United States Patent
Abeywardane et al.

(10) Patent No.: US 8,586,748 B2
(45) Date of Patent: Nov. 19, 2013

(54) 2-SULFONYLAMINO-4-HETEROARYL BUTYRAMIDE ANTAGONISTS OF CCR10

(75) Inventors: Asitha Abeywardane, Danbury, CT (US); Derek Cogan, Sandy Hook, CT (US); Younggi Choi, Brookfield, CT (US); Donghong A. Gao, Hopewell Junction, NY (US); Daniel R. Goldberg, Redding, CT (US); Alexander Heim-Riether, Newtown, CT (US); Craig Andrew Miller, Mount Vernon, NY (US); Philip Dean Ramsden, Mount Vernon, NY (US); Lana Louise Smith Keenan, Poughquag, NY (US); Roger John Snow, Danbury, CT (US); Yang Yu, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 238 days.

(21) Appl. No.: 12/937,006

(22) PCT Filed: Apr. 8, 2009

(86) PCT No.: PCT/US2009/039850
§ 371 (c)(1),
(2), (4) Date: Mar. 21, 2011

(87) PCT Pub. No.: WO2009/126675
PCT Pub. Date: Oct. 15, 2009

(65) Prior Publication Data
US 2011/0275800 A1    Nov. 10, 2011

Related U.S. Application Data

(60) Provisional application No. 61/043,416, filed on Apr. 9, 2008.

(51) Int. Cl.
*C07D 401/12* (2006.01)
*C07D 401/14* (2006.01)
*A61K 31/454* (2006.01)

(52) U.S. Cl.
USPC ............................ 546/208; 546/211; 514/326

(58) Field of Classification Search
USPC .................. 546/208, 211; 514/326
See application file for complete search history.

(56) References Cited

U.S. PATENT DOCUMENTS 6,680,329 B2 * 1/2004 Altenburger et al. ......... 514/318

FOREIGN PATENT DOCUMENTS

| DE | 19548797 | * | 7/1997 |
| WO | 2008008374 | A2 | 1/2008 |
| WO | 2009052078 | A1 | 4/2009 |
| WO | 2009142984 | A1 | 11/2009 |

OTHER PUBLICATIONS

Quinones et. al. "The complex role of the chemokine receptor CCR2 in collagen-induced arthritis: implications for therapeutic targeting of CCR2 in rheumatoid arthritis" Journal of Molecular Medicine 2005 83: 672-681.*
Wagner et al.; Syntheses von 4-(4-Amidino-phenyl)-2-arylsulfonylaminobuttersaeureamiden; Die Pharmazie; vol. 37; No. 1; Jan. 1, 1982; pp. 13-16.
International Search Report for corresponding PCT/US2009/039850; date of mailing Sep. 24, 2009.

* cited by examiner

*Primary Examiner* — David K O Dell
(74) *Attorney, Agent, or Firm* — Michael P. Morris; Edward S. Lazer

(57) ABSTRACT

This invention relates to a compound of formula (I) and the pharmaceutically acceptable salts thereof wherein $R^1$, $R^2$, $R^4$. Ar and Het are as defined herein. The invention also relates to methods of using the compound of formula (I) to treat a diseases and disorders that are mediated or sustained through the activity of CCR10.

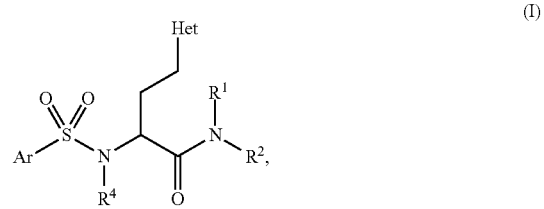

5 Claims, No Drawings

2-SULFONYLAMINO-4-HETEROARYL BUTYRAMIDE ANTAGONISTS OF CCR10

BACKGROUND OF THE INVENTION

1. Field of the Invention

This invention relates to substituted amides that are useful as inhibitors of CCR10 activity and are thus useful for treating a variety of diseases and disorders that are mediated or sustained through the activity of CCR10 including inflammatory skin diseases, allergic asthma and melanoma. This invention also relates to pharmaceutical compositions comprising these compounds, methods of using these compounds in the treatment of various diseases and disorders, processes for preparing these compounds and intermediates useful in these processes.

2. Brief Description of the Art

Chemokine receptors play an important role in mediating tissue specific recruitment of leukocytes to sites of inflammation. Within the blood there is a subset of memory T cells that preferentially homes to the skin. This subset is defined by expression of the cutaneous lymphocyte antigen (CLA), a lectin, which binds to E-selectin on dermal endothelial cells and promotes trafficking. Although the subset of CLA-expressing cells constitutes only 10-15% of the circulating T cell pool, these cells are found in abundance within several inflammatory skin lesions, for example, psoriasis, contact sensitivity and allergic dermatitis.

Recent studies have revealed that $CLA^+$ memory cells also express the chemokine receptor CCR10 and that cells expressing CCR10 are enriched in inflammatory skin lesions. One ligand for this receptor, CCL27, is also markedly up-regulated at these sites suggesting that this chemokine receptor may participate in mediating the tissue-specific trafficking of $CLA^+$ memory T cells. Within the skin, expression of CCR10 has been reported on $CLA^+$ T cells, melanocytes, fibroblasts, and microvascular endothelial cells. CCL27 expression has been shown to be tightly regulated with abundant expression in the epidermis, predominantly by keratinocytes.

There is evidence in both humans and in rodents that the CCR10-CCL27 interaction plays an important role in the trafficking of inflammatory T cell subsets to skin lesions. By histological analysis, it is clear that, in addition to the increase in epidermal expression of CCL27 observed in psoriatic and atopic dermatitis biopsies, there is also expanded expression of CCL27 into the dermal layer as well. Further, endothelial cells within the vasculature of these lesions also display CCL27, though they are negative for CCL27 message, suggesting that keratinocyte-derived CCL27 can be captured by endothelial cells and presented to circulating leukocytes. Accompanying these changes in the skin is a marked increase in the recruitment of lymphocytes that co-express CLA and CCR10. Consistent with the role of CCL27 in skin inflammation, IL-1 beta and TNF alpha treatment of cultured keratinocytes induces expression of CCL27.

Cutaneous application of nickel, in nickel-allergic humans, led to the up-regulated expression of CCL27 and the subsequent recruitment of $CCR10^+$ lymphocytes. Thus, these studies provide temporal support for the role of CCL27 in attracting $CCR10^+$ cells. Furthermore, in vivo proof of concept has been shown in wild-type mice where treatment with a function blocking antibody against CCL27 clearly diminished recruitment and swelling in both DNFB-induced and ovalbumin DTH models of dermatitis. These authors also demonstrated the ability of cutaneous injection of CCL27 to promote local lymphocyte trafficking and inflammation, thus providing proof of concept using both ligand and antibody in relevant animal models. Consistent with its ascribed in vivo role, CCL27 induces calcium flux in $CCR10^+$ cells and mediates the selective chemotaxis of $CLA^+$ $CCR10^+$ lymphocytes in vitro.

Studies, such as those described above, suggest that antagonism of the interaction between CCR10 and its skin derived ligand CCL27 could therefore be of benefit in the treatment of inflammatory skin diseases by blocking the entry and activation of T cells within the skin. One indication for a CCR10 antagonist would be psoriasis. The rationale is based on histological studies of receptor/ligand expression in humans with psoriasis and proof of concept studies in animal models of skin inflammation. From analysis of normal and diseased skin samples, it is clear that the expression of CCR10 is highly regulated and restricted primarily to a subset of skin homing ($CLA^+$) lymphocytes, dermal endothelial cells, and dermal fibroblasts. In addition, CCL27, a ligand for CCR10, is also expressed in keratinocytes. In normal skin, CCL27 is expressed by keratinocytes in the basal layers of the epidermis. However, in the skin of atopic dermatitis and psoriasis patients this ligand is up-regulated with expression extending to the suprabasal layers of the epidermis and histological staining also evident on the dermal microvasculature. The enhanced expression of CCL27 is accompanied by an increased presence of $CCR10^+$ lymphocytes. Finally the proof of concept studies described above demonstrated that a function blocking antibody directed against CCL27 blocked trafficking of lymphocytes and swelling in two murine models of dermatitis.

Based on the pattern of expression for both CCR10 and CCL27 and the above proof of concept studies, CCR10 may also be a promising target for treatment of contact sensitivity and allergic dermatitis. It has been shown recently that CCL27 is increased in the sera of patients with systemic sclerosis and in the dermis of UV-induced cutaneous SLE (systemic lupus erythematosus) lesions. Therefore, systemic sclerosis and cutaneous SLE could also be additional indications. In addition, inflammation of the respiratory tract in a murine model of allergic asthma is associated with CCL28 and CCR10 expression suggesting that inhibition of CCR10 activity may also be useful in treatment of allergic asthma.

Antagonism of CCR10 may also be beneficial for the treatment of melanoma. In a mouse model of melanoma metastasis, it has been demonstrated that melanoma lines expressing CCR10 form tumors more readily than matched CCR10 deficient melanomas and that a blocking antibody against CCL27 can block the growth of these $CCR10^+$ melanoma cells in vivo. These observations, coupled with the finding that many human melanomas express CCR10, provide the rationale for considering this as a further indication.

BRIEF SUMMARY OF THE INVENTION

In a general aspect, the present invention is directed to the compounds of the following formula (I):

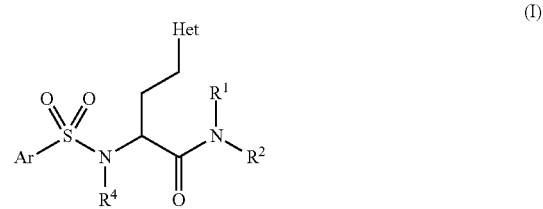

wherein Ar, Het, $R^1R^2$ and $R^4$ are as defined herein, as well as the tautomers thereof, and salts thereof. It has been found that the compounds of formula (I) have valuable pharmacological properties, particularly an inhibiting activity of CCR10 activity.

In another aspect, the present invention is directed to a method of inhibiting CCR10 activity in an individual comprising administering to the individual a therapeutically effective amount of a compound of formula (I), or a pharmaceutically acceptable salt thereof.

In another aspect, the present invention is directed to a method of treating a disease or disorder associated with the activation of CCR10 comprising administering to an individual a therapeutically effective amount of a compound of formula (I), or a pharmaceutically acceptable salt thereof.

In another aspect, the present invention is directed to a method of treating an inflammatory skin disease comprising administering to an individual a therapeutically effective amount of a compound of formula (I), or a pharmaceutically acceptable salt thereof. Examples of such diseases that may be treated include, for example, psoriasis, contact sensitivity, allergic dermatitis, systemic sclerosis, and cutaneous SLE.

In another aspect, the present invention is directed to a method of treating allergic asthma comprising administering to an individual a therapeutically effective amount of a compound of formula (I), or a pharmaceutically acceptable salt thereof.

In another aspect, the present invention is directed to a method of treating melanoma comprising administering to an individual in need of such treatment a therapeutically effective amount of a compound of formula (I), or a pharmaceutically acceptable salt thereof.

In yet additional aspects, the present invention is directed to pharmaceutical compositions comprising a compound of formula (I), or a pharmaceutically acceptable salt thereof, and a pharmaceutically acceptable carrier.

The present invention also includes the processes for preparing the above-mentioned compounds and intermediates used in these processes.

DETAILED DESCRIPTION OF THE INVENTION

In an embodiment there is provided compounds of formula (I):

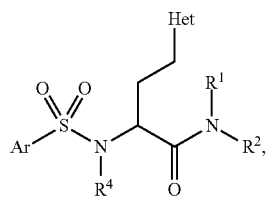

wherein:
Ar is phenyl, naphthyl or heteroaryl. selected from indolyl, pyridyl, thienyl, pyrazolyl, oxazolyl, indazolyl, benzimidazolyl, isoquinolinyl, 1H-pyrrolo[2,3-b]pyridinyl, benzothienyl, benzofuranyl, 2,1,3-benzothiadiazolyl and 6H-imidazo[2,1-b]thiazolyl, wherein said phenyl naphthyl or heteroaryl is optionally substituted with one to four groups selected from $C_{1-6}$alkyl, $C_{1-6}$alkoxy, phenyl, heteroaryl, phenyloxy, halogen, —$NH_2$, —NHC(O)$NH_2$, —NHC(O)$C_{1-6}$alkyl, —$NO_2$, —$CF_3$, —$OCF_3$, —CN, —C(O)$C_{1-6}$alkyl, —$(CH_2)_{0-2}$ $CO_2C_{1-6}$alkyl, —$(CH_2)_{0-2}CO_2H$, 5-tetrazolyl, —CHO, —C(O)$NH_2$, —C(O)NH($C_{1-6}$alkyl) and —C(O)N($C_{1-6}$alkyl)$_2$; or
if Ar is phenyl, two adjacent groups together with the phenyl they are bonded to may form a 2,3-dihydrobenzofuranyl, 1,3-dihydroindol-2-one, or 2-acetyl-3,4-dihydro-1H-isoquinolinyl group;
Het is a heteroaryl group selected from:

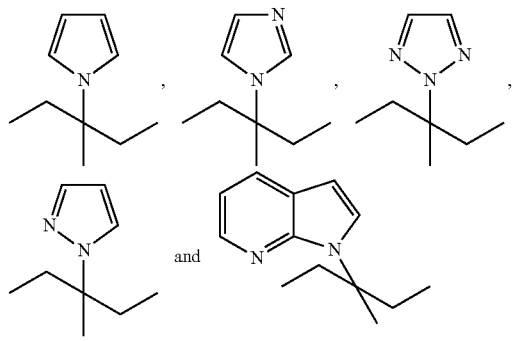

and is optionally substituted with one to two groups independently selected from
—CN, —$NO_2$, halogen, —$C_{1-6}$alkyl, —C(O)$NH_2$ and $CO_2Me$;
$R^1$ and $R^2$ are independently selected from $C_{1-6}$alkyl, aryl$C_{1-2}$alkyl, phenyl, naphthyl and $C_{3-8}$cycloalkyl, wherein said aryl$C_{1-2}$alkyl is optionally substituted with one to two groups selected from halogen, $C_{1-6}$alkoxy, $C_{1-6}$alkyl, —$CF_3$, imidazolyl, pyridyl, pyrimidinyl, pyrazolyl, 5-methyloxadiazolyl, morpholinyl, piperidinyl and N-methyl-1,2,3,4-tetrahydroisoquinolinyl; or
$R^1$ and $R^2$, together with the N they are bonded to form a heterocycle selected from piperidine, morpholine, tetrahydroisoquinoline, decahydroisoquinoline, piperazine, azepane, 6-aza-spiro[2.5]octane, 2,3,4,5-tetrahydro-1H-benzo[b]azepine, [1,4]-diazepane, [1,4]-oxazepane, thiomorpholine, thiomorpholine, thiomorpholine 1,1-dioxide, 4,5,6,7-tetrahydrothieno[3,2-c]pyridine, 5,6,7,8-tetrahydro-[1,2,4]triazolo[4,3-a]pyrazine, 5,6,7,8-tetrahydro-imidazo[1,5-a]pyrazine, 4,5,6,7-tetrahydro-thiazolo[5,4-c]pyridine, 1,2,3,6-tetrahydropyridine and octahydropyrido[1,2-a]pyrazine, wherein said heterocycle is optionally substituted by one to two groups selected from $C_{1-6}$alkyl, $C_{1-6}$alkenyl, phenyl, benzyl, hydroxy$C_{1-6}$alkyl, —OH, —$CF_3$, —CN, halogen, —$NO_2$, —$NH_2$, oxo, 1,3-dioxolane, —CH=$NOCH_3$, —$SO_2NH_2$, —$SO_2N(C_{1-6}$alkyl$)_2$, —$SO_3H$, —$SO_2(C_{1-6}$ alkyl$)_2$, —C(O)N($C_{1-6}$alkyl$)_2$, —C(O)NH$C_{1-6}$alkyl, —$(CH_2)_{0-2}$C(O)$NH_2$, —$(CH_2)_{0-4}CO_2H$, —$(CH_2)_{0-4}$ $CO_2C_{1-6}$ alkyl, =C—$CO_2C_{1-6}$alkyl, —CH=CH—$CO_2H$, —CH=CH—$CO_2C_{1-6}$alkyl, —$OCH_2CO_2H$, —$OCH_2CO_2C_{1-6}$alkyl, —$OC(CH_3)_2CO_2H$, —$OC(CH_3)_2$ $CO_2C_{1-6}$alkyl, —C(O)$CH_2CO_2H$, —C(O)$CH_2CO_2C_{1-6}$ alkyl, —C(O)$C_{1-6}$alkyl, —C(O)$C_{1-4}$alkyl(OH), —$CH_2OC_{1-6}$ alkyl, —$(CH_2)_{0-2}$NHC(O)$C_{1-6}$alkyl, —C(O)morpholinyl, thiazole, 3-methyl-1,2,4-oxadiazolyl, pyrimidine and 2-[1,2,4]oxadiazol-3-ylpyrazine; and
$R^4$ is hydrogen or $C_{1-6}$alkyl;
or a pharmaceutically acceptable salt thereof.

In another embodiment, there are provided compounds of formula (I), wherein:
Ar is phenyl, naphthyl or heteroaryl selected from indolyl, pyridyl, thienyl, pyrazolyl, indazolyl, isoquinolinyl, benzothienyl, benzofuranyl, and 6H-imidazo[2,1-b]thiazolyl, wherein said phenyl naphthyl or heteroaryl is optionally substituted with one to four groups selected from $CH_3$, $-CH_2CH_3$, $-OCH_3$, Cl, Br, F, $-NH_2$, $C(O)CH_3$, $NHC(O)CH_3$, $-CF_3$, $-OCF_3$, $-CN$ and $-CO_2CH_3$; or if Ar is phenyl, two adjacent groups together with the phenyl they are bonded to may form a 2,3-dihydrobenzofuranyl or oxindolyl group;

Het is a heteroaryl group selected from

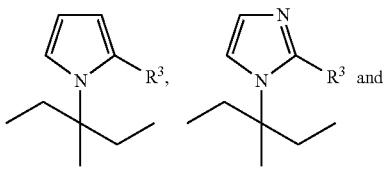

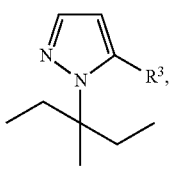

wherein $R^3$ is selected from $-CN$, $-NO_2$, Cl, Br, $-C(O)NH_2$ and $CO_2Me$;

$R^1$ is $CH_3$ and $R^2$ is benzyl, wherein said benzyl is optionally substituted with one to two groups selected from halogen, $C_{1-6}$alkoxy, $C_{1-6}$alkyl, $-CF_3$, imidazolyl, pyridyl, pyrimidinyl, pyrazolyl, 5-methyloxadiazolyl, morpholinyl, piperidinyl and N-methyl-1,2,3,4-tetrahydroisoquinolinyl; or $R^1$ and $R^2$, together with the N they are bonded to form a heterocycle selected from piperidine, tetrahydroisoquinoline, decahydroisoquinoline, piperazine, 6-aza-spiro[2.5]octane, azepane, [1,4]-diazepane and [1,4]-oxazepane, 4,5,6,7-tetrahydrothieno[3,2-c]pyridine, 5,6,7,8-tetrahydro-imidazo[1,5-a]pyrazine, 1,2,3,6-tetrahydropyridine, 5,6,7,8-tetrahydro-[1,2,4]triazolo[4,3-a]pyrazine, 2,3,4,5-tetrahydro-1H-benzo[b]azepine and 1,2,3,6-tetrahydropyridine, wherein said heterocycle is optionally substituted by one to two groups selected from $C_{1-6}$alkyl, $C_{1-6}$alkenyl, phenyl, benzyl, $-CF_3$, $-CN$, Cl, Br, F, $-NO_2$, oxo, $-CH=NOCH_3$, $SO_2NH_2$, $-SO_2N(CH_3)_2$, $-SO_3H$, $-SO_2(CH_3)$, $-C(O)N(CH_3)_2$, $-C(O)NHCH_3$, $-(CH_2)_{0-2}C(O)NH_2$, $-(CH_2)_{0-4}CO_2H$, $-(CH_2)_{0-4}CO_2C_{1-2}$alkyl, $-(CH_2)_{0-4}OH$, $-CH=CH-CO_2H$, $-CH=CH-CO_2C_{1-2}$alkyl, $=C-CO_2C_{1-6}$alkyl, $-OCH_2CO_2H$, $-OCH_2CO_2C_{1-2}$alkyl, $-OC(CH_3)_2CO_2H$, $-OC(CH_3)_2CO_2C_{1-2}$alkyl, $-C(O)CH_2CO_2H$, $-C(O)CH_2CO_2C_{1-2}$alkyl, $-C(O)CH_3$, $-C(O)C_{1-4}$alkyl(OH), $-CH_2OCH_3$, $-(CH_2)_{0-2}NHC(O)CH_3$, $-C(O)$morpholinyl, thiazole, 3-methyl-1,2,4-oxadiazolyl, pyrimidine and 2-[1,2,4]oxadiazol-3-ylpyrazine; and $R^4$ is hydrogen;

or a pharmaceutically acceptable salt thereof.

In still another embodiment, there are provided compounds of formula (I), wherein:

Ar is phenyl, indolyl, thienyl or indazolyl, wherein each is optionally substituted with one to three groups selected from $CH_3$, $-CH_2CH_3$, $-OCH_3$, Cl, Br, F, $-NH_2$, and $-CF_3$;

Het is a heteroaryl group selected from

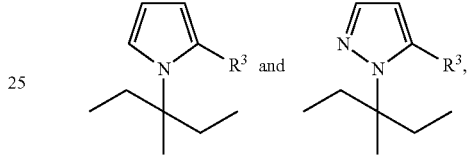

wherein $R^3$ is selected from $-CN$, $-NO_2$, Cl, Br, $-C(O)NH_2$ and $CO_2Me$;

$R^1$ and $R^2$, together with the N they are bonded to, form a heterocycle selected from piperidine, tetrahydroisoquinoline, decahydroisoquinoline, piperazine, 6-aza-spiro[2.5]octane, azepane, [1,4]-diazepane and [1,4]-oxazepane, 1,2,3,6-tetrahydrpyridine and 4,5,6,7-tetrahydrothieno[3,2-c]pyridine, wherein said heterocycle is optionally substituted by one to two groups selected from $C_{1-6}$alkyl, $(CH_2)_{0-2}OH$, $-CF_3$, $-CN$, Cl, Br, F, $-(CH_2)_{0-4}CO_2H$, $-(CH_2)_{0-4}CO_2C_{1-6}$alkyl, $-C(O)N(CH_3)_2$, $-C(O)NHCH_3$, $-C(O)NH_2$, $-C(O)CH_3$, $-CH=CH-CO_2H$, $-OC(CH_3)_2CO_2H$, $-OC(CH_3)_2CO_2H$ and $-C(O)CH_2CO_2H$; and $R^4$ is hydrogen;

or a pharmaceutically acceptable salt thereof.

In still a further embodiment of the invention, there are provided compounds of the formula (I) selected from the group below or a tautomer thereof or a salt thereof:

| Example | Structure | Name |
|---------|-----------|------|
| 1 | 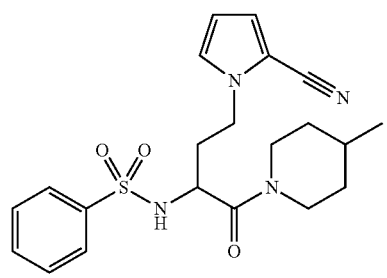 [SMILES: CC1CCN(C(=O)C(CCn2cccc2C#N)NS(=O)(=O)c2ccccc2)CC1] | N-{3-(2-cyano-1H-pyrrol-1-yl)-1[(4-methylpiperidin-1-yl)carbonyl]propyl} benzenesulfonamide |

-continued

| Example | Structure | Name |
|---|---|---|
| 2 | 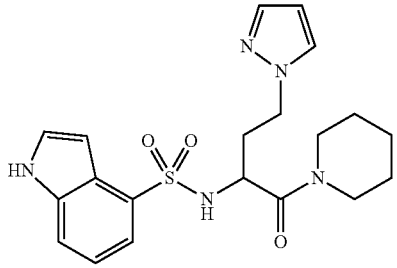 [SMILES: O=C(C(CCn1cccn1)NS(=O)(=O)c1cccc2[nH]ccc12)N1CCCCC1] | N-[1-(piperidin-1-ylcarbonyl)-3-(1H-pyrazol-1-yl)propyl]-1H-indole-4-sulfonamide |
| 3 | 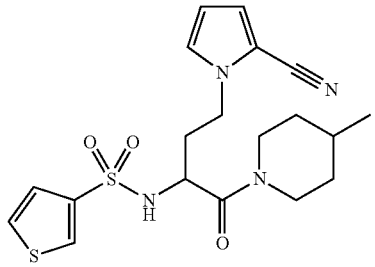 [SMILES: CC1CCN(C(=O)C(CCn2cccc2C#N)NS(=O)(=O)c2ccsc2)CC1] | N-{3-(2-cyano-1H-pyrrol-1-yl)-1-[(4-methylpiperidin-1-yl)carbonyl]propyl}thiophene-3-sulfonamide |
| 4 | 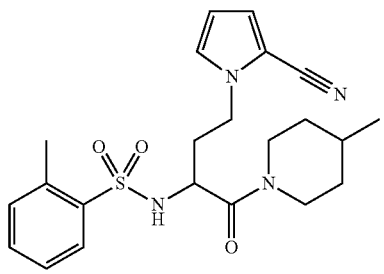 [SMILES: Cc1ccccc1S(=O)(=O)NC(CCn1cccc1C#N)C(=O)N1CCC(C)CC1] | N-{3-(2-cyano-1H-pyrrol-1-yl)-1-[(4-methylpiperidin-1-yl)carbonyl]propyl}-2-methylbenzenesulfonamide |
| 5 | 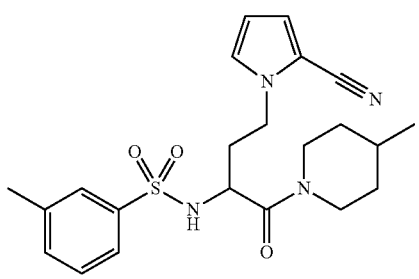 | N-{3-(2-cyano-1H-pyrrol-1-yl)-1-[(4-methylpiperidin-1-yl)carbonyl]propyl}-3-methylbenzenesulfonamide |
| 6 | 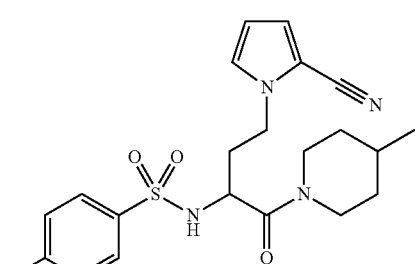 | N-{3-(2-cyano-1H-pyrrol-1-yl)-1-[(4-methylpiperidin-1-yl)carbonyl]propyl}-4-methylbenzenesulfonamide |

-continued

| Example | Structure | Name |
|---|---|---|
| 7 | 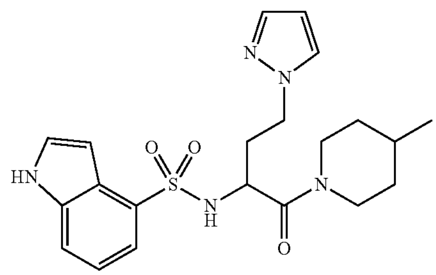 [SMILES: CC1CCN(C(=O)C(CCn2cccn2)NS(=O)(=O)c2cccc3[nH]ccc23)CC1] | N-{1-[(4-methylpiperidin-1-yl)carbonyl]-3-(1H-pyrazol-1-yl)propyl}-1H-indole-4-sulfonamide |
| 8 | 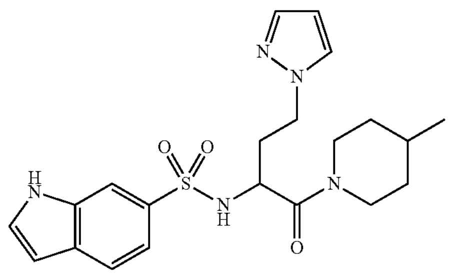 [SMILES: CC1CCN(C(=O)C(CCn2cccn2)NS(=O)(=O)c2ccc3cc[nH]c3c2)CC1] | N-{1-[(4-methylpiperidin-1-yl)carbonyl]-3-(1H-pyrazol-1-yl)propyl}-1H-indole-6-sulfonamide |
| 9 | 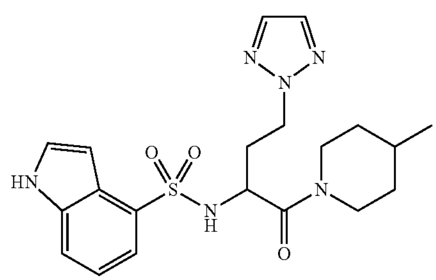 [SMILES: CC1CCN(C(=O)C(CCn2nccn2)NS(=O)(=O)c2cccc3[nH]ccc23)CC1] | N-{1-[(4-methylpiperidin-1-yl)carbonyl]-3-(2H-1,2,3-triazol-2-yl)propyl}-1H-indole-4-sulfonamide |
| 10 | 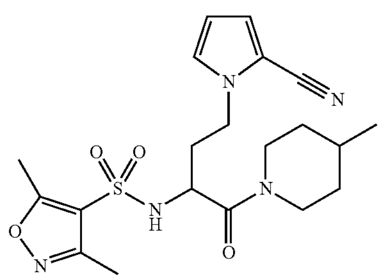 [SMILES: Cc1noc(C)c1S(=O)(=O)NC(CCn1cccc1C#N)C(=O)N1CCC(C)CC1] | N-{3-(2-cyano-1H-pyrrol-1-yl)-1-[(4-methylpiperidin-1-yl)carbonyl]propyl}-3,5-dimethylisoxazole-4-sulfonamide |
| 11 | 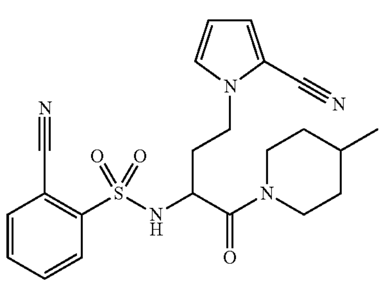 [SMILES: CC1CCN(C(=O)C(CCn2cccc2C#N)NS(=O)(=O)c2ccccc2C#N)CC1] | 2-cyano-N-{3-(2-cyano-1H-pyrrol-1-yl)-1-[(4-methylpiperidin-1-yl)carbonyl]propyl}benzenesulfonamide |

-continued

| Example | Structure | Name |
|---|---|---|
| 12 | 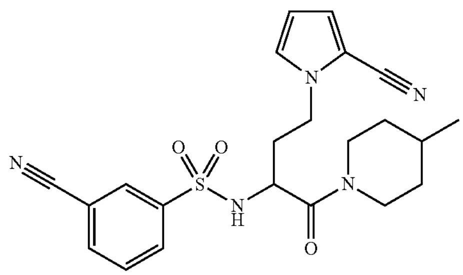 [SMILES: CC1CCN(C(=O)C(CCn2cccc2C#N)NS(=O)(=O)c2cccc(C#N)c2)CC1] | 3-cyano-N-{3-(2-cyano-1H-pyrrol-1-yl)-1-[(4-methylpiperidin-1-yl)carbonyl]propyl} benzenesulfonamide |
| 13 | 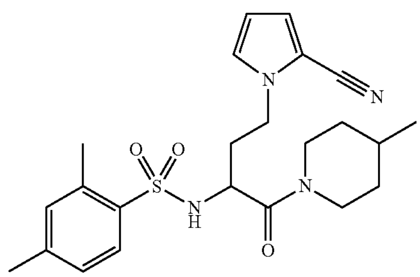 | N-{3-(2-cyano-1H-pyrrol-1-yl)-1-[(4-methylpiperidin-1-yl)carbonyl]propyl}-2,4-dimethylbenzenesulfonamide |
| 14 | 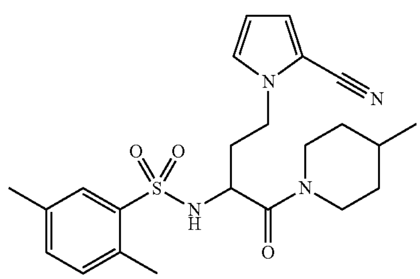 | N-{3-(2-cyano-1H-pyrrol-1-yl)-1-[(4-methylpiperidin-1-yl)carbonyl]propyl}-2,5-dimethylbenzenesulfonamide |
| 15 | 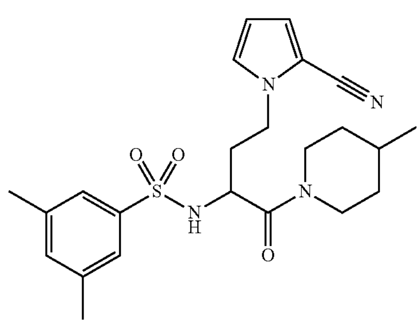 | N-{3-(2-cyano-1H-pyrrol-1-yl)-1-[(4-methylpiperidin-1-yl)carbonyl]propyl}-3,5-dimethylbenzenesulfonamide |
| 16 | 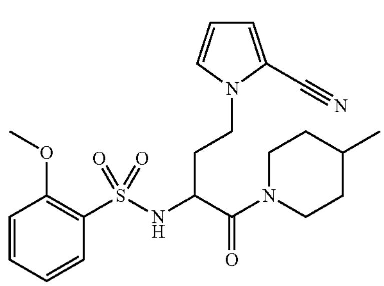 [SMILES: COc1ccccc1S(=O)(=O)NC(CCn1cccc1C#N)C(=O)N1CCC(C)CC1] | N-{3-(2-cyano-1H-pyrrol-1-yl)-1-[(4-methylpiperidin-1-yl)carbonyl]propyl}-2-methoxybenzenesulfonamide |

-continued

| Example | Structure | Name |
|---|---|---|
| 17 | 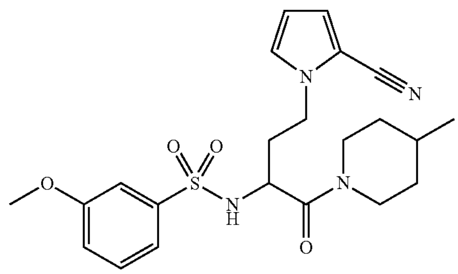 | N-{3-(2-cyano-1H-pyrrol-1-yl)-1-[(4-methylpiperidin-1-yl)carbonyl]propyl}-3-methoxybenzenesulfonamide |
| 18 | 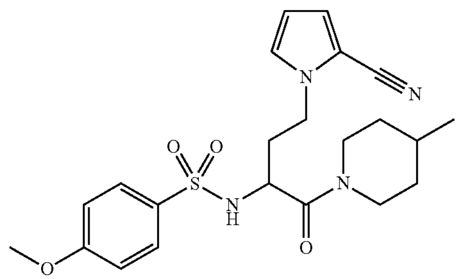 | N-{3-(2-cyano-1H-pyrrol-1-yl)-1-[(4-methylpiperidin-1-yl)carbonyl]propyl}-4-methoxybenzenesulfonamide |
| 19 | 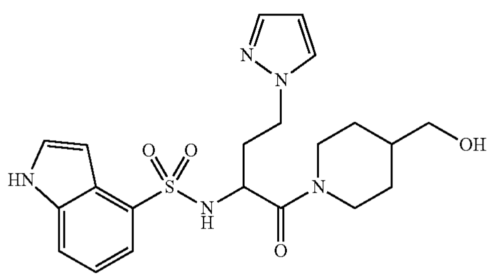 [SMILES: O=C(C(CCn1cccn1)NS(=O)(=O)c1cccc2[nH]ccc12)N1CCC(CO)CC1] | N-[1-{[4-(hydroxymethyl)piperidin-1-yl]carbonyl}-3-(1H-pyrazol-1-yl)propyl]-1H-indole-4-sulfonamide |
| 20 | 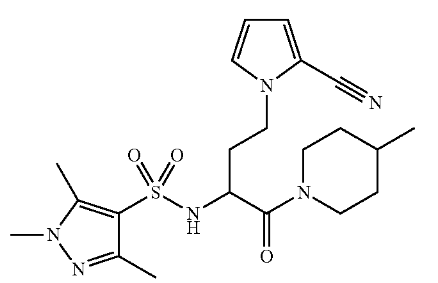 | N-{3-(2-cyano-1H-pyrrol-1-yl)-1-[(4-methylpiperidin-1-yl)carbonyl]propyl}-1,3,5-trimethyl-1H-pyrazole-4-sulfonamide |
| 21 | 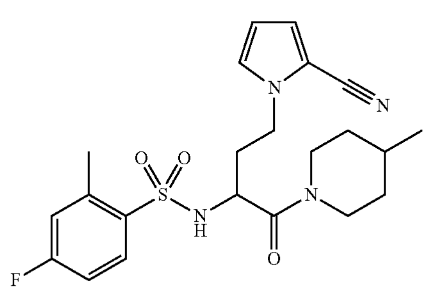 | N-{3-(2-cyano-1H-pyrrol-1-yl)-1-[(4-methylpiperidin-1-yl)carbonyl]propyl}-4-fluoro-2-methylbenzenesulfonamide |

| Example | Structure | Name |
|---|---|---|
| 22 | 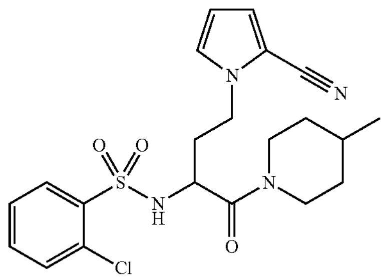 [SMILES: CC1CCN(C(=O)C(CCn2cccc2C#N)NS(=O)(=O)c2ccccc2Cl)CC1] | 2-chloro-N-{3-(2-cyano-1H-pyrrol-1-yl)-1-[(4-methylpiperidin-1-yl)carbonyl]propyl} benzenesulfonamide |
| 23 | 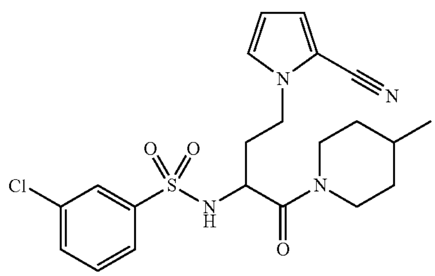 [SMILES: CC1CCN(C(=O)C(CCn2cccc2C#N)NS(=O)(=O)c2cccc(Cl)c2)CC1] | 3-chloro-N-{3-(2-cyano-1H-pyrrol-1-yl)-1-[(4-methylpiperidin-1-yl)carbonyl]propyl} benzenesulfonamide |
| 24 | 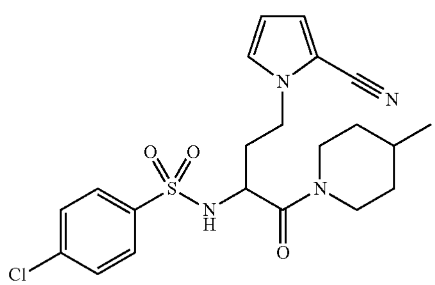 [SMILES: CC1CCN(C(=O)C(CCn2cccc2C#N)NS(=O)(=O)c2ccc(Cl)cc2)CC1] | 4-chloro-N-{3-(2-cyano-1H-pyrrol-1-yl)-1-[(4-methylpiperidin-1-yl)carbonyl]propyl} benzenesulfonamide |
| 25 | 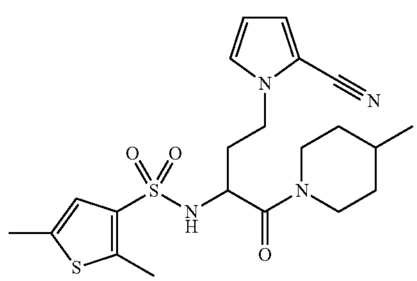 | N-{3-(2-cyano-1H-pyrrol-1-yl)-1-[(4-methylpiperidin-1-yl)carbonyl]propyl}-2,5-dimethylthiophene-3-sulfonamide |
| 26 | 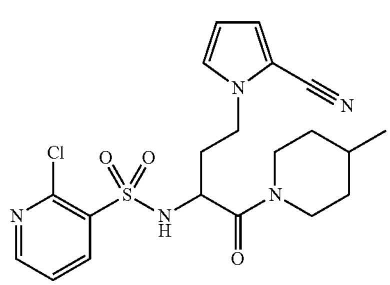 [SMILES: CC1CCN(C(=O)C(CCn2cccc2C#N)NS(=O)(=O)c2cccnc2Cl)CC1] | 2-chloro-N-{3-(2-cyano-1H-pyrrol-1-yl)-1-[(4-methylpiperidin-1-yl)carbonyl]propyl} pyridine-2-sulfonamide |

-continued

| Example | Structure | Name |
|---|---|---|
| 27 | 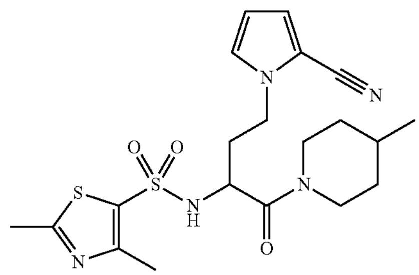 | N-{3-(2-cyano-1H-pyrrol-1-yl)-1-[(4-methylpiperidin-1-yl)carbonyl]propyl}-2,4-dimethyl-1,3-thiazole-5-sulfonamide |
| 28 | 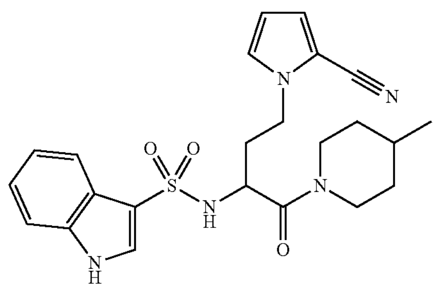 [SMILES: CC1CCN(C(=O)C(CCn2cccc2C#N)NS(=O)(=O)c2c[nH]c3ccccc23)CC1] | N-{3-(2-cyano-1H-pyrrol-1-yl)-1-[(4-methylpiperidin-1-yl)carbonyl]propyl}-1H-indole-3-sulfonamide |
| 29 | 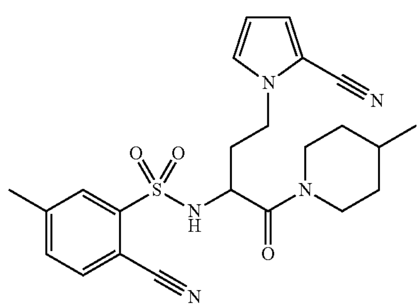 | 2-cyano-N-{3-(2-cyano-1H-pyrrol-1-yl)-1-[(4-methylpiperidin-1-yl)carbonyl]propyl}-5-methylbenzenesulfonamide |
| 30 | 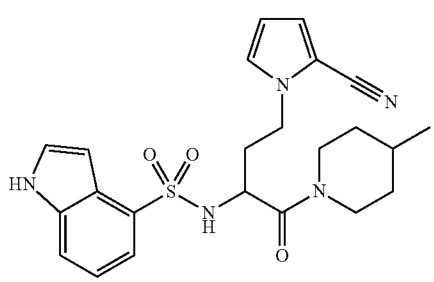 [SMILES: CC1CCN(C(=O)C(CCn2cccc2C#N)NS(=O)(=O)c2cccc3[nH]ccc23)CC1] | N-{3-(2-cyano-1H-pyrrol-1-yl)-1-[(4-methylpiperidin-1-yl)carbonyl]propyl}-1H-indole-4-sulfonamide |
| 31 | 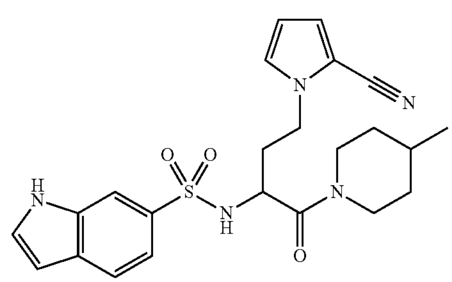 [SMILES: CC1CCN(C(=O)C(CCn2cccc2C#N)NS(=O)(=O)c2ccc3cc[nH]c3c2)CC1] | N-{3-(2-cyano-1H-pyrrol-1-yl)-1-[(4-methylpiperidin-1-yl)carbonyl]propyl}-1H-indole-6-sulfonamide |

-continued

| Example | Structure | Name |
|---|---|---|
| 32 | 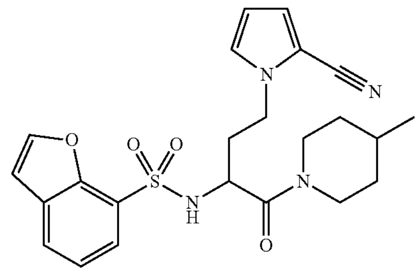 [SMILES: CC1CCN(C(=O)C(CCn2cccc2C#N)NS(=O)(=O)c2cccc3ccoc23)CC1] | N-{3-(2-cyano-1H-pyrrol-1-yl)-1-[(4-methylpiperidin-1-yl)carbonyl]propyl}-1-benzofuran-7-sulfonamide |
| 33 | 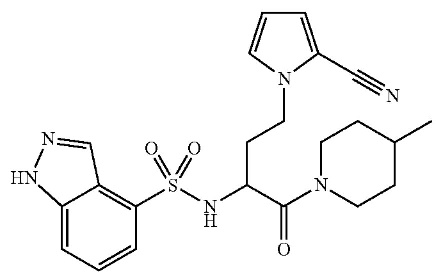 [SMILES: CC1CCN(C(=O)C(CCn2cccc2C#N)NS(=O)(=O)c2cccc3[nH]ncc23)CC1] | N-{3-(2-cyano-1H-pyrrol-1-yl)-1-[(4-methylpiperidin-1-yl)carbonyl]propyl}-1H-indazole-4-sulfonamide |
| 34 | 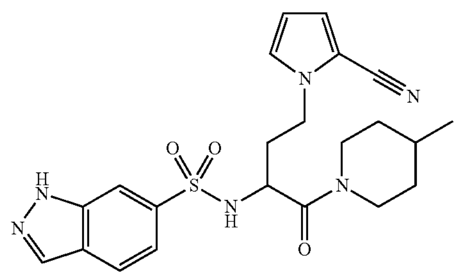 [SMILES: CC1CCN(C(=O)C(CCn2cccc2C#N)NS(=O)(=O)c2ccc3cn[nH]c3c2)CC1] | N-{3-(2-cyano-1H-pyrrol-1-yl)-1-[(4-methylpiperidin-1-yl)carbonyl]propyl}-1H-indazole-6-sulfonamide |
| 35 | 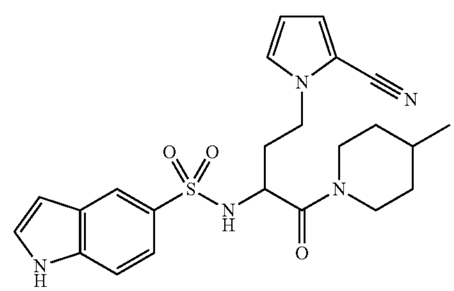 [SMILES: CC1CCN(C(=O)C(CCn2cccc2C#N)NS(=O)(=O)c2ccc3[nH]ccc3c2)CC1] | N-{3-(2-cyano-1H-pyrrol-1-yl)-1-[(4-methylpiperidin-1-yl)carbonyl]propyl}-1H-indole-5-sulfonamide |
| 36 | 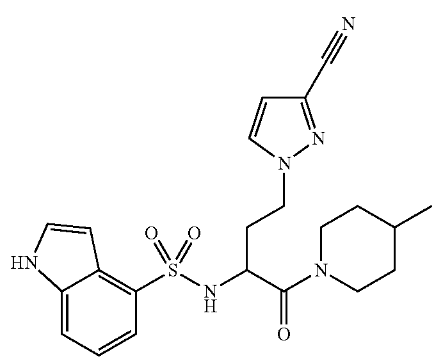 [SMILES: CC1CCN(C(=O)C(CCn2ccc(C#N)n2)NS(=O)(=O)c2cccc3[nH]ccc23)CC1] | N-{3-(3-cyano-1H-pyrazol-1-yl)-1-[(4-methylpiperidin-1-yl)carbonyl]propyl}-1H-indole-4-sulfonamide |

-continued

| Example | Structure | Name |
|---|---|---|
| 37 | 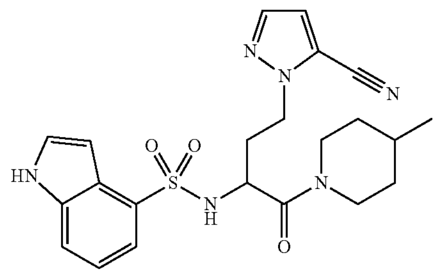 | N-{3-(5-cyano-1H-pyrazol-1-yl)-1-[(4-methylpiperidin-1-yl)carbonyl]propyl}-1H-indole-4-sulfonamide |
| 38 | 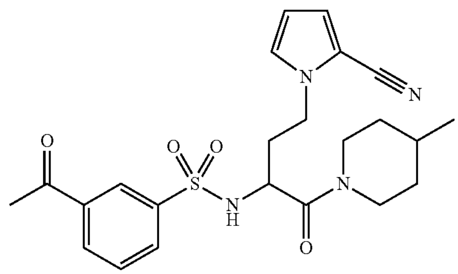 [SMILES: CC(=O)c1cccc(S(=O)(=O)NC(CCn2cccc2C#N)C(=O)N2CCC(C)CC2)c1] | 3-acetyl-N-{3-(2-cyano-1H-pyrrol-1-yl)-1-[(4-methylpiperidin-1-yl)carbonyl]propyl}benzenesulfonamide |
| 39 | 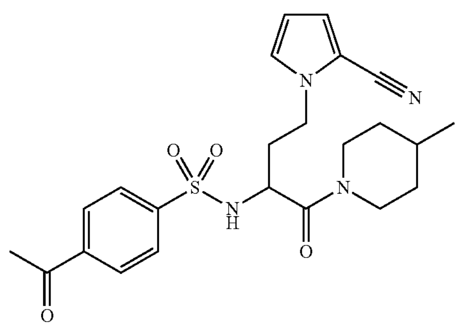 [SMILES: CC(=O)c1ccc(S(=O)(=O)NC(CCn2cccc2C#N)C(=O)N2CCC(C)CC2)cc1] | 4-acetyl-N-{3-(2-cyano-1H-pyrrol-1-yl)-1-[(4-methylpiperidin-1-yl)carbonyl]propyl}benzenesulfonamide |
| 40 | 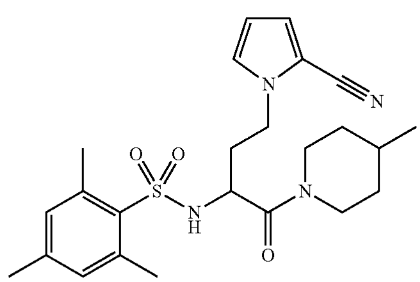 | N-{3-(5-cyano-1H-pyrrol-1-yl)-1-[(4-methylpiperidin-1-yl)carbonyl]propyl}-2,4,6-trimethylbenzenesulfonamide |
| 41 | 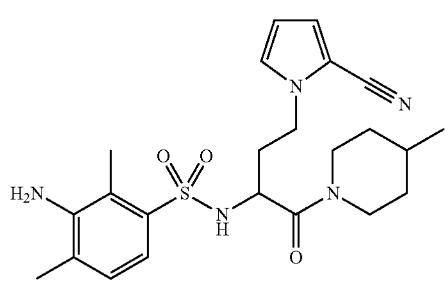 | 3-amino-N-{3-(2-cyano-1H-pyrrol-1-yl)-1-[(4-methylpiperidin-1-yl)carbonyl]propyl}-2,4-dimethylbenzenesulfonamide |

-continued

| Example | Structure | Name |
|---|---|---|
| 42 | 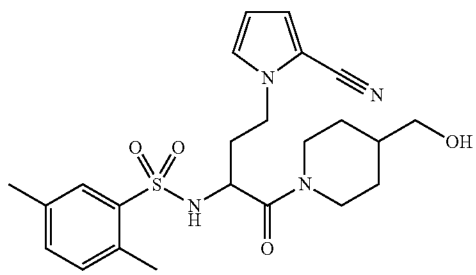 [SMILES: Cc1ccc(C)c(S(=O)(=O)NC(CCn2cccc2C#N)C(=O)N2CCC(CO)CC2)c1] | N-[3-(2-cyano-1H-pyrrol-1-yl)-1-{[4-(hydroxymethyl)piperidin-1-yl]carbonyl}propyl]-2,5-dimethylbenzenesulfonamide |
| 43 | 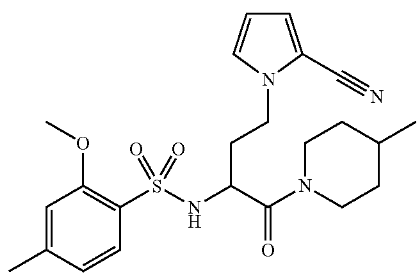 | N-{3-(2-cyano-1H-pyrrol-1-yl)-1-[(4-methylpiperidin-1-yl)carbonyl]propyl}-2-methoxy-4-methylbenzenesulfonamide |
| 44 | 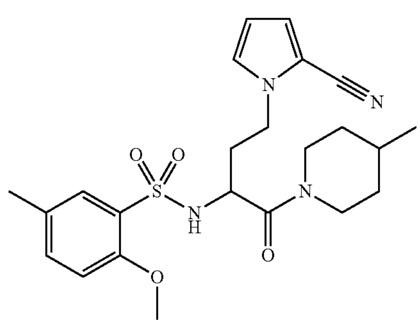 | N-{3-(2-cyano-1H-pyrrol-1-yl)-1-[(4-methylpiperidin-1-yl)carbonyl]propyl}-2-methoxy-5-methylbenzenesulfonamide |
| 45 | 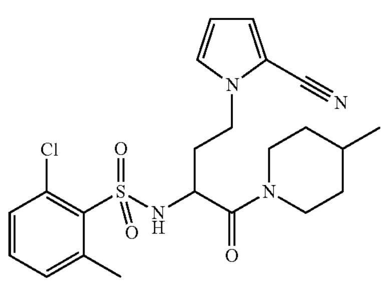 [SMILES: Cc1cccc(Cl)c1S(=O)(=O)NC(CCn1cccc1C#N)C(=O)N1CCC(C)CC1] | 2-chloro-N-{3-(2-cyano-1H-pyrrol-1-yl)-1-[(4-methylpiperidin-1-yl)carbonyl]propyl}-6-methylbenzenesulfonamide |
| 46 | 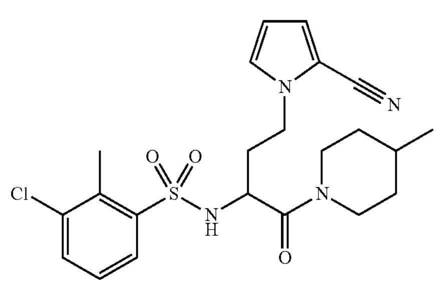 [SMILES: Cc1c(Cl)cccc1S(=O)(=O)NC(CCn1cccc1C#N)C(=O)N1CCC(C)CC1] | 3-chloro-N-{3-(2-cyano-1H-pyrrol-1-yl)-1-[(4-methylpiperidin-1-yl)carbonyl]propyl}-2-methylbenzenesulfonamide |

-continued

| Example | Structure | Name |
|---|---|---|
| 47 | 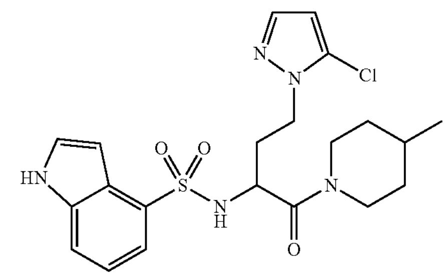 [SMILES: CC1CCN(C(=O)C(CCn2nccc2Cl)NS(=O)(=O)c2cccc3[nH]ccc23)CC1] | N-{3-(5-chloro-1H-pyrazol-1-yl)-1-[(4-methylpiperidin-1-yl)carbonyl]propyl}-1H-indole-4-sulfonamide |
| 48 | 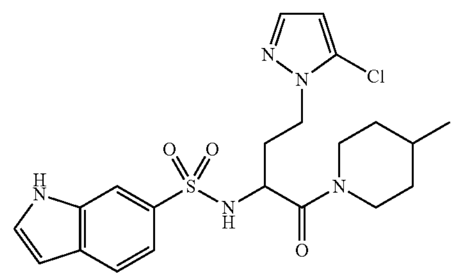 [SMILES: CC1CCN(C(=O)C(CCn2nccc2Cl)NS(=O)(=O)c2ccc3cc[nH]c3c2)CC1] | N-{3-(5-chloro-1H-pyrazol-1-yl)-1-[(4-methylpiperidin-1-yl)carbonyl]propyl}-1H-indole-6-sulfonamide |
| 49 | 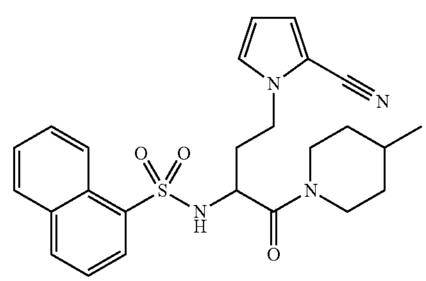 [SMILES: CC1CCN(C(=O)C(CCn2cccc2C#N)NS(=O)(=O)c2cccc3ccccc23)CC1] | N-{3-(2-cyano-1H-pyrrol-1-yl)-1-[(4-methylpiperidin-1-yl)carbonyl]propyl}naphthalene-1-sulfonamide |
| 50 | 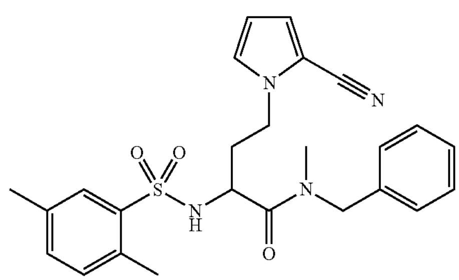 [SMILES: Cc1ccc(C)c(S(=O)(=O)NC(CCn2cccc2C#N)C(=O)N(C)Cc2ccccc2)c1] | N-benzyl-4-(2-cyano-1H-pyrrol-1-yl)-2-{[(2,5-dimethylphenyl)sulfonyl]amino}-N-methylbutanamide |
| 51 | 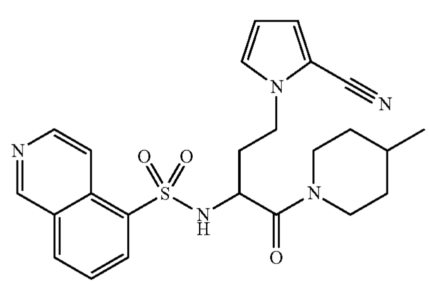 [SMILES: CC1CCN(C(=O)C(CCn2cccc2C#N)NS(=O)(=O)c2cccc3cnccc23)CC1] | N-{3-(2-cyano-1H-pyrrol-1-yl)-1-[(4-methylpiperidin-1-yl)carbonyl]propyl}isoquinoline-5-sulfonamide |

-continued

| Example | Structure | Name |
|---|---|---|
| 52 | 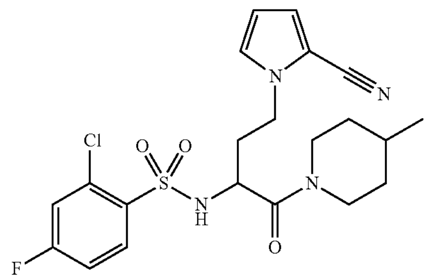 [SMILES: CC1CCN(C(=O)C(CCn2cccc2C#N)NS(=O)(=O)c2ccc(F)cc2Cl)CC1] | 2-chloro-N-{3-(2-cyano-1H-pyrrol-1-yl)-1-[(4-methylpiperidin-1-yl)carbonyl]propyl}-4-fluorobenzenesulfonamide |
| 53 | 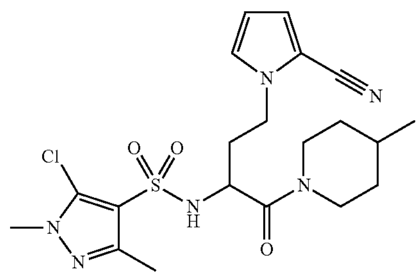 | 5-chloro-N-{3-(2-cyano-1H-pyrrol-1-yl)-1-[(4-methylpiperidin-1-yl)carbonyl]propyl}-1,3-dimethyl-1H-pyrazole-4-sulfonamide |
| 54 | 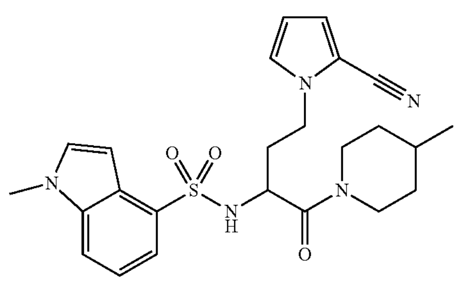 | N-{3-(2-cyano-1H-pyrrol-1-yl)-1-[(4-methylpiperidin-1-yl)carbonyl]propyl}-1-methyl-1H-indole-4-sulfonamide |
| 55 | 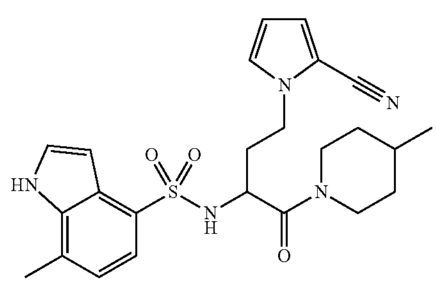 | N-{3-(2-cyano-1H-pyrrol-1-yl)-1-[(4-methylpiperidin-1-yl)carbonyl]propyl}-7-methyl-1H-indole-4-sulfonamide |
| 56 | 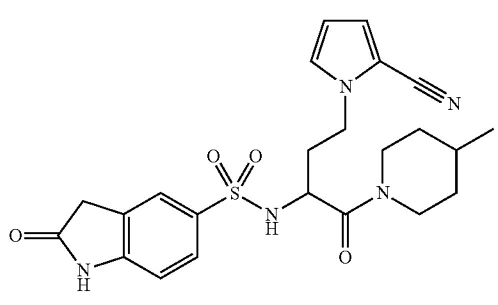 [SMILES: CC1CCN(C(=O)C(CCn2cccc2C#N)NS(=O)(=O)c2ccc3c(c2)CC(=O)N3)CC1] | N-{3-(2-cyano-1H-pyrrol-1-yl)-1-[(4-methylpiperidin-1-yl)carbonyl]propyl}-2-oxoindoline-5-sulfonamide |

| Example | Structure | Name |
| --- | --- | --- |
| 57 | 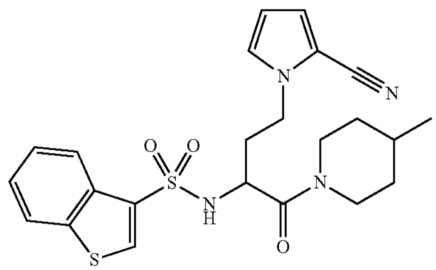 [SMILES: CC1CCN(C(=O)C(CCn2cccc2C#N)NS(=O)(=O)c2csc3ccccc23)CC1] | N-{3-(2-cyano-1H-pyrrol-1-yl)-1-[(4-methylpiperidin-1-yl)carbonyl]propyl}-1-benzothiophene-3-sulfonamide |
| 58 | 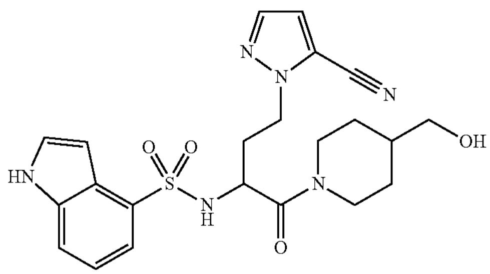 [SMILES: N#Cc1ccnn1CCC(NS(=O)(=O)c1cccc2[nH]ccc12)C(=O)N1CCC(CO)CC1] | N-[3-(5-cyano-1H-pyrazol-1-yl)-1-{[4-(hydroxymethyl)piperidin-1-yl]carbonyl}propyl]-1H-indole-4-sulfonamide |
| 59 | 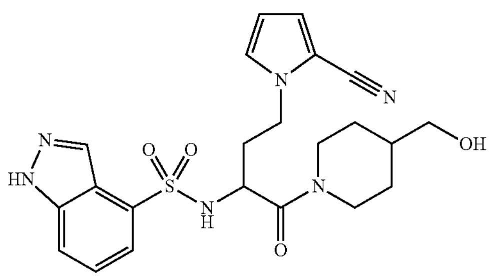 [SMILES: N#Cc1cccn1CCC(NS(=O)(=O)c1cccc2[nH]ncc12)C(=O)N1CCC(CO)CC1] | N-[3-(2-cyano-1H-pyrrol-1-yl)-1-{[4-(hydroxymethyl)piperidin-1-yl]carbonyl}propyl]-1H-indazole-4-sulfonamide |
| 60 | 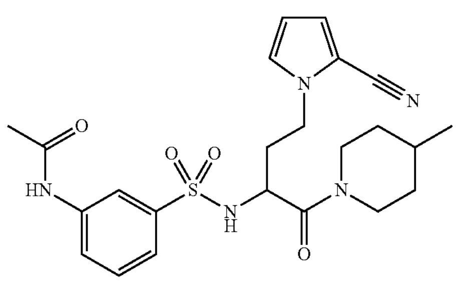 [SMILES: CC(=O)Nc1cccc(S(=O)(=O)NC(CCn2cccc2C#N)C(=O)N2CCC(C)CC2)c1] | N-{3-[({3-(2-cyano-1H-pyrrol-1-yl)-1-[(4-methylpiperidin-1-yl)carbonyl]propyl}amino)sulfonyl]phenyl}acetamide |
| 61 | 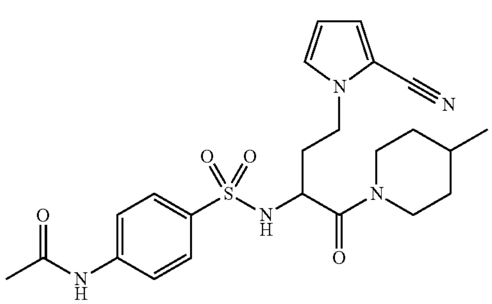 [SMILES: CC(=O)Nc1ccc(S(=O)(=O)NC(CCn2cccc2C#N)C(=O)N2CCC(C)CC2)cc1] | N-{4-[({3-(2-cyano-1H-pyrrol-1-yl)-1-[(4-methylpiperidin-1-yl)carbonyl]propyl}amino)sulfonyl]phenyl}acetamide |

-continued

| Example | Structure | Name |
|---|---|---|
| 62 | 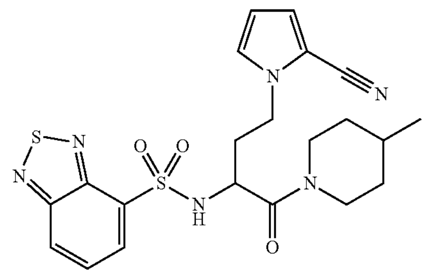 [SMILES: CC1CCN(C(=O)C(CCn2cccc2C#N)NS(=O)(=O)c2cccc3nsnc23)CC1] | N-{3-(2-cyano-1H-pyrrol-1-yl)-1-[(4-methylpiperidin-1-yl)carbonyl]propyl}-2,1,3-benzothiadiazole-4-sulfonamide |
| 63 | 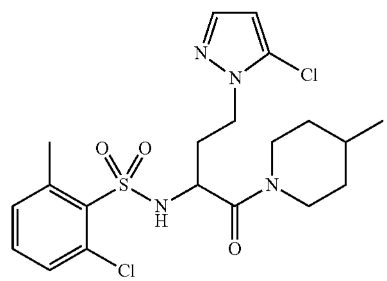 [SMILES: Cc1cccc(Cl)c1S(=O)(=O)NC(CCn1nccc1Cl)C(=O)N1CCC(C)CC1] | 2-chloro-N-{3-(5-chloro-1H-pyrazol-1-yl)-1-[4-methylpiperidin-1-yl)carbonyl]propyl}-6-methylbenzenesulfonamide |
| 64 | 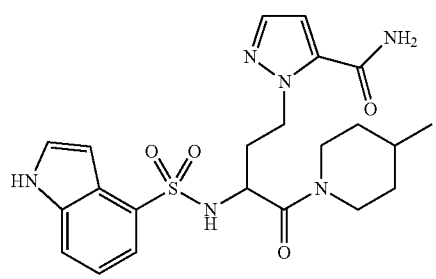 [SMILES: CC1CCN(C(=O)C(CCn2nccc2C(N)=O)NS(=O)(=O)c2cccc3[nH]ccc23)CC1] | 1-{3-[(1H-indol-4-ylsulfonyl)amino]-4-(4-methylpiperidin-1-yl)-4-oxobutyl}-1H-pyrazole-5-carboxamide |
| 65 | 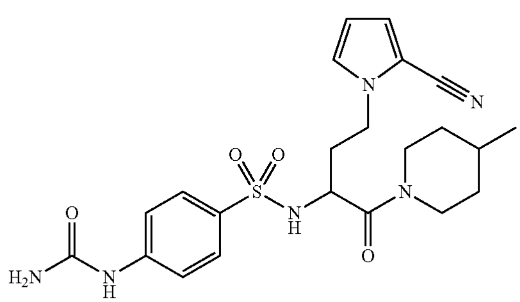 [SMILES: CC1CCN(C(=O)C(CCn2cccc2C#N)NS(=O)(=O)c2ccc(NC(N)=O)cc2)CC1] | 4-(carbamoylamino)-N-{3-(2-cyano-1H-pyrrol-1-yl)-1-[(4-methylpiperidin-1-yl)carbonyl]propyl}benzenesulfonamide |
| 66 | 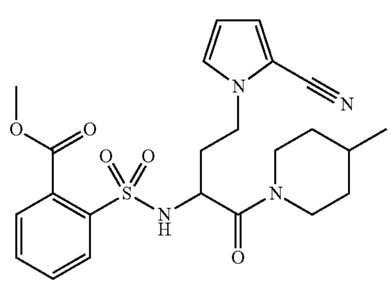 [SMILES: COC(=O)c1ccccc1S(=O)(=O)NC(CCn1cccc1C#N)C(=O)N1CCC(C)CC1] | methyl 2-[({3-(2-cyano-1H-pyrrol-1-yl)-1-[(4-methylpiperidin-1-yl)carbonyl]propyl}amino)sulfonyl]benzoate |

-continued

| Example | Structure | Name |
|---|---|---|
| 67 | 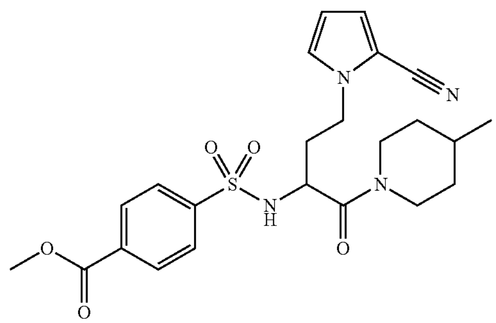 | methyl 4-[({3-(2-cyano-1H-pyrrol-1-yl)-1-[(4-methylpiperidin-1-yl)carbonyl]propyl}amino)sulfonyl]benzoate |
| 68 | 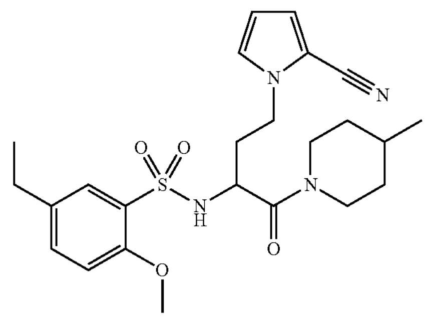 [SMILES: CCc1ccc(OC)c(S(=O)(=O)NC(CCn2cccc2C#N)C(=O)N2CCC(C)CC2)c1] | N-{3-(2-cyano-1H-pyrrol-1-yl)-1-[(4-methylpiperidin-1-yl)carbonyl]propyl}-5-ethyl-2-methoxybenzenesulfonamide |
| 69 | 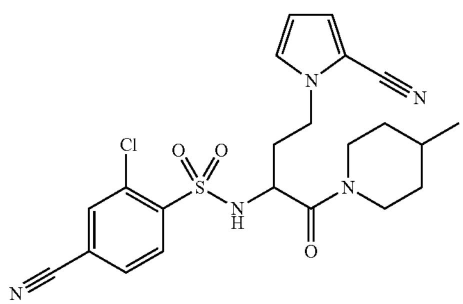 [SMILES: CC1CCN(C(=O)C(CCn2cccc2C#N)NS(=O)(=O)c2ccc(C#N)cc2Cl)CC1] | 2-chloro-4-cyano-N-{3-(2-cyano-1H-pyrrol-1-yl)-1-[(4-methylpiperidin-1-yl)carbonyl]propyl}benzenesulfonamide |
| 70 | 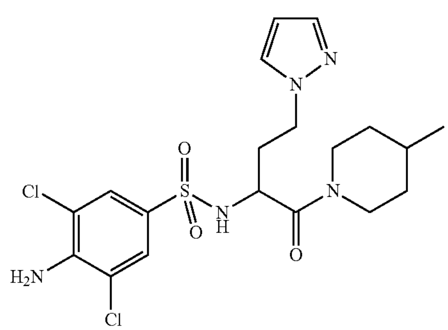 [SMILES: CC1CCN(C(=O)C(CCn2cccn2)NS(=O)(=O)c2cc(Cl)c(N)c(Cl)c2)CC1] | 4-amino-3,5-dichloro-N-{1-[(4-methylpiperidin-1-yl)carbonyl]-3-(1H-pyrazol-1-yl)propyl}benzenesulfonamide |
| 71 | 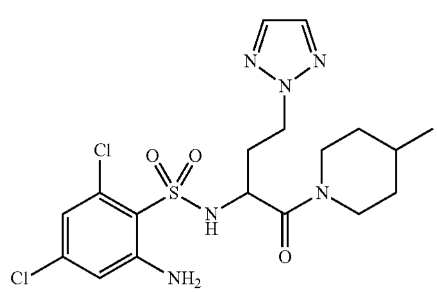 [SMILES: CC1CCN(C(=O)C(CCn2nccn2)NS(=O)(=O)c2c(N)cc(Cl)cc2Cl)CC1] | 2-amino-4,6-dichloro-N-{1-[(4-methylpiperidin-1-yl)carbonyl]-3-(2H-1,2,3-triazol-2-yl)propyl}benzenesulfonamide |

| Example | Structure | Name |
|---|---|---|
| 72 | 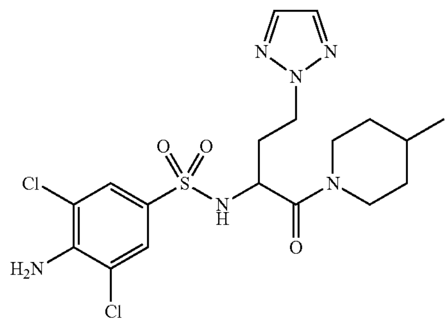 [SMILES: CC1CCN(C(=O)C(CCn2nccn2)NS(=O)(=O)c2cc(Cl)c(N)c(Cl)c2)CC1] | 4-amino-3,5-dichloro-N-{1-[(4-methyl piperidin-1-yl)carbonyl]-3-(2H-1,2,3-triazol-2-yl)propyl}benzenesulfonamide |
| 73 | 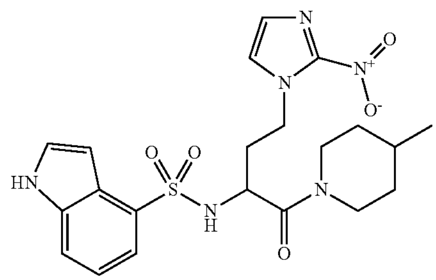 [SMILES: CC1CCN(C(=O)C(CCn2ccnc2[N+](=O)[O-])NS(=O)(=O)c2cccc3[nH]ccc23)CC1] | N-{1-[(4-methylpiperidin-1-yl)carbonyl]-3-(2-nitro-1H-imidazol-1-yl)propyl}-1H-indole-4-sulfonamide |
| 74 | 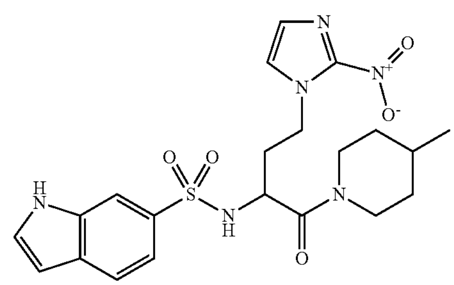 [SMILES: CC1CCN(C(=O)C(CCn2ccnc2[N+](=O)[O-])NS(=O)(=O)c2ccc3cc[nH]c3c2)CC1] | N-{1-[(4-methylpiperidin-1-yl)carbonyl]-3-(2-nitro-1H-imidazol-1-yl)propyl}-1H-indole-6-sulfonamide |
| 75 | 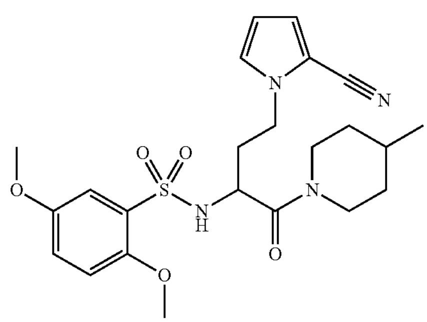 [SMILES: COc1ccc(OC)c(S(=O)(=O)NC(CCn2cccc2C#N)C(=O)N2CCC(C)CC2)c1] | N-{3-(2-cyano-1H-pyrrol-1-yl)-1-[(4-methylpiperidin-1-yl)carbonyl]propyl}-2,5-dimethoxybenzenesulfonamide |
| 76 | 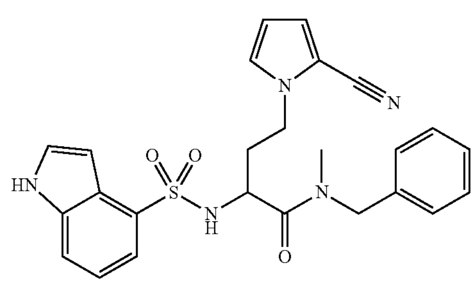 [SMILES: CN(Cc1ccccc1)C(=O)C(CCn1cccc1C#N)NS(=O)(=O)c1cccc2[nH]ccc12] | N-benzyl-4-(2-cyano-1H-pyrrol-1-yl)-2-[(1H-indol-4-ylsulfonyl)amino]-N-methylbutanamide |

-continued

| Example | Structure | Name |
|---|---|---|
| 77 | 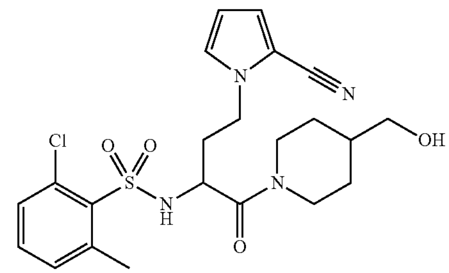 [SMILES: Cc1cccc(Cl)c1S(=O)(=O)NC(CCn1cccc1C#N)C(=O)N1CCC(CO)CC1] | 2-chloro-N-[3-(2-cyano-1H-pyrrol-1-yl)-1-{[4-(hydroxymethyl)piperidin-1-yl]carbonyl}propyl]-6-methylbenzenesulfonamide |
| 78 | 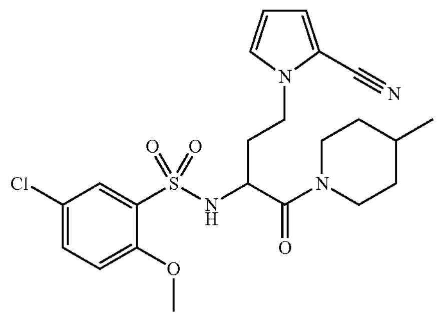 [SMILES: COc1ccc(Cl)cc1S(=O)(=O)NC(CCn1cccc1C#N)C(=O)N1CCC(C)CC1] | 5-chloro-N-{3-(2-cyano-1H-pyrrol-1-yl)-1-[(4-methylpiperidin-1-yl)carbonyl]propyl}-2-methoxybenzenesulfonamide |
| 79 | 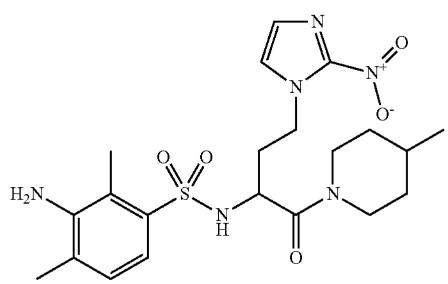 [SMILES: Cc1ccc(S(=O)(=O)NC(CCn2ccnc2[N+](=O)[O-])C(=O)N2CCC(C)CC2)c(C)c1N] | 3-amino-2,4-dimethyl-N-{1-[(4-methyl piperidin-1-yl)carbonyl]-3-(2-nitro-1H-imidazol-1-yl)propyl}benzenesulfonamide |
| 80 | Chiral | 4-(2-cyano-1H-pyrrol-1-yl)-2-{[(2,5-dimethylphenyl)sulfonyl]amino}-N-methyl-N-[(1R)-1-phenylethyl]butanamide |
| 81 | 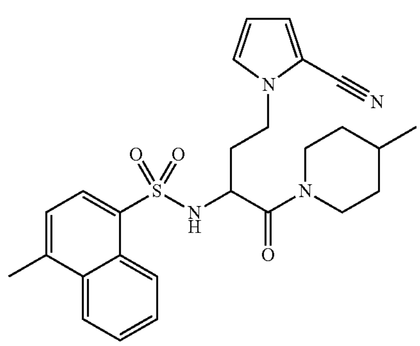 | N-{3-(2-cyano-1H-pyrrol-1-yl)-1-[(4-methylpiperidin-1-yl)carbonyl]propyl}-4-methylnaphthalene-1-sulfonamide |

-continued

| Example | Structure | Name |
|---|---|---|
| 82 | 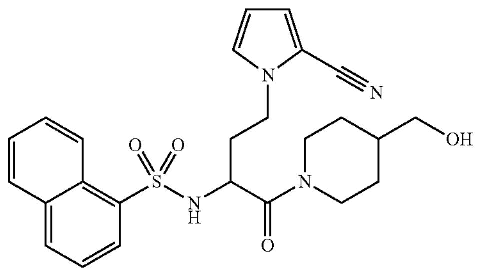 [SMILES: N#Cc1cccn1CCC(NS(=O)(=O)c1cccc2ccccc12)C(=O)N1CCC(CO)CC1] | N-[3-(2-cyano-1H-pyrrol-1-yl)-1-{[4-(hydroxymethyl)piperidin-1-yl]carbonyl}propyl]naphthalene-1-sulfonamide |
| 83 | 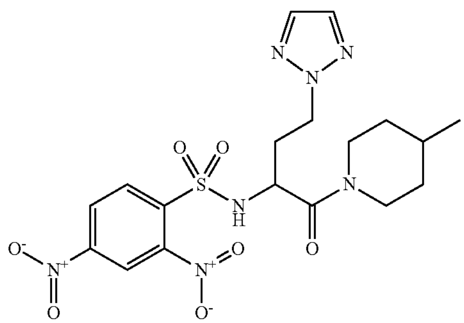 [SMILES: CC1CCN(C(=O)C(CCn2nccn2)NS(=O)(=O)c2ccc([N+](=O)[O-])cc2[N+](=O)[O-])CC1] | N-{1-[(4-methylpiperidin-1-yl)carbonyl]-3-(2H-1,2,3-triazol-2-yl)propyl}-2,4-dinitrobenzenesulfonamide |
| 84 | 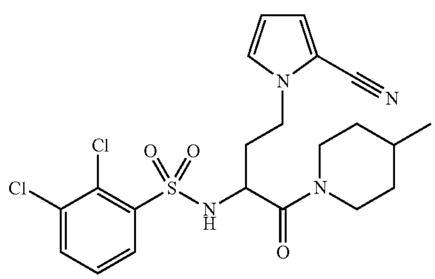 [SMILES: CC1CCN(C(=O)C(CCn2cccc2C#N)NS(=O)(=O)c2cccc(Cl)c2Cl)CC1] | 2,3-dichloro-N-{3-(2-cyano-1H-pyrrol-1-yl)-1-[(4-methylpiperidin-1-yl)carbonyl]propyl}benzenesulfonamide |
| 85 | 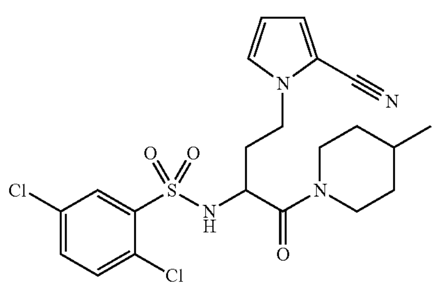 [SMILES: CC1CCN(C(=O)C(CCn2cccc2C#N)NS(=O)(=O)c2cc(Cl)ccc2Cl)CC1] | 2,5-dichloro-N-{3-(2-cyano-1H-pyrrol-1-yl)-1-[(4-methylpiperidin-1-yl)carbonyl]propyl}benzenesulfonamide |
| 86 | 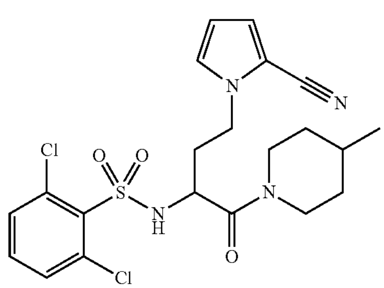 [SMILES: CC1CCN(C(=O)C(CCn2cccc2C#N)NS(=O)(=O)c2c(Cl)cccc2Cl)CC1] | 2,6-dichloro-N-{3-(2-cyano-1H-pyrrol-1-yl)-1-[(4-methylpiperidin-1-yl)carbonyl]propyl}benzenesulfonamide |

-continued

| Example | Structure | Name |
| --- | --- | --- |
| 87 | 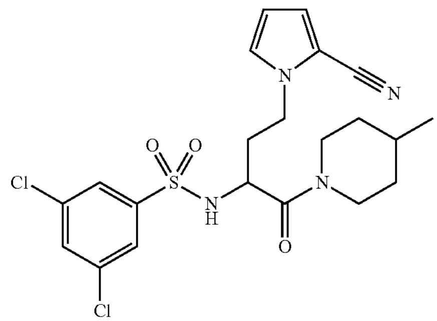 [SMILES: CC1CCN(C(=O)C(CCn2cccc2C#N)NS(=O)(=O)c2cc(Cl)cc(Cl)c2)CC1] | 3,5-dichloro-N-{3-(2-cyano-1H-pyrrol-1-yl)-1-[(4-methylpiperidin-1-yl)carbonyl]propyl}benzenesulfonamide |
| 88 | 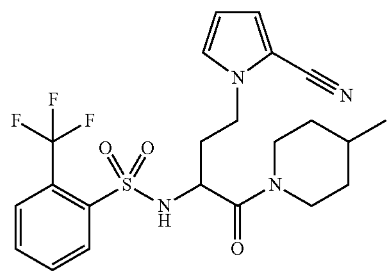 [SMILES: CC1CCN(C(=O)C(CCn2cccc2C#N)NS(=O)(=O)c2ccccc2C(F)(F)F)CC1] | N-{3-(2-cyano-1H-pyrrol-1-yl)-1-[(4-methylpiperidin-1-yl)carbonyl]propyl}-2-(trifluoromethyl)benzenesulfonamide |
| 89 | 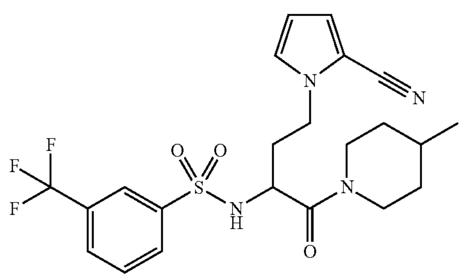 [SMILES: CC1CCN(C(=O)C(CCn2cccc2C#N)NS(=O)(=O)c2cccc(C(F)(F)F)c2)CC1] | N-{3-(2-cyano-1H-pyrrol-1-yl)-1-[(4-methylpiperidin-1-yl)carbonyl]propyl}-3-(trifluoromethyl)benzenesulfonamide |
| 90 | 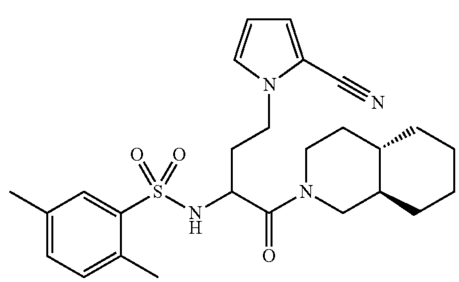 [SMILES: Cc1ccc(C)c(S(=O)(=O)NC(CCn2cccc2C#N)C(=O)N2CC[C@@H]3CCCC[C@H]3C2)c1] | N-{3-(2-cyano-1H-pyrrol-1-yl)-1-[(trans)-octahydroisoquinolin-2(1H)-ylcarbonyl]propyl}-2,5-dimethylbenzenesulfonamide |
| 91 | 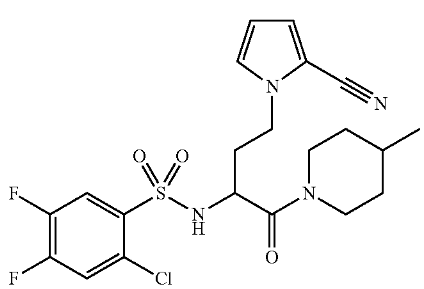 [SMILES: CC1CCN(C(=O)C(CCn2cccc2C#N)NS(=O)(=O)c2cc(F)c(F)cc2Cl)CC1] | 2-chloro-N-{3-(2-cyano-1H-pyrrol-1-yl)-1-[(4-methylpiperidin-1-yl)carbonyl]propyl}-4,5-difluorobenzenesulfonamide |

| Example | Structure | Name |
|---|---|---|
| 92 | 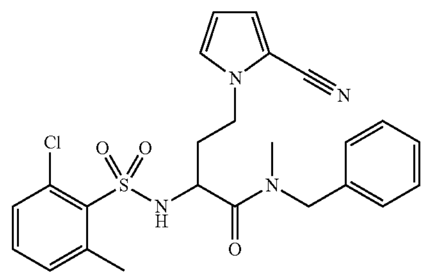 [SMILES: Cc1cccc(Cl)c1S(=O)(=O)NC(CCn1cccc1C#N)C(=O)N(C)Cc1ccccc1] | N-benzyl-2-{[(2-chloro-6-methylphenyl)sulfonyl]amino}-4-(2-cyano-1H-pyrrol-1-yl)-N-methylbutanamide |
| 93 | 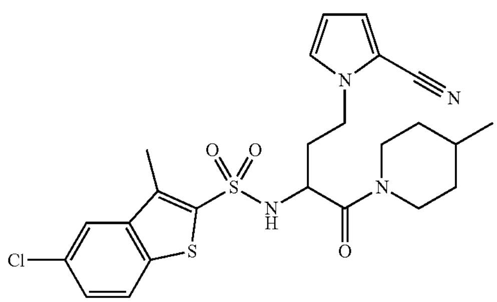 [SMILES: Cc1c(S(=O)(=O)NC(CCn2cccc2C#N)C(=O)N2CCC(C)CC2)sc2ccc(Cl)cc12] | 5-chloro-N-{3-(2-cyano-1H-pyrrol-1-yl)-1-[(4-methylpiperidin-1-yl)carbonyl]propyl}-3-methyl-1-benzothiophene-2-sulfonamide |
| 94 | 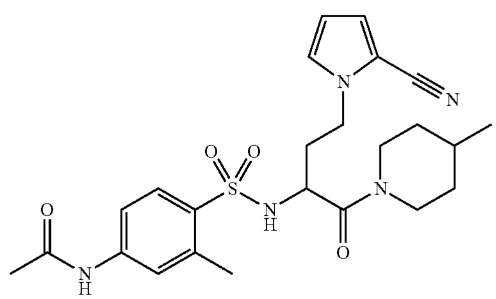 [SMILES: CC(=O)Nc1ccc(S(=O)(=O)NC(CCn2cccc2C#N)C(=O)N2CCC(C)CC2)c(C)c1] | N-{4-[({3-(2-cyano-1H-pyrrol-1-yl)-1-[(4-methylpiperidin-1-yl)carbonyl]propyl}amino) sulfonyl]-3-methylphenyl}acetamide |
| 95 | 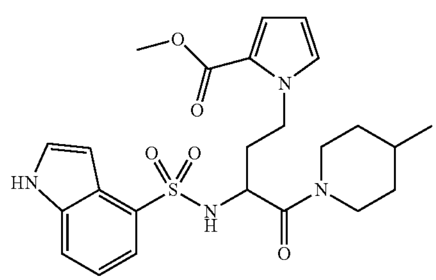 [SMILES: COC(=O)c1cccn1CCC(NS(=O)(=O)c1cccc2[nH]ccc12)C(=O)N1CCC(C)CC1] | methyl 1-{3-[(1H-indol-4-ylsulfonyl)amino]-4-(4-methylpiperidin-1-yl)-4-oxobutyl}-1H-pyrrole-2-carboxylate |
| 96 | 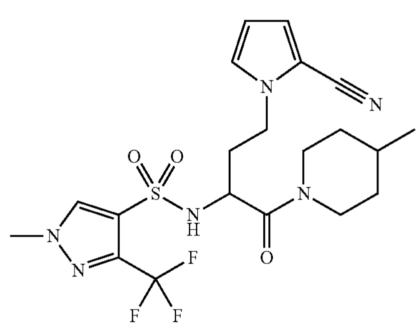 | N-{3-(2-cyano-1H-pyrrol-1-yl)-1-[(4-methylpiperidin-1-yl)carbonyl]propyl}-1-methyl-3-(trifluoromethyl)-1H-pyrazole-4-sulfonamide |

-continued

| Example | Structure | Name |
|---|---|---|
| 97 | 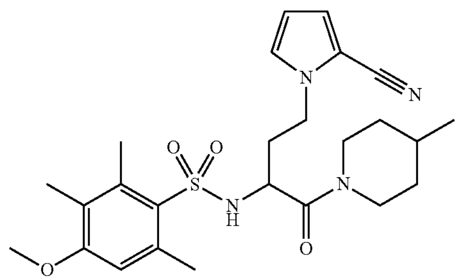 | N-{3-(2-cyano-1H-pyrrol-1-yl)-1-[(4-methylpiperidin-1-yl)carbonyl]propyl}-4-methoxy-2,3,6-trimethylbenzenesulfonamide |
| 98 | 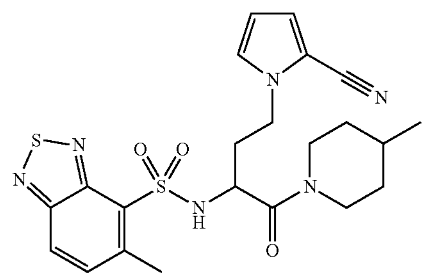 [SMILES: Cc1ccc2nsnc2c1S(=O)(=O)NC(CCn1cccc1C#N)C(=O)N1CCC(C)CC1] | N-{3-(2-cyano-1H-pyrrol-1-yl)-1-[(4-methylpiperidin-1-yl)carbonyl]propyl}-5-methyl-2,1,3-benzothiadiazole-4-sulfonamide |
| 99 | 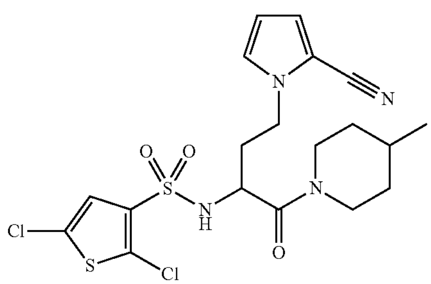 [SMILES: CC1CCN(C(=O)C(CCn2cccc2C#N)NS(=O)(=O)c2cc(Cl)sc2Cl)CC1] | 2,5-dichloro-N-{3-(2-cyano-1H-pyrrol-1-yl)-1-[(4-methylpiperidin-1-yl)carbonyl]propyl}thiophene-3-sulfonamide |
| 100 | 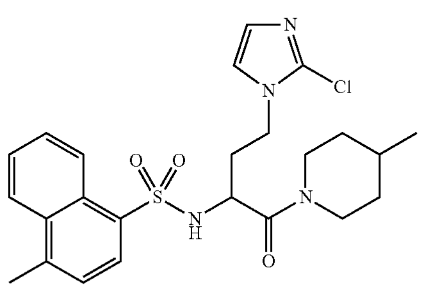 [SMILES: Cc1ccc(S(=O)(=O)NC(CCn2ccnc2Cl)C(=O)N2CCC(C)CC2)c2ccccc12] | N-{3-(2-chloro-1H-imidazol-1-yl)-1-[(4-methylpiperidin-1-yl)carbonyl]propyl}-4-methylnaphthalene-1-sulfonamide |
| 101 | 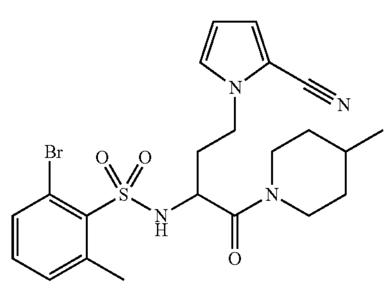 [SMILES: Cc1cccc(Br)c1S(=O)(=O)NC(CCn1cccc1C#N)C(=O)N1CCC(C)CC1] | 2-bromo-N-[3-(2-cyano-1H-pyrrol-1-yl)-1-(piperidin-1-ylcarbonyl)propyl]-6-methylbenzenesulfonamide |

-continued

| Example | Structure | Name |
| --- | --- | --- |
| 102 | 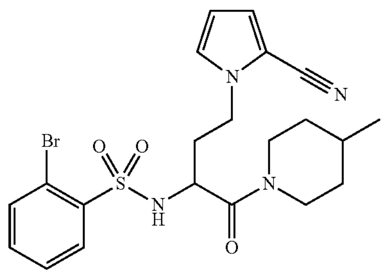 [SMILES: CC1CCN(C(=O)C(CCn2cccc2C#N)NS(=O)(=O)c2ccccc2Br)CC1] | 2-bromo-N-{3-(2-cyano-1H-pyrrol-1-yl)-1-[(4-methylpiperidin-1-yl)carbonyl]propyl} benzenesulfonamide |
| 103 | 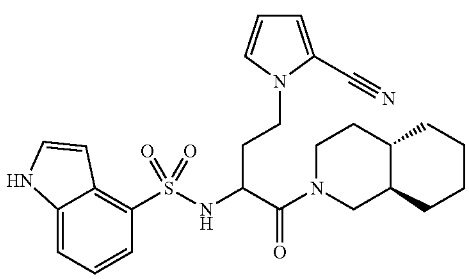 [SMILES: N#Cc1cccn1CCC(NS(=O)(=O)c1cccc2[nH]ccc12)C(=O)N1CC[C@@H]2CCCC[C@H]2C1] | N-{3-(2-cyano-1H-pyrrol-1-yl)-1-[(trans)-octahydroisoquinolin-2(1H)-ylcarbonyl]propyl}-1H-indole-4-sulfonamide |
| 104 | 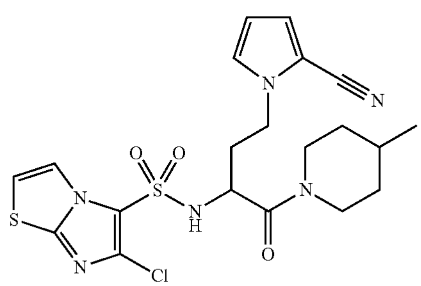 [SMILES: CC1CCN(C(=O)C(CCn2cccc2C#N)NS(=O)(=O)c2c(Cl)nc3sccn23)CC1] | 6-chloro-N-{3-(2-cyano-1H-pyrrol-1-yl)-1-[(4-methylpiperidin-1-yl)carbonyl]propyl} imidazo[2,1-b][1,3]thiazole-5-sulfonamide |
| 105 | 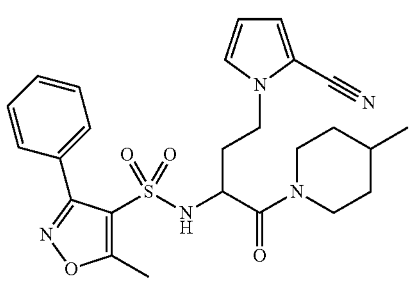 [SMILES: Cc1onc(-c2ccccc2)c1S(=O)(=O)NC(CCn1cccc1C#N)C(=O)N1CCC(C)CC1] | N-{3-(2-cyano-1H-pyrrol-1-yl)-1-[(4-methylpiperidin-1-yl)carbonyl]propyl}-5-methyl-3-phenylisoxazole-4-sulfonamide |
| 106 | 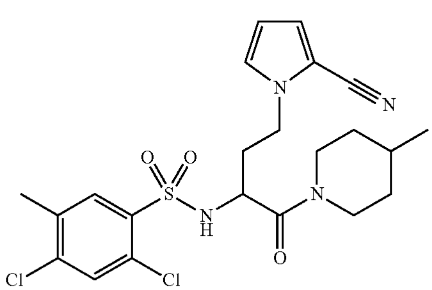 | 2,4-dichloro-N-{3-(2-cyano-1H-pyrrol-1-yl)-1-[(4-methylpiperidin-1-yl)carbonyl]propyl}-5-methylbenzenesulfonamide |

-continued

| Example | Structure | Name |
|---|---|---|
| 107 | 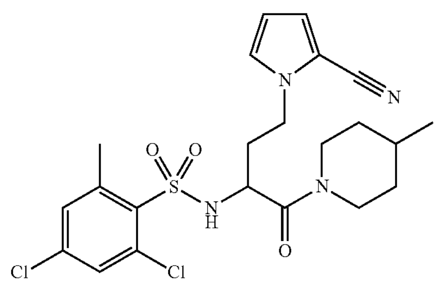 [SMILES: Cc1cc(Cl)cc(Cl)c1S(=O)(=O)NC(CCn1cccc1C#N)C(=O)N1CCC(C)CC1] | 2,4-dichloro-N-{3-(2-cyano-1H-pyrrol-1-yl)-1-[(4-methylpiperidin-1-yl)carbonyl]propyl}-6-methylbenzenesulfonamide |
| 108 | 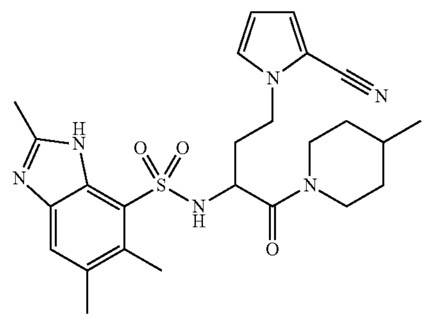 | N-{3-(2-cyano-1H-pyrrol-1-yl)-1-[(4-methylpiperidin-1-yl)carbonyl]propyl}-2,5,6-trimethyl-1H-benzimidazole-7-sulfonamide |
| 109 | 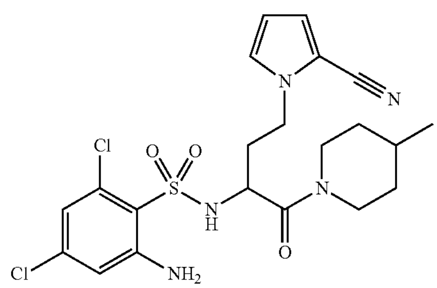 [SMILES: CC1CCN(C(=O)C(CCn2cccc2C#N)NS(=O)(=O)c2c(N)cc(Cl)cc2Cl)CC1] | 2-amino-4,6-dichloro-N-{3-(2-cyano-1H-pyrrol-1-yl)-1-[(4-methylpiperidin-1-yl)carbonyl]propyl}benzenesulfonamide |
| 110 | 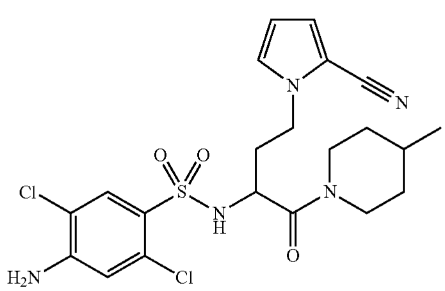 [SMILES: CC1CCN(C(=O)C(CCn2cccc2C#N)NS(=O)(=O)c2cc(Cl)c(N)cc2Cl)CC1] | 4-amino-2,5-dichloro-N-{3-(2-cyano-1H-pyrrol-1-yl)-1-[(4-methylpiperidin-1-yl)carbonyl]propyl}benzenesulfonamide |
| 111 | 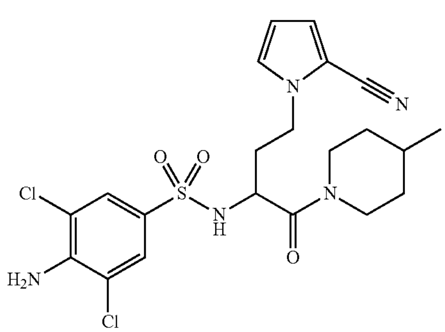 [SMILES: CC1CCN(C(=O)C(CCn2cccc2C#N)NS(=O)(=O)c2cc(Cl)c(N)c(Cl)c2)CC1] | 4-amino-3,5-dichloro-N-{3-(2-cyano-1H-pyrrol-1-yl)-1-[(4-methylpiperidin-1-yl)carbonyl]propyl}benzenesulfonamide |

-continued

| Example | Structure | Name |
|---|---|---|
| 112 | 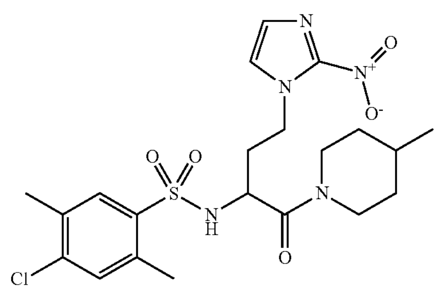 | 4-chloro-2,5-dimethyl-N-{1-[(4-methylpiperidin-1-yl)carbonyl]-3-(2-nitro-1H-imidazol-1-yl)propyl}benzenesulfonamide |
| 113 | 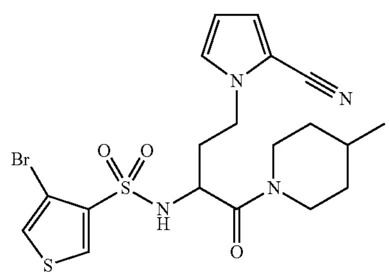 [SMILES: CC1CCN(C(=O)C(CCn2cccc2C#N)NS(=O)(=O)c2cscc2Br)CC1] | 4-bromo-N-{3-(2-cyano-1H-pyrrol-1-yl)-1-[(4-methylpiperidin-1-yl)carbonyl]propyl}thiophene-3-sulfonamide |
| 114 | 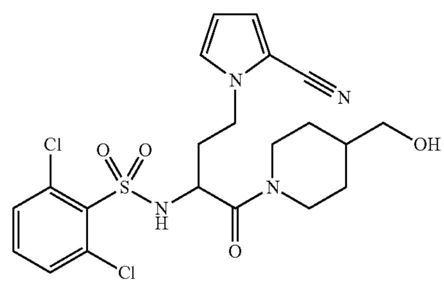 [SMILES: N#Cc1cccn1CCC(NS(=O)(=O)c1c(Cl)cccc1Cl)C(=O)N1CCC(CO)CC1] | 2,6-dichloro-N-[3-(2-cyano-1H-pyrrol-1-yl)-1-{[4-(hydroxymethyl)piperidin-1-yl]carbonyl}propyl]benzenesulfonamide |
| 115 | 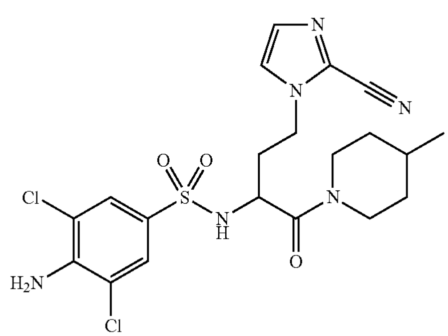 [SMILES: CC1CCN(C(=O)C(CCn2ccnc2C#N)NS(=O)(=O)c2cc(Cl)c(N)c(Cl)c2)CC1] | 4-amino-3,5-dichloro-N-{3-(2-cyano-1H-imidazol-1-yl)-1-[(4-methylpiperidin-1-1-yl)carbonyl]propyl}benzenesulfonamide |
| 116 | 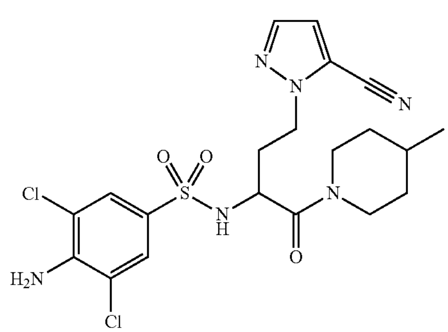 [SMILES: CC1CCN(C(=O)C(CCn2nccc2C#N)NS(=O)(=O)c2cc(Cl)c(N)c(Cl)c2)CC1] | 4-amino-3,5-dichloro-N-{3-(5-cyano-1H-pyrazol-1-yl)-1-[(4-methylpiperidin-1-1-yl)carbonyl]propyl}benzenesulfonamide |

| Example | Structure | Name |
|---|---|---|
| 117 | 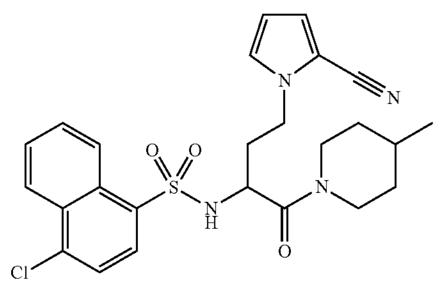 [SMILES: CC1CCN(C(=O)C(CCn2cccc2C#N)NS(=O)(=O)c2ccc(Cl)c3ccccc23)CC1] | 4-chloro-N-{3-(2-cyano-1H-pyrrol-1-yl)-1-[(4-methylpiperidin-1-yl)carbonyl]propyl} naphthalene-1-sulfonamide |
| 118 | 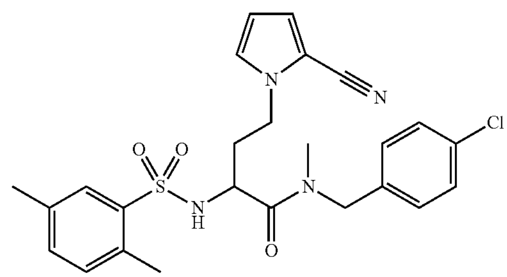 [SMILES: Cc1ccc(C)c(S(=O)(=O)NC(CCn2cccc2C#N)C(=O)N(C)Cc2ccc(Cl)cc2)c1] | N-(4-chlorobenzyl)-4-(2-cyano-1H-pyrrol-1-yl)-2-{[(2,5-dimethylphenyl)sulfonyl]amino}-N-methylbutanamide |
| 119 | 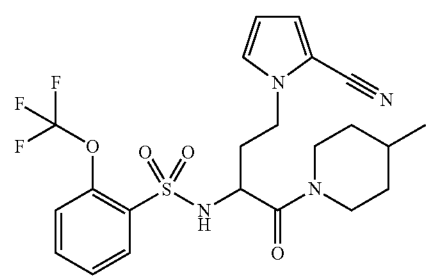 [SMILES: CC1CCN(C(=O)C(CCn2cccc2C#N)NS(=O)(=O)c2ccccc2OC(F)(F)F)CC1] | N-{3-(2-cyano-1H-pyrrol-1-yl)-1-[(4-methylpiperidin-1-yl)carbonyl]propyl}-2-(trifluoromethoxy)benzenesulfonamide |
| 120 | 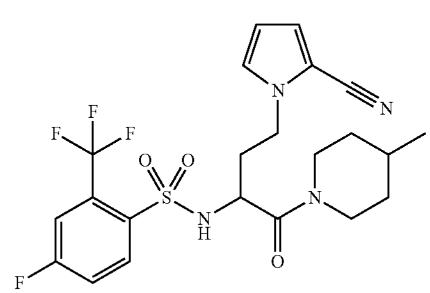 [SMILES: CC1CCN(C(=O)C(CCn2cccc2C#N)NS(=O)(=O)c2ccc(F)cc2C(F)(F)F)CC1] | N-{3-(2-cyano-1H-pyrrol-1-yl)-1-[(4-methylpiperidin-1-yl)carbonyl]propyl}-4-fluoro-2-(trifluoromethyl)benzenesulfonamide |
| 121 | 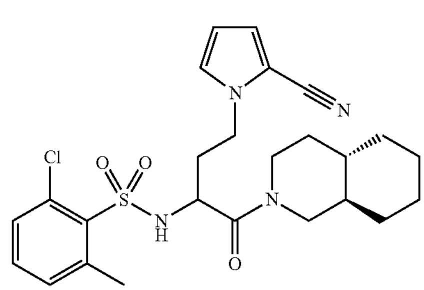 [SMILES: Cc1cccc(Cl)c1S(=O)(=O)NC(CCn1cccc1C#N)C(=O)N1CC[C@@H]2CCCC[C@H]2C1] | 2-chloro-N-{3-(2-cyano-1H-pyrrol-1-yl)-1-[(trans)-octahydroisoquinolin-2(1H)-ylcarbonyl]propyl}-6-methylbenzenesulfonamide |

-continued

| Example | Structure | Name |
|---|---|---|
| 122 | 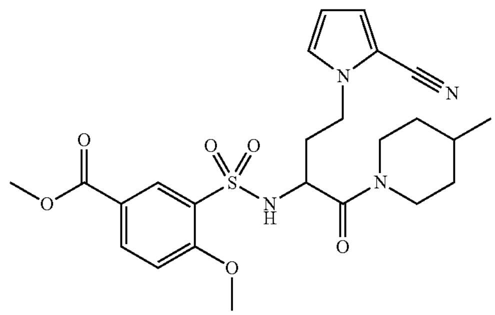 | methyl 3-[({3-(2-cyano-1H-pyrrol-1-yl)-1-[(4-methylpiperidin-1-yl)carbonyl]propyl}amino)sulfonyl]-4-methoxybenzoate |
| 123 | 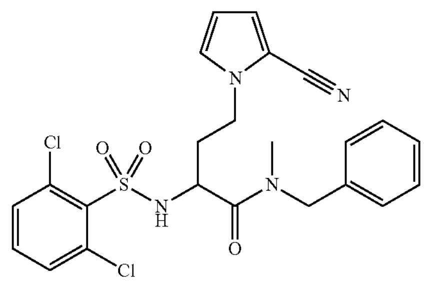 [SMILES: CN(Cc1ccccc1)C(=O)C(CCn1cccc1C#N)NS(=O)(=O)c1c(Cl)cccc1Cl] | N-benzyl-4-(2-cyano-1H-pyrrol-1-yl)-2-{[(2,6-dichlorophenyl)sulfonyl]amino}-N-methylbutanamide |
| 124 | 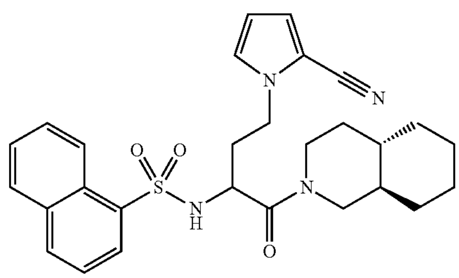 [SMILES: N#Cc1cccn1CCC(NS(=O)(=O)c1cccc2ccccc12)C(=O)N1CC[C@@H]2CCCC[C@H]2C1] | N-{3-(2-cyano-1H-pyrrol-1-yl)-1-[(trans)-octahydroisoquinolin-2(1H)-ylcarbonyl] propyl}naphthalene-1-sulfonamide |
| 125 | 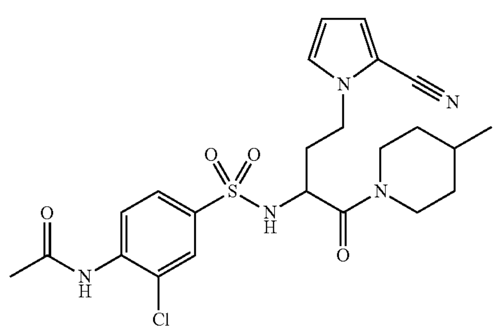 [SMILES: CC(=O)Nc1ccc(S(=O)(=O)NC(CCn2cccc2C#N)C(=O)N2CCC(C)CC2)cc1Cl] | N-{2-chloro-4-[({3-(2-cyano-1H-pyrrol-1-yl)-1-[(4-methylpiperidin-1-yl)carbonyl]propyl}amino)sulfonyl]phenyl}acetamide |
| 126 | 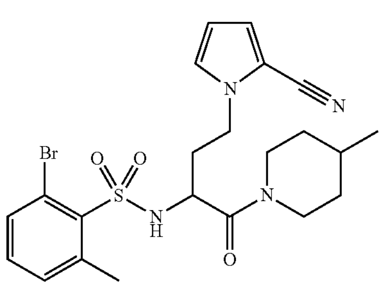 [SMILES: Cc1cccc(Br)c1S(=O)(=O)NC(CCn1cccc1C#N)C(=O)N1CCC(C)CC1] | 2-bromo-N-{3-(2-cyano-1H-pyrrol-1-yl)-1-[(4-methylpiperidin-1-yl)carbonyl]propyl}-6-methylbenzenesulfonamide |

-continued

| Example | Structure | Name |
|---|---|---|
| 127 | 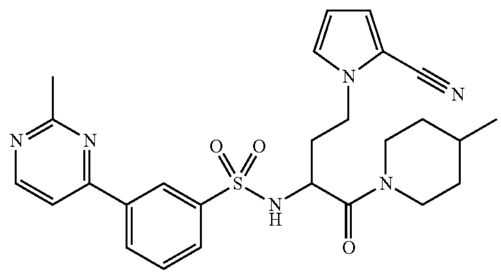 [SMILES: Cc1nccc(-c2cccc(S(=O)(=O)NC(CCn3cccc3C#N)C(=O)N3CCC(C)CC3)c2)n1] | N-{3-(2-cyano-1H-pyrrol-1-yl)-1-[(4-methylpiperidin-1-yl)carbonyl]propyl}-3-(2-methylpyrimidin-4-yl)benzenesulfonamide |
| 128 | 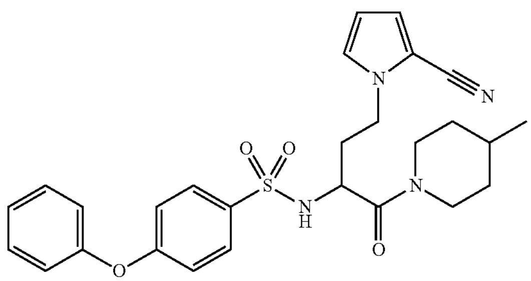 [SMILES: CC1CCN(C(=O)C(CCn2cccc2C#N)NS(=O)(=O)c2ccc(Oc3ccccc3)cc2)CC1] | N-{3-(2-cyano-1H-pyrrol-1-yl)-1-[(4-methylpiperidin-1-yl)carbonyl]propyl}-4-phenoxybenzenesulfonamide |
| 129 | 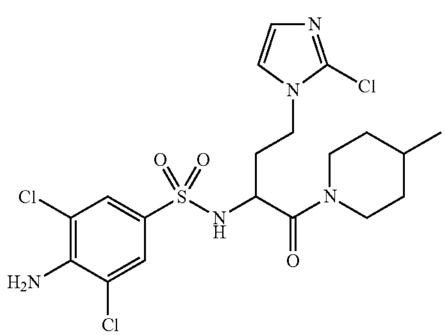 [SMILES: CC1CCN(C(=O)C(CCn2ccnc2Cl)NS(=O)(=O)c2cc(Cl)c(N)c(Cl)c2)CC1] | 4-amino-3,5-dichloro-N-{3-(2-chloro-1H-imidazol-1-yl)-1-[(4-methylpiperidin-1-1-yl)carbonyl]propyl}benzenesulfonamide |
| 130 | 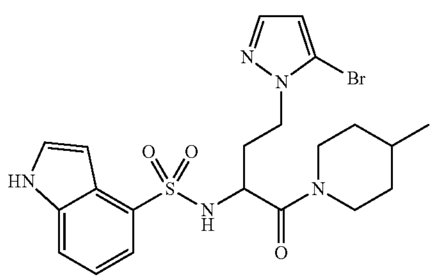 [SMILES: CC1CCN(C(=O)C(CCn2nccc2Br)NS(=O)(=O)c2cccc3[nH]ccc23)CC1] | N-{3-(5-bromo-1H-pyrazol-1-yl)-1-[(4-methylpiperidin-1-yl)carbonyl]propyl}-1H-indole-4-sulfonamide |
| 131 | 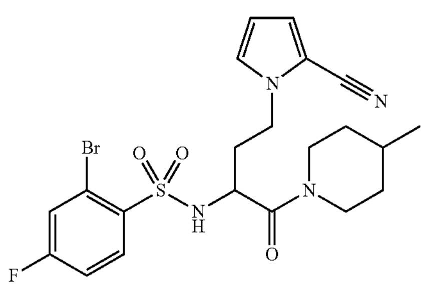 | 2-bromo-N-{3-(2-cyano-1H-pyrrol-1-yl)-1-[(4-methylpiperidin-1-yl)carbonyl]propyl}-4-fluorobenzenesulfonamide |

-continued

| Example | Structure | Name |
|---|---|---|
| 132 | 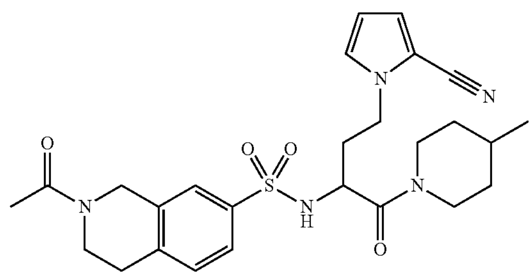 [SMILES: CC(=O)N1CCc2ccc(S(=O)(=O)NC(CCn3cccc3C#N)C(=O)N3CCC(C)CC3)cc2C1] | 2-acetyl-N-{3-(2-cyano-1H-pyrrol-1-yl)-1-[(4-methylpiperidin-1-yl)carbonyl]propyl}-1,2,3,4-tetrahydroisoquinoline-7-sulfonamide |
| 133 | 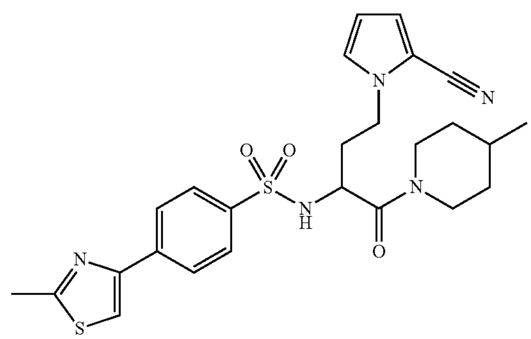 | N-{3-(2-cyano-1H-pyrrol-1-yl)-1-[(4-methylpiperidin-1-yl)carbonyl]propyl}-4-(2-methyl-1,3-thiazol-4-yl)benzenesulfonamide |
| 134 | 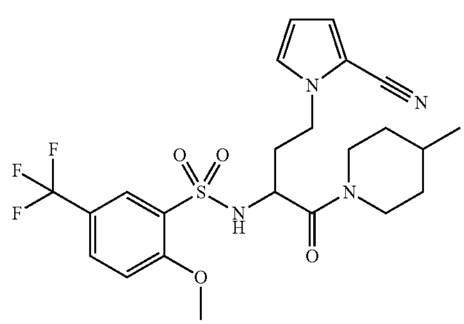 [SMILES: COc1ccc(C(F)(F)F)cc1S(=O)(=O)NC(CCn1cccc1C#N)C(=O)N1CCC(C)CC1] | N-{3-(2-cyano-1H-pyrrol-1-yl)-1-[(4-methylpiperidin-1-yl)carbonyl]propyl}-2-methoxy-5-(trifluoromethyl)benzenesulfonamide |
| 135 | 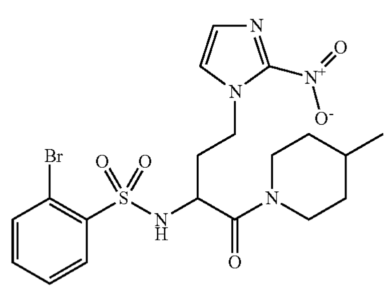 [SMILES: CC1CCN(C(=O)C(CCn2ccnc2[N+](=O)[O-])NS(=O)(=O)c2ccccc2Br)CC1] | 2-bromo-N-{1-[(4-methylpiperidin-1-yl)carbonyl]-3-(2-nitro-1H-imidazol-1-yl)propyl}benzenesulfonamide |
| 136 | 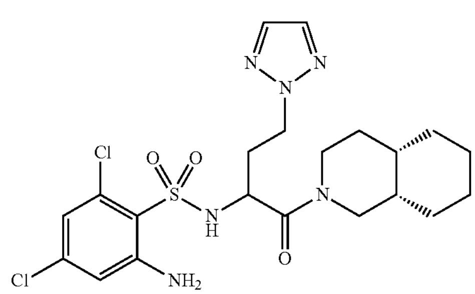 [SMILES: Nc1cc(Cl)cc(Cl)c1S(=O)(=O)NC(CCn1nccn1)C(=O)N1CC[C@@H]2CCCC[C@@H]2C1] | 2-amino-4,6-dichloro-N-{1-[(cis)-octahydroisoquinolin-2(1H)-ylcarbonyl]-3-(2H-1,2,3-triazol-2-yl)propyl}benzenesulfonamide |

-continued

| Example | Structure | Name |
|---|---|---|
| 137 | 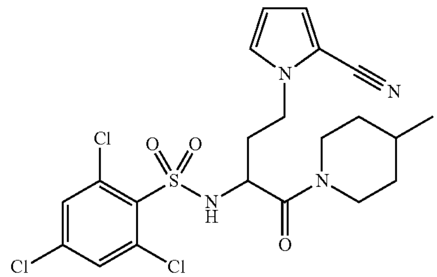 [SMILES: CC1CCN(C(=O)C(CCn2cccc2C#N)NS(=O)(=O)c2c(Cl)cc(Cl)cc2Cl)CC1] | 2,4,6-trichloro-N-{3-(2-cyano-1H-pyrrol-1-yl)-1-[(4-methylpiperidin-1-yl)carbonyl]propyl}benzenesulfonamide |
| 139 | 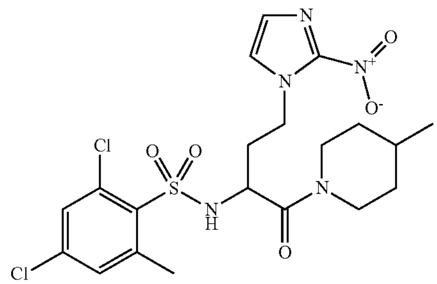 [SMILES: Cc1cc(Cl)cc(Cl)c1S(=O)(=O)NC(CCn1ccnc1[N+](=O)[O-])C(=O)N1CCC(C)CC1] | 2,4-dichloro-6-methyl-N-{1-[(4-methylpiperidin-1-yl)carbonyl]-3-(2-nitro-1H-imidazol-1-yl)propyl}benzenesulfonamide |
| 140 | | N-{3-(2-cyano-1H-pyrrol-1-yl)-1-[(2-methylpiperidin-1-yl)carbonyl]propyl}-1H-indole-4-sulfonamide |
| 140 | Chiral | 4-(2-cyano-1H-pyrrol-1-yl)-2-{[(2,6-dichlorophenyl)sulfonyl]amino}-N-methyl-N-[(1R)-1-phenylethyl]butanamide |
| 141 | 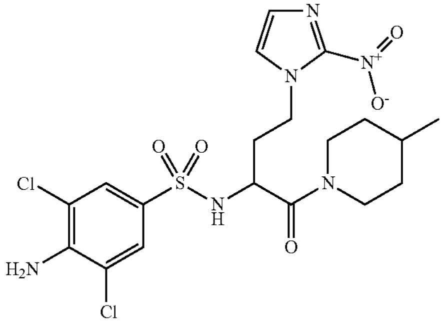 [SMILES: CC1CCN(C(=O)C(CCn2ccnc2[N+](=O)[O-])NS(=O)(=O)c2cc(Cl)c(N)c(Cl)c2)CC1] | 4-amino-3,5-dichloro-N-{1-[(4-methylpiperidin-1-yl)carbonyl]-3-(2-nitro-1H-imidazol-1-yl)propyl}benzenesulfonamide |

-continued

| Example | Structure | Name |
| --- | --- | --- |
| 142 | 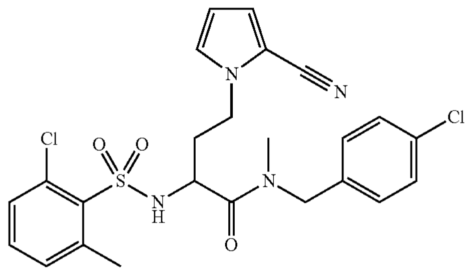 [SMILES: Cc1cccc(Cl)c1S(=O)(=O)NC(CCn1cccc1C#N)C(=O)N(C)Cc1ccc(Cl)cc1] | N-(4-chlorobenzyl)-2-{[(2-chloro-6-methylphenyl)sulfonyl]amino}-4-(2-cyano-1H-pyrrol-1-yl)-N-methylbutanamide |
| 143 | 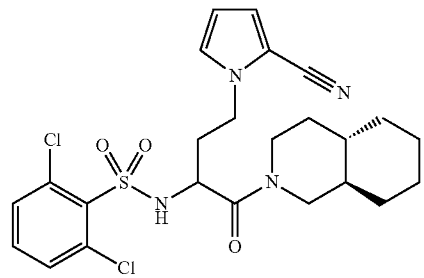 [SMILES: N#Cc1cccn1CCC(NS(=O)(=O)c1c(Cl)cccc1Cl)C(=O)N1CC[C@@H]2CCCC[C@H]2C1] | 2,6-dichloro-N-{3-(2-cyano-1H-pyrrol-1-yl)-1-[(trans)-octahydroisoquinolin-2(1H)-ylcarbonyl]propyl}benzenesulfonamide |
| 144 | 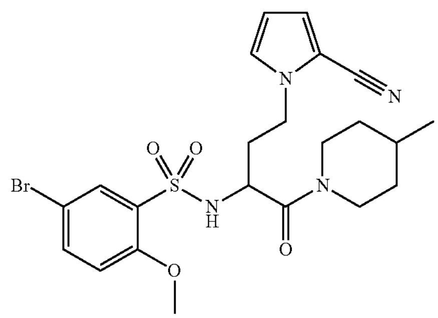 [SMILES: COc1ccc(Br)cc1S(=O)(=O)NC(CCn1cccc1C#N)C(=O)N1CCC(C)CC1] | 5-bromo-N-{3-(2-cyano-1H-pyrrol-1-yl)-1-[(4-methylpiperidin-1-yl)carbonyl]propyl}-2-methoxybenzenesulfonamide |
| 145 | 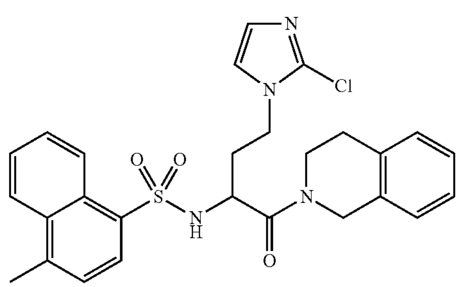 [SMILES: Cc1ccc(S(=O)(=O)NC(CCn2ccnc2Cl)C(=O)N2CCc3ccccc3C2)c2ccccc12] | N-[3-(2-chloro-1H-imidazol-1-yl)-1-(3,4-dihydroisoquinolin-2(1H)-ylcarbonyl)propyl]-4-methylnaphthalene-1-sulfonamide |
| 146 | 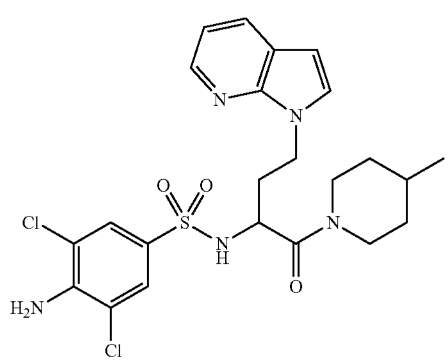 [SMILES: CC1CCN(C(=O)C(CCn2ccc3cccnc32)NS(=O)(=O)c2cc(Cl)c(N)c(Cl)c2)CC1] | 4-amino-3,5-dichloro-N-{1-[(4-methylpiperidin-1-yl)carbonyl]-3-(1H-pyrrolo[2,3-b]pyridin-1-yl)propyl}benzenesulfonamide |

| Example | Structure | Name |
| --- | --- | --- |
| 147 | 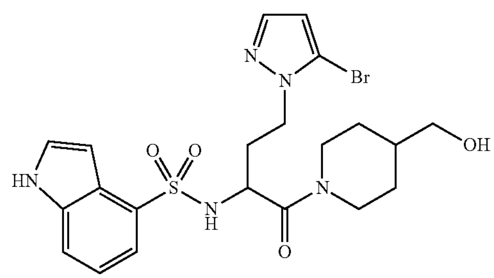 [SMILES: O=C(C(CCn1nccc1Br)NS(=O)(=O)c1cccc2[nH]ccc12)N1CCC(CO)CC1] | N-[3-(5-bromo-1H-pyrazol-1-yl)-1-{[4-(hydroxymethyl)piperidin-1-yl]carbonyl}propyl]-1H-indole-4-sulfonamide |
| 148 | 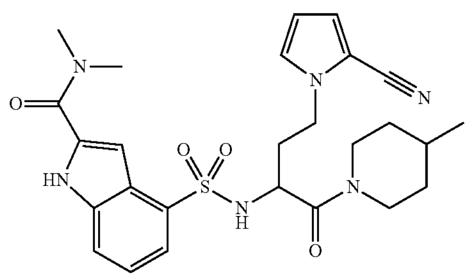 [SMILES: CC1CCN(C(=O)C(CCn2cccc2C#N)NS(=O)(=O)c2cccc3[nH]c(C(=O)N(C)C)cc23)CC1] | 4-({3-(2-cyano-1H-pyrrol-1-yl)-1-[(4-methylpiperidin-1-yl)carbonyl]propyl}sulfamoyl)-N,N-dimethyl-1H-indole-2-carboxamide |
| 149 | 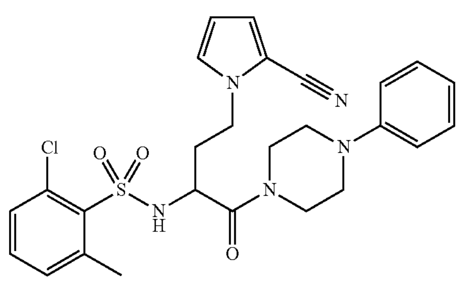 [SMILES: Cc1cccc(Cl)c1S(=O)(=O)NC(CCn1cccc1C#N)C(=O)N1CCN(c2ccccc2)CC1] | 2-chloro-N-{3-(2-cyano-1H-pyrrol-1-yl)-1-[(4-phenylpiperazin-1-yl)carbonyl]propyl}-6-methylbenzenesulfonamide |
| 150 | 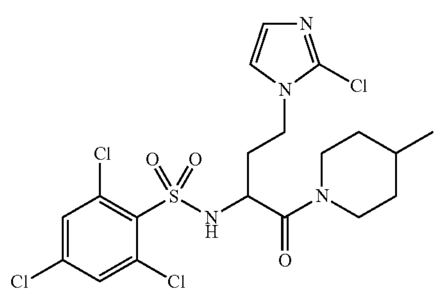 [SMILES: CC1CCN(C(=O)C(CCn2ccnc2Cl)NS(=O)(=O)c2c(Cl)cc(Cl)cc2Cl)CC1] | 2,4,6-trichloro-N-{3-(2-chloro-1H-imidazol-1-yl)-1-[(4-methylpiperidin-1-yl)carbonyl]propyl}benzenesulfonamide |
| 151 | 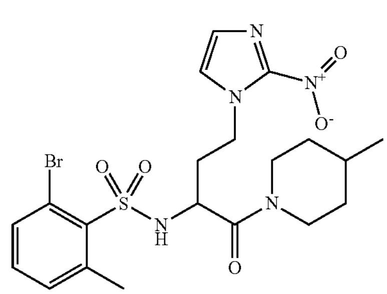 | 2-bromo-6-methyl-N-{1-[(4-methylpiperidin-1-yl)carbonyl]-3-(2-nitro-1H-imidazol-1-yl)propyl}benzenesulfonamide |

-continued

| Example | Structure | Name |
|---|---|---|
| 152 | 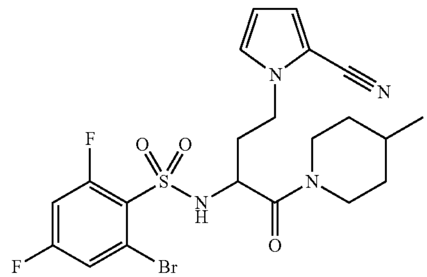 [SMILES: CC1CCN(C(=O)C(CCn2cccc2C#N)NS(=O)(=O)c2c(F)cc(F)cc2Br)CC1] | 2-bromo-N-{3-(2-cyano-1H-pyrrol-1-yl)-1-[(4-methylpiperidin-1-yl)carbonyl]propyl}-4,6-difluorobenzenesulfonamide |
| 153 | 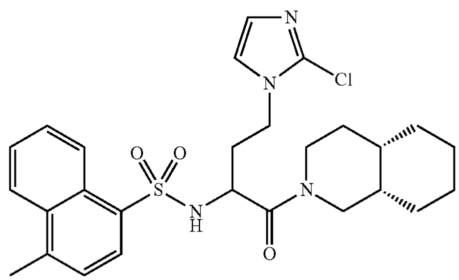 [SMILES: Cc1ccc(S(=O)(=O)NC(CCn2ccnc2Cl)C(=O)N2CC[C@@H]3CCCC[C@@H]3C2)c2ccccc12] | N-{3-(2-chloro-1H-imidazol-1-yl)-1-[(cis)-octahydroisoquinolin-2(1H)-ylcarbonyl]propyl}-4-methylnaphthalene-1-sulfonamide |
| 154 | 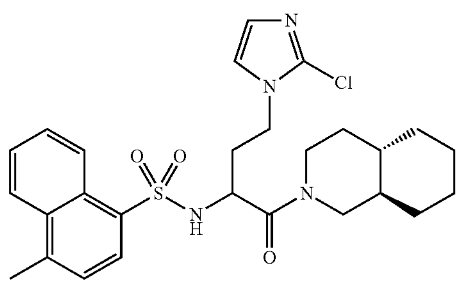 [SMILES: Cc1ccc(S(=O)(=O)NC(CCn2ccnc2Cl)C(=O)N2CC[C@@H]3CCCC[C@H]3C2)c2ccccc12] | N-{3-(2-chloro-1H-imidazol-1-yl)-1-[(trans)-octahydroisoquinolin-2(1H)-ylcarbonyl]propyl}-4-methylnaphthalene-1-sulfonamide |
| 155 | 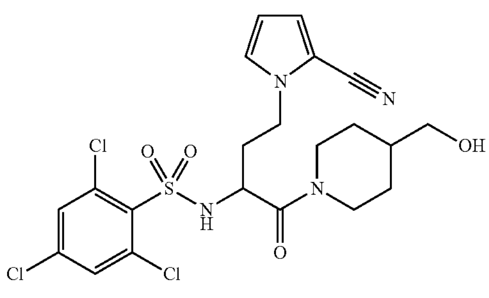 [SMILES: N#Cc1cccn1CCC(NS(=O)(=O)c1c(Cl)cc(Cl)cc1Cl)C(=O)N1CCC(CO)CC1] | 2,4,6-trichloro-N-[3-(2-cyano-1H-pyrrol-1-yl)-1-{[4-(hydroxymethyl)piperidin-1-yl]carbonyl}propyl]benzenesulfonamide |
| 156 | 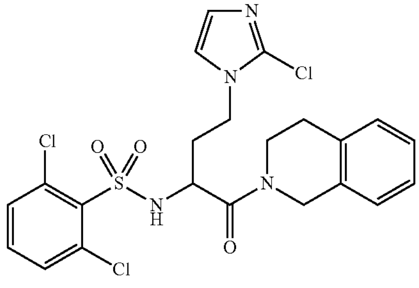 [SMILES: O=C(C(CCn1ccnc1Cl)NS(=O)(=O)c1c(Cl)cccc1Cl)N1CCc2ccccc2C1] | 2,6-dichloro-N-[3-(2-chloro-1H-imidazol-1-yl)-1-(3,4-dihydroisoquinolin-2(1H)-ylcarbonyl)propyl]benzenesulfonamide |

-continued

| Example | Structure | Name |
|---|---|---|
| 157 | 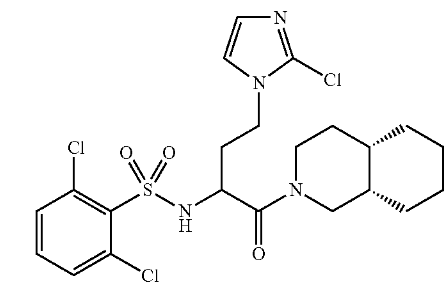 [SMILES: O=C(C(CCn1ccnc1Cl)NS(=O)(=O)c1c(Cl)cccc1Cl)N1CC[C@@H]2CCCC[C@@H]2C1] | 2,6-dichloro-N-{3-(2-chloro-1H-imidazol-1-yl)-1-[(cis-octahydroisoquinolin-2(1H)-yl)carbonyl]propyl}benzenesulfonamide |
| 158 | 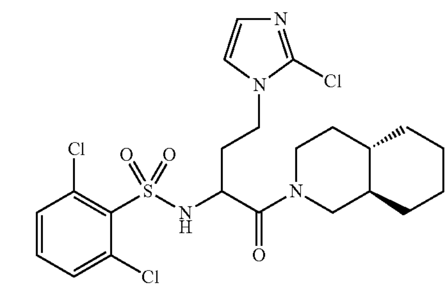 [SMILES: O=C(C(CCn1ccnc1Cl)NS(=O)(=O)c1c(Cl)cccc1Cl)N1CC[C@@H]2CCCC[C@H]2C1] | 2,6-dichloro-N-{3-(2-chloro-1H-imidazol-1-yl)-1-[(trans-octahydroisoquinolin-2(1H)-yl)carbonyl]propyl}benzenesulfonamide |
| 159 | 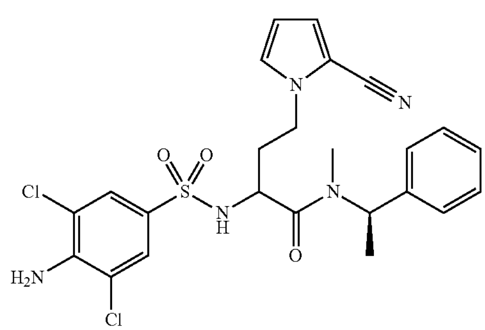 [SMILES: C[C@H](c1ccccc1)N(C)C(=O)C(CCn1cccc1C#N)NS(=O)(=O)c1cc(Cl)c(N)c(Cl)c1] | 2-{[(4-amino-3,5-dichlorophenyl)sulfonyl]amino}-4-(2-cyano-1H-pyrrol-1-yl)-N-methyl-N-[(1R)-1-phenylethyl]butanamide |
| 160 | | N-[3-(2-cyano-1H-pyrrol-1-yl)-1-{[4-(hydroxymethyl)piperidin-1-yl]carbonyl}propyl]-1H-indole-6-sulfonamide |
| 160 | | N-[1-(3,4-dihydroisoquinolin-2(1H)-ylcarbonyl)-3-(2-nitro-1H-imidazol-1-yl)propyl]-4-methylnaphthalene-1-sulfonamide |

| Example | Structure | Name |
|---|---|---|
| 161 | 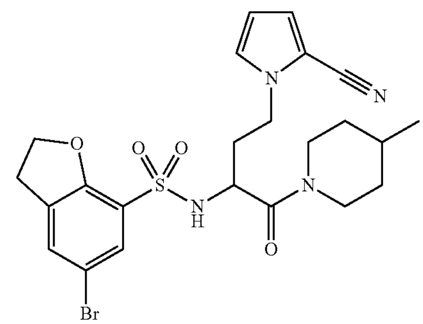 [SMILES: CC1CCN(C(=O)C(CCn2cccc2C#N)NS(=O)(=O)c2cc(Br)cc3c2OCC3)CC1] | 5-bromo-N-{3-(2-cyano-1H-pyrrol-1-yl)-1-[(4-methylpiperidin-1-yl)carbonyl]propyl}-2,3-dihydro-1-benzofuran-7-sulfonamide |
| 162 | 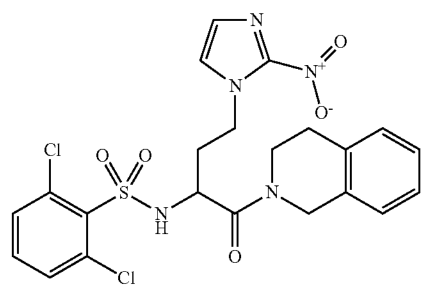 [SMILES: O=C(C(CCn1ccnc1[N+](=O)[O-])NS(=O)(=O)c1c(Cl)cccc1Cl)N1CCc2ccccc2C1] | 2,6-dichloro-N-[1-(3,4-dihydroisoquinolin-2(1H)-ylcarbonyl)-3-(2-nitro-1H-imidazol-1-yl)propyl]benzenesulfonamide |
| 163 | 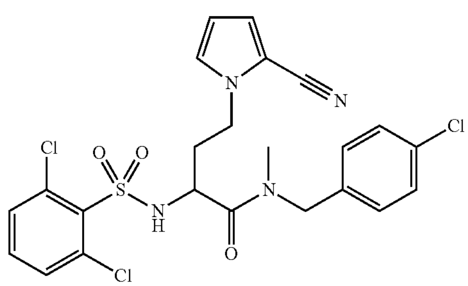 [SMILES: CN(Cc1ccc(Cl)cc1)C(=O)C(CCn1cccc1C#N)NS(=O)(=O)c1c(Cl)cccc1Cl] | N-(4-chlorobenzyl)-4-(2-cyano-1H-pyrrol-1-yl)-2-{[(2,6-dichlorophenyl)sulfonyl]amino}-N-methylbutanamide |
| 164 | 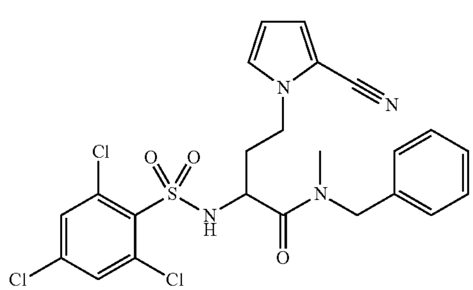 [SMILES: CN(Cc1ccccc1)C(=O)C(CCn1cccc1C#N)NS(=O)(=O)c1c(Cl)cc(Cl)cc1Cl] | N-benzyl-4-(2-cyano-1H-pyrrol-1-yl)-N-methyl-2-{[(2,4,6-trichlorophenyl)sulfonyl]amino}butanamide |
| 165 | 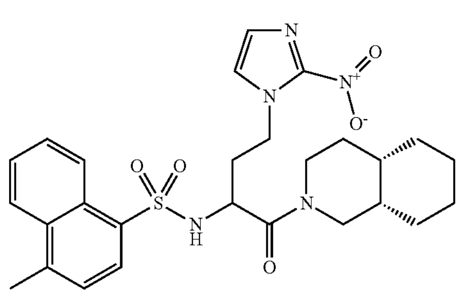 [SMILES: Cc1ccc(S(=O)(=O)NC(CCn2ccnc2[N+](=O)[O-])C(=O)N2CC[C@@H]3CCCC[C@@H]3C2)c2ccccc12] | 4-methyl-N-{3-(2-nitro-1H-imidazol-1-yl)-1-[(cis)-octahydroisoquinolin-2(1H)-ylcarbonyl]propyl}naphthalene-1-sulfonamide |

| Example | Structure | Name |
|---|---|---|
| 166 | 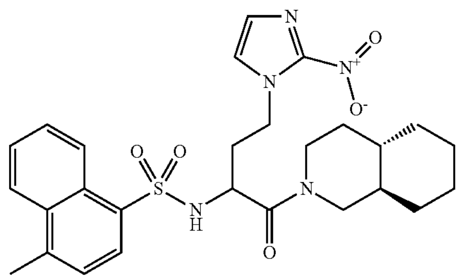 [SMILES: Cc1ccc(S(=O)(=O)NC(CCn2ccnc2[N+](=O)[O-])C(=O)N2CC[C@@H]3CCCC[C@H]3C2)c2ccccc12] | 4-methyl-N-{3-(2-nitro-1H-imidazol-1-yl)-1-[(trans)-octahydroisoquinolin-2(1H)-ylcarbonyl]propyl}naphthalene-1-sulfonamide |
| 167 | 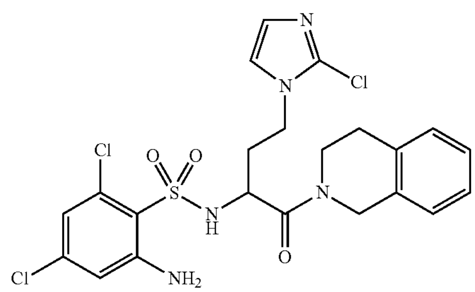 [SMILES: Nc1cc(Cl)cc(Cl)c1S(=O)(=O)NC(CCn1ccnc1Cl)C(=O)N1CCc2ccccc2C1] | 2-amino-4,6-dichloro-N-[3-(2-chloro-1H-imidazol-yl)-1-(3,4-dihydroisoquinolin-2(1H)-ylcarbonyl)propyl]benzenesulfonamide |
| 168 | 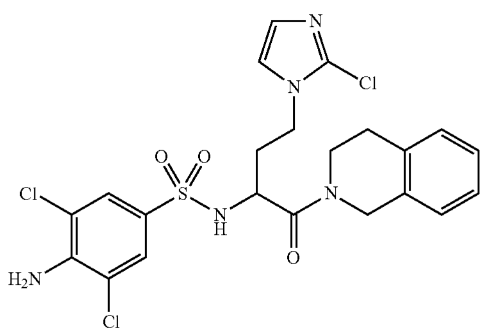 [SMILES: Nc1c(Cl)cc(S(=O)(=O)NC(CCn2ccnc2Cl)C(=O)N2CCc3ccccc3C2)cc1Cl] | 4-amino-3,5-dichloro-N-[3-(2-chloro-1H-imidazol-yl)-1-(3,4-dihydroisoquinolin-2(1H)-ylcarbonyl)propyl]benzenesulfonamide |
| 169 | 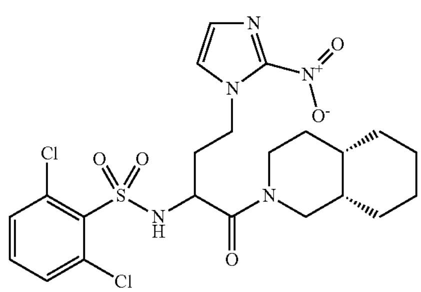 [SMILES: O=C(C(CCn1ccnc1[N+](=O)[O-])NS(=O)(=O)c1c(Cl)cccc1Cl)N1CC[C@@H]2CCCC[C@@H]2C1] | 2,6-dichloro-N-{3-(2-nitro-1H-imidazol-1-yl)-1-[(cis)-octahydroisoquinolin-2(1H)-ylcarbonyl]propyl}benzenesulfonamide |
| 170 | 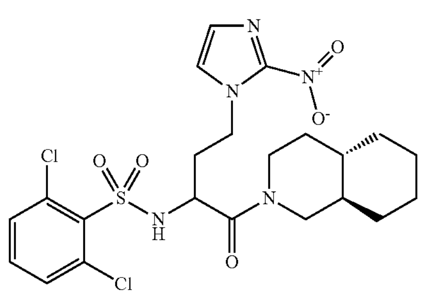 [SMILES: O=C(C(CCn1ccnc1[N+](=O)[O-])NS(=O)(=O)c1c(Cl)cccc1Cl)N1CC[C@@H]2CCCC[C@H]2C1] | 2,6-dichloro-N-{3-(2-nitro-1H-imidazol-1-yl)-1-[(trans)-octahydroisoquinolin-2(1H)-ylcarbonyl]propyl}benzenesulfonamide |

-continued

| Example | Structure | Name |
|---|---|---|
| 171 | 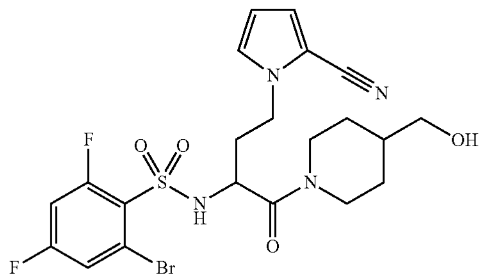 [SMILES: N#Cc1cccn1CCC(NS(=O)(=O)c1c(F)cc(F)cc1Br)C(=O)N1CCC(CO)CC1] | 2-bromo-N-[3-(2-cyano-1H-pyrrol-1-yl)-1-{[4-(hydroxymethyl)piperidin-1-yl]carbonyl}propyl]-4,6-difluorobenzenesulfonamide |
| 172 | 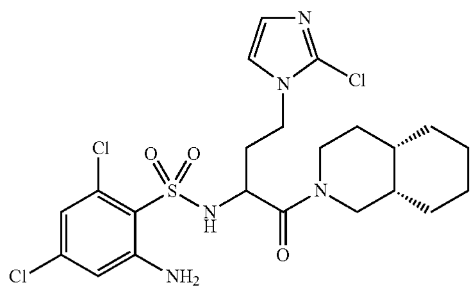 [SMILES: Nc1cc(Cl)cc(Cl)c1S(=O)(=O)NC(CCn1ccnc1Cl)C(=O)N1CC[C@@H]2CCCC[C@@H]2C1] | 2-amino-4,6-dichloro-N-{3-(2-chloro-1H-imidazol-1-yl)-1-[(cis)-octahydroisoquinolin-2(1H)-ylcarbonyl]propyl}benzenesulfonamide |
| 173 | 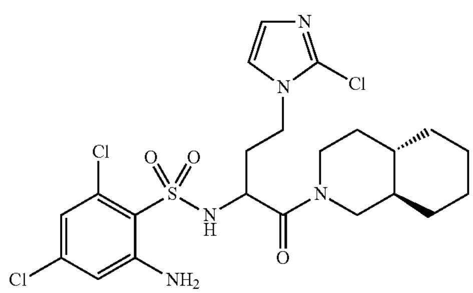 [SMILES: Nc1cc(Cl)cc(Cl)c1S(=O)(=O)NC(CCn1ccnc1Cl)C(=O)N1CC[C@@H]2CCCC[C@H]2C1] | 2-amino-4,6-dichloro-N-{3-(2-chloro-1H-imidazol-1-yl)-1-[(trans)-octahydroisoquinolin-2(1H)-ylcarbonyl]propyl}benzenesulfonamide |
| 174 | 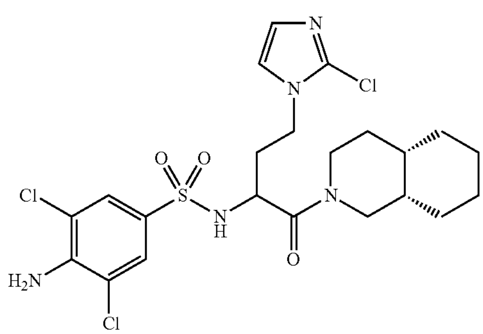 [SMILES: Nc1c(Cl)cc(S(=O)(=O)NC(CCn2ccnc2Cl)C(=O)N2CC[C@@H]3CCCC[C@@H]3C2)cc1Cl] | 4-amino-3,5-dichloro-N-{3-(2-chloro-1H-imidazol-1-yl)-1-[(cis)-octahydroisoquinolin-2(1H)-ylcarbonyl]propyl}benzenesulfonamide |
| 175 | 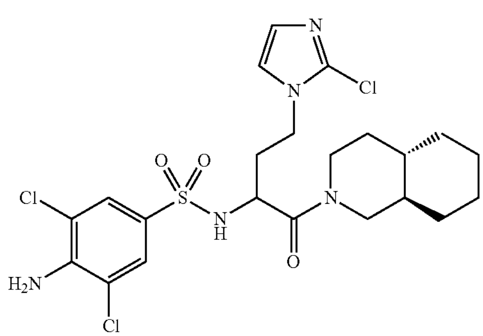 [SMILES: Nc1c(Cl)cc(S(=O)(=O)NC(CCn2ccnc2Cl)C(=O)N2CC[C@@H]3CCCC[C@H]3C2)cc1Cl] | 4-amino-3,5-dichloro-N-{3-(2-chloro-1H-imidazol-1-yl)-1-[(trans)-octahydroisoquinolin-2(1H)-ylcarbonyl]propyl}benzenesulfonamide |

-continued

| Example | Structure | Name |
| --- | --- | --- |
| 176 | 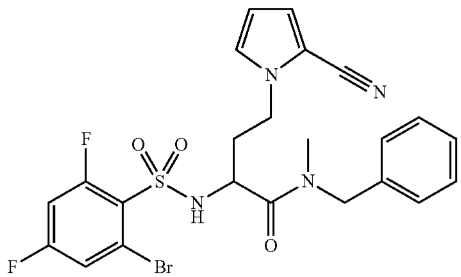 [SMILES: CN(Cc1ccccc1)C(=O)C(CCn1cccc1C#N)NS(=O)(=O)c1c(F)cc(F)cc1Br] | N-benzyl-2-{[(2-bromo-4,6-difluorophenyl)sulfonyl]amino}-4-(2-cyano-1H-pyrrol-1-yl)-N-methylbutanamide |
| 177 | 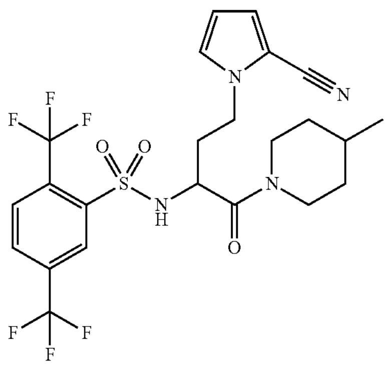 [SMILES: CC1CCN(C(=O)C(CCn2cccc2C#N)NS(=O)(=O)c2cc(C(F)(F)F)ccc2C(F)(F)F)CC1] | N-{3-(2-cyano-1H-pyrrol-1-yl)-1-[(4-methylpiperidin-1-yl)carbonyl]propyl}-2,5-bis(trifluoromethyl)benzenesulfonamide |
| 178 | 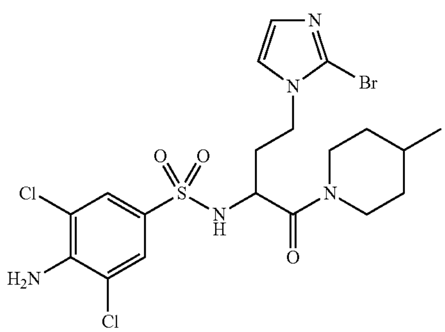 [SMILES: CC1CCN(C(=O)C(CCn2ccnc2Br)NS(=O)(=O)c2cc(Cl)c(N)c(Cl)c2)CC1] | 4-amino-N-{3-(2-bromo-1H-imidazol-1-yl)-1-[(4-methylpiperidin-1-yl)carbonyl]propyl}-3,5-dichlorobenzenesulfonamide |
| 179 | 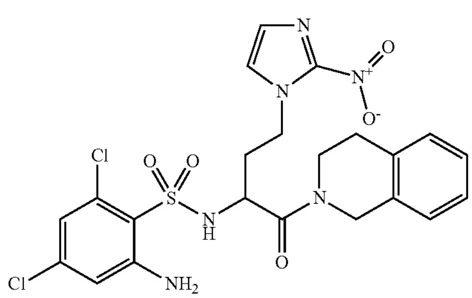 [SMILES: Nc1cc(Cl)cc(Cl)c1S(=O)(=O)NC(CCn1ccnc1[N+](=O)[O-])C(=O)N1CCc2ccccc2C1] | 2-amino-4,6-dichloro-N-[1-(3,4-dihydroisoquinolin-2(1H)-ylcarbonyl)-3-(2-nitro-1H-imidazol-1-yl)propyl]benzenesulfonamide |
| 180 | 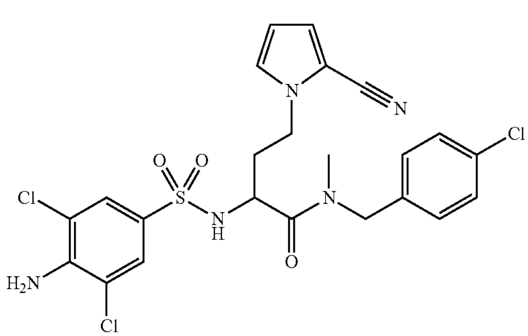 [SMILES: CN(Cc1ccc(Cl)cc1)C(=O)C(CCn1cccc1C#N)NS(=O)(=O)c1cc(Cl)c(N)c(Cl)c1] | 2-{[(4-amino-3,5-dichlorophenyl)sulfonyl]amino}-N-(4-chlorobenzyl)-4-(2-cyano-1H-pyrrol-1-yl)-N-methylbutanamide |

-continued

| Example | Structure | Name |
|---|---|---|
| 182 | 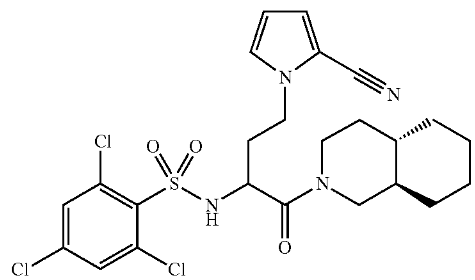 [SMILES: N#Cc1cccn1CCC(NS(=O)(=O)c1c(Cl)cc(Cl)cc1Cl)C(=O)N1CC[C@@H]2CCCC[C@H]2C1] | 2,4,6-trichloro-N-{3-(2-cyano-1H-pyrrol-1-yl)-1-[(trans)-octahydroisoquinolin-2(1H)-ylcarbonyl]propyl}benzenesulfonamide |
| 183 | 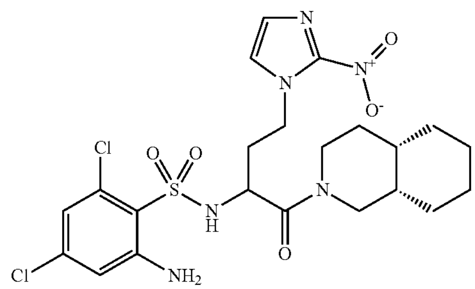 [SMILES: Nc1cc(Cl)cc(Cl)c1S(=O)(=O)NC(CCn1ccnc1[N+](=O)[O-])C(=O)N1CC[C@@H]2CCCC[C@@H]2C1] | 2-amino-4,6-trichloro-N-{3-(2-nitro-1H-imidazol-1-yl)-1-[(cis)-octahydroisoquinolin-2(1H)-ylcarbonyl]propyl}benzenesulfonamide |
| 184 | 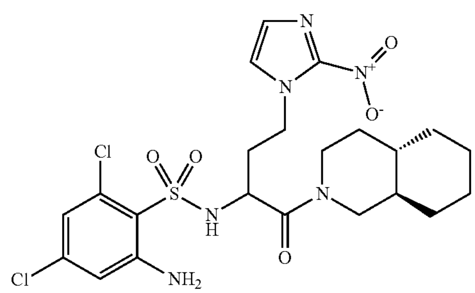 [SMILES: Nc1cc(Cl)cc(Cl)c1S(=O)(=O)NC(CCn1ccnc1[N+](=O)[O-])C(=O)N1CC[C@@H]2CCCC[C@H]2C1] | 2-amino-4,6-trichloro-N-{3-(2-nitro-1H-imidazol-1-yl)-1-[(trans)-octahydroisoquinolin-2(1H)-ylcarbonyl]propyl}benzenesulfonamide |
| 185 | 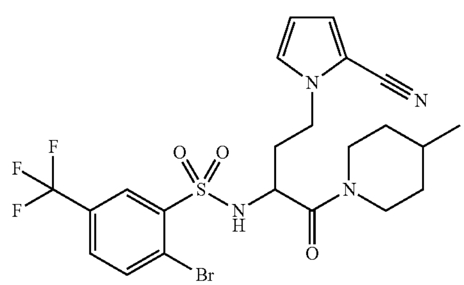 [SMILES: CC1CCN(C(=O)C(CCn2cccc2C#N)NS(=O)(=O)c2cc(C(F)(F)F)ccc2Br)CC1] | 2-bromo-N-{3-(2-cyano-1H-pyrrol-1-yl)-1-[(4-methylpiperidin-1-yl)carbonyl]propyl}-5-(trifluoromethyl)benzenesulfonamide |
| 186 | 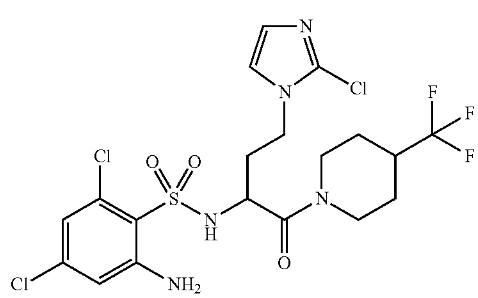 [SMILES: Nc1cc(Cl)cc(Cl)c1S(=O)(=O)NC(CCn1ccnc1Cl)C(=O)N1CCC(C(F)(F)F)CC1] | 2-amino-4,6-dichloro-N-[3-(2-chloro-1H-imidazol-1-yl)-1-{[4-(trifluoromethyl)piperidin-1-yl]carbonyl}propyl]benzenesulfonamide |

| Example | Structure | Name |
|---|---|---|
| 187 | Chiral | 2-{[(2-bromo-4,6-difluorophenyl)sulfonyl]amino}-4-(2-cyano-1H-pyrrol-1-yl)-N-methyl-N-[(1R)-1-phenylethyl]butanamide |
| 188 | 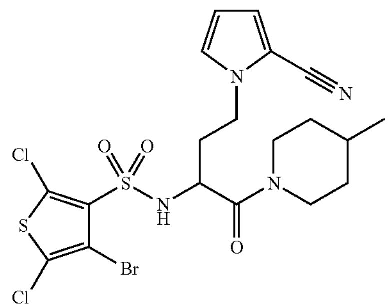 [SMILES: CC1CCN(C(=O)C(CCn2cccc2C#N)NS(=O)(=O)c2c(Cl)sc(Cl)c2Br)CC1] | 4-bromo-2,5-dichloro-N-{3-(2-cyano-1H-pyrrol-1-yl)-1-[(4-methylpiperidin-1-yl)carbonyl]propyl}thiophene-3-sulfonamide |
| 189 | 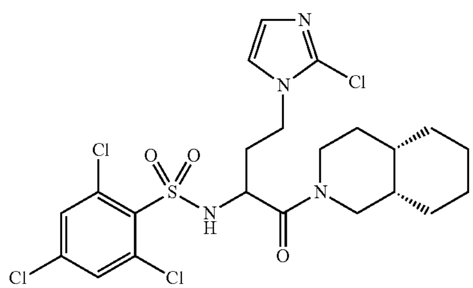 [SMILES: O=C(C(CCn1ccnc1Cl)NS(=O)(=O)c1c(Cl)cc(Cl)cc1Cl)N1CC[C@@H]2CCCC[C@@H]2C1] | 2,4,6-trichloro-N-{3-(2-chloro-1H-imidazol-1-yl)-1-[(cis)-octahydroisoquinolin-2(1H)-ylcarbonyl]propyl}benzenesulfonamide |
| 190 | 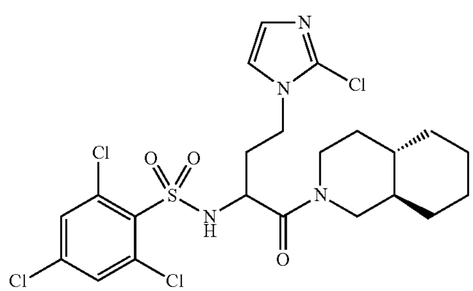 [SMILES: O=C(C(CCn1ccnc1Cl)NS(=O)(=O)c1c(Cl)cc(Cl)cc1Cl)N1CC[C@@H]2CCCC[C@H]2C1] | 2,4,6-trichloro-N-{3-(2-chloro-1H-imidazol-1-yl)-1-[(trans)-octahydroisoquinolin-2(1H)-ylcarbonyl]propyl}benzenesulfonamide |
| 191 | 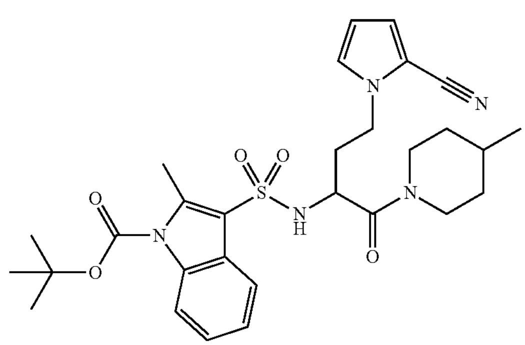 [SMILES: Cc1c(S(=O)(=O)NC(CCn2cccc2C#N)C(=O)N2CCC(C)CC2)c2ccccc2n1C(=O)OC(C)(C)C] | tert-butyl 3-[({3-(2-cyano-1H-pyrrol-1-yl)-1-[(4-methylpiperidin-1-yl)carbonyl]propyl}amino)sulfonyl]-2-methyl-1H-indole-1-carboxylate |

| Example | Structure | Name |
|---|---|---|
| 192 | 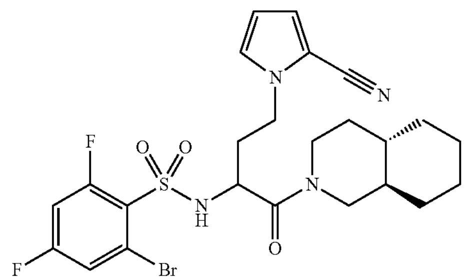 [SMILES: N#Cc1cccn1CCC(NS(=O)(=O)c1c(F)cc(F)cc1Br)C(=O)N1CC[C@@H]2CCCC[C@H]2C1] | 2-bromo-N-{3-(2-cyano-1H-pyrrol-1-yl)-1-[(trans)-octahydroisoquinolin-2(1H)-ylcarbonyl]propyl}-4,6-difluorobenzenesulfonamide |
| 193 | 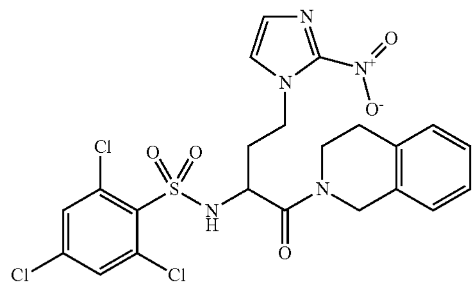 [SMILES: O=C(C(CCn1ccnc1[N+](=O)[O-])NS(=O)(=O)c1c(Cl)cc(Cl)cc1Cl)N1CCc2ccccc2C1] | 2,4,6-trichloro-N-[1-(3,4-dihydroisoquinolin-2(1H)-ylcarbonyl)-3-(2-nitro-1H-imidazol-1-yl)propyl]benzenesulfonamide |
| 196 | 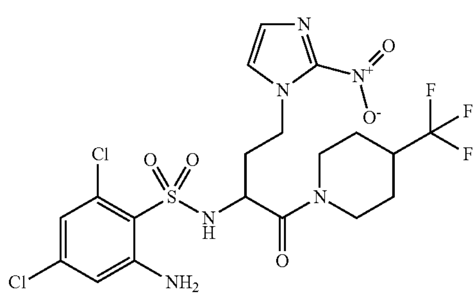 [SMILES: Nc1cc(Cl)cc(Cl)c1S(=O)(=O)NC(CCn1ccnc1[N+](=O)[O-])C(=O)N1CCC(C(F)(F)F)CC1] | 2-amino-4,6-dichloro-N-[3-(2-nitro-1H-imidazol-1-yl)-1-{[4-(trifluoromethyl)piperidin-1-yl]carbonyl}propyl]benzenesulfonamide |
| 197 | 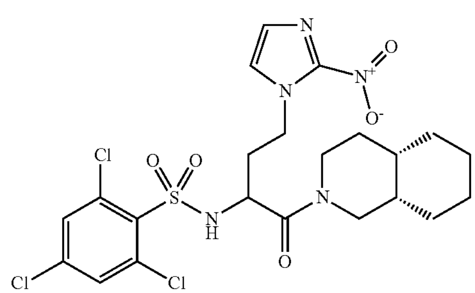 [SMILES: O=C(C(CCn1ccnc1[N+](=O)[O-])NS(=O)(=O)c1c(Cl)cc(Cl)cc1Cl)N1CC[C@@H]2CCCC[C@@H]2C1] | 2,4,6-trichloro-N-{3-(2-nitro-1H-imidazol-1-yl)-1-[(cis)-octahydroisoquinolin-2(1H)-ylcarbonyl]propyl}benzenesulfonamide |
| 198 | 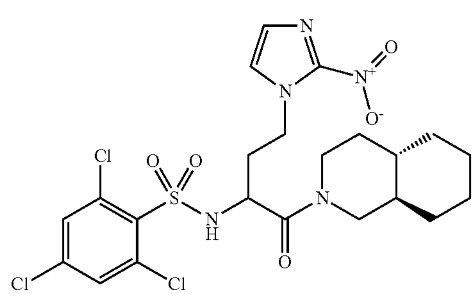 [SMILES: O=C(C(CCn1ccnc1[N+](=O)[O-])NS(=O)(=O)c1c(Cl)cc(Cl)cc1Cl)N1CC[C@@H]2CCCC[C@H]2C1] | 2,4,6-trichloro-N-{3-(2-nitro-1H-imidazol-1-yl)-1-[(trans)-octahydroisoquinolin-2(1H)-ylcarbonyl]propyl}benzenesulfonamide |

| Example | Structure | Name |
|---|---|---|
| 199 | 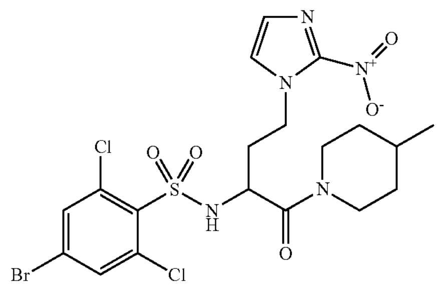 [SMILES: CC1CCN(C(=O)C(CCn2ccnc2[N+](=O)[O-])NS(=O)(=O)c2c(Cl)cc(Br)cc2Cl)CC1] | 4-bromo-2,6-dichloro-N-{1-[(4-methylpiperidin-1-yl)carbonyl]-3-(2-nitro-1H-imidazol-1-yl)propyl}benzenesulfonamide |
| 200 | 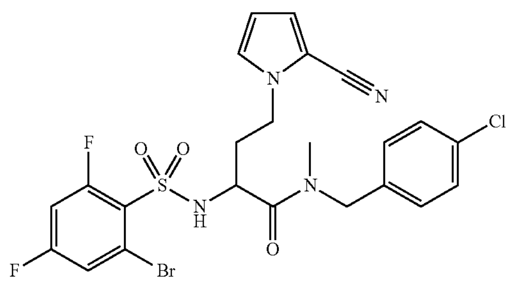 [SMILES: CN(Cc1ccc(Cl)cc1)C(=O)C(CCn1cccc1C#N)NS(=O)(=O)c1c(F)cc(F)cc1Br] | 2-{[(2-bromo-4,6-difluorophenyl)sulfonyl]amino}-N-(4-chlorobenzyl)-4-(2-cyano-1H-pyrrol-1-yl)-N-methylbutanamide |
| 201 | 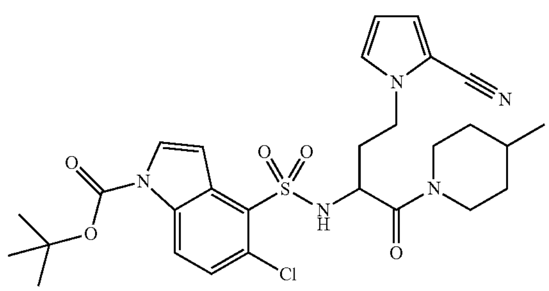 [SMILES: CC1CCN(C(=O)C(CCn2cccc2C#N)NS(=O)(=O)c2c(Cl)ccc3c2ccn3C(=O)OC(C)(C)C)CC1] | 5-chloro-4-[3-(2-cyano-pyrrol-1-yl)-1-(4-methyl-piperidine-1-carbonyl)-propylsulfamoyl]-indole-1-carboxylic acid tert-butyl ester |
| 202 | 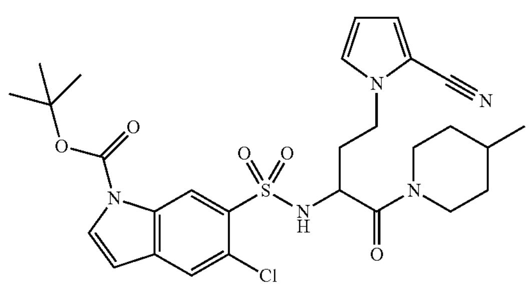 [SMILES: CC1CCN(C(=O)C(CCn2cccc2C#N)NS(=O)(=O)c2cc3c(ccn3C(=O)OC(C)(C)C)cc2Cl)CC1] | 5-chloro-6-[3-(2-cyano-pyrrol-1-yl)-1-(4-methyl-piperidine-1-carbonyl)-propylsulfamoyl]-indole-1-carboxylic acid tert-butyl ester |
| 203 | 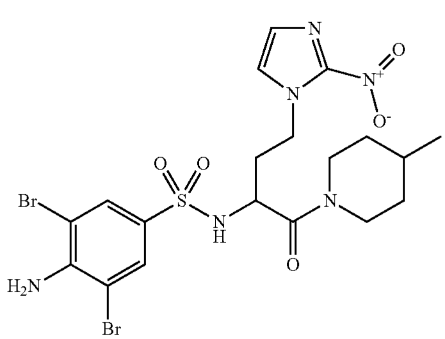 [SMILES: CC1CCN(C(=O)C(CCn2ccnc2[N+](=O)[O-])NS(=O)(=O)c2cc(Br)c(N)c(Br)c2)CC1] | 4-amino-3,5-dibromo-N-{1-[(4-methylpiperidin-1-yl)carbonyl]-3-(2-nitro-1H-imidazol-1-yl)propyl}benzenesulfonamide |

-continued

| Example | Structure | Name |
|---|---|---|
| 207 | 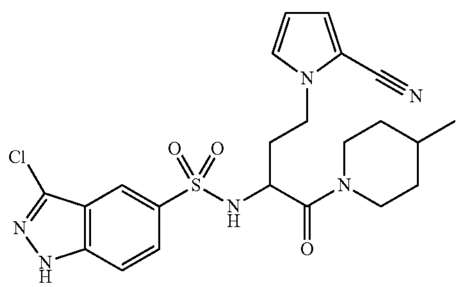 [SMILES: CC1CCN(C(=O)C(CCn2cccc2C#N)NS(=O)(=O)c2ccc3[nH]nc(Cl)c3c2)CC1] | 3-chloro-N-{3-(2-cyano-1H-pyrrol-1-yl)-1-[(4-methylpiperidin-1-yl)carbonyl]propyl}-1H-indazole-5-sulfonamide |
| 209 | 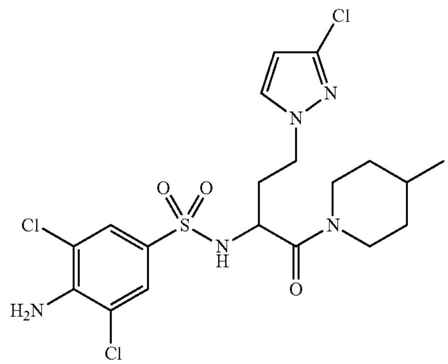 [SMILES: CC1CCN(C(=O)C(CCn2ccc(Cl)n2)NS(=O)(=O)c2cc(Cl)c(N)c(Cl)c2)CC1] | 4-amino-3,5-dichloro-N-{3-(3-chloro-1H-pyrazol-1-yl)-1-[(4-methylpiperidin-1-yl)carbonyl]propyl}benzenesulfonamide |
| 210 | 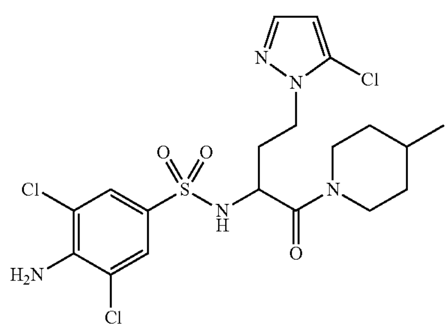 [SMILES: CC1CCN(C(=O)C(CCn2nccc2Cl)NS(=O)(=O)c2cc(Cl)c(N)c(Cl)c2)CC1] | 4-amino-3,5-dichloro-N-{3-(5-chloro-1H-pyrazol-1-yl)-1-[(4-methylpiperidin-1-yl)carbonyl]propyl}benzenesulfonamide |
| 211 | 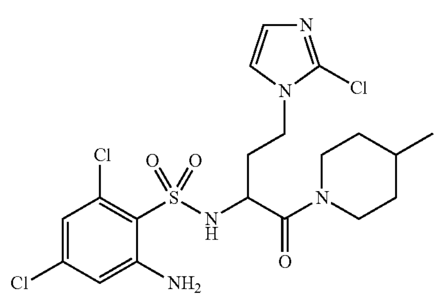 [SMILES: CC1CCN(C(=O)C(CCn2ccnc2Cl)NS(=O)(=O)c2c(N)cc(Cl)cc2Cl)CC1] | 2-amino-4,6-dichloro-N-{3-(2-chloro-1H-imidazol-1-yl)-1-[(4-methylpiperidin-1-yl)carbonyl]propyl}benzenesulfonamide |
| 212 | 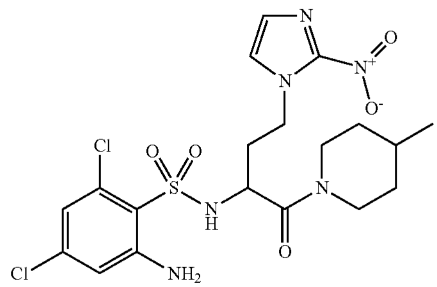 [SMILES: CC1CCN(C(=O)C(CCn2ccnc2[N+](=O)[O-])NS(=O)(=O)c2c(N)cc(Cl)cc2Cl)CC1] | 2-amino-4,6-dichloro-N-{1-[(4-methylpiperidin-1-yl)carbonyl]-3-(2-nitro-1H-imidazol-1-yl)propyl}benzenesulfonamide |

-continued

| Example | Structure | Name |
|---|---|---|
| 213 | 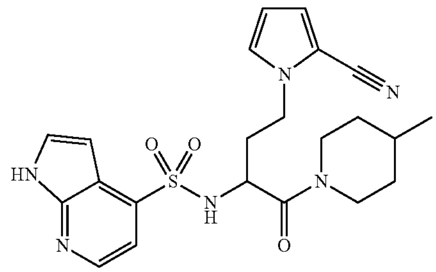 [SMILES: CC1CCN(C(=O)C(CCn2cccc2C#N)NS(=O)(=O)c2ccnc3[nH]ccc23)CC1] | N-{3-(2-cyano-1H-pyrrol-1-yl)-1-[(4-methylpiperidin-1-yl)carbonyl]propyl}-1H-pyrrolo[2,3-b]pyridine-4-sulfonamide |
| 214 | 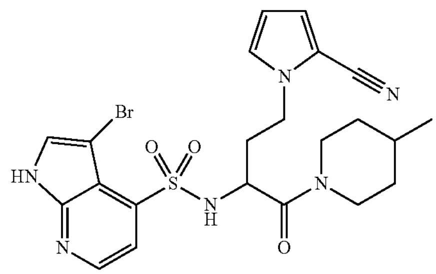 [SMILES: CC1CCN(C(=O)C(CCn2cccc2C#N)NS(=O)(=O)c2ccnc3[nH]cc(Br)c23)CC1] | 3-bromo-N-{3-(2-cyano-1H-pyrrol-1-yl)-1-[(4-methylpiperidin-1-yl)carbonyl]propyl}-1H-pyrrolo[2,3-b]pyridine-4-sulfonamide |
| 215 | 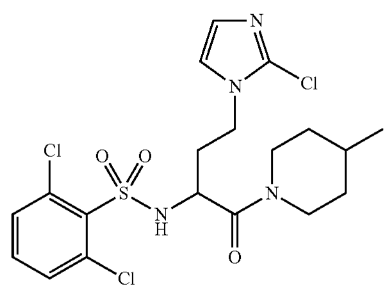 [SMILES: CC1CCN(C(=O)C(CCn2ccnc2Cl)NS(=O)(=O)c2c(Cl)cccc2Cl)CC1] | 2,6-dichloro-N-{3-(2-chloro-1H-imidazol-1-yl)-1-[(4-methylpiperidin-1-yl)carbonyl]propyl}benzenesulfonamide |
| 216 | 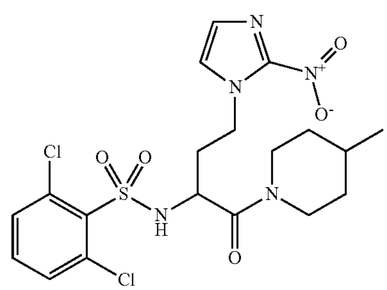 [SMILES: CC1CCN(C(=O)C(CCn2ccnc2[N+](=O)[O-])NS(=O)(=O)c2c(Cl)cccc2Cl)CC1] | 2,6-dichloro-N-{1-[(4-methylpiperidin-1-yl)carbonyl]-3-(2-nitro-1H-imidazol-1-yl)propyl}benzenesulfonamide |
| 217 | 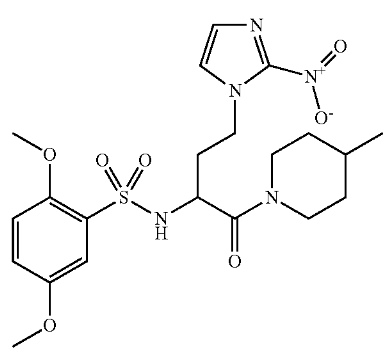 [SMILES: COc1ccc(OC)c(S(=O)(=O)NC(CCn2ccnc2[N+](=O)[O-])C(=O)N2CCC(C)CC2)c1] | 2,5-dimethoxy-N-{1-[(4-methylpiperidin-1-yl)carbonyl]-3-(2-nitro-1H-imidazol-1-yl)propyl}benzenesulfonamide |

-continued

| Example | Structure | Name |
|---|---|---|
| 218 | 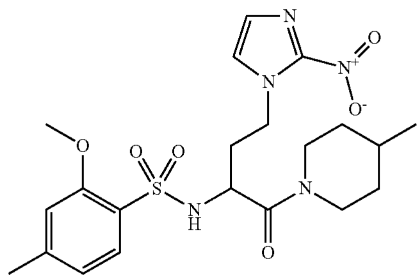 | 2-methoxy-4-methyl-N-{1-[(4-methylpiperidin-1-yl)carbonyl]-3-(2-nitro-1H-imidazol-1-yl)propyl}benzenesulfonamide |
| 219 | 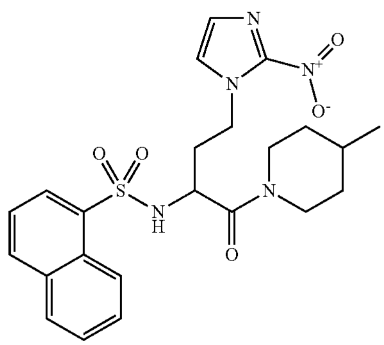 [SMILES: CC1CCN(C(=O)C(CCn2ccnc2[N+](=O)[O-])NS(=O)(=O)c2cccc3ccccc23)CC1] | N-{1-[(4-methylpiperidin-1-yl)carbonyl]-3-(2-nitro-1H-imidazol-1-yl)propyl}naphthalene-1-sulfonamide |
| 220 | 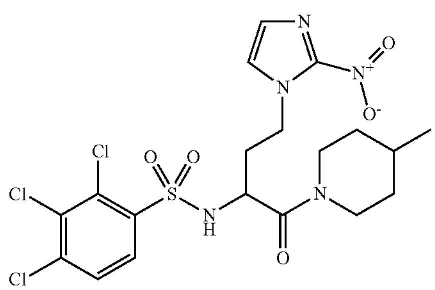 [SMILES: CC1CCN(C(=O)C(CCn2ccnc2[N+](=O)[O-])NS(=O)(=O)c2ccc(Cl)c(Cl)c2Cl)CC1] | 2,3,4-trichloro-N-{1-[(4-methylpiperidin-1-yl)carbonyl]-3-(2-nitro-1H-imidazol-1-yl)propyl}benzenesulfonamide |
| 221 | 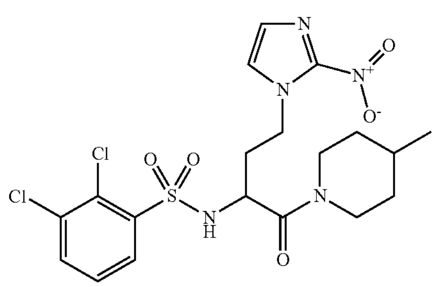 | 2,3-dichloro-N-{1-[(4-methylpiperidin-1-yl)carbonyl]-3-(2-nitro-1H-imidazol-1-yl)propyl}benzenesulfonamide |
| 222 | 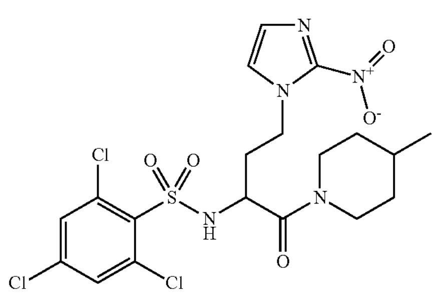 [SMILES: CC1CCN(C(=O)C(CCn2ccnc2[N+](=O)[O-])NS(=O)(=O)c2c(Cl)cc(Cl)cc2Cl)CC1] | 2,4,6-trichloro-N-{1-[(4-methylpiperidin-1-yl)carbonyl]-3-(2-nitro-1H-imidazol-1-yl)propyl}benzenesulfonamide |

-continued

| Example | Structure | Name |
|---|---|---|
| 223 | 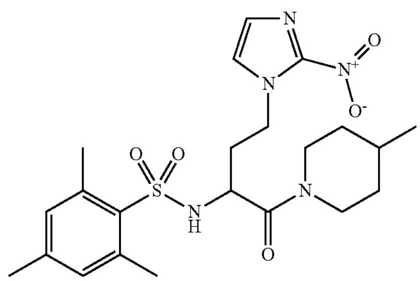 | 2,4,6-trimethyl-N-{1-[(4-methylpiperidin-1-yl)carbonyl]-3-(2-nitro-1H-imidazol-1-yl)propyl}benzenesulfonamide |
| 224 | 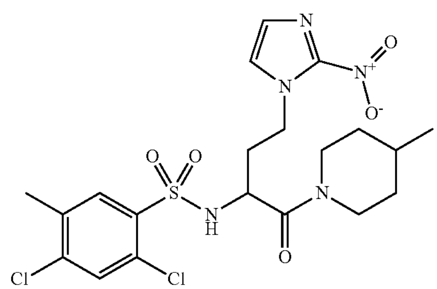 [SMILES: Cc1cc(S(=O)(=O)NC(CCn2ccnc2[N+](=O)[O-])C(=O)N2CCC(C)CC2)c(Cl)cc1Cl] | 2,4-dichloro-5-methyl-N-{1-[(4-methylpiperidin-1-yl)carbonyl]-3-(2-nitro-1H-imidazol-1-yl)propyl}benzenesulfonamide |
| 225 | 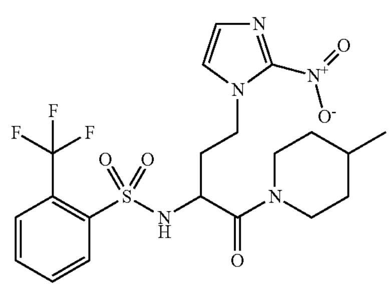 [SMILES: CC1CCN(C(=O)C(CCn2ccnc2[N+](=O)[O-])NS(=O)(=O)c2ccccc2C(F)(F)F)CC1] | 2-Trifluoromethyl-N-{1-[(4-methylpiperidin-1-yl)carbonyl]-3-(2-nitro-1H-imidazol-1-yl)propyl}benzenesulfonamide |
| 226 | 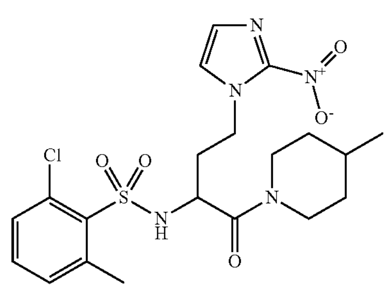 [SMILES: Cc1cccc(Cl)c1S(=O)(=O)NC(CCn1ccnc1[N+](=O)[O-])C(=O)N1CCC(C)CC1] | 2-chloro-6-methyl-N-{1-[(4-methylpiperidin-1-yl)carbonyl]-3-(2-nitro-1H-imidazol-1-yl)propyl}benzenesulfonamide |
| 227 | 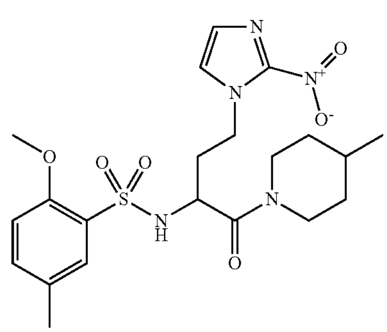 [SMILES: COc1ccc(C)cc1S(=O)(=O)NC(CCn1ccnc1[N+](=O)[O-])C(=O)N1CCC(C)CC1] | 2-methoxy-5-methyl-N-{1-[(4-methylpiperidin-1-yl)carbonyl]-3-(2-nitro-1H-imidazol-1-yl)propyl}benzenesulfonamide |

| Example | Structure | Name |
|---|---|---|
| 228 | 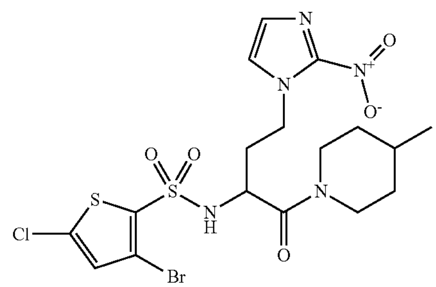 [SMILES: CC1CCN(C(=O)C(CCn2ccnc2[N+](=O)[O-])NS(=O)(=O)c2sc(Cl)cc2Br)CC1] | 3-bromo-5-chloro-N-{1-[(4-methylpiperidin-1-yl)carbonyl]-3-(2-nitro-1H-imidazol-1-yl)propyl}thiophene-2-sulfonamide |
| 229 | 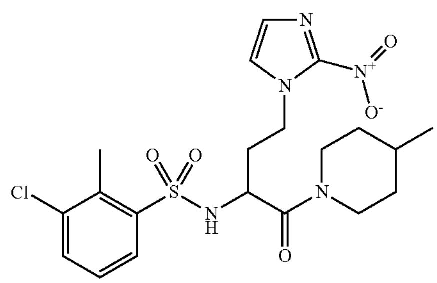 [SMILES: Cc1c(Cl)cccc1S(=O)(=O)NC(CCn1ccnc1[N+](=O)[O-])C(=O)N1CCC(C)CC1] | 3-chloro-2-methyl-N-{1-[(4-methylpiperidin-1-yl)carbonyl]-3-(2-nitro-1H-imidazol-1-yl)propyl}benzenesulfonamide |
| 230 | 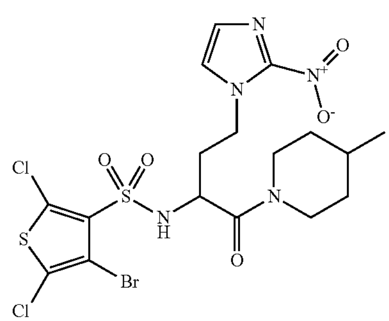 [SMILES: CC1CCN(C(=O)C(CCn2ccnc2[N+](=O)[O-])NS(=O)(=O)c2c(Cl)sc(Cl)c2Br)CC1] | 4-bromo-2,5-dichloro-N-{1-[(4-methylpiperidin-1-yl)carbonyl]-3-(2-nitro-1H-imidazol-1-yl)propyl}thiophene-3-sulfonamide |
| 231 | 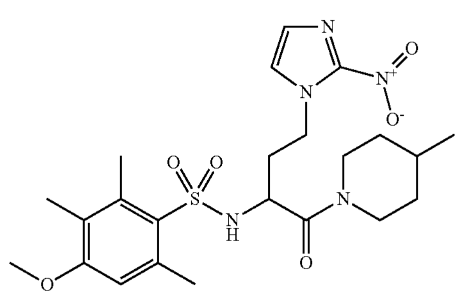 | 4-methoxy-2,3,6-trimethyl-N-{1-[(4-methylpiperidin-1-yl)carbonyl]-3-(2-nitro-1H-imidazol-1-yl)propyl}benzenesulfonamide |
| 232 | 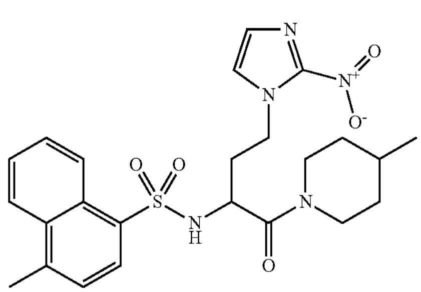 [SMILES: Cc1ccc(S(=O)(=O)NC(CCn2ccnc2[N+](=O)[O-])C(=O)N2CCC(C)CC2)c2ccccc12] | 4-methyl-N-{1-[(4-methylpiperidin-1-yl)carbonyl]-3-(2-nitro-1H-imidazol-1-yl)propyl}naphthalene-1-sulfonamide |

| Example | Structure | Name |
| --- | --- | --- |
| 234 | 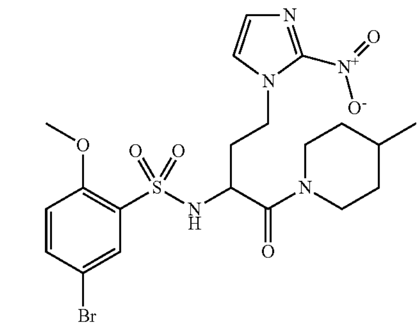 [SMILES: COc1ccc(Br)cc1S(=O)(=O)NC(CCn1ccnc1[N+](=O)[O-])C(=O)N1CCC(C)CC1] | 5-bromo-2-methoxy-N-{1-[(4-methylpiperidin-1-yl)carbonyl]-3-(2-nitro-1H-imidazol-1-yl)propyl}benzenesulfonamide |
| 235 | 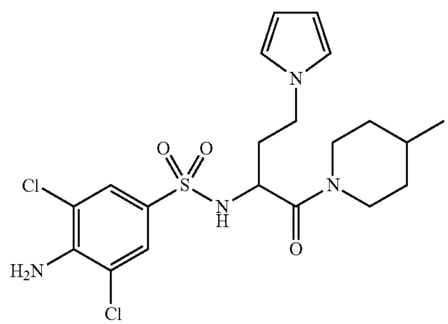 [SMILES: CC1CCN(C(=O)C(CCn2cccc2)NS(=O)(=O)c2cc(Cl)c(N)c(Cl)c2)CC1] | 4-amino-3,5-dichloro-N-{1-[(4-methylpiperidin-1-yl)carbonyl]-3-(1H-pyrrol-1-yl)propyl}benzenesulfonamide |
| 236 | 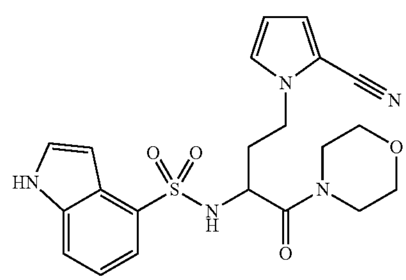 [SMILES: N#Cc1cccn1CCC(NS(=O)(=O)c1cccc2[nH]ccc12)C(=O)N1CCOCC1] | N-[3-(2-cyano-1H-pyrrol-1-yl)-1-(morpholin-4-ylcarbonyl)propyl]-1H-indole-4-sulfonamide |
| 237 | 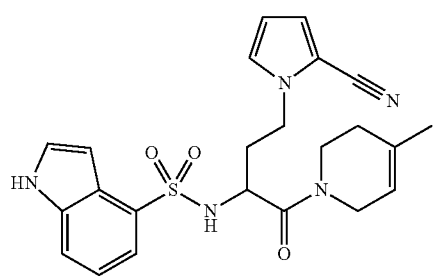 [SMILES: CC1=CCN(C(=O)C(CCn2cccc2C#N)NS(=O)(=O)c2cccc3[nH]ccc23)CC1] | N-{3-(2-cyano-1H-pyrrol-1-yl)-1-[(4-methyl-3,6-dihydropyridin-1(2H)-yl)carbonyl]propyl}-1H-indole-4-sulfonamide |
| 238 | 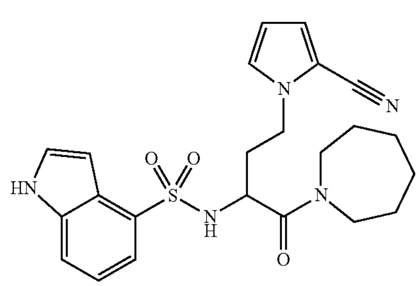 [SMILES: N#Cc1cccn1CCC(NS(=O)(=O)c1cccc2[nH]ccc12)C(=O)N1CCCCCC1] | N-[1-(azepan-1-ylcarbonyl)-3-(2-cyano-1H-pyrrol-1-yl)propyl]-1H-indole-4-sulfonamide |

| Example | Structure | Name |
|---|---|---|
| 239 | 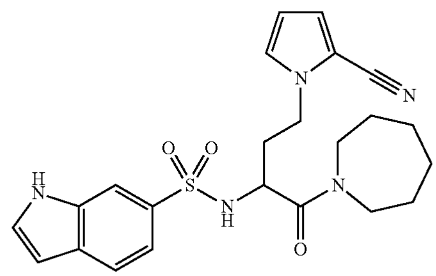 [SMILES: N#Cc1cccn1CCC(NS(=O)(=O)c1ccc2cc[nH]c2c1)C(=O)N1CCCCCC1] | N-[1-(azepan-1-ylcarbonyl)-3-(2-cyano-1H-pyrrol-1-yl)propyl]-1H-indole-6-sulfonamide |
| 241 | 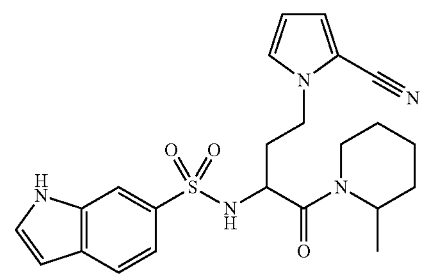 [SMILES: CC1CCCCN1C(=O)C(CCn1cccc1C#N)NS(=O)(=O)c1ccc2cc[nH]c2c1] | N-{3-(2-cyano-1H-pyrrol-1-yl)-1-[(2-methylpiperidin-1-yl)carbonyl]propyl}-1H-indole-6-sulfonamide |
| 242 | 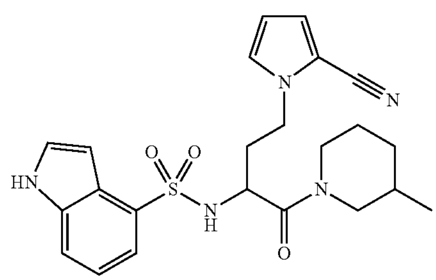 [SMILES: CC1CCCN(C(=O)C(CCn2cccc2C#N)NS(=O)(=O)c2cccc3[nH]ccc23)C1] | N-{3-(2-cyano-1H-pyrrol-1-yl)-1-[(3-methylpiperidin-1-yl)carbonyl]propyl}-1H-indole-4-sulfonamide |
| 243 | 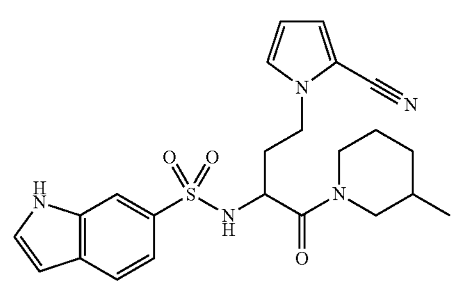 [SMILES: CC1CCCN(C(=O)C(CCn2cccc2C#N)NS(=O)(=O)c2ccc3cc[nH]c3c2)C1] | N-{3-(2-cyano-1H-pyrrol-1-yl)-1-[(3-methylpiperidin-1-yl)carbonyl]propyl}-1H-indole-6-sulfonamide |
| 244 | 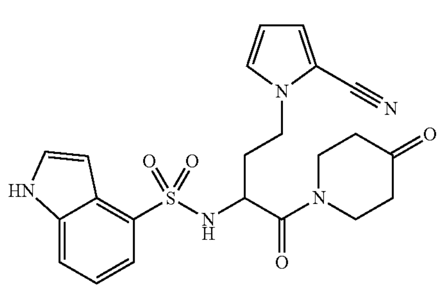 [SMILES: N#Cc1cccn1CCC(NS(=O)(=O)c1cccc2[nH]ccc12)C(=O)N1CCC(=O)CC1] | N-{3-(2-cyano-1H-pyrrol-1-yl)-1-[(4-oxopiperidin-1-yl)carbonyl]propyl}-1H-indole-4-sulfonamide |

| Example | Structure | Name |
|---|---|---|
| 245 | 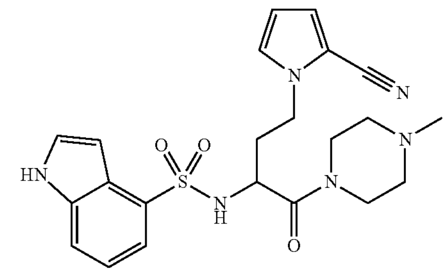 [SMILES: CN1CCN(C(=O)C(CCn2cccc2C#N)NS(=O)(=O)c2cccc3[nH]ccc23)CC1] | N-{3-(2-cyano-1H-pyrrol-1-yl)-1-[(4-methylpiperazin-1-yl)carbonyl]propyl}-1H-indole-4-sulfonamide |
| 246 | 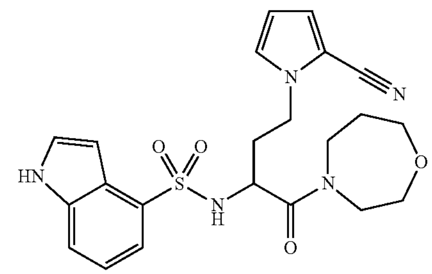 [SMILES: N#Cc1cccn1CCC(NS(=O)(=O)c1cccc2[nH]ccc12)C(=O)N1CCCOCC1] | N-[3-(2-cyano-1H-pyrrol-1-yl)-1-(1,4-oxazepan-4-ylcarbonyl)propyl]-1H-indole-4-sulfonamide |
| 247 | 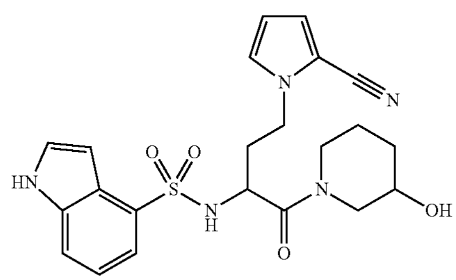 [SMILES: N#Cc1cccn1CCC(NS(=O)(=O)c1cccc2[nH]ccc12)C(=O)N1CCCC(O)C1] | N-{3-(2-cyano-1H-pyrrol-1-yl)-1-[(3-hydroxypiperidin-1-yl)carbonyl]propyl}-1H-indole-4-sulfonamide |
| 248 | 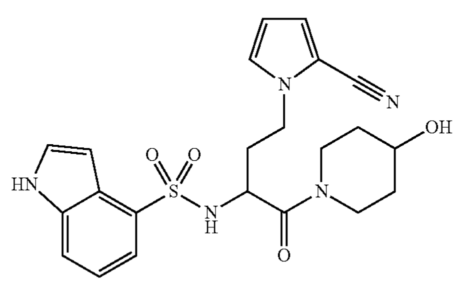 [SMILES: N#Cc1cccn1CCC(NS(=O)(=O)c1cccc2[nH]ccc12)C(=O)N1CCC(O)CC1] | N-{3-(2-cyano-1H-pyrrol-1-yl)-1-[(4-hydroxypiperidin-1-yl)carbonyl]propyl}-1H-indole-4-sulfonamide |
| 249 | 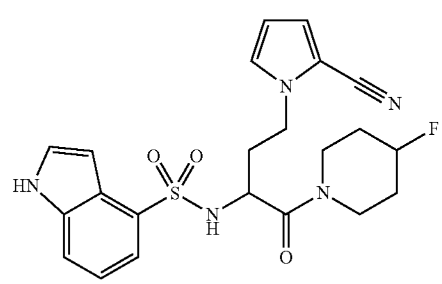 [SMILES: N#Cc1cccn1CCC(NS(=O)(=O)c1cccc2[nH]ccc12)C(=O)N1CCC(F)CC1] | N-{3-(2-cyano-1H-pyrrol-1-yl)-1-[(4-fluoropiperidin-1-yl)carbonyl]propyl}-1H-indole-4-sulfonamide |

| Example | Structure | Name |
|---|---|---|
| 250 | 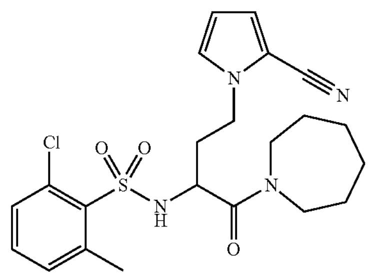 [SMILES: Cc1cccc(Cl)c1S(=O)(=O)NC(CCn1cccc1C#N)C(=O)N1CCCCCC1] | N-[1-(azepan-1-ylcarbonyl)-3-(2-cyano-1H-pyrrol-1-yl)propyl]-2-chloro-6-methylbenzenesulfonamide |
| 251 | 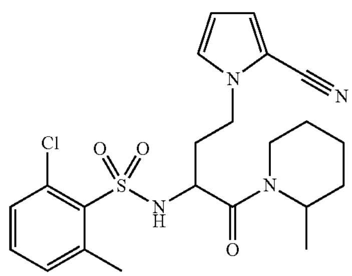 [SMILES: Cc1cccc(Cl)c1S(=O)(=O)NC(CCn1cccc1C#N)C(=O)N1CCCCC1C] | 2-chloro-N-{3-(2-cyano-1H-pyrrol-1-yl)-1-[(2-methylpiperidin-1-yl)carbonyl]propyl}-6-methylbenzenesulfonamide |
| 252 | 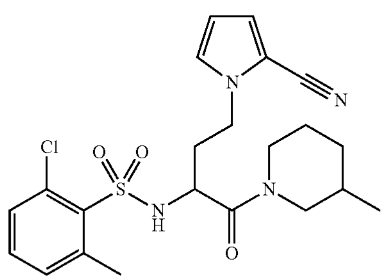 [SMILES: Cc1cccc(Cl)c1S(=O)(=O)NC(CCn1cccc1C#N)C(=O)N1CCCC(C)C1] | 2-chloro-N-{3-(2-cyano-1H-pyrrol-1-yl)-1-[(3-methylpiperidin-1-yl)carbonyl]propyl}-6-methylbenzenesulfonamide |
| 253 | 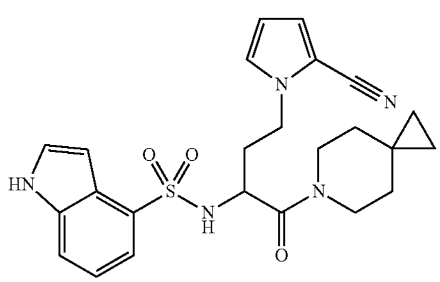 [SMILES: N#Cc1cccn1CCC(NS(=O)(=O)c1cccc2[nH]ccc12)C(=O)N1CCC2(CC1)CC2] | N-[1-(6-azaspiro[2.5]oct-6-ylcarbonyl)-3-(2-cyano-1H-pyrrol-1-yl)propyl]-1H-indole-4-sulfonamide |
| 254 | 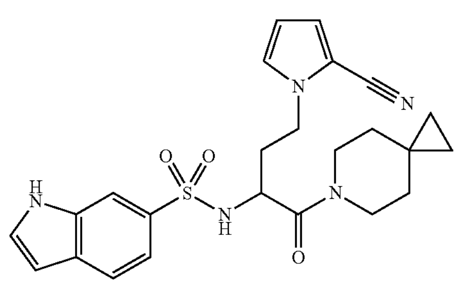 [SMILES: N#Cc1cccn1CCC(NS(=O)(=O)c1ccc2cc[nH]c2c1)C(=O)N1CCC2(CC1)CC2] | N-[1-(6-azaspiro[2.5]oct-6-ylcarbonyl)-3-(2-cyano-1H-pyrrol-1-yl)propyl]-1H-indole-6-sulfonamide |

| Example | Structure | Name |
|---|---|---|
| 255 | 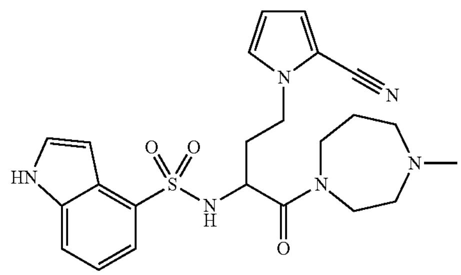 [SMILES: CN1CCCN(C(=O)C(CCn2cccc2C#N)NS(=O)(=O)c2cccc3[nH]ccc23)CC1] | N-{3-(2-cyano-1H-pyrrol-1-yl)-1-[(4-methyl-1,4-diazepan-1-yl)carbonyl]propyl}-1H-indole-4-sulfonamide |
| 256 | 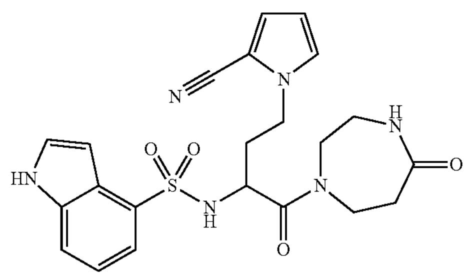 [SMILES: N#Cc1cccn1CCC(NS(=O)(=O)c1cccc2[nH]ccc12)C(=O)N1CCNC(=O)CC1] | N-{3-(2-cyano-1H-pyrrol-1-yl)-1-[(5-oxo-1,4-diazepan-1-yl)carbonyl]propyl}-1H-indole-4-sulfonamide |
| 257 | 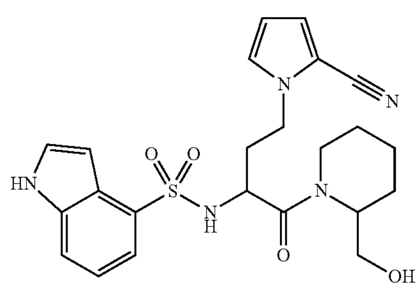 [SMILES: N#Cc1cccn1CCC(NS(=O)(=O)c1cccc2[nH]ccc12)C(=O)N1CCCCC1CO] | N-[3-(2-cyano-1H-pyrrol-1-yl)-1-{[2-(hydroxymethyl)piperidin-1-yl]carbonyl}propyl]-1H-indole-4-sulfonamide |
| 258 | 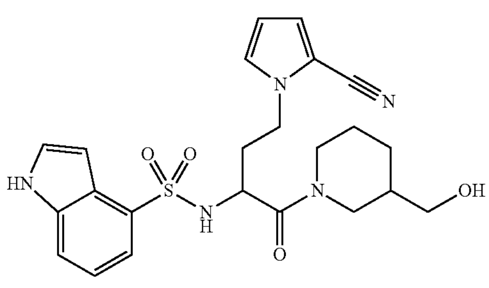 [SMILES: N#Cc1cccn1CCC(NS(=O)(=O)c1cccc2[nH]ccc12)C(=O)N1CCCC(CO)C1] | N-[3-(2-cyano-1H-pyrrol-1-yl)-1-{[3-(hydroxymethyl)piperidin-1-yl]carbonyl}propyl]-1H-indole-4-sulfonamide |
| 259 | 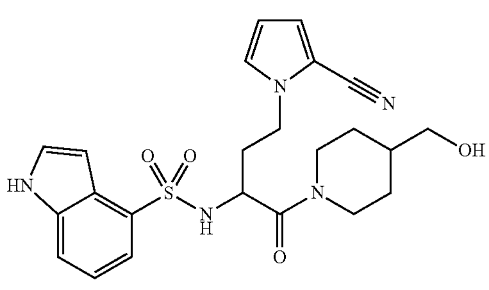 | N-[3-(2-cyano-1H-pyrrol-1-yl)-1-{[4-(hydroxymethyl)piperidin-1-yl]carbonyl}propyl]-1H-indole-4-sulfonamide |

| Example | Structure | Name |
|---|---|---|
| 261 | 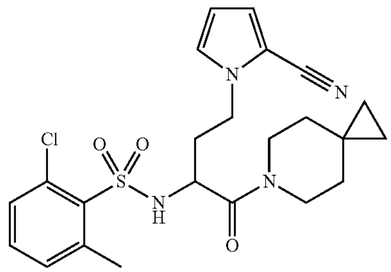 [SMILES: Cc1cccc(Cl)c1S(=O)(=O)NC(CCn1cccc1C#N)C(=O)N1CCC2(CC1)CC2] | N-[1-(6-azaspiro[2.5]oct-6-ylcarbonyl)-3-(2-cyano-1H-pyrrol-1-yl)propyl]-2-chloro-6-methylbenzenesulfonamide |
| 262 | | N-{3-(2-cyano-1H-pyrrol-1-yl)-1-[(4-propylpiperidin-1-yl)carbonyl]propyl}-1H-indole-4-sulfonamide |
| 262 | | 2-{[(2-chloro-6-methylphenyl)sulfonyl]amino}-4-(2-cyano-1H-pyrrol-1-yl)-N-cyclohexyl-N-methylbutanamide |
| 264 | 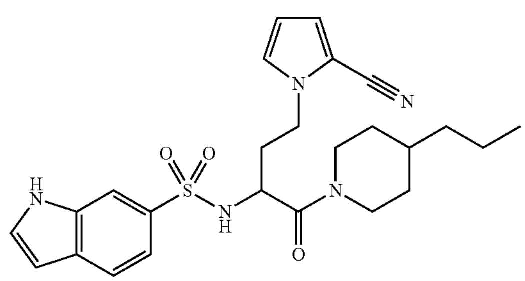 [SMILES: CCCC1CCN(C(=O)C(CCn2cccc2C#N)NS(=O)(=O)c2ccc3cc[nH]c3c2)CC1] | N-{3-(2-cyano-1H-pyrrol-1-yl)-1-[(4-propylpiperidin-1-yl)carbonyl]propyl}-1H-indole-6-sulfonamide |
| 265 | 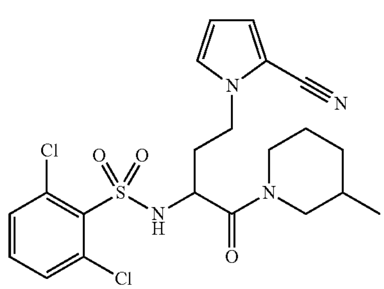 [SMILES: CC1CCCN(C(=O)C(CCn2cccc2C#N)NS(=O)(=O)c2c(Cl)cccc2Cl)C1] | 2,6-dichloro-N-{3-(2-cyano-1H-pyrrol-1-yl)-1-[(3-methylpiperidin-1-yl)carbonyl]propyl}benzenesulfonamide |

-continued

| Example | Structure | Name |
|---------|-----------|------|
| 266 | 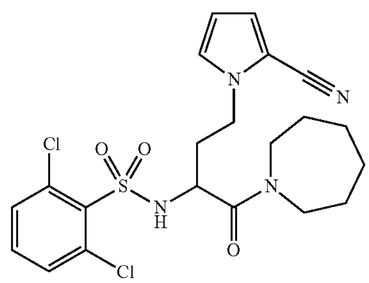 [SMILES: N#Cc1cccn1CCC(NS(=O)(=O)c1c(Cl)cccc1Cl)C(=O)N1CCCCCC1] | N-[1-(azepan-1-ylcarbonyl)-3-(2-cyano-1H-pyrrol-1-yl)propyl]-2,6-dichlorobenzenesulfonamide |
| 267 | 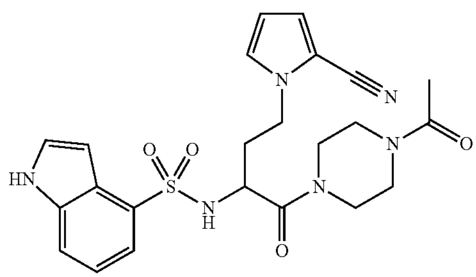 [SMILES: CC(=O)N1CCN(C(=O)C(CCn2cccc2C#N)NS(=O)(=O)c2cccc3[nH]ccc23)CC1] | N-{1-[(4-acetylpiperazin-1-yl)carbonyl]-3-(2-cyano-1H-pyrrol-1-yl)propyl}-1H-indole-4-sulfonamide |
| 268 | 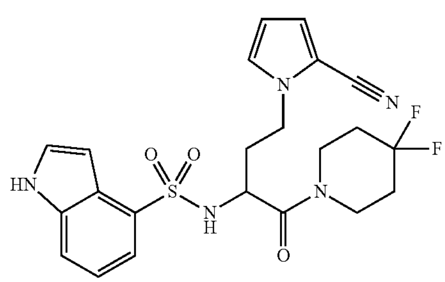 [SMILES: N#Cc1cccn1CCC(NS(=O)(=O)c1cccc2[nH]ccc12)C(=O)N1CCC(F)(F)CC1] | N-{3-(2-cyano-1H-pyrrol-1-yl)-1-[(4,4-difluoropiperidin-1-yl)carbonyl]propyl}-1H-indole-4-sulfonamide |
| 269 | 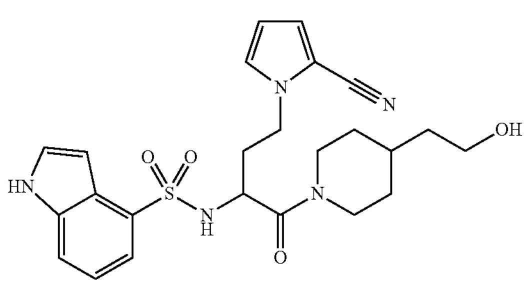 [SMILES: N#Cc1cccn1CCC(NS(=O)(=O)c1cccc2[nH]ccc12)C(=O)N1CCC(CCO)CC1] | N-[3-(2-cyano-1H-pyrrol-1-yl)-1-{[4-(2-hydroxyethyl)piperidin-1-yl]carbonyl}propyl]-1H-indole-4-sulfonamide |
| 270 | 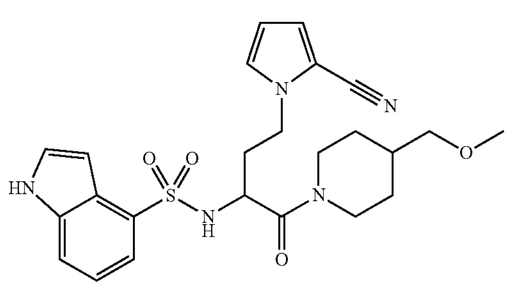 [SMILES: COCC1CCN(C(=O)C(CCn2cccc2C#N)NS(=O)(=O)c2cccc3[nH]ccc23)CC1] | N-[3-(2-cyano-1H-pyrrol-1-yl)-1-{[4-(methoxymethyl)piperidin-1-yl]carbonyl}propyl]-1H-indole-4-sulfonamide |

| Example | Structure | Name |
|---|---|---|
| 271 | 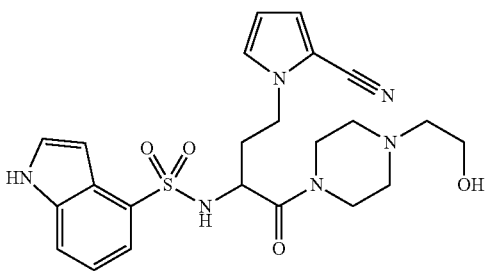 [SMILES: N#Cc1cccn1CCC(NS(=O)(=O)c1cccc2[nH]ccc12)C(=O)N1CCN(CCO)CC1] | N-[3-(2-cyano-1H-pyrrol-1-yl)-1-{[4-(2-hydroxyethyl)piperazin-1-yl]carbonyl}propyl]-1H-indole-4-sulfonamide |
| 272 | 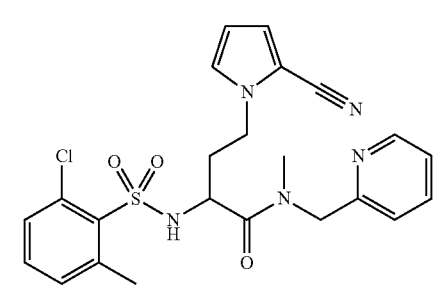 [SMILES: Cc1cccc(Cl)c1S(=O)(=O)NC(CCn1cccc1C#N)C(=O)N(C)Cc1ccccn1] | 2-{[(2-chloro-6-methylphenyl)sulfonyl]amino}-4-(2-cyano-1H-pyrrol-1-yl)-N-methyl-N-(pyridin-2-ylmethyl)butanamide |
| 273 | 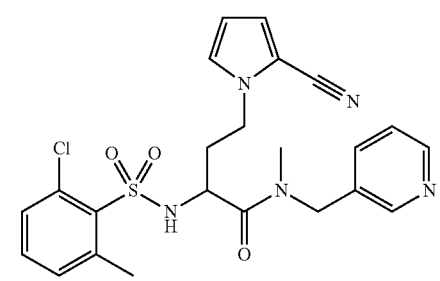 [SMILES: Cc1cccc(Cl)c1S(=O)(=O)NC(CCn1cccc1C#N)C(=O)N(C)Cc1cccnc1] | 2-{[(2-chloro-6-methylphenyl)sulfonyl]amino}-4-(2-cyano-1H-pyrrol-1-yl)-N-methyl-N-(pyridin-3-ylmethyl)butanamide |
| 274 | 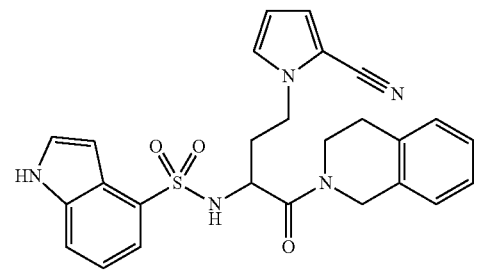 [SMILES: N#Cc1cccn1CCC(NS(=O)(=O)c1cccc2[nH]ccc12)C(=O)N1CCc2ccccc2C1] | N-[3-(2-cyano-1H-pyrrol-1-yl)-1-(3,4-dihydroisoquinolin-2(1H)-ylcarbonyl)propyl]-1H-indole-4-sulfonamide |
| 275 | 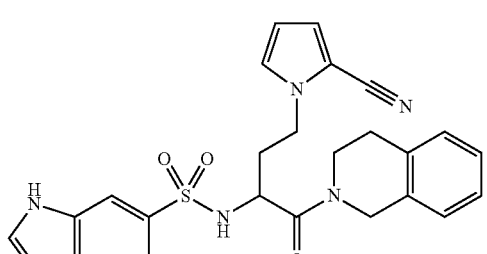 | N-[3-(2-cyano-1H-pyrrol-1-yl)-1-(3,4-dihydroisoquinolin-2(1H)-ylcarbonyl)propyl]-1H-indole-6-sulfonamide |

-continued

| Example | Structure | Name |
|---|---|---|
| 276 | 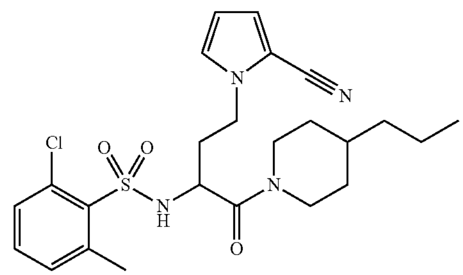 [SMILES: CCCC1CCN(C(=O)C(CCn2cccc2C#N)NS(=O)(=O)c2c(C)cccc2Cl)CC1] | 2-chloro-N-{3-(2-cyano-1H-pyrrol-1-yl)-1-[(4-propylpiperidin-1-yl)carbonyl]propyl}-6-methylbenzenesulfonamide |
| 277 | 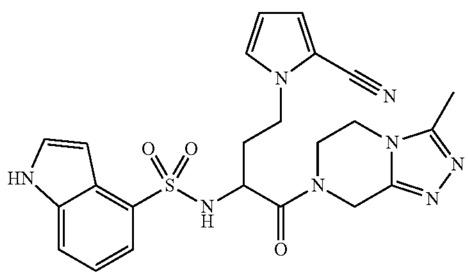 [SMILES: Cc1nnc2n1CCN(C(=O)C(CCn1cccc1C#N)NS(=O)(=O)c1cccc3[nH]ccc13)C2] | N-[3-(2-cyano-1H-pyrrol-1-yl)-1-(3-methyl-5,6-dihydro[1,2,4]triazolo[4,3-a]pyrazin-7(8H)-ylcarbonyl)propyl]-1H-indole-4-sulfonamide |
| 278 | 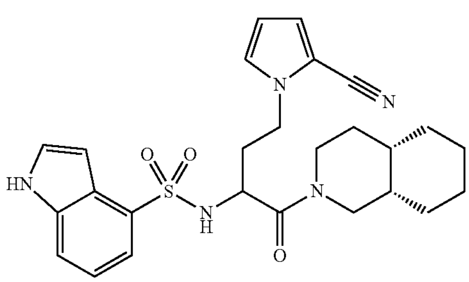 [SMILES: N#Cc1cccn1CCC(NS(=O)(=O)c1cccc2[nH]ccc12)C(=O)N1CC[C@@H]2CCCC[C@@H]2C1] | N-{3-(2-cyano-1H-pyrrol-1-yl)-1-[(cis)-octahydroisoquinolin-2(1H)-ylcarbonyl]propyl}-1H-indole-4-sulfonamide |
| 279 | 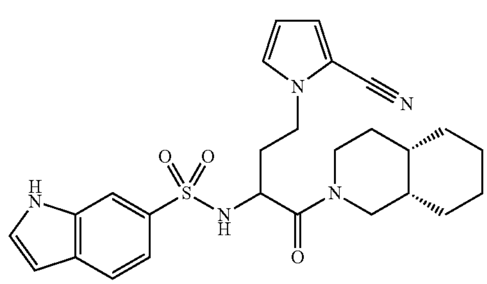 [SMILES: N#Cc1cccn1CCC(NS(=O)(=O)c1ccc2cc[nH]c2c1)C(=O)N1CC[C@@H]2CCCC[C@@H]2C1] | N-{3-(2-cyano-1H-pyrrol-1-yl)-1-[(cis)-octahydroisoquinolin-2(1H)-ylcarbonyl]propyl}-1H-indole-6-sulfonamide |
| 280 | 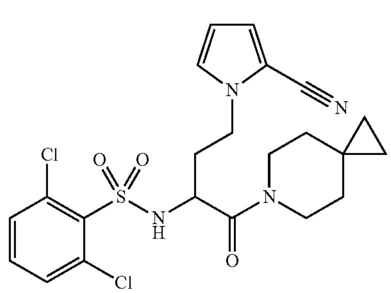 [SMILES: N#Cc1cccn1CCC(NS(=O)(=O)c1c(Cl)cccc1Cl)C(=O)N1CCC2(CC1)CC2] | N-[1-(6-azaspiro[2.5]oct-6-ylcarbonyl)-3-(2-cyano-1H-pyrrol-1-yl)propyl]-2,6-dichlorobenzenesulfonamide |

-continued

| Example | Structure | Name |
|---|---|---|
| 281 | 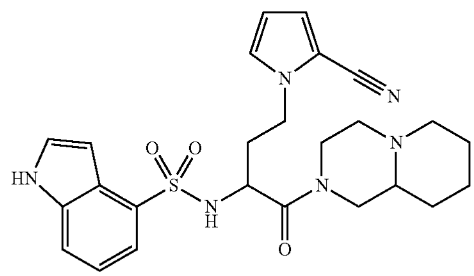 [SMILES: N#Cc1cccn1CCC(NS(=O)(=O)c1cccc2[nH]ccc12)C(=O)N1CCN2CCCCC2C1] | N-[3-(2-cyano-1H-pyrrol-1-yl)-1-(octahydro-2H-pyrido[1,2-a]pyrazin-2-ylcarbonyl)propyl]-1H-indole-4-sulfonamide |
| 282 | 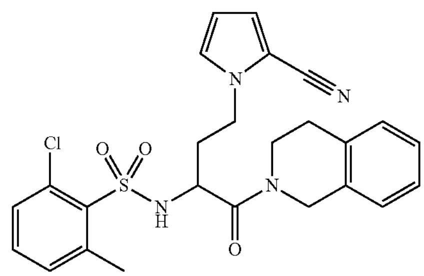 [SMILES: Cc1cccc(Cl)c1S(=O)(=O)NC(CCn1cccc1C#N)C(=O)N1CCc2ccccc2C1] | 2-chloro-N-[3-(2-cyano-1H-pyrrol-1-yl)-1-(3,4-dihydroisoquinolin-2(1H)-ylcarbonyl)propyl]-6-methylbenzenesulfonamide |
| 283 | 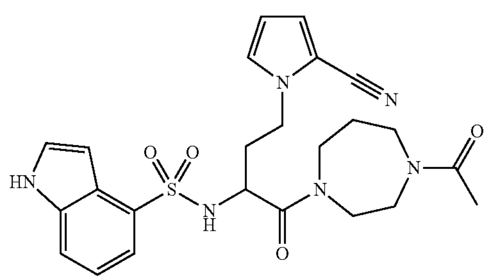 [SMILES: CC(=O)N1CCCN(C(=O)C(CCn2cccc2C#N)NS(=O)(=O)c2cccc3[nH]ccc23)CC1] | N-{1-[(4-acetyl-1,4-diazepan-1-yl)carbonyl]-3-(2-cyano-1H-pyrrol-1-yl)propyl}-1H-indole-4-sulfonamide |
| 284 | 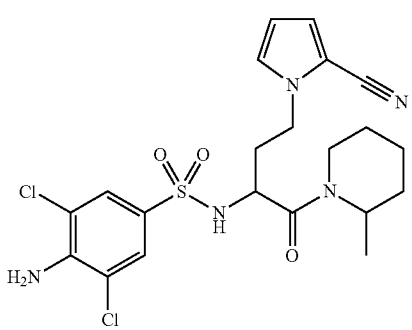 [SMILES: CC1CCCCN1C(=O)C(CCn1cccc1C#N)NS(=O)(=O)c1cc(Cl)c(N)c(Cl)c1] | 4-amino-3,5-dichloro-N-{3-(2-cyano-1H-pyrrol-1-yl)-1-[(2-methylpiperidin-1-yl)carbonyl]propyl}benzenesulfonamide |
| 285 | 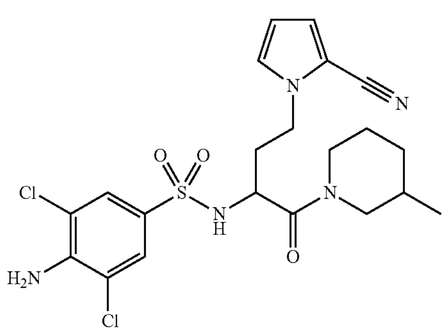 [SMILES: CC1CCCN(C(=O)C(CCn2cccc2C#N)NS(=O)(=O)c2cc(Cl)c(N)c(Cl)c2)C1] | 4-amino-3,5-dichloro-N-{3-(2-cyano-1H-pyrrol-1-yl)-1-[(3-methylpiperidin-1-yl)carbonyl]propyl}benzenesulfonamide |

| Example | Structure | Name |
|---|---|---|
| 286 | 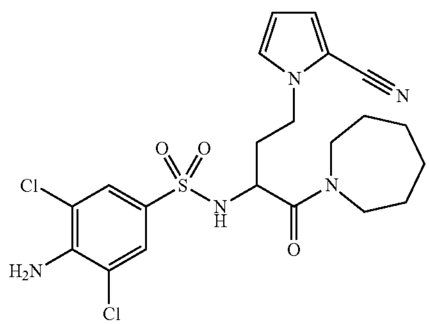 [SMILES: N#Cc1cccn1CCC(NS(=O)(=O)c1cc(Cl)c(N)c(Cl)c1)C(=O)N1CCCCCC1] | 4-amino-N-[1-(azepan-1-ylcarbonyl)-3-(2-cyano-1H-pyrrol-1-yl)propyl]-3,5-dichlorobenzenesulfonamide |
| 287 | 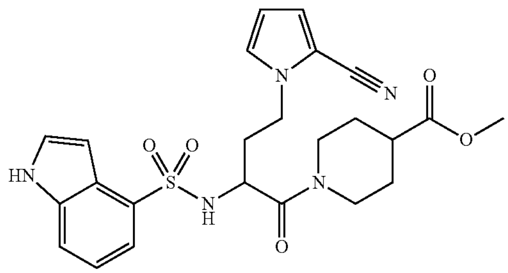 [SMILES: COC(=O)C1CCN(C(=O)C(CCn2cccc2C#N)NS(=O)(=O)c2cccc3[nH]ccc23)CC1] | methyl 1-{4-(2-cyano-1H-pyrrol-1-yl)-2-[(1H-indol-4-ylsulfonyl)amino]butanoyl}piperidine-4-carboxylate |
| 288 | 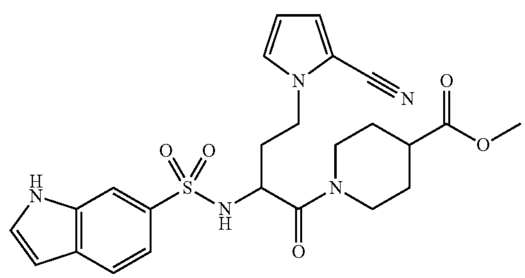 [SMILES: COC(=O)C1CCN(C(=O)C(CCn2cccc2C#N)NS(=O)(=O)c2ccc3cc[nH]c3c2)CC1] | methyl 1-{4-(2-cyano-1H-pyrrol-1-yl)-2-[(1H-indol-6-ylsulfonyl)amino]butanoyl}piperidine-4-carboxylate |
| 289 | 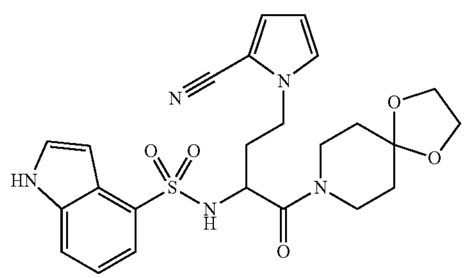 [SMILES: N#Cc1cccn1CCC(NS(=O)(=O)c1cccc2[nH]ccc12)C(=O)N1CCC2(CC1)OCCO2] | N-[3-(2-cyano-1H-pyrrol-1-yl)-1-(1,4-dioxa-8-azaspiro[4.5]dec-8-ylcarbonyl)propyl]-1H-indole-4-sulfonamide |
| 290 | 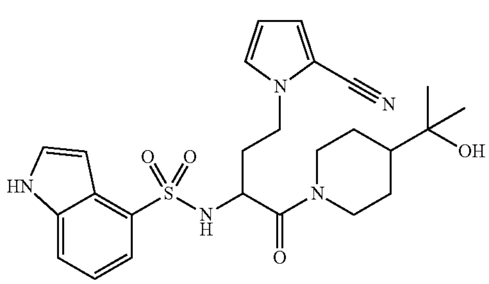 [SMILES: CC(C)(O)C1CCN(C(=O)C(CCn2cccc2C#N)NS(=O)(=O)c2cccc3[nH]ccc23)CC1] | N-[3-(2-cyano-1H-pyrrol-1-yl)-1-{[4-(1-hydroxy-1-methylethyl)piperidin-1-yl]carbonyl}propyl]-1H-indole-4-sulfonamide |

-continued

| Example | Structure | Name |
|---|---|---|
| 291 | 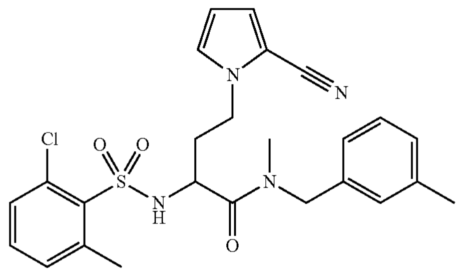 [SMILES: Cc1cccc(CN(C)C(=O)C(CCn2cccc2C#N)NS(=O)(=O)c2c(C)cccc2Cl)c1] | 2-{[(2-chloro-6-methylphenyl)sulfonyl]amino}-4-(2-cyano-1H-pyrrol-1-yl)-N-methyl-N-(3-methylbenzyl)butanamide |
| 292 | 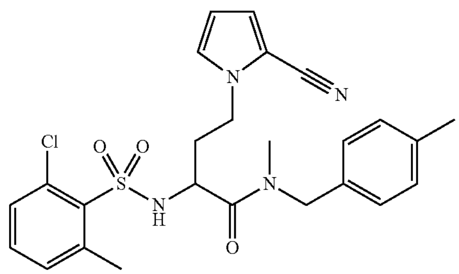 [SMILES: Cc1ccc(CN(C)C(=O)C(CCn2cccc2C#N)NS(=O)(=O)c2c(C)cccc2Cl)cc1] | 2-{[(2-chloro-6-methylphenyl)sulfonyl]amino}-4-(2-cyano-1H-pyrrol-1-yl)-N-methyl-N-(4-methylbenzyl)butanamide |
| 293 | Chiral | 2-{[(2-chloro-6-methylphenyl)sulfonyl]amino}-4-(2-cyano-1H-pyrrol-1-yl)-N-methyl-N-[(1S)-1-phenylethyl]butanamide |
| 294 | 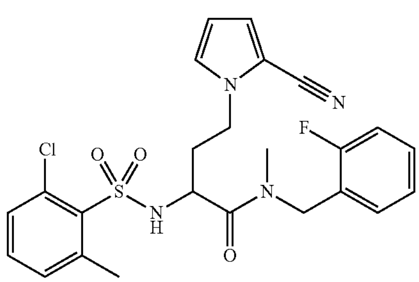 [SMILES: Cc1cccc(Cl)c1S(=O)(=O)NC(CCn1cccc1C#N)C(=O)N(C)Cc1ccccc1F] | 2-{[(2-chloro-6-methylphenyl)sulfonyl]amino}-4-(2-cyano-1H-pyrrol-1-yl)-N-(2-fluorobenzyl)-N-methylbutanamide |
| 295 | 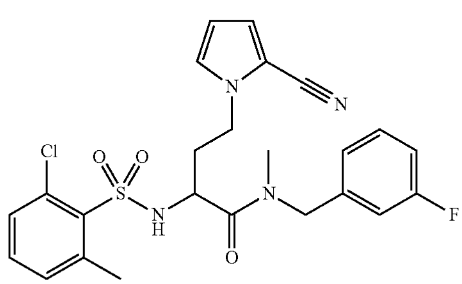 [SMILES: Cc1cccc(Cl)c1S(=O)(=O)NC(CCn1cccc1C#N)C(=O)N(C)Cc1cccc(F)c1] | 2-{[(2-chloro-6-methylphenyl)sulfonyl]amino}-4-(2-cyano-1H-pyrrol-1-yl)-N-(3-fluorobenzyl)-N-methylbutanamide |

-continued

| Example | Structure | Name |
|---|---|---|
| 296 | 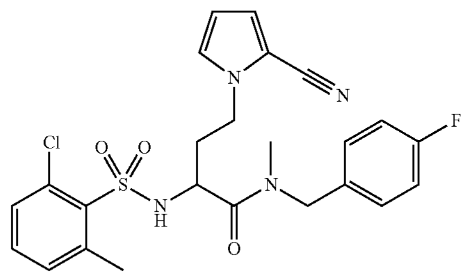 [SMILES: Cc1cccc(Cl)c1S(=O)(=O)NC(CCn1cccc1C#N)C(=O)N(C)Cc1ccc(F)cc1] | 2-{[(2-chloro-6-methylphenyl)sulfonyl]amino}-4-(2-cyano-1H-pyrrol-1-yl)-N-(4-fluorobenzyl)-N-methylbutanamide |
| 297 | 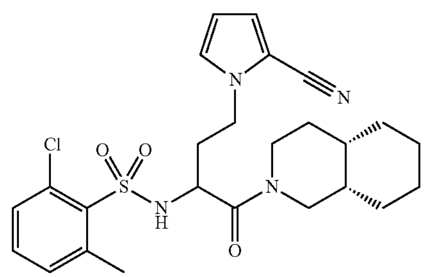 [SMILES: Cc1cccc(Cl)c1S(=O)(=O)NC(CCn1cccc1C#N)C(=O)N1CC[C@@H]2CCCC[C@@H]2C1] | 2-chloro-N-{3-(2-cyano-1H-pyrrol-1-yl)-1-[(cis)-octahydroisoquinolin-2(1H)-ylcarbonyl]propyl}-6-methylbenzenesulfonamide |
| 298 | 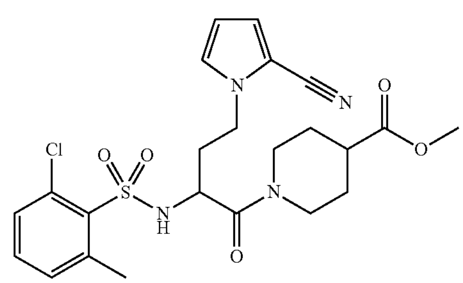 [SMILES: COC(=O)C1CCN(C(=O)C(CCn2cccc2C#N)NS(=O)(=O)c2c(C)cccc2Cl)CC1] | methyl 1-[2-{[(2-chloro-6-methylphenyl)sulfonyl]amino}-4-(2-cyano-1H-pyrrol-1-yl)butanoyl]piperidine-4-carboxylate |
| 299 | 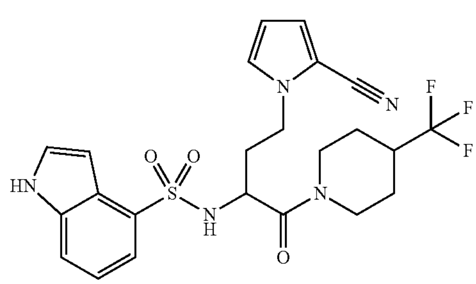 [SMILES: N#Cc1cccn1CCC(NS(=O)(=O)c1cccc2[nH]ccc12)C(=O)N1CCC(C(F)(F)F)CC1] | N-[3-(2-cyano-1H-pyrrol-1-yl)-1-{[4-(trifluoromethyl)piperidin-1-yl]carbonyl}propyl]-1H-indole-4-sulfonamide |
| 300 | 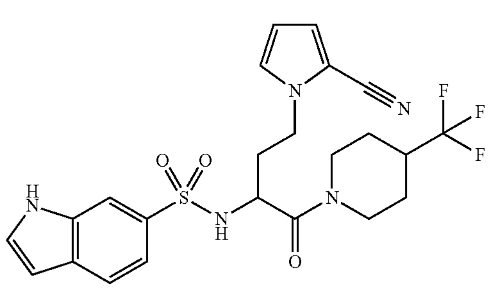 [SMILES: N#Cc1cccn1CCC(NS(=O)(=O)c1ccc2cc[nH]c2c1)C(=O)N1CCC(C(F)(F)F)CC1] | N-[3-(2-cyano-1H-pyrrol-1-yl)-1-{[4-(trifluoromethyl)piperidin-1-yl]carbonyl}propyl]-1H-indole-6-sulfonamide |

-continued

| Example | Structure | Name |
|---|---|---|
| 301 | 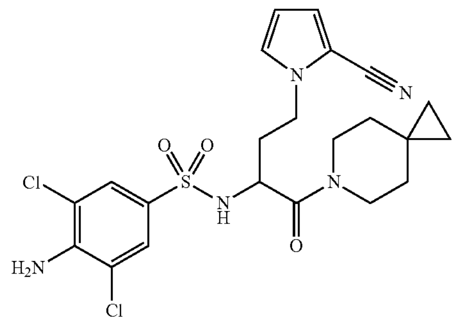 [SMILES: N#Cc1cccn1CCC(NS(=O)(=O)c1cc(Cl)c(N)c(Cl)c1)C(=O)N1CCC2(CC1)CC2] | 4-amino-N-[1-(6-azaspiro[2.5]oct-6-ylcarbonyl)-3-(2-cyano-1H-pyrrol-1-yl)propyl]-3,5-dichlorobenzenesulfonamide |
| 302 | 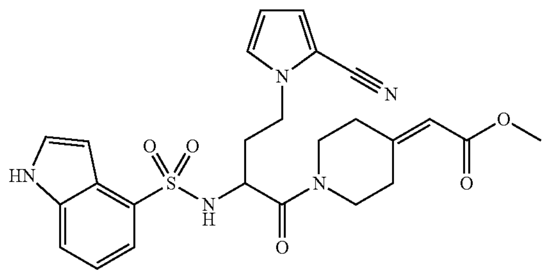 [SMILES: COC(=O)C=C1CCN(C(=O)C(CCn2cccc2C#N)NS(=O)(=O)c2cccc3[nH]ccc23)CC1] | methyl (1-{4-(2-cyano-1H-pyrrol-1-yl)-2-[(1H-indol-4-ylsulfonyl)amino]butanoyl}piperdin-4-ylidene)acetate |
| 303 | 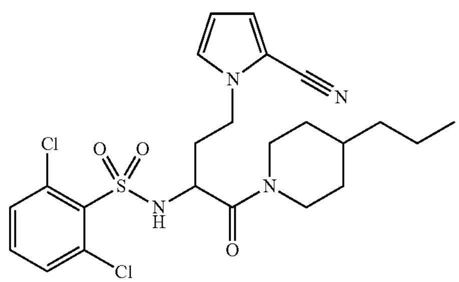 [SMILES: CCCC1CCN(C(=O)C(CCn2cccc2C#N)NS(=O)(=O)c2c(Cl)cccc2Cl)CC1] | 2,6-dichloro-N-{3-(2-cyano-1H-pyrrol-1-yl)-1-[(4-propylpiperidin-1-yl)carbonyl]propyl}benzenesulfonamide |
| 304 | 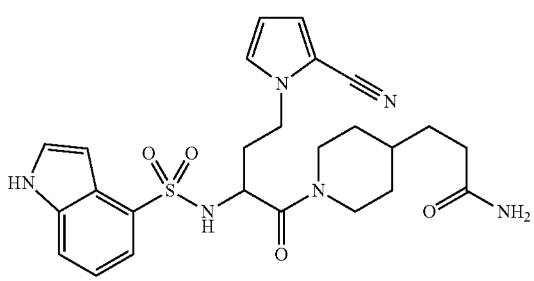 [SMILES: N#Cc1cccn1CCC(NS(=O)(=O)c1cccc2[nH]ccc12)C(=O)N1CCC(CCC(N)=O)CC1] | 3-(1-{4-(2-cyano-1H-pyrrol-1-yl)-2-[(1H-indol-4-ylsulfonyl)amino]butanoyl}piperdin-4-yl)propanamide |
| 305 | 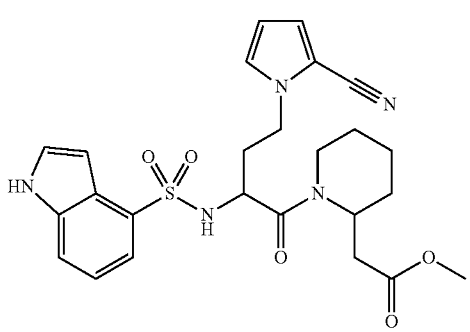 [SMILES: COC(=O)CC1CCCCN1C(=O)C(CCn1cccc1C#N)NS(=O)(=O)c1cccc2[nH]ccc12] | methyl (1-{4-(2-cyano-1H-pyrrol-1-yl)-2-[(1H-indol-4-ylsulfonyl)amino]butanoyl}piperidin-2-yl)acetate |

| Example | Structure | Name |
|---|---|---|
| 306 | 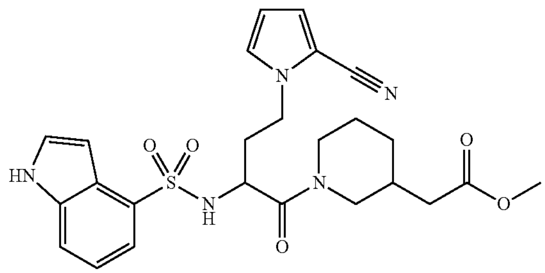 [SMILES: COC(=O)CC1CCCN(C(=O)C(CCn2cccc2C#N)NS(=O)(=O)c2cccc3[nH]ccc23)C1] | methyl (1-{4-(2-cyano-1H-pyrrol-1-yl)-2-[(1H-indol-4-ylsulfonyl)amino]butanoyl}piperidin-3-yl)acetate |
| 307 | 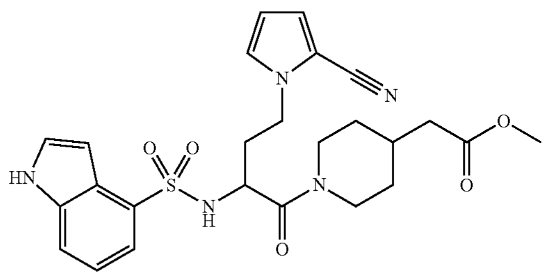 [SMILES: COC(=O)CC1CCN(C(=O)C(CCn2cccc2C#N)NS(=O)(=O)c2cccc3[nH]ccc23)CC1] | methyl (1-{4-(2-cyano-1H-pyrrol-1-yl)-2-[(1H-indol-4-ylsulfonyl)amino]butanoyl}piperidin-4-yl)acetate |
| 308 | 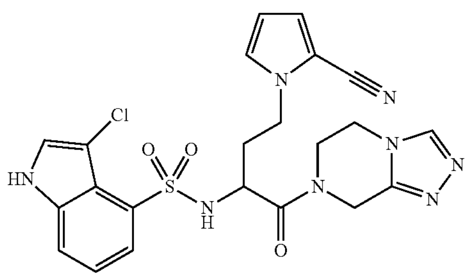 [SMILES: N#Cc1cccn1CCC(NS(=O)(=O)c1cccc2[nH]cc(Cl)c12)C(=O)N1CCn2cnnc2C1] | 3-chloro-N-[3-(2-cyano-1H-pyrrol-1-yl)-1-(5,6-dihydro[1,2,4]triazolo[4,3-a]pyrazin-7(8H)-ylcarbonyl)propyl]-1H-indole-4-sulfonamide |
| 309 | 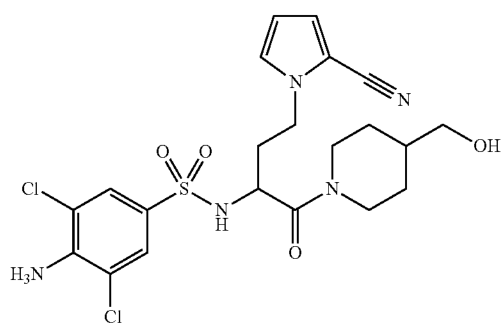 [SMILES: N#Cc1cccn1CCC(NS(=O)(=O)c1cc(Cl)c(N)c(Cl)c1)C(=O)N1CCC(CO)CC1] | 4-amino-3,5-dichloro-N-[3-(2-cyano-1H-pyrrol-1-yl)-1-{[4-(hydroxymethyl)piperidin-1-yl]carbonyl}propyl]benzenesulfonamide |
| 310 | 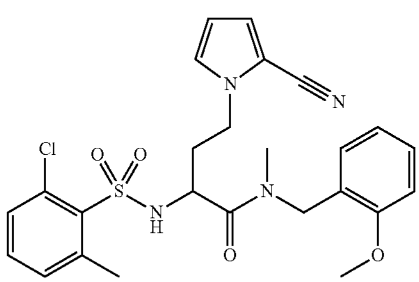 [SMILES: COc1ccccc1CN(C)C(=O)C(CCn1cccc1C#N)NS(=O)(=O)c1c(C)cccc1Cl] | 2-{[(2-chloro-6-methylphenyl)sulfonyl]amino}-4-(2-cyano-1H-pyrrol-1-yl)-N-(2-methoxybenzyl)-N-methylbutanamide |

| Example | Structure | Name |
| --- | --- | --- |
| 311 | 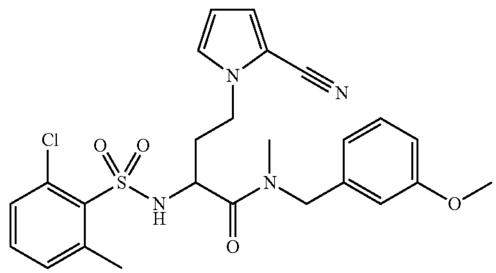 [SMILES: COc1cccc(CN(C)C(=O)C(CCn2cccc2C#N)NS(=O)(=O)c2c(C)cccc2Cl)c1] | 2-{[(2-chloro-6-methylphenyl)sulfonyl]amino}-4-(2-cyano-1H-pyrrol-1-yl)-N-(3-methoxybenzyl)-N-methylbutanamide |
| 312 | 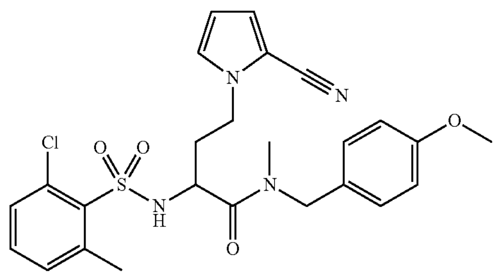 [SMILES: COc1ccc(CN(C)C(=O)C(CCn2cccc2C#N)NS(=O)(=O)c2c(C)cccc2Cl)cc1] | 2-{[(2-chloro-6-methylphenyl)sulfonyl]amino}-4-(2-cyano-1H-pyrrol-1-yl)-N-(4-methoxybenzyl)-N-methylbutanamide |
| 313 | 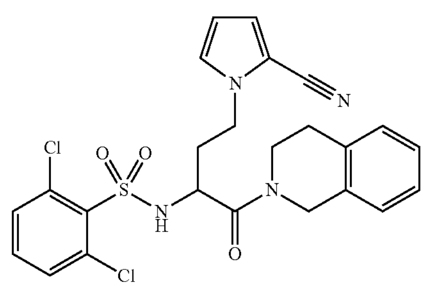 [SMILES: N#Cc1cccn1CCC(NS(=O)(=O)c1c(Cl)cccc1Cl)C(=O)N1CCc2ccccc2C1] | 2,6-dichloro-N-[3-(2-cyano-1H-pyrrol-1-yl)-1-(3,4-dihydroisoquinolin-2(1H)-ylcarbonyl)propyl]benzenesulfonamide |
| 314 | 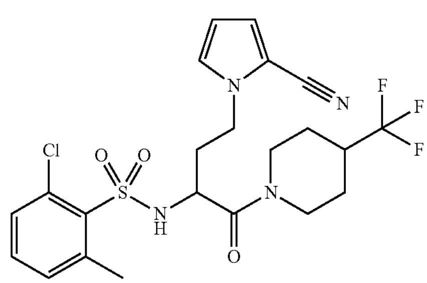 [SMILES: Cc1cccc(Cl)c1S(=O)(=O)NC(CCn1cccc1C#N)C(=O)N1CCC(C(F)(F)F)CC1] | 2-chloro-N-[3-(2-cyano-1H-pyrrol-1-yl)-1-{[4-(trifluoromethyl)piperidin-1-yl]carbonyl}propyl]-6-methylbenzenesulfonamide |
| 315 | 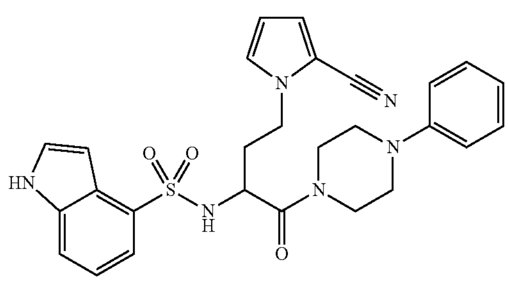 [SMILES: N#Cc1cccn1CCC(NS(=O)(=O)c1cccc2[nH]ccc12)C(=O)N1CCN(c2ccccc2)CC1] | N-{3-(2-cyano-1H-pyrrol-1-yl)-1-[(4-phenylpiperazin-1-yl)carbonyl]propyl}-1H-indole-4-sulfonamide |

| Example | Structure | Name |
|---|---|---|
| 316 | 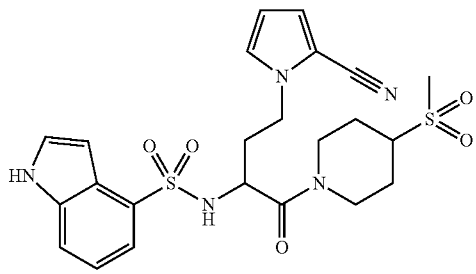 [SMILES: CS(=O)(=O)C1CCN(C(=O)C(CCn2cccc2C#N)NS(=O)(=O)c2cccc3[nH]ccc23)CC1] | N-[3-(2-cyano-1H-pyrrol-1-yl)-1-{[4-(methylsulfonyl)piperidin-1-yl]carbonyl}propyl]-1H-indole-4-sulfonamide |
| 317 | 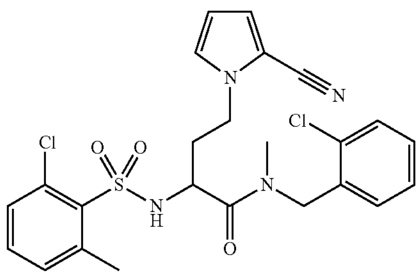 [SMILES: Cc1cccc(Cl)c1S(=O)(=O)NC(CCn1cccc1C#N)C(=O)N(C)Cc1ccccc1Cl] | N-(2-chlorobenzyl)-2-{[(2-chloro-6-methylphenyl)sulfonyl]amino}-4-(2-cyano-1H-pyrrol-1-yl)-N-methylbutanamide |
| 318 | 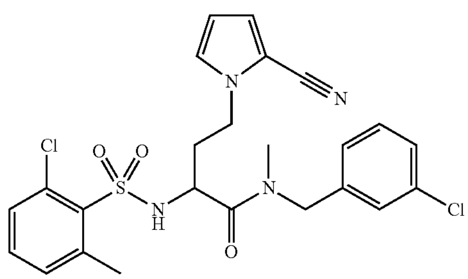 [SMILES: Cc1cccc(Cl)c1S(=O)(=O)NC(CCn1cccc1C#N)C(=O)N(C)Cc1cccc(Cl)c1] | N-(3-chlorobenzyl)-2-{[(2-chloro-6-methylphenyl)sulfonyl]amino}-4-(2-cyano-1H-pyrrol-1-yl)-N-methylbutanamide |
| 319 | 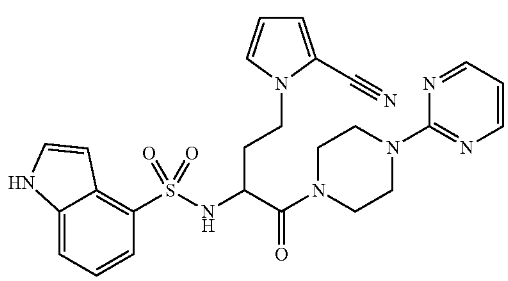 [SMILES: N#Cc1cccn1CCC(NS(=O)(=O)c1cccc2[nH]ccc12)C(=O)N1CCN(c2ncccn2)CC1] | N-{3-(2-cyano-1H-pyrrol-1-yl)-1-[(4-pyrimidin-2-ylpiperazin-1-yl)carbonyl]propyl}-1H-indole-4-sulfonamide |
| 320 | 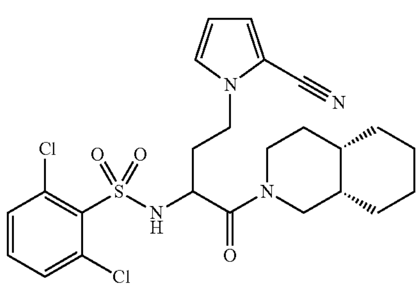 [SMILES: N#Cc1cccn1CCC(NS(=O)(=O)c1c(Cl)cccc1Cl)C(=O)N1CC[C@@H]2CCCC[C@@H]2C1] | 2,6-dichloro-N-{3-(2-cyano-1H-pyrrol-1-yl)-1-[(cis)-octahydroisoquinolin-2(1H)-ylcarbonyl]propyl}benzenesulfonamide |

| Example | Structure | Name |
| --- | --- | --- |
| 321 | 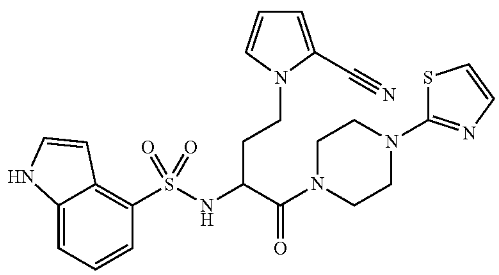 [SMILES: N#Cc1cccn1CCC(NS(=O)(=O)c1cccc2[nH]ccc12)C(=O)N1CCN(c2nccs2)CC1] | N-[3-(2-cyano-1H-pyrrol-1-yl)-1-{[4-(1,3-thiazol-2-yl)piperazin-1-yl]carbonyl}propyl]-1H-indole-4-sulfonamide |
| 322 | 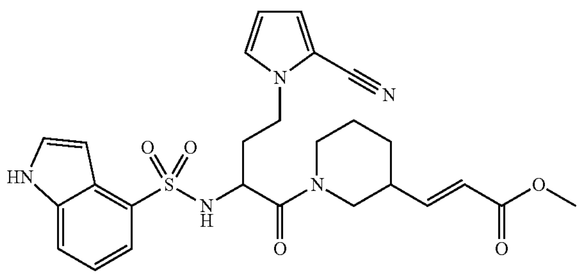 [SMILES: COC(=O)/C=C/C1CCCN(C(=O)C(CCn2cccc2C#N)NS(=O)(=O)c2cccc3[nH]ccc23)C1] | methyl (2E)-3-(1-{4-(2-cyano-1H-pyrrol-1-yl)-2-[(1H-indol-4-ylsulfonyl)amino]butanoyl}piperidin-3-yl)prop-2-enoate |
| 323 | 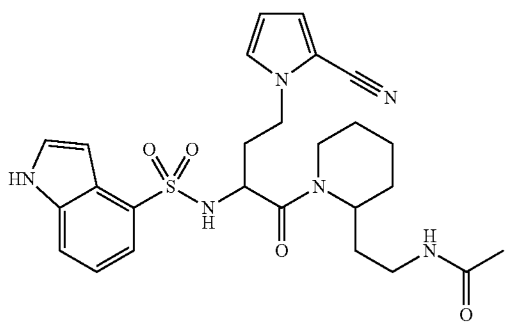 [SMILES: CC(=O)NCCC1CCCCN1C(=O)C(CCn1cccc1C#N)NS(=O)(=O)c1cccc2[nH]ccc12] | N-[2-(1-{4-(2-cyano-1H-pyrrol-1-yl)-2-[(1H-indol-4-ylsulfonyl)amino]butanoyl}piperidin-2-yl)ethyl]acetamide |
| 324 | 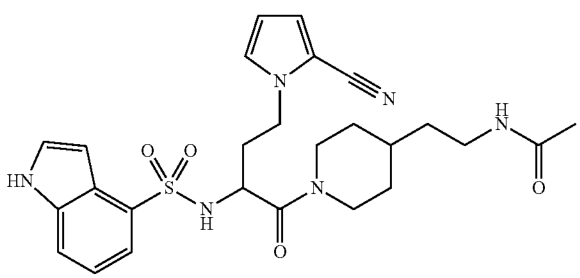 [SMILES: CC(=O)NCCC1CCN(C(=O)C(CCn2cccc2C#N)NS(=O)(=O)c2cccc3[nH]ccc23)CC1] | N-[2-(1-{4-(2-cyano-1H-pyrrol-1-yl)-2-[(1H-indol-4-ylsulfonyl)amino]butanoyl}piperidin-4-yl)ethyl]acetamide |
| 325 | 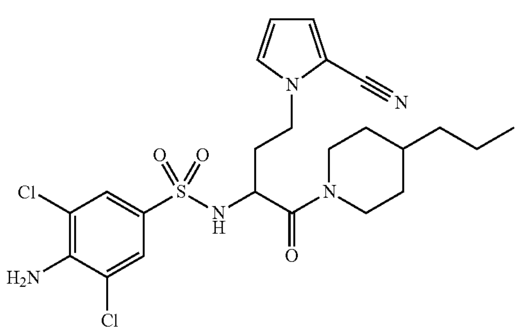 [SMILES: CCCC1CCN(C(=O)C(CCn2cccc2C#N)NS(=O)(=O)c2cc(Cl)c(N)c(Cl)c2)CC1] | 4-amino-3,5-dichloro-N-{3-(2-cyano-1H-pyrrol-1-yl)-1-[(4-propylpiperidin-1-yl)carbonyl]propyl}benzenesulfonamide |

-continued

| Example | Structure | Name |
|---|---|---|
| 326 | 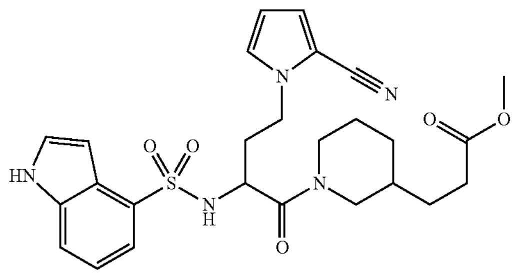 [SMILES: COC(=O)CCC1CCCN(C(=O)C(CCn2cccc2C#N)NS(=O)(=O)c2cccc3[nH]ccc23)C1] | methyl 3-(1-{4-(2-cyano-1H-pyrrol-1-yl)-2-[(1H-indol-4-ylsulfonyl)amino]butanoyl}piperidin-3-yl)propanoate |
| 327 | 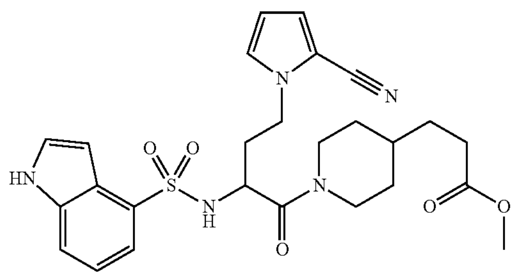 [SMILES: COC(=O)CCC1CCN(C(=O)C(CCn2cccc2C#N)NS(=O)(=O)c2cccc3[nH]ccc23)CC1] | methyl 3-(1-{4-(2-cyano-1H-pyrrol-1-yl)-2-[(1H-indol-4-ylsulfonyl)amino]butanoyl}piperidin-4-yl)propanoate |
| 328 | 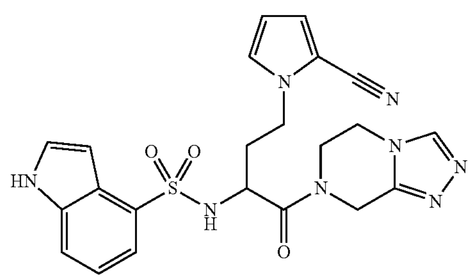 [SMILES: N#Cc1cccn1CCC(NS(=O)(=O)c1cccc2[nH]ccc12)C(=O)N1CCn2cnnc2C1] | N-[3-(2-cyano-1H-pyrrol-1-yl)-1-(5,6-dihydro[1,2,4]triazolo[4,3-a]pyrazin-7(8H)-ylcarbonyl)propyl]-1H-indole-4-sulfonamide |
| 329 | 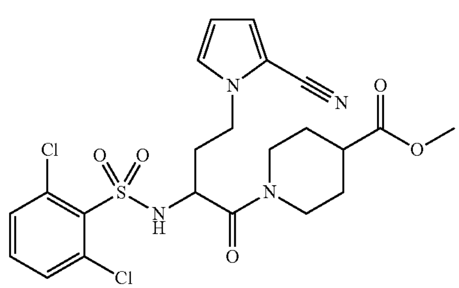 [SMILES: COC(=O)C1CCN(C(=O)C(CCn2cccc2C#N)NS(=O)(=O)c2c(Cl)cccc2Cl)CC1] | methyl 1-[4-(2-cyano-1H-pyrrol-1-yl)-2-{[(2,6-dichlorophenyl)sulfonyl]amino}butanoyl]piperidine-4-carboxylate |
| 330 | 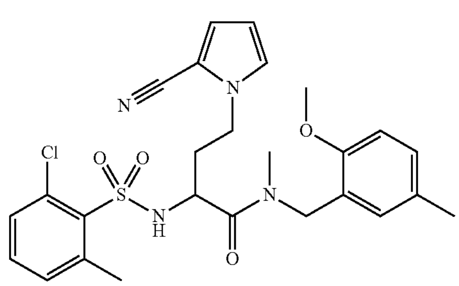 [SMILES: COc1ccc(C)cc1CN(C)C(=O)C(CCn1cccc1C#N)NS(=O)(=O)c1c(C)cccc1Cl] | 2-{[(2-chloro-6-methylphenyl)sulfonyl]amino}-4-(2-cyano-1H-pyrrol-1-yl)-N-(2-methoxy-5-methylbenzyl)-N-methylbutanamide |

-continued

| Example | Structure | Name |
|---|---|---|
| 331 | 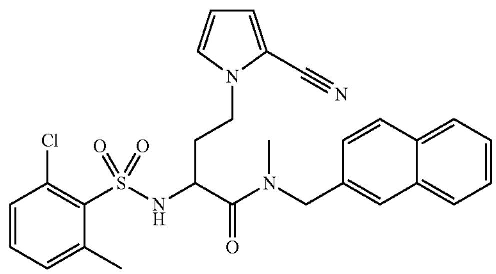 [SMILES: Cc1cccc(Cl)c1S(=O)(=O)NC(CCn1cccc1C#N)C(=O)N(C)Cc1ccc2ccccc2c1] | 2-{[(2-chloro-6-methylphenyl)sulfonyl]amino}-4-(2-cyano-1H-pyrrol-1-yl)-N-methyl-N-(2-naphthylmethyl)butanamide |
| 332 | 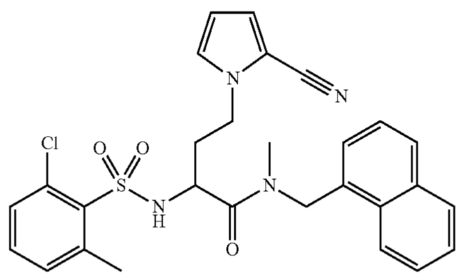 [SMILES: Cc1cccc(Cl)c1S(=O)(=O)NC(CCn1cccc1C#N)C(=O)N(C)Cc1cccc2ccccc12] | 2-{[(2-chloro-6-methylphenyl)sulfonyl]amino}-4-(2-cyano-1H-pyrrol-1-yl)-N-methyl-N-(1-naphthylmethyl)butanamide |
| 333 | 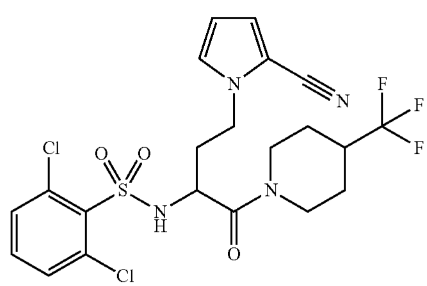 [SMILES: N#Cc1cccn1CCC(NS(=O)(=O)c1c(Cl)cccc1Cl)C(=O)N1CCC(C(F)(F)F)CC1] | 2,6-dichloro-N-[3-(2-cyano-1H-pyrrol-1-yl)-1-{[4-(trifluoromethyl)piperidin-1-yl]carbonyl}propyl]benzenesulfonamide |
| 334 | 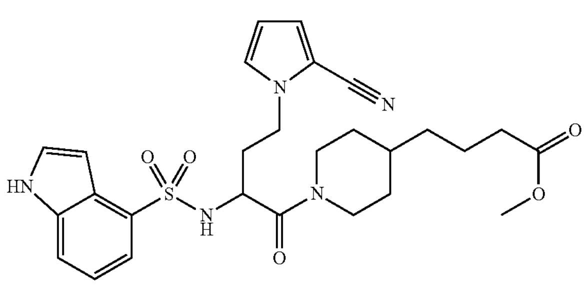 [SMILES: COC(=O)CCCC1CCN(C(=O)C(CCn2cccc2C#N)NS(=O)(=O)c2cccc3[nH]ccc23)CC1] | methyl 4-(1-{4-(2-cyano-1H-pyrrol-1-yl)-2-[(1H-indol-4-ylsulfonyl)amino]butanoyl}piperidin-4-yl)butanoate |
| 335 | 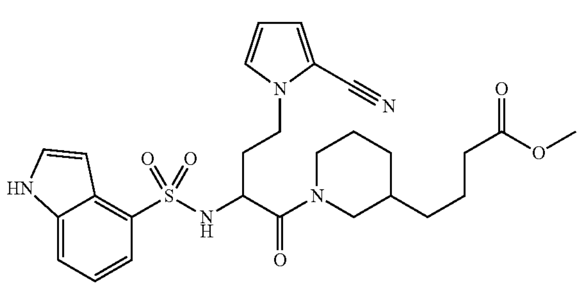 [SMILES: COC(=O)CCCC1CCCN(C(=O)C(CCn2cccc2C#N)NS(=O)(=O)c2cccc3[nH]ccc23)C1] | methyl 4-(1-{4-(2-cyano-1H-pyrrol-1-yl)-2-[(1H-indol-4-ylsulfonyl)amino]butanoyl}piperidin-3-yl)butanoate |

| Example | Structure | Name |
|---|---|---|
| 336 | 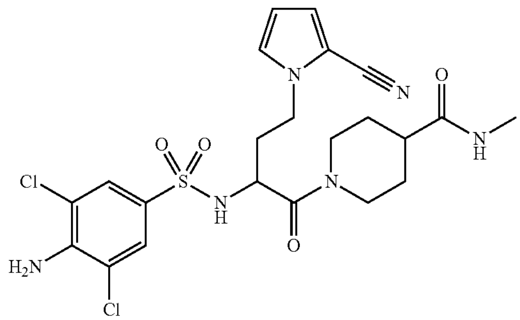 [SMILES: CNC(=O)C1CCN(C(=O)C(CCn2cccc2C#N)NS(=O)(=O)c2cc(Cl)c(N)c(Cl)c2)CC1] | 1-[2-{[(4-amino-3,5-dichlorophenyl)sulfonyl]amino}-4-(2-cyano-1H-pyrrol-1-yl)butanoyl]-N-methylpiperidine-4-carboxamide |
| 337 | 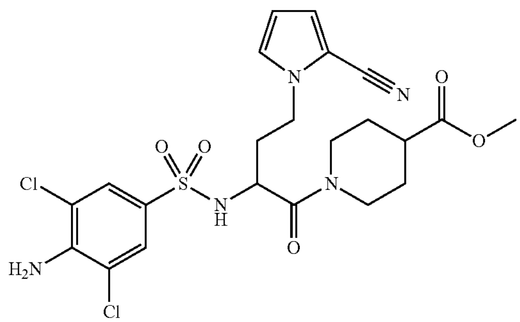 [SMILES: COC(=O)C1CCN(C(=O)C(CCn2cccc2C#N)NS(=O)(=O)c2cc(Cl)c(N)c(Cl)c2)CC1] | methyl 1-[2-{[(4-amino-3,5-dichlorophenyl)sulfonyl]amino}-4-(2-cyano-1H-pyrrol-1-yl)butanoyl]piperidine-4-carboxylate |
| 338 | 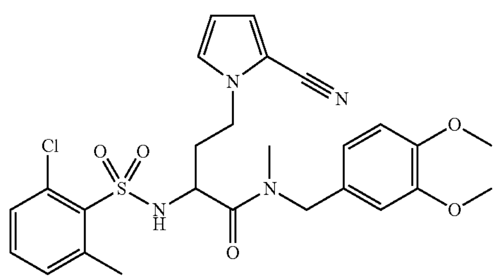 [SMILES: COc1ccc(CN(C)C(=O)C(CCn2cccc2C#N)NS(=O)(=O)c2c(C)cccc2Cl)cc1OC] | 2-{[(2-chloro-6-methylphenyl)sulfonyl]amino}-4-(2-cyano-1H-pyrrol-1-yl)-N-(3,4-dimethoxybenzyl)-N-methylbutanamide |
| 339 | 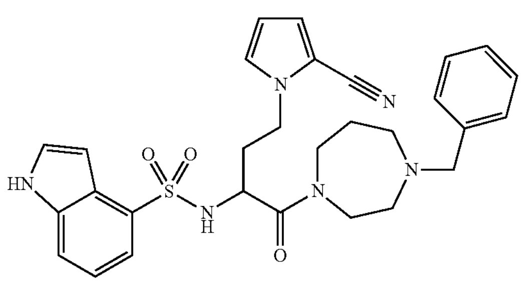 [SMILES: N#Cc1cccn1CCC(NS(=O)(=O)c1cccc2[nH]ccc12)C(=O)N1CCCN(Cc2ccccc2)CC1] | N-{1-[(4-benzyl-1,4-diazepan-1-yl)carbonyl]-3-(2-cyano-1H-pyrrol-1-yl)propyl}-1H-indole-4-sulfonamide |
| 340 | 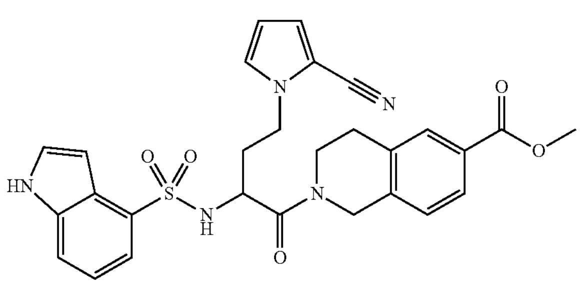 [SMILES: COC(=O)c1ccc2c(c1)CCN(C(=O)C(CCn1cccc1C#N)NS(=O)(=O)c1cccc3[nH]ccc13)C2] | methyl 2-{4-(2-cyano-1H-pyrrol-1-yl)-2-[(1H-indol-4-ylsulfonyl)amino]butanoyl}-1,2,3,4-tetrahydroisoquinoline-6-carboxylate |

-continued

| Example | Structure | Name |
|---|---|---|
| 341 | 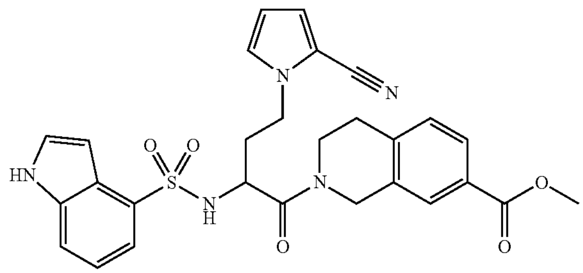 [SMILES: COC(=O)c1ccc2c(c1)CN(C(=O)C(CCn1cccc1C#N)NS(=O)(=O)c1cccc3[nH]ccc13)CC2] | 2-{4-(2-cyano-1H-pyrrol-1-yl)-2-[(1H-indol-4-ylsulfonyl)amino]butanoyl}-1,2,3,4-tetrahydroisoquinoline-7-carboxylic acid methyl ester |
| 342 | 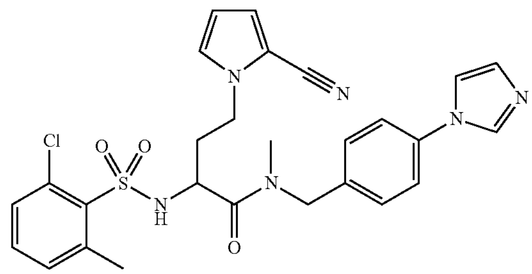 [SMILES: Cc1cccc(Cl)c1S(=O)(=O)NC(CCn1cccc1C#N)C(=O)N(C)Cc1ccc(-n2ccnc2)cc1] | 2-{[(2-chloro-6-methylphenyl)sulfonyl]amino}-4-(2-cyano-1H-pyrrol-1-yl)-N-[4-(1H-imidazol-1-yl)benzyl]-N-methylbutanamide |
| 343 | 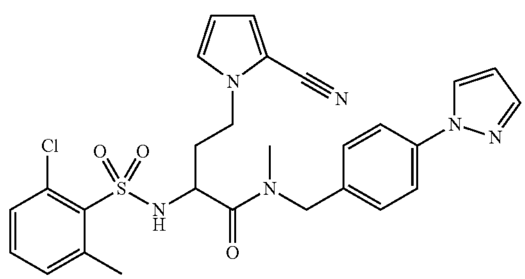 [SMILES: Cc1cccc(Cl)c1S(=O)(=O)NC(CCn1cccc1C#N)C(=O)N(C)Cc1ccc(-n2cccn2)cc1] | 2-{[(2-chloro-6-methylphenyl)sulfonyl]amino}-4-(2-cyano-1H-pyrrol-1-yl)-N-methyl-N-[4-(1H-pyrazol-1-yl)benzyl]butanamide |
| 344 | 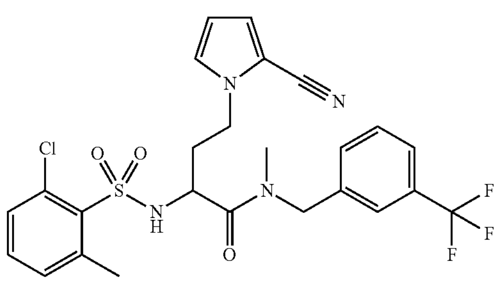 [SMILES: Cc1cccc(Cl)c1S(=O)(=O)NC(CCn1cccc1C#N)C(=O)N(C)Cc1cccc(C(F)(F)F)c1] | 2-{[(2-chloro-6-methylphenyl)sulfonyl]amino}-4-(2-cyano-1H-pyrrol-1-yl)-N-methyl-N-[3-(trifluoromethyl)benzyl]butanamide |
| 345 | 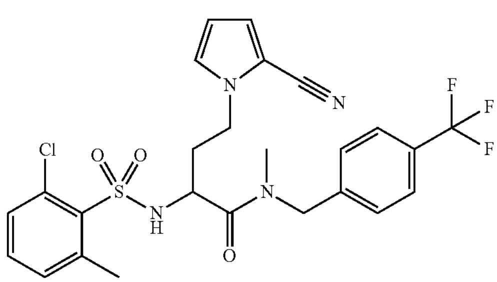 [SMILES: Cc1cccc(Cl)c1S(=O)(=O)NC(CCn1cccc1C#N)C(=O)N(C)Cc1ccc(C(F)(F)F)cc1] | 2-{[(2-chloro-6-methylphenyl)sulfonyl]amino}-4-(2-cyano-1H-pyrrol-1-yl)-N-methyl-N-[4-(trifluoromethyl)benzyl]butanamide |

| Example | Structure | Name |
|---|---|---|
| 346 | 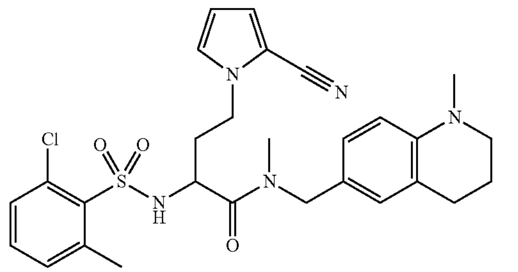 [SMILES: Cc1cccc(Cl)c1S(=O)(=O)NC(CCn1cccc1C#N)C(=O)N(C)Cc1ccc2c(c1)CCCN2C] | 2-{[(2-chloro-6-methylphenyl)sulfonyl]amino}-4-(2-cyano-1H-pyrrol-1-yl)-N-methyl-N-[(1-methyl-1,2,3,4-tetrahydroquinolin-6-yl)methyl]butanamide |
| 347 | 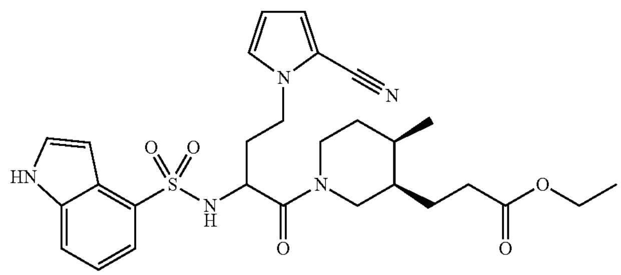 [SMILES: CCOC(=O)CC[C@H]1CN(C(=O)C(CCn2cccc2C#N)NS(=O)(=O)c2cccc3[nH]ccc23)CC[C@H]1C] | 3-[(cis)-1-{4-(2-cyano-1H-pyrrol-1-yl)-2-[(1H-indol-4-ylsulfonyl)amino]butanoyl}-4-methylpiperidin-3-yl]propanoic acid |
| 348 | 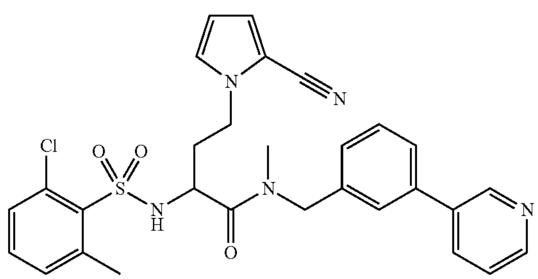 [SMILES: Cc1cccc(Cl)c1S(=O)(=O)NC(CCn1cccc1C#N)C(=O)N(C)Cc1cccc(-c2cccnc2)c1] | 2-{[(2-chloro-6-methylphenyl)sulfonyl]amino}-4-(2-cyano-1H-pyrrol-1-yl)-N-methyl-N-(3-pyridin-3-ylbenzyl)butanamide |
| 349 | 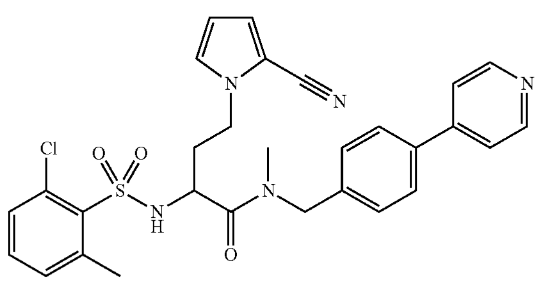 [SMILES: Cc1cccc(Cl)c1S(=O)(=O)NC(CCn1cccc1C#N)C(=O)N(C)Cc1ccc(-c2ccncc2)cc1] | 2-{[(2-chloro-6-methylphenyl)sulfonyl]amino}-4-(2-cyano-1H-pyrrol-1-yl)-N-methyl-N-(4-pyridin-4-ylbenzyl)butanamide |
| 350 | 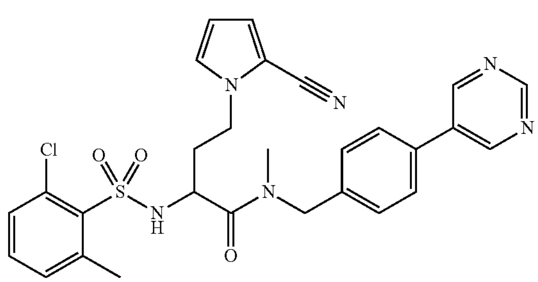 [SMILES: Cc1cccc(Cl)c1S(=O)(=O)NC(CCn1cccc1C#N)C(=O)N(C)Cc1ccc(-c2cncnc2)cc1] | 2-{[(2-chloro-6-methylphenyl)sulfonyl]amino}-4-(2-cyano-1H-pyrrol-1-yl)-N-methyl-N-(4-pyrimidin-5-ylbenzyl)butanamide |

| Example | Structure | Name |
|---|---|---|
| 351 | 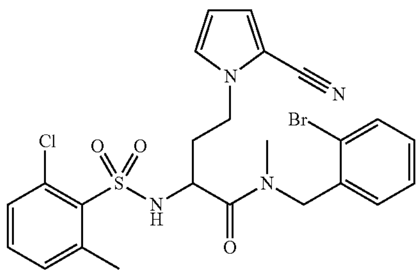 [SMILES: Cc1cccc(Cl)c1S(=O)(=O)NC(CCn1cccc1C#N)C(=O)N(C)Cc1ccccc1Br] | N-(2-bromobenzyl)-2-{[(2-chloro-6-methylphenyl)sulfonyl]amino}-4-(2-cyano-1H-pyrrol-1-yl)-N-methylbutanamide |
| 352 | 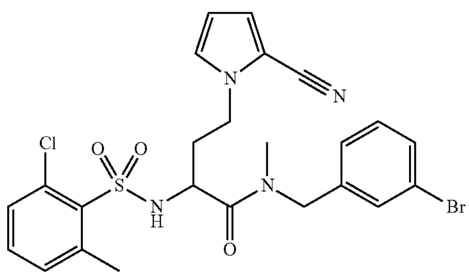 [SMILES: Cc1cccc(Cl)c1S(=O)(=O)NC(CCn1cccc1C#N)C(=O)N(C)Cc1cccc(Br)c1] | N-(3-bromobenzyl)-2-{[(2-chloro-6-methylphenyl)sulfonyl]amino}-4-(2-cyano-1H-pyrrol-1-yl)-N-methylbutanamide |
| 353 | 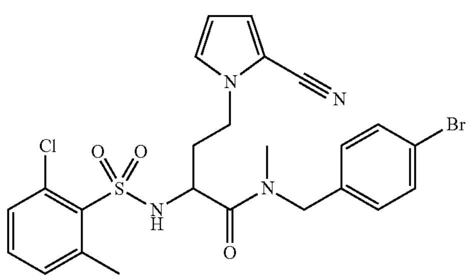 [SMILES: Cc1cccc(Cl)c1S(=O)(=O)NC(CCn1cccc1C#N)C(=O)N(C)Cc1ccc(Br)cc1] | N-(4-bromobenzyl)-2-{[(2-chloro-6-methylphenyl)sulfonyl]amino}-4-(2-cyano-1H-pyrrol-1-yl)-N-methylbutanamide |
| 354 | 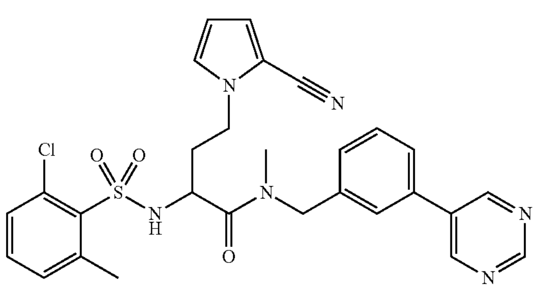 [SMILES: Cc1cccc(Cl)c1S(=O)(=O)NC(CCn1cccc1C#N)C(=O)N(C)Cc1cccc(-c2cncnc2)c1] | 2-{[(2-chloro-6-methylphenyl)sulfonyl]amino}-4-(2-cyano-1H-pyrrol-1-yl)-N-methyl-N-(3-pyrimidin-5-ylbenzyl)butanamide |
| 355 | 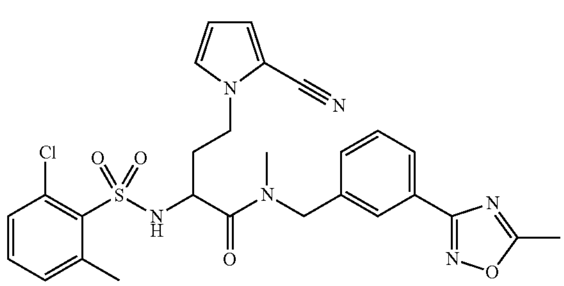 [SMILES: Cc1nc(-c2cccc(CN(C)C(=O)C(CCn3cccc3C#N)NS(=O)(=O)c3c(C)cccc3Cl)c2)no1] | 2-{[(2-chloro-6-methylphenyl)sulfonyl]amino}-4-(2-cyano-1H-pyrrol-1-yl)-N-methyl-N-[3-(5-methyl-1,2,4-oxadiazol-3-yl)benzyl]butanamide |

| Example | Structure | Name |
| --- | --- | --- |
| 356 | 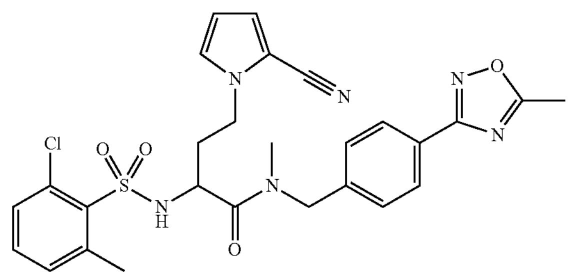 [SMILES: Cc1nc(-c2ccc(CN(C)C(=O)C(CCn3cccc3C#N)NS(=O)(=O)c3c(C)cccc3Cl)cc2)no1] | 2-{[(2-chloro-6-methylphenyl)sulfonyl]amino}-4-(2-cyano-1H-pyrrol-1-yl)-N-methyl-N-[4-(5-methyl-1,2,4-oxadiazol-3-yl)benzyl]butanamide |
| 357 | 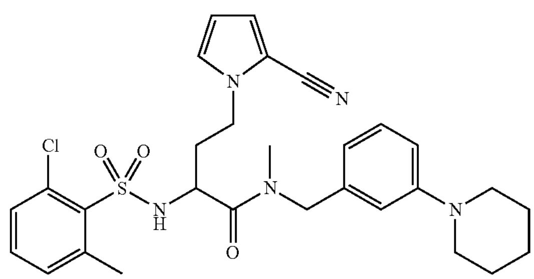 [SMILES: Cc1cccc(Cl)c1S(=O)(=O)NC(CCn1cccc1C#N)C(=O)N(C)Cc1cccc(N2CCCCC2)c1] | 2-{[(2-chloro-6-methylphenyl)sulfonyl]amino}-4-(2-cyano-1H-pyrrol-1-yl)-N-methyl-N-(3-piperidin-1-ylbenzyl)butanamide |
| 358 | 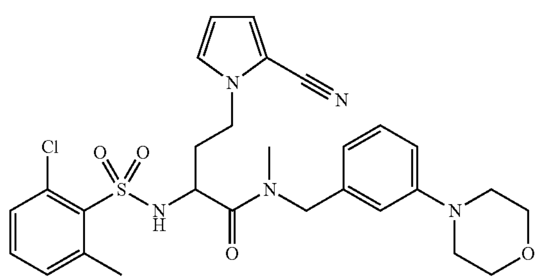 [SMILES: Cc1cccc(Cl)c1S(=O)(=O)NC(CCn1cccc1C#N)C(=O)N(C)Cc1cccc(N2CCOCC2)c1] | 2-{[(2-chloro-6-methylphenyl)sulfonyl]amino}-4-(2-cyano-1H-pyrrol-1-yl)-N-methyl-N-(3-morpholin-4-ylbenzyl)butanamide |
| 359 | 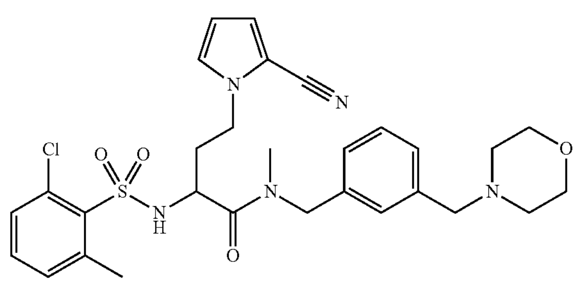 [SMILES: Cc1cccc(Cl)c1S(=O)(=O)NC(CCn1cccc1C#N)C(=O)N(C)Cc1cccc(CN2CCOCC2)c1] | 2-{[(2-chloro-6-methylphenyl)sulfonyl]amino}-4-(2-cyano-1H-pyrrol-1-yl)-N-methyl-N-[3-(morpholin-4-ylmethyl)benzyl]butanamide |
| 360 | 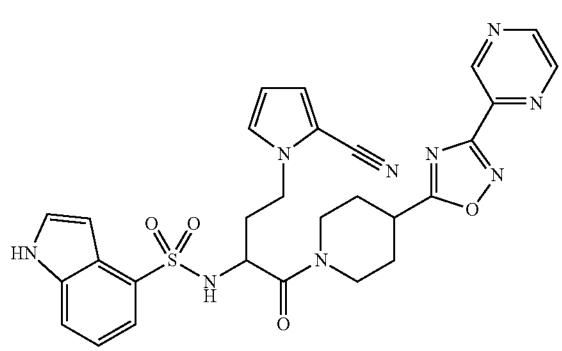 [SMILES: N#Cc1cccn1CCC(NS(=O)(=O)c1cccc2[nH]ccc12)C(=O)N1CCC(c2nc(-c3cnccn3)no2)CC1] | N-[3-(2-cyano-1H-pyrrol-1-yl)-1-{[4-(3-pyrazin-2-yl-1,2,4-oxadiazol-5-yl)piperidin-1-yl]carbonyl}propyl]-1H-indole-4-sulfonamide |

| Example | Structure | Name |
|---|---|---|
| 361 | 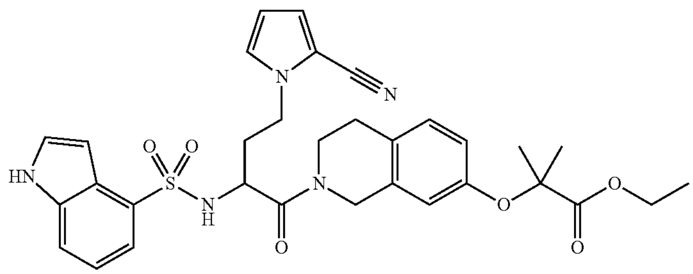 [SMILES: CCOC(=O)C(C)(C)Oc1ccc2c(c1)CN(C(=O)C(CCn1cccc1C#N)NS(=O)(=O)c1cccc3[nH]ccc13)CC2] | ethyl 2-[(2-{4-(2-cyano-1H-pyrrol-1-yl)-2-[(1H-indol-4-ylsulfonyl)amino]butanoyl}-1,2,3,4-tetrahydroisoquinolin-7-yl)oxy]-2-methylpropanoate |
| 362 | 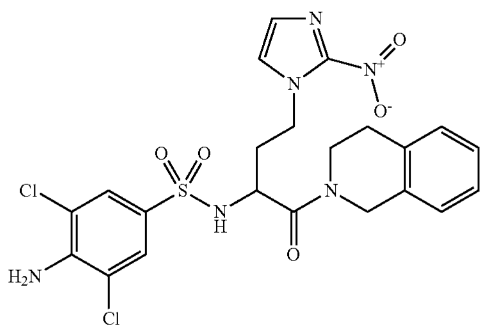 [SMILES: Nc1c(Cl)cc(S(=O)(=O)NC(CCn2ccnc2[N+](=O)[O-])C(=O)N2CCc3ccccc3C2)cc1Cl] | 4-amino-3,5-dichloro-N-[1-(3,4-dihydroisoquinolin-2(1H)-ylcarbonyl)-3-(2-nitro-1H-imidazol-1-yl)propyl]benzenesulfonamide |
| 363 | 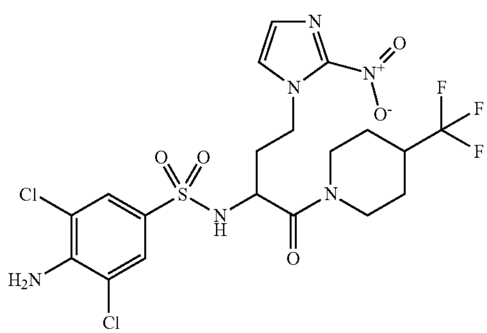 [SMILES: Nc1c(Cl)cc(S(=O)(=O)NC(CCn2ccnc2[N+](=O)[O-])C(=O)N2CCC(C(F)(F)F)CC2)cc1Cl] | 4-amino-3,5-dichloro-N-[3-(2-nitro-1H-imidazol-1-yl)-1-{[4-(trifluoromethyl)piperidin-1-yl]carbonyl}propyl]benzenesulfonamide |
| 364 | 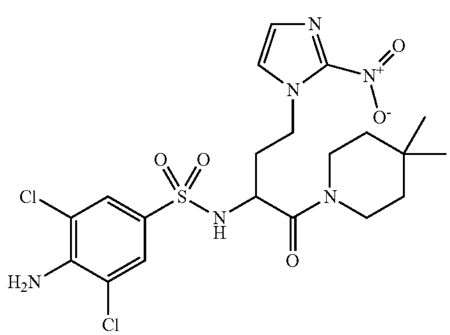 [SMILES: CC1(C)CCN(C(=O)C(CCn2ccnc2[N+](=O)[O-])NS(=O)(=O)c2cc(Cl)c(N)c(Cl)c2)CC1] | 4-amino-3,5-dichloro-N-{1-[(4,4-dimethylpiperidin-1-yl)carbonyl]-3-(2-nitro-1H-imidazol-1-yl)propyl}benzenesulfonamide |
| 365 | 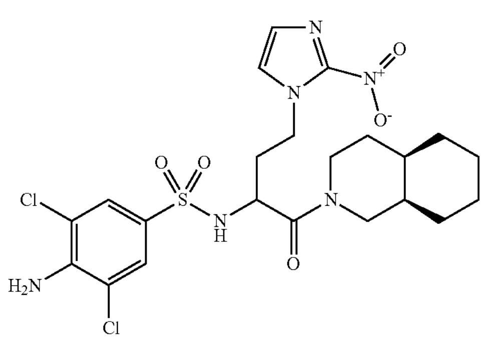 [SMILES: Nc1c(Cl)cc(S(=O)(=O)NC(CCn2ccnc2[N+](=O)[O-])C(=O)N2CC[C@H]3CCCC[C@H]3C2)cc1Cl] | 4-amino-3,5-dichloro-N-{3-(2-nitro-1H-imidazol-1-yl)-1-[(cis)-octahydroisoquinolin-2(1H)-ylcarbonyl]propyl}benzenesulfonamide |

-continued

| Example | Structure | Name |
|---|---|---|
| 366 | 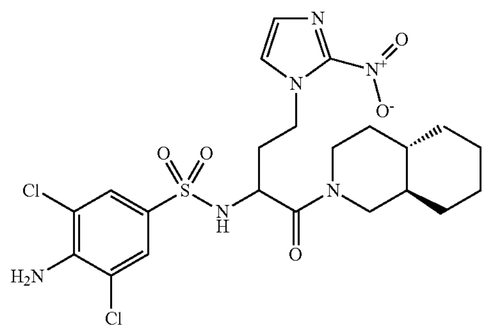 [SMILES: Nc1c(Cl)cc(S(=O)(=O)NC(CCn2ccnc2[N+](=O)[O-])C(=O)N2CC[C@@H]3CCCC[C@H]3C2)cc1Cl] | 4-amino-3,5-dichloro-N-{3-(2-nitro-1H-imidazol-1-yl)-1-[(trans)-octahydroisoquinolin-2(1H)-ylcarbonyl]propyl}benzenesulfonamide |
| 367 | 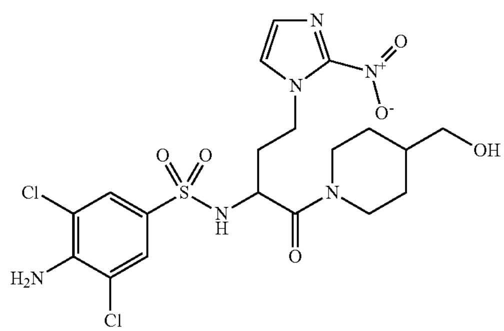 [SMILES: Nc1c(Cl)cc(S(=O)(=O)NC(CCn2ccnc2[N+](=O)[O-])C(=O)N2CCC(CO)CC2)cc1Cl] | 4-amino-3,5-dichloro-N-[1-{[4-(hydroxymethyl)piperidin-1-yl]carbonyl}-3-(2-nitro-1H-imidazol-1-yl)propyl]benzenesulfonamide |
| 368 | 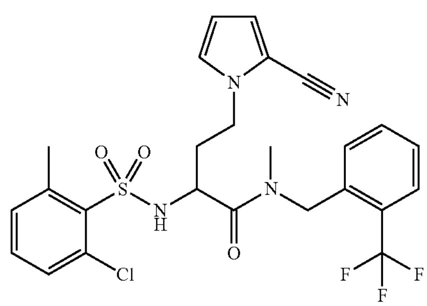 [SMILES: Cc1cccc(Cl)c1S(=O)(=O)NC(CCn1cccc1C#N)C(=O)N(C)Cc1ccccc1C(F)(F)F] | 2-{[(2-chloro-6-methylphenyl)sulfonyl]amino}-4-(2-cyano-1H-pyrrol-1-yl)-N-methyl-N-[2-(trifluoromethyl)benzyl]butanamide |
| 369 | 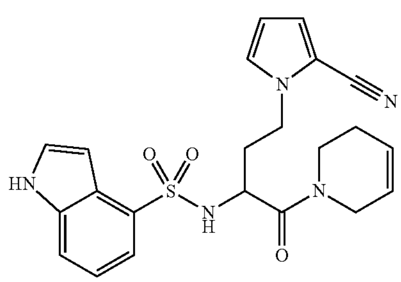 [SMILES: N#Cc1cccn1CCC(NS(=O)(=O)c1cccc2[nH]ccc12)C(=O)N1CC=CCC1] | N-[3-(2-cyano-1H-pyrrol-1-yl)-1-(3,6-dihydropyridin-1(2H)-ylcarbonyl)propyl]-1H-indole-4-sulfonamide |
| 370 | 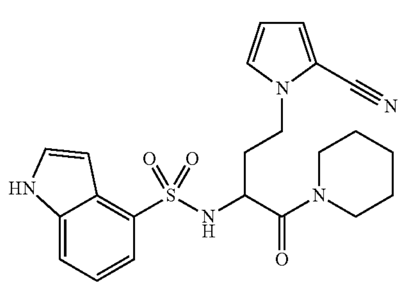 [SMILES: N#Cc1cccn1CCC(NS(=O)(=O)c1cccc2[nH]ccc12)C(=O)N1CCCCC1] | N-[3-(2-cyano-1H-pyrrol-1-yl)-1-(piperidin-1-ylcarbonyl)propyl]-1H-indole-4-sulfonamide |

-continued

| Example | Structure | Name |
|---|---|---|
| 371 | 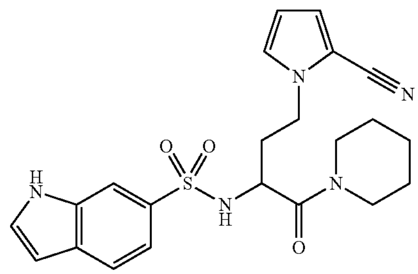 [SMILES: N#Cc1cccn1CCC(NS(=O)(=O)c1ccc2cc[nH]c2c1)C(=O)N1CCCCC1] | N-[3-(2-cyano-1H-pyrrol-1-yl)-1-(piperidin-1-ylcarbonyl)propyl]-1H-indole-6-sulfonamide |
| 372 | 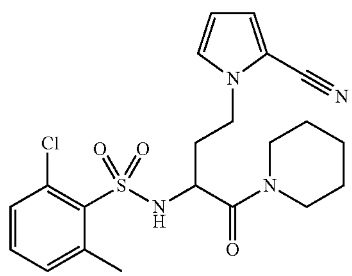 [SMILES: Cc1cccc(Cl)c1S(=O)(=O)NC(CCn1cccc1C#N)C(=O)N1CCCCC1] | 2-chloro-N-[3-(2-cyano-1H-pyrrol-1-yl)-1-(piperidin-1-ylcarbonyl)propyl]-6-methylbenzenesulfonamide |
| 373 | 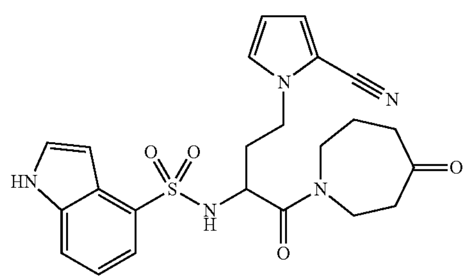 [SMILES: N#Cc1cccn1CCC(NS(=O)(=O)c1cccc2[nH]ccc12)C(=O)N1CCCC(=O)CC1] | N-{3-(2-cyano-1H-pyrrol-1-yl)-1-[(4-oxoazepan-1-yl)carbonyl]propyl}-1H-indole-4-sulfonamide |
| 374 | 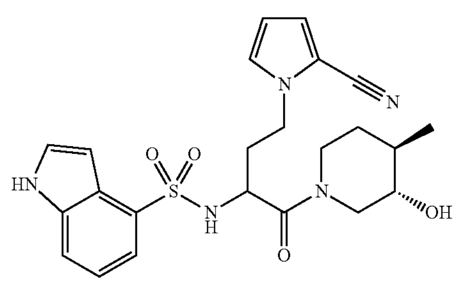 [SMILES: C[C@@H]1CCN(C(=O)C(CCn2cccc2C#N)NS(=O)(=O)c2cccc3[nH]ccc23)C[C@H]1O] | N-[3-(2-cyano-1H-pyrrol-1-yl)-1-{[(trans)-3-hydroxy-4-methylpiperidin-1-yl]carbonyl}propyl]-1H-indole-4-sulfonamide |
| 375 | 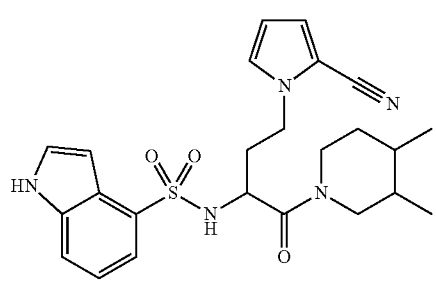 [SMILES: CC1CCN(C(=O)C(CCn2cccc2C#N)NS(=O)(=O)c2cccc3[nH]ccc23)CC1C] | N-{3-(2-cyano-1H-pyrrol-1-yl)-1-[(3,4-dimethylpiperidin-1-yl)carbonyl]propyl}-1H-indole-4-sulfonamide |

| Example | Structure | Name |
|---|---|---|
| 376 | 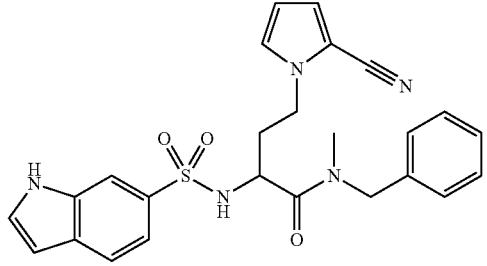 [SMILES: CN(Cc1ccccc1)C(=O)C(CCn1cccc1C#N)NS(=O)(=O)c1ccc2cc[nH]c2c1] | N-benzyl-4-(2-cyano-1H-pyrrol-1-yl)-2-[(1H-indol-6-ylsulfonyl)amino]-N-methylbutanamide |
| 377 | 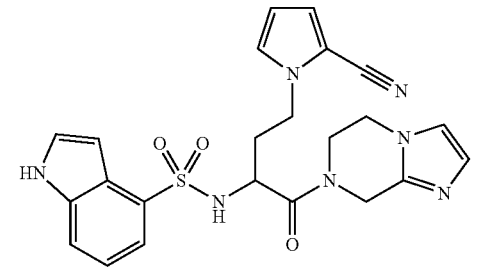 [SMILES: N#Cc1cccn1CCC(NS(=O)(=O)c1cccc2[nH]ccc12)C(=O)N1CCn2ccnc2C1] | N-[3-(2-cyano-1H-pyrrol-1-yl)-1-(5,6-dihydro-imidazo[4,3-a]pyrazin-7(8H)-ylcarbonyl)propyl]-1H-indole-4-sulfonamide |
| 378 | 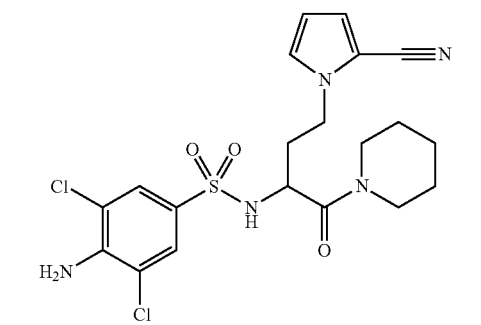 [SMILES: N#Cc1cccn1CCC(NS(=O)(=O)c1cc(Cl)c(N)c(Cl)c1)C(=O)N1CCCCC1] | 4-amino-3,5-dichloro-N-[3-(2-cyano-1H-pyrrol-1-yl)-1-(piperidin-1-ylcarbonyl)propyl]benzenesulfonamide |
| 379 | 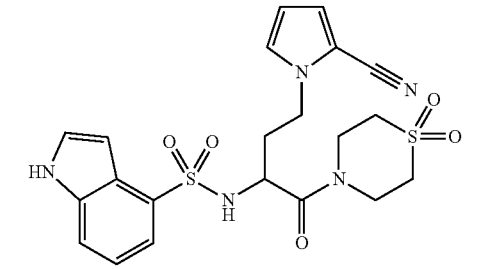 [SMILES: N#Cc1cccn1CCC(NS(=O)(=O)c1cccc2[nH]ccc12)C(=O)N1CCS(=O)(=O)CC1] | N-{3-(2-cyano-1H-pyrrol-1-yl)-1-[(1,1-dioxidothiomorpholin-4-yl)carbonyl]propyl}-1H-indole-4-sulfonamide |
| 380 | 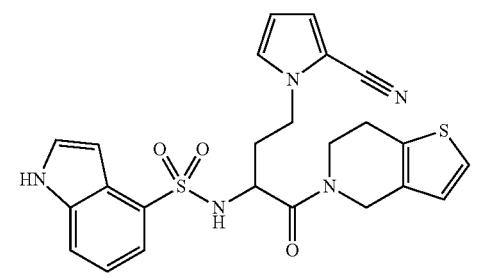 [SMILES: N#Cc1cccn1CCC(NS(=O)(=O)c1cccc2[nH]ccc12)C(=O)N1CCc2sccc2C1] | N-[3-(2-cyano-1H-pyrrol-1-yl)-1-(6,7-dihydrothieno[3,2-c]pyridin-5(4H)-ylcarbonyl)propyl]-1H-indole-4-sulfonamide |

-continued

| Example | Structure | Name |
|---|---|---|
| 381 | 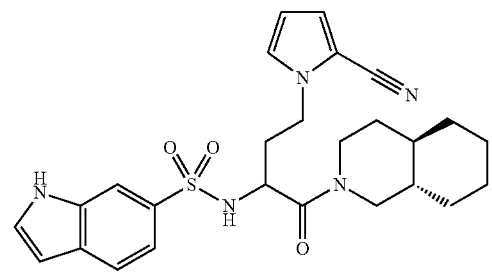 [SMILES: N#Cc1cccn1CCC(NS(=O)(=O)c1ccc2cc[nH]c2c1)C(=O)N1CC[C@H]2CCCC[C@@H]2C1] | N-{3-(2-cyano-1H-pyrrol-1-yl)-1-[(trans)-octahydroisoquinolin-2(1H)-ylcarbonyl]propyl}-1H-indole-6-sulfonamide |
| 382 | 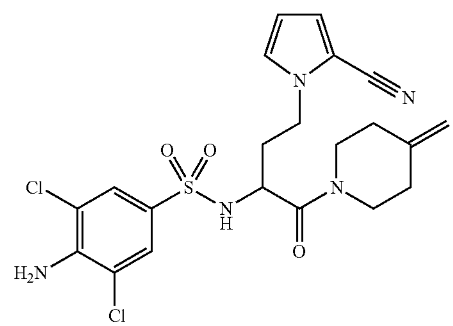 [SMILES: C=C1CCN(C(=O)C(CCn2cccc2C#N)NS(=O)(=O)c2cc(Cl)c(N)c(Cl)c2)CC1] | 4-amino-3,5-dichloro-N-{3-(2-cyano-1H-pyrrol-1-yl)-1-[(4-methylenepiperidin-1-yl)carbonyl]propyl}benzenesulfonamide |
| 383 | 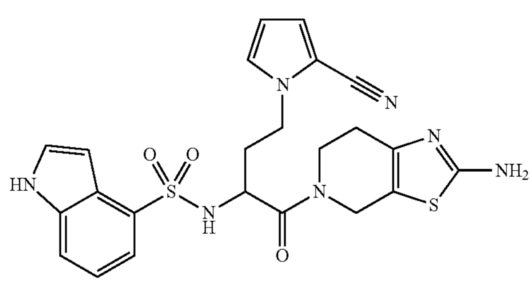 [SMILES: N#Cc1cccn1CCC(NS(=O)(=O)c1cccc2[nH]ccc12)C(=O)N1CCc2nc(N)sc2C1] | N-{1-[(2-amino-6,7-dihydro[1,3]thiazolo[5,4-c]pyridin-5(4H)-yl)carbonyl]-3-(2-cyano-1H-pyrrol-1-yl)propyl}-1H-indole-4-sulfonamide |
| 384 | 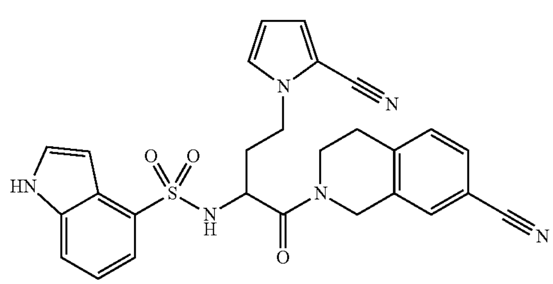 [SMILES: N#Cc1ccc2c(c1)CN(C(=O)C(CCn1cccc1C#N)NS(=O)(=O)c1cccc3[nH]ccc13)CC2] | 1H-indole-4-sulfonic acid [3-(2-cyano-pyrrol-1-yl)-1-(7-cyano-3,4-dihydro-1H-isoquinoline-2-carbonyl)-propyl]-amide |
| 385 | 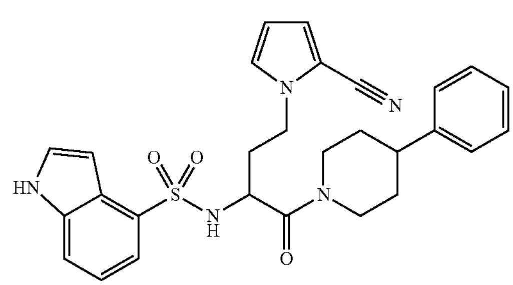 [SMILES: N#Cc1cccn1CCC(NS(=O)(=O)c1cccc2[nH]ccc12)C(=O)N1CCC(c2ccccc2)CC1] | N-{3-(2-cyano-1H-pyrrol-1-yl)-1-[(4-phenylpiperidin-1-yl)carbonyl]propyl}-1H-indole-4-sulfonamide |

-continued

| Example | Structure | Name |
|---|---|---|
| 386 | 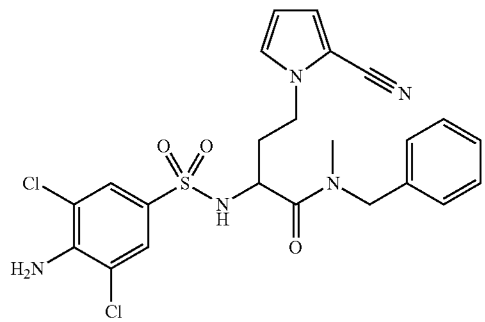 [SMILES: CN(Cc1ccccc1)C(=O)C(CCn1cccc1C#N)NS(=O)(=O)c1cc(Cl)c(N)c(Cl)c1] | 2-{[(4-amino-3,5-dichlorophenyl)sulfonyl]amino}-N-benzyl-4-(2-cyano-1H-pyrrol-1-yl)-N-methylbutanamide |
| 387 | 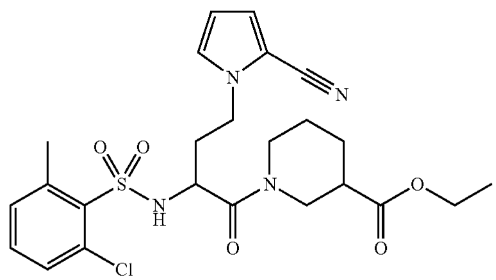 [SMILES: CCOC(=O)C1CCCN(C(=O)C(CCn2cccc2C#N)NS(=O)(=O)c2c(C)cccc2Cl)C1] | ethyl 1-[2-{[(2-chloro-6-methylphenyl)sulfonyl]amino}-4-(2-cyano-1H-pyrrol-1-yl)butanoyl]piperidine-3-carboxylate |
| 388 | 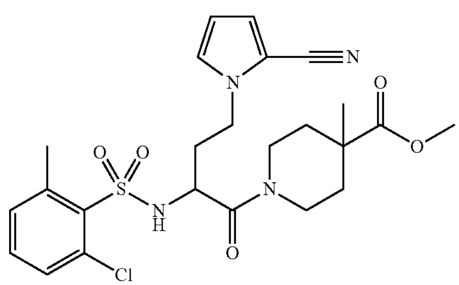 [SMILES: COC(=O)C1(C)CCN(C(=O)C(CCn2cccc2C#N)NS(=O)(=O)c2c(C)cccc2Cl)CC1] | methyl 1-[2-{[(2-chloro-6-methylphenyl)sulfonyl]amino}-4-(2-cyano-1H-pyrrol-1-yl)butanoyl]-4-methylpiperidine-4-carboxylate |
| 389 | 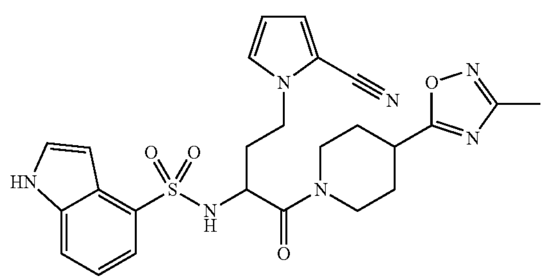 [SMILES: Cc1noc(C2CCN(C(=O)C(CCn3cccc3C#N)NS(=O)(=O)c3cccc4[nH]ccc34)CC2)n1] | N-[3-(2-cyano-1H-pyrrol-1-yl)-1-{[4-(3-methyl-1,2,4-oxadiazol-5-yl)piperidin-1-yl]carbonyl}propyl]-1H-indole-4-sulfonamide |
| 390 | 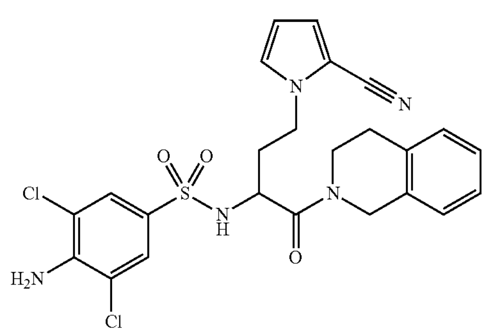 [SMILES: N#Cc1cccn1CCC(NS(=O)(=O)c1cc(Cl)c(N)c(Cl)c1)C(=O)N1CCc2ccccc2C1] | 4-amino-3,5-dichloro-N-[3-(2-cyano-1H-pyrrol-1-yl)-1-(3,4-dihydroisoquinolin-2(1H)-ylcarbonyl)propyl]benzenesulfonamide |

| Example | Structure | Name |
|---|---|---|
| 391 | 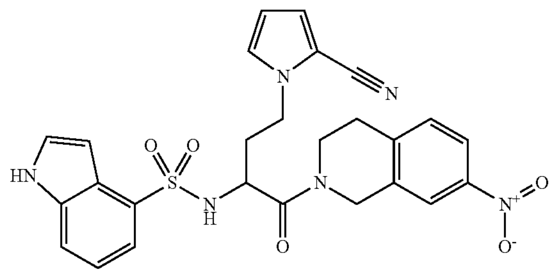 [SMILES: N#Cc1cccn1CCC(NS(=O)(=O)c1cccc2[nH]ccc12)C(=O)N1CCc2ccc([N+](=O)[O-])cc2C1] | 1H-indole-4-sulfonic acid [3-(2-cyano-pyrrol-1-yl)-1-(7-nitro-3,4-dihydro-1H-isoquinoline-2-carbonyl)-propyl]-amide |
| 392 | 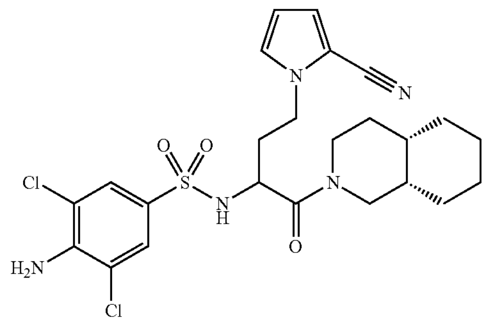 [SMILES: N#Cc1cccn1CCC(NS(=O)(=O)c1cc(Cl)c(N)c(Cl)c1)C(=O)N1CC[C@@H]2CCCC[C@@H]2C1] | 4-amino-3,5-dichloro-N-{3-(2-cyano-1H-pyrrol-1-yl)-1-[(cis)-octahydroisoquinolin-2(1H)-ylcarbonyl]propyl}benzenesulfonamide |
| 393 | 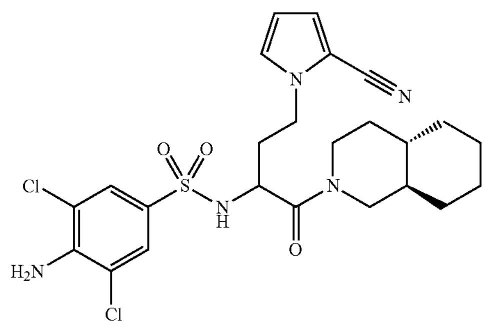 [SMILES: N#Cc1cccn1CCC(NS(=O)(=O)c1cc(Cl)c(N)c(Cl)c1)C(=O)N1CC[C@@H]2CCCC[C@H]2C1] | 4-amino-3,5-dichloro-N-{3-(2-cyano-1H-pyrrol-1-yl)-1-[(trans)-octahydroisoquinolin-2(1H)-ylcarbonyl]propyl}benzenesulfonamide |
| 394 | 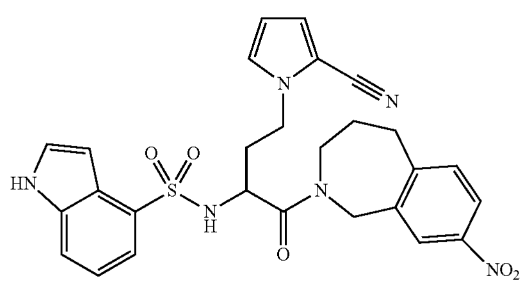 [SMILES: N#Cc1cccn1CCC(NS(=O)(=O)c1cccc2[nH]ccc12)C(=O)N1CCCc2ccc([N+](=O)[O-])cc2C1] | 1H-indole-4-sulfonic acid [3-(2-cyano-pyrrol-1-yl)-1-(8-nitro-1,3,4,5-tetrahydro-2-benzazepine-2-carbonyl)-propyl]-amide |
| 395 | 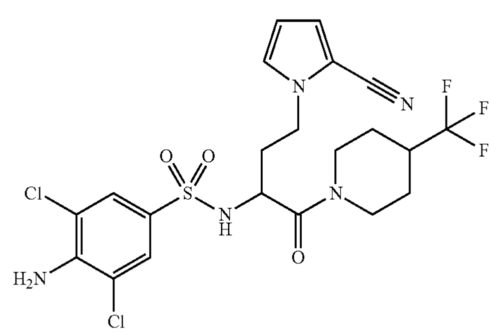 [SMILES: N#Cc1cccn1CCC(NS(=O)(=O)c1cc(Cl)c(N)c(Cl)c1)C(=O)N1CCC(C(F)(F)F)CC1] | 4-amino-3,5-dichloro-N-[3-(2-cyano-1H-pyrrol-1-yl)-1-{[4-(trifluoromethyl)piperidin-1-yl]carbonyl}propyl]benzenesulfonamide |

| Example | Structure | Name |
|---|---|---|
| 397 | 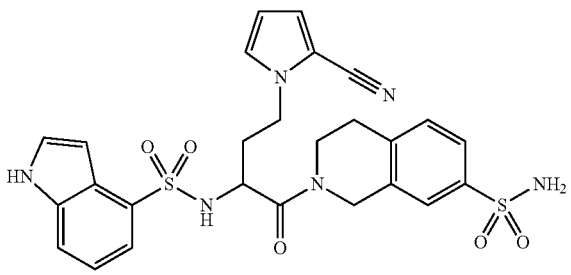 [SMILES: N#Cc1cccn1CCC(NS(=O)(=O)c1cccc2[nH]ccc12)C(=O)N1CCc2ccc(S(N)(=O)=O)cc2C1] | 2-{4-(2-cyano-1H-pyrrol-1-yl)-2-[(1H-indol-4-ylsulfonyl)amino]butanoyl}-1,2,3,4-tetrahydroisoquinoline-7-sulfonamide |
| 398 | 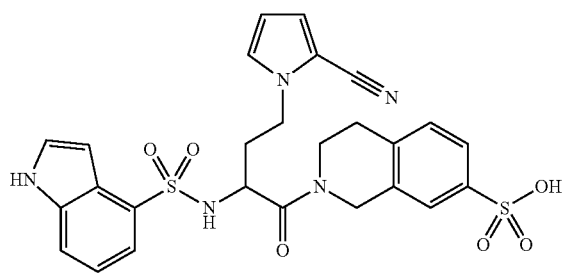 [SMILES: N#Cc1cccn1CCC(NS(=O)(=O)c1cccc2[nH]ccc12)C(=O)N1CCc2ccc(S(=O)(=O)O)cc2C1] | 2-{4-(2-cyano-1H-pyrrol-1-yl)-2-[(1H-indol-4-ylsulfonyl)amino]butanoyl}-1,2,3,4-tetrahydroisoquinoline-7-sulfonic acid |
| 399 | 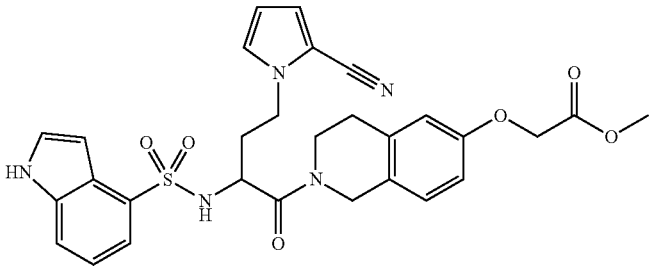 [SMILES: COC(=O)COc1ccc2c(c1)CCN(C(=O)C(CCn1cccc1C#N)NS(=O)(=O)c1cccc3[nH]ccc13)C2] | methyl [(2-{4-(2-cyano-1H-pyrrol-1-yl)-2-[(1H-indol-4-ylsulfonyl)amino]butanoyl}-1,2,3,4-tetrahydroisoquinolin-6-yl)oxy]acetate |
| 400 | 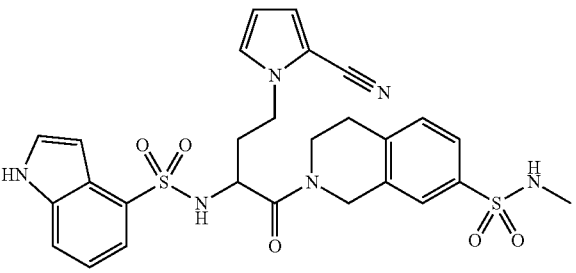 [SMILES: CNS(=O)(=O)c1ccc2c(c1)CN(C(=O)C(CCn1cccc1C#N)NS(=O)(=O)c1cccc3[nH]ccc13)CC2] | 2-{4-(2-cyano-1H-pyrrol-1-yl)-2-[(1H-indol-4-ylsulfonyl)amino]butanoyl}-N-methyl-1,2,3,4-tetrahydroisoquinoline-7-sulfonamide |
| 401 | 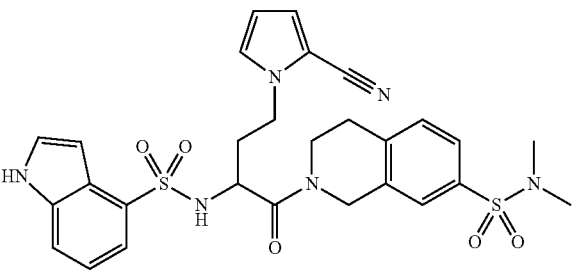 [SMILES: CN(C)S(=O)(=O)c1ccc2c(c1)CN(C(=O)C(CCn1cccc1C#N)NS(=O)(=O)c1cccc3[nH]ccc13)CC2] | 2-{4-(2-cyano-1H-pyrrol-1-yl)-2-[(1H-indol-4-ylsulfonyl)amino]butanoyl}-N,N-dimethyl-1,2,3,4-tetrahydroisoquinoline-7-sulfonamide |

-continued

| Example | Structure | Name |
|---|---|---|
| 402 | 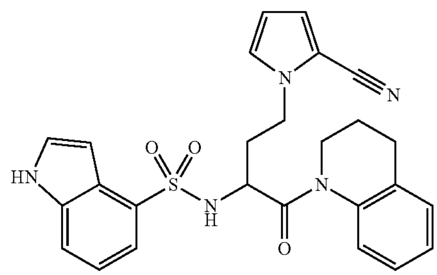 [SMILES: N#Cc1cccn1CCC(NS(=O)(=O)c1cccc2[nH]ccc12)C(=O)N1CCCc2ccccc21] | N-[3-(2-cyano-1H-pyrrol-1-yl)-1-(3,4-dihydroquinolin-1(2H)-ylcarbonyl)propyl]-1H-indole-4-sulfonamide |
| 403 | 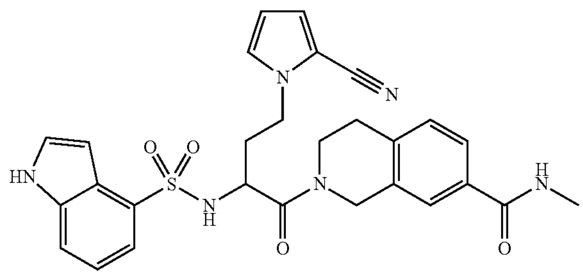 [SMILES: CNC(=O)c1ccc2c(c1)CN(C(=O)C(CCn1cccc1C#N)NS(=O)(=O)c1cccc3[nH]ccc13)CC2] | 2-{4-(2-cyano-1H-pyrrol-1-yl)-2-[(1H-indol-4-ylsulfonyl)amino]butanoyl}-N-methyl-1,2,3,4-tetrahydroisoquinoline-7-carboxamide |
| 404 | 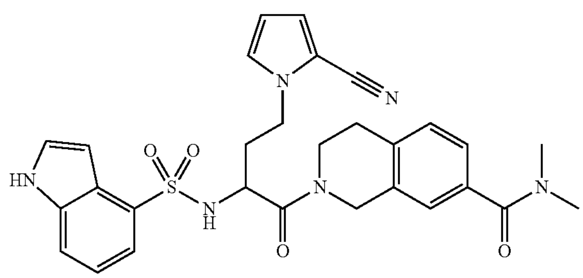 [SMILES: CN(C)C(=O)c1ccc2c(c1)CN(C(=O)C(CCn1cccc1C#N)NS(=O)(=O)c1cccc3[nH]ccc13)CC2] | 2-{4-(2-cyano-1H-pyrrol-1-yl)-2-[(1H-indol-4-ylsulfonyl)amino]butanoyl}-N,N-dimethyl-1,2,3,4-tetrahydroisoquinoline-7-carboxamide |
| 405 | 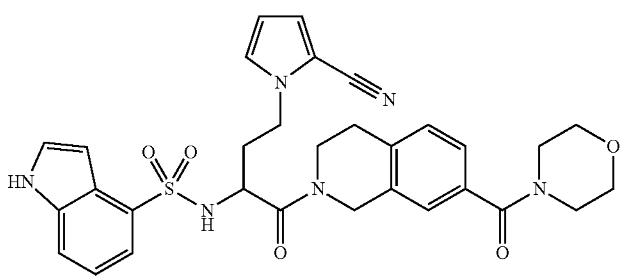 [SMILES: N#Cc1cccn1CCC(NS(=O)(=O)c1cccc2[nH]ccc12)C(=O)N1CCc2ccc(C(=O)N3CCOCC3)cc2C1] | N-[3-(2-cyano-1H-pyrrol-1-yl)-1-{[7-(morpholin-4-ylcarbonyl)-3,4-dihydroisoquinolin-2(1H)-yl]carbonyl}propyl]-1H-indole-4-sulfonamide |
| 406 | 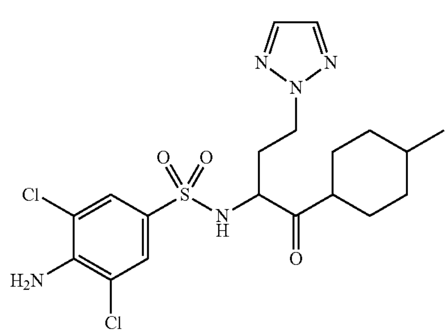 [SMILES: CC1CCC(C(=O)C(CCn2nccn2)NS(=O)(=O)c2cc(Cl)c(N)c(Cl)c2)CC1] | 4-amino-3,5-dichloro-N-{1-[(4-methylcyclohexyl)carbonyl]-3-(2H-1,2,3-triazol-2-yl)propyl}benzenesulfonamide |

| Example | Structure | Name |
| --- | --- | --- |
| 407 | 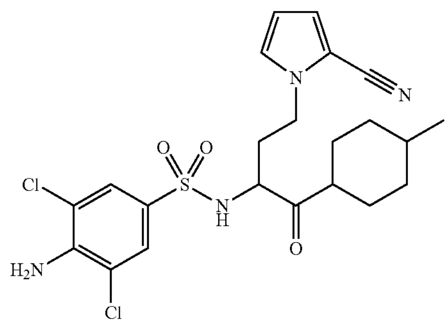 [SMILES: CC1CCC(C(=O)C(CCn2cccc2C#N)NS(=O)(=O)c2cc(Cl)c(N)c(Cl)c2)CC1] | 4-amino-3,5-dichloro-N-{3-(2-cyano-1H-pyrrol-1-yl)-1-[(4-methylcyclohexyl)carbonyl]propyl}benzenesulfonamide |
| 408 | 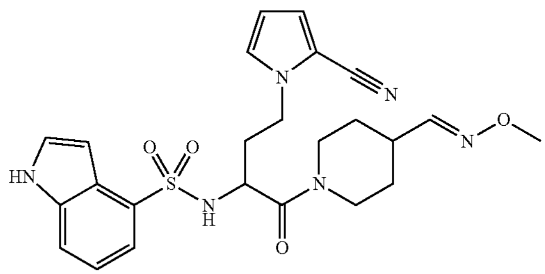 [SMILES: CO/N=C/C1CCN(C(=O)C(CCn2cccc2C#N)NS(=O)(=O)c2cccc3[nH]ccc23)CC1] | N-[3-(2-cyano-1H-pyrrol-1-yl)-1-({4-[(E/Z)-(methoxyimino)methyl]piperidin-1-yl}carbonyl)propyl]-1H-indole-4-sulfonamide |
| 409 | 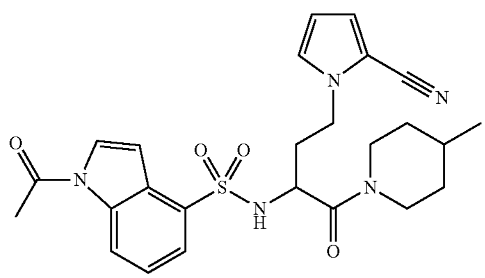 [SMILES: CC(=O)n1ccc2c(S(=O)(=O)NC(CCn3cccc3C#N)C(=O)N3CCC(C)CC3)cccc21] | 1-acetyl-N-{3-(2-cyano-1H-pyrrol-1-yl)-1-[(4-methylpiperidin-1-yl)carbonyl]propyl}-1H-indole-4-sulfonamide |
| 410 | 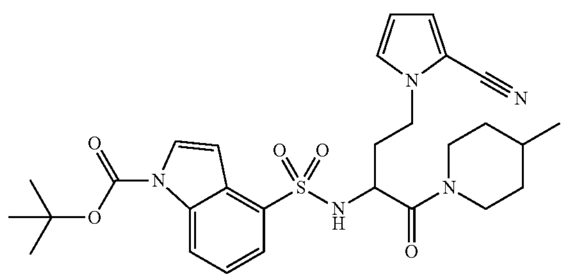 [SMILES: CC1CCN(C(=O)C(CCn2cccc2C#N)NS(=O)(=O)c2cccc3c2ccn3C(=O)OC(C)(C)C)CC1] | tert-butyl 4-[({3-(2-cyano-1H-pyrrol-1-yl)-1-[(4-methylpiperidin-1-yl)carbonyl]propyl}amino)sulfonyl]-1H-indole-1-carboxylate |
| 411 | 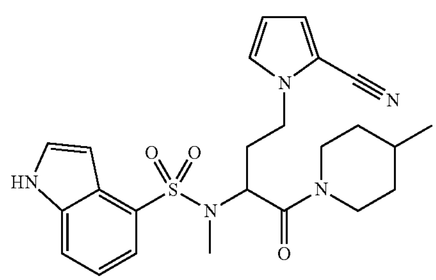 [SMILES: CC1CCN(C(=O)C(CCn2cccc2C#N)N(C)S(=O)(=O)c2cccc3[nH]ccc23)CC1] | N-{3-(2-cyano-1H-pyrrol-1-yl)-1-[(4-methylpiperidin-1-yl)carbonyl]propyl}-N-methyl-1H-indole-4-sulfonamide |

-continued

| Example | Structure | Name |
|---|---|---|
| 413 | 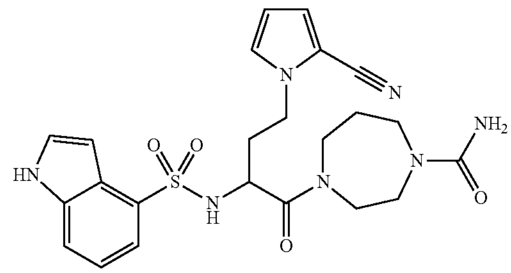 [SMILES: N#Cc1cccn1CCC(NS(=O)(=O)c1cccc2[nH]ccc12)C(=O)N1CCCN(C(N)=O)CC1] | 4-{4-(2-cyano-1H-pyrrol-1-yl)-2-[(1H-indol-4-ylsulfonyl)amino]butanoyl}-1,4-diazepane-1-carboxamide |
| 414 | 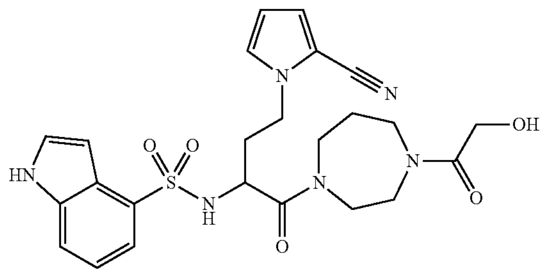 [SMILES: N#Cc1cccn1CCC(NS(=O)(=O)c1cccc2[nH]ccc12)C(=O)N1CCCN(C(=O)CO)CC1] | N-{3-(2-cyano-1H-pyrrol-1-yl)-1-[(4-glycoloyl-1,4-diazepan-1-yl)carbonyl]propyl}-1H-indole-4-sulfonamide |
| 415 | 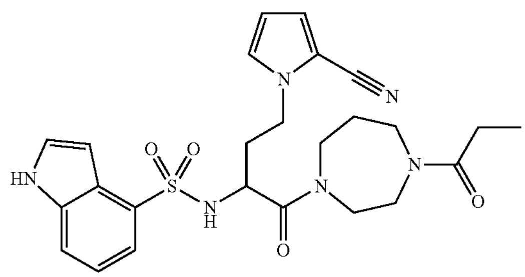 [SMILES: CCC(=O)N1CCCN(C(=O)C(CCn2cccc2C#N)NS(=O)(=O)c2cccc3[nH]ccc23)CC1] | N-{3-(2-cyano-1H-pyrrol-1-yl)-1-[(4-propionyl-1,4-diazepan-1-yl)carbonyl]propyl}-1H-indole-4-sulfonamide |
| 416 | 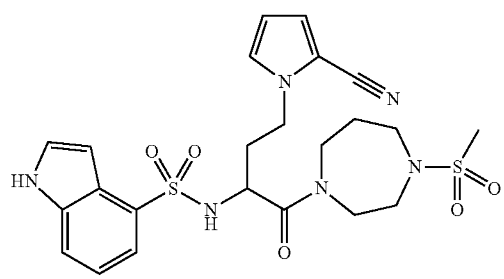 [SMILES: CS(=O)(=O)N1CCCN(C(=O)C(CCn2cccc2C#N)NS(=O)(=O)c2cccc3[nH]ccc23)CC1] | N-[3-(2-cyano-1H-pyrrol-1-yl)-1-{[4-(methylsulfonyl)-1,4-diazepan-1-yl]carbonyl}propyl]-1H-indole-4-sulfonamide |
| 417 | 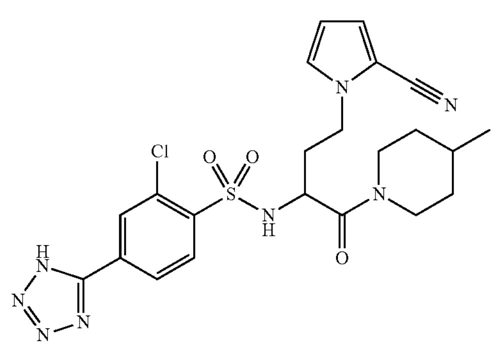 [SMILES: CC1CCN(C(=O)C(CCn2cccc2C#N)NS(=O)(=O)c2ccc(-c3nnn[nH]3)cc2Cl)CC1] | 2-chloro-N-{3-(2-cyano-1H-pyrrol-1-yl)-1-[(4-methylpiperidin-1-yl)carbonyl]propyl}-4-(1H-tetrazol-5-yl)benzenesulfonamide |

| Example | Structure | Name |
| --- | --- | --- |
| 418 | 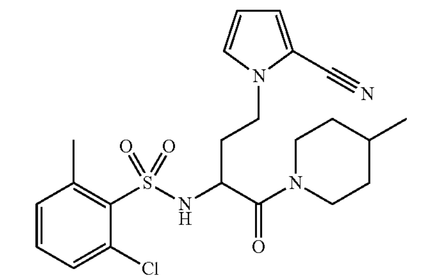 [SMILES: Cc1cccc(Cl)c1S(=O)(=O)NC(CCn1cccc1C#N)C(=O)N1CCC(C)CC1] | 2-chloro-N-{3-(5-cyano-1H-pyrazol-1-yl)-1-[(4-methylpiperidin-1-yl)carbonyl]propyl}-6-methylbenzenesulfonamide |
| 419 | 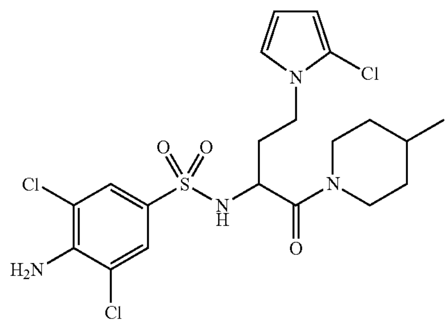 [SMILES: CC1CCN(C(=O)C(CCn2cccc2Cl)NS(=O)(=O)c2cc(Cl)c(N)c(Cl)c2)CC1] | 4-amino-3,5-dichloro-N-{3-(2-chloro-1H-pyrrol-1-yl)-1-[(4-methylpiperidin-1-yl)carbonyl]propyl}benzenesulfonamide |
| 420 | 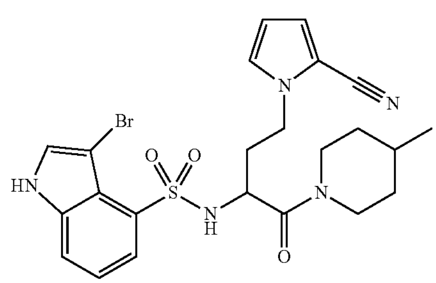 | 3-bromo-N-{3-(2-cyano-1H-pyrrol-1-yl)-1-[(4-methylpiperidin-1-yl)carbonyl]propyl}-1H-indole-4-sulfonamide |
| 421 | 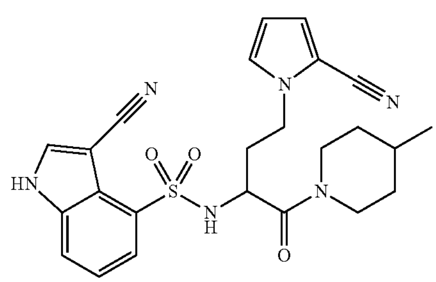 [SMILES: CC1CCN(C(=O)C(CCn2cccc2C#N)NS(=O)(=O)c2cccc3[nH]cc(C#N)c23)CC1] | 3-cyano-N-{3-(2-cyano-1H-pyrrol-1-yl)-1-[(4-methylpiperidin-1-yl)carbonyl]propyl}-1H-indole-4-sulfonamide |
| 422 | 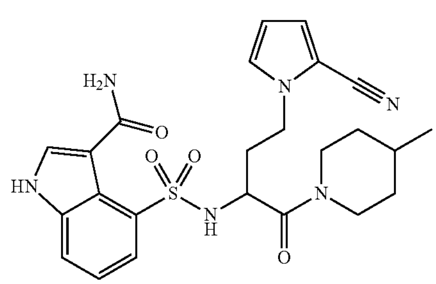 [SMILES: CC1CCN(C(=O)C(CCn2cccc2C#N)NS(=O)(=O)c2cccc3[nH]cc(C(N)=O)c23)CC1] | 4-[({3-(2-cyano-1H-pyrrol-1-yl)-1-[(4-methylpiperidin-1-yl)carbonyl]propyl}amino)sulfonyl]-1H-indole-3-carboxamide |

-continued

| Example | Structure | Name |
|---|---|---|
| 423 | 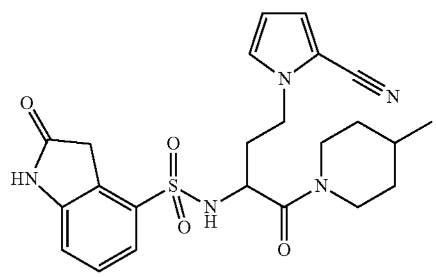 [SMILES: CC1CCN(C(=O)C(CCn2cccc2C#N)NS(=O)(=O)c2cccc3c2CC(=O)N3)CC1] | N-{3-(2-cyano-1H-pyrrol-1-yl)-1-[(4-methylpiperidin-1-yl)carbonyl]propyl}-2-oxoindoline-4-sulfonamide |
| 424 | 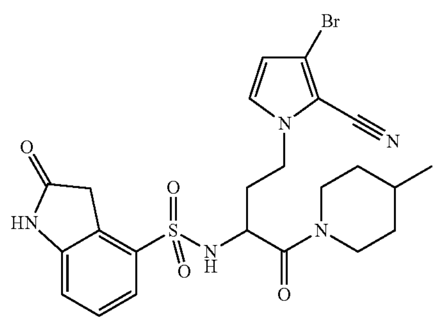 [SMILES: CC1CCN(C(=O)C(CCn2ccc(Br)c2C#N)NS(=O)(=O)c2cccc3c2CC(=O)N3)CC1] | N-{3-(3-bromo-2-cyano-1H-pyrrol-1-yl)-1-[(4-methylpiperidin-1-yl)carbonyl]propyl}-2-oxoindoline-4-sulfonamide |
| 425 | 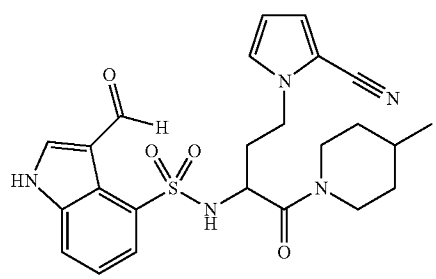 [SMILES: CC1CCN(C(=O)C(CCn2cccc2C#N)NS(=O)(=O)c2cccc3[nH]cc(C=O)c23)CC1] | N-{3-(2-cyano-1H-pyrrol-1-yl)-1-[(4-methylpiperidin-1-yl)carbonyl]propyl}-3-formyl-1H-indole-4-sulfonamide |
| 426 | 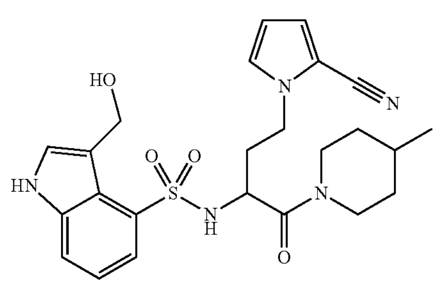 [SMILES: CC1CCN(C(=O)C(CCn2cccc2C#N)NS(=O)(=O)c2cccc3[nH]cc(CO)c23)CC1] | N-{3-(2-cyano-1H-pyrrol-1-yl)-1-[(4-methylpiperidin-1-yl)carbonyl]propyl}-3-(hydroxymethyl)-1H-indole-4-sulfonamide |
| 427 | 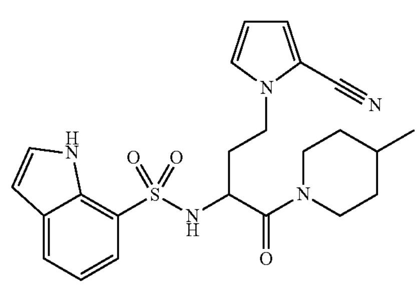 [SMILES: CC1CCN(C(=O)C(CCn2cccc2C#N)NS(=O)(=O)c2cccc3cc[nH]c23)CC1] | N-{3-(2-cyano-1H-pyrrol-1-yl)-1-[(4-methylpiperidin-1-yl)carbonyl]propyl}-1H-indole-7-sulfonamide |

-continued

| Example | Structure | Name |
|---|---|---|
| 428 | 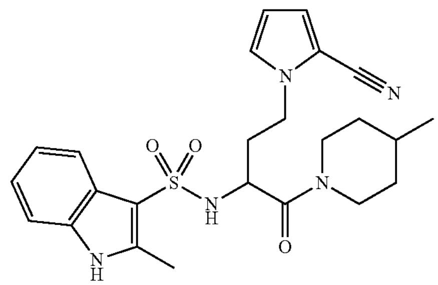 [SMILES: Cc1[nH]c2ccccc2c1S(=O)(=O)NC(CCn1cccc1C#N)C(=O)N1CCC(C)CC1] | N-{3-(2-cyano-1H-pyrrol-1-yl)-1-[(4-methylpiperidin-1-yl)carbonyl]propyl}-2-methyl-1H-indole-3-sulfonamide |
| 429 | 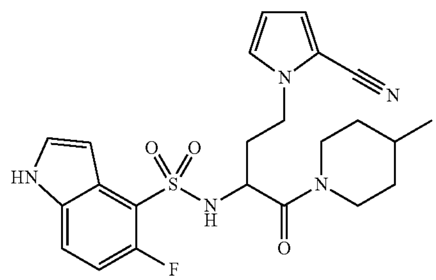 [SMILES: CC1CCN(C(=O)C(CCn2cccc2C#N)NS(=O)(=O)c2c(F)ccc3[nH]ccc23)CC1] | N-{3-(2-cyano-1H-pyrrol-1-yl)-1-[(4-methylpiperidin-1-yl)carbonyl]propyl}-5-fluoro-1H-indole-4-sulfonamide |
| 430 | 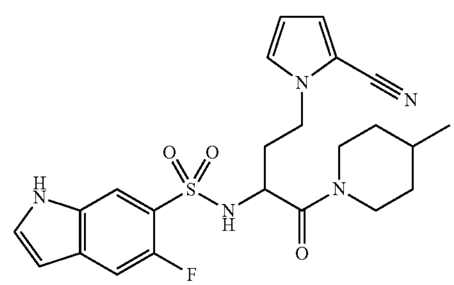 [SMILES: CC1CCN(C(=O)C(CCn2cccc2C#N)NS(=O)(=O)c2cc3[nH]ccc3cc2F)CC1] | N-{3-(2-cyano-1H-pyrrol-1-yl)-1-[(4-methylpiperidin-1-yl)carbonyl]propyl}-5-fluoro-1H-indole-6-sulfonamide |
| 431 | 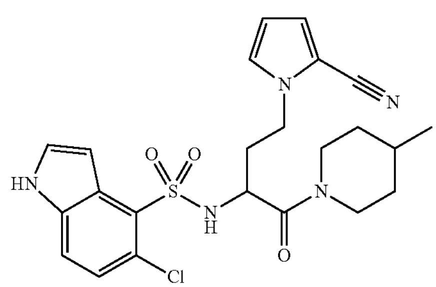 [SMILES: CC1CCN(C(=O)C(CCn2cccc2C#N)NS(=O)(=O)c2c(Cl)ccc3[nH]ccc23)CC1] | 5-chloro-N-{3-(2-cyano-1H-pyrrol-1-yl)-1-[(4-methylpiperidin-1-yl)carbonyl]propyl}-1H-indole-4-sulfonamide |
| 433 | 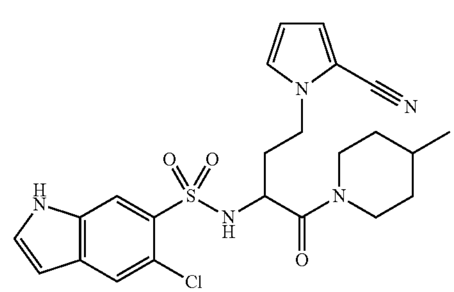 [SMILES: CC1CCN(C(=O)C(CCn2cccc2C#N)NS(=O)(=O)c2cc3[nH]ccc3cc2Cl)CC1] | 5-chloro-N-{3-(2-cyano-1H-pyrrol-1-yl)-1-[(4-methylpiperidin-1-yl)carbonyl]propyl}-1H-indole-6-sulfonamide |

| Example | Structure | Name |
|---|---|---|
| 433 | 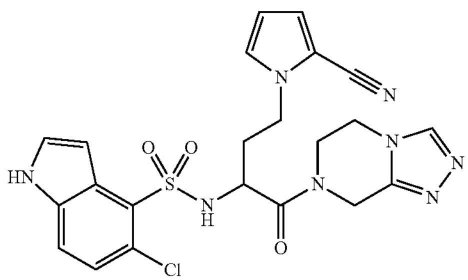 [SMILES: N#Cc1cccn1CCC(NS(=O)(=O)c1c(Cl)ccc2[nH]ccc12)C(=O)N1CCn2cnnc2C1] | N-[3-(2-cyano-1H-pyrrol-1-yl)-1-(5,6-dihydro[1,2,4]triazolo[4,3-a]pyrazin-7(8H)-ylcarbonyl)propyl]-5-chloro-1H-indole-4-sulfonamide |
| 434 | 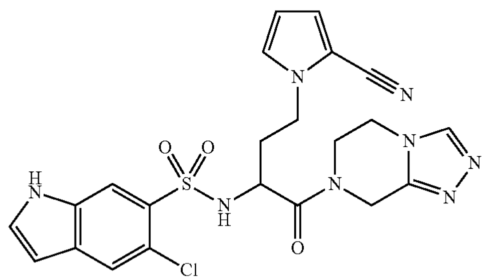 [SMILES: N#Cc1cccn1CCC(NS(=O)(=O)c1cc2[nH]ccc2cc1Cl)C(=O)N1CCn2cnnc2C1] | 5-chloro-1H-indole-6-sulfonic acid [3-(2-cyano-pyrrol-1-yl)-1-(5,6-dihydro-8H-[1,2,4]triazolo[4,3-a]pyrazine-7-carbonyl)-propyl]-amide |
| 435 | 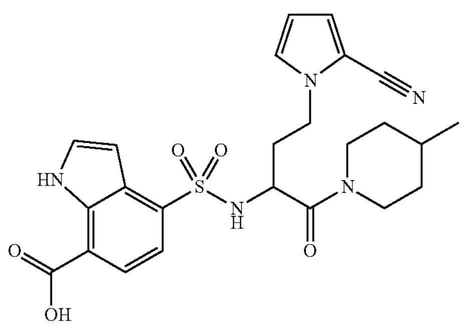 [SMILES: CC1CCN(C(=O)C(CCn2cccc2C#N)NS(=O)(=O)c2ccc(C(=O)O)c3[nH]ccc23)CC1] | 4-({3-(2-cyano-1H-pyrrol-1-yl)-1-[(4-methylpiperidin-1-yl)carbonyl]propyl}sulfamoyl)-1H-indole-7-carboxylic acid |
| 436 | 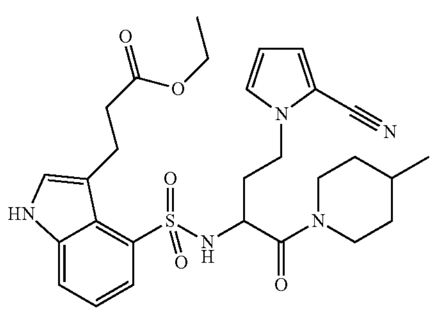 [SMILES: CCOC(=O)CCc1c[nH]c2cccc(S(=O)(=O)NC(CCn3cccc3C#N)C(=O)N3CCC(C)CC3)c12] | ethyl 3-{4-[({3-(2-cyano-1H-pyrrol-1-yl)-1-[(4-methylpiperidin-1-yl)carbonyl]propyl}amino)sulfonyl]-1H-indol-3-yl}propanoate |
| 437 | 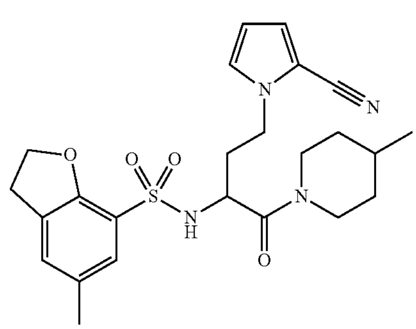 [SMILES: Cc1cc2c(c(S(=O)(=O)NC(CCn3cccc3C#N)C(=O)N3CCC(C)CC3)c1)OCC2] | N-{3-(2-cyano-1H-pyrrol-1-yl)-1-[(4-methylpiperidin-1-yl)carbonyl]propyl}-5-methyl-2,3-dihydro-1-benzofuran-7-sulfonamide |

| Example | Structure | Name |
| --- | --- | --- |
| 438 | 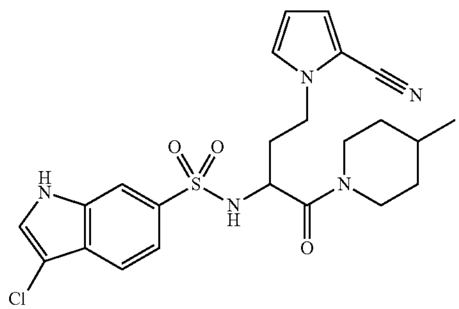 [SMILES: CC1CCN(C(=O)C(CCn2cccc2C#N)NS(=O)(=O)c2ccc3c(Cl)c[nH]c3c2)CC1] | 3-chloro-N-{3-(2-cyano-1H-pyrrol-1-yl)-1-[(4-methylpiperidin-1-yl)carbonyl]propyl}-1H-indole-6-sulfonamide |
| 439 | 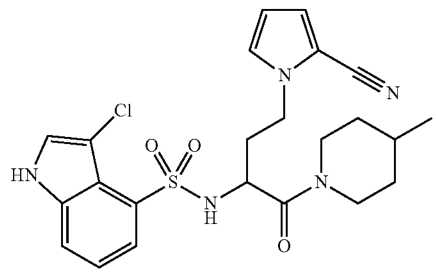 [SMILES: CC1CCN(C(=O)C(CCn2cccc2C#N)NS(=O)(=O)c2cccc3[nH]cc(Cl)c23)CC1] | 3-chloro-N-{3-(2-cyano-1H-pyrrol-1-yl)-1-[(4-methylpiperidin-1-yl)carbonyl]propyl}-1H-indole-4-sulfonamide |
| 440 | 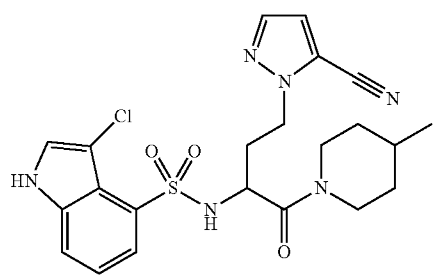 [SMILES: CC1CCN(C(=O)C(CCn2nccc2C#N)NS(=O)(=O)c2cccc3[nH]cc(Cl)c23)CC1] | 3-chloro-N-{3-(5-cyano-1H-pyrazol-1-yl)-1-[(4-methylpiperidin-1-yl)carbonyl]propyl}-1H-indole-4-sulfonamide |
| 441 | 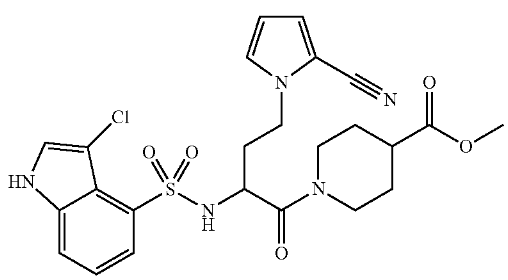 [SMILES: COC(=O)C1CCN(C(=O)C(CCn2cccc2C#N)NS(=O)(=O)c2cccc3[nH]cc(Cl)c23)CC1] | methyl 1-[2-{[(3-chloro-1H-indol-4-yl)sulfonyl]amino}-4-(2-cyano-1H-pyrrol-1-yl)butanoyl]piperidine-4-carboxylate |
| 442 | 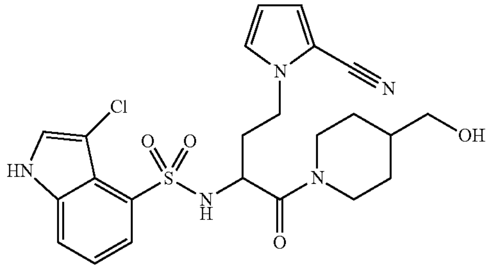 [SMILES: N#Cc1cccn1CCC(NS(=O)(=O)c1cccc2[nH]cc(Cl)c12)C(=O)N1CCC(CO)CC1] | 3-chloro-N-[3-(2-cyano-1H-pyrrol-1-yl)-1-{[4-(hydroxymethyl)piperidin-1-yl]carbonyl}propyl]-1H-indole-4-sulfonamide |

| Example | Structure | Name |
|---|---|---|
| 443 | 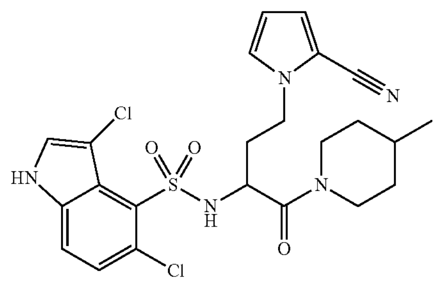 [SMILES: CC1CCN(C(=O)C(CCn2cccc2C#N)NS(=O)(=O)c2c(Cl)ccc3[nH]cc(Cl)c23)CC1] | 3,5-dichloro-1H-indole-4-sulfonic acid [3-(2-cyano-pyrrol-1-yl)-1-(4-methyl-piperidine-1-carbonyl)-propyl]-amide |
| 444 | 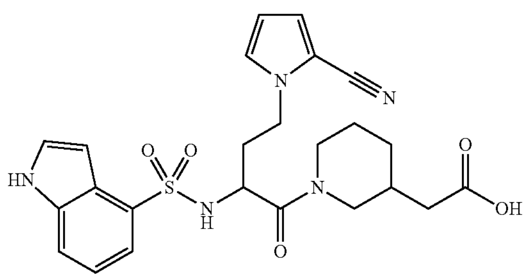 [SMILES: N#Cc1cccn1CCC(NS(=O)(=O)c1cccc2[nH]ccc12)C(=O)N1CCCC(CC(=O)O)C1] | (1-{4-(2-cyano-1H-pyrrol-1-yl)-2-[(1H-indol-4-ylsulfonyl)amino]butanoyl}piperidin-3-yl)acetic acid |
| 445 | 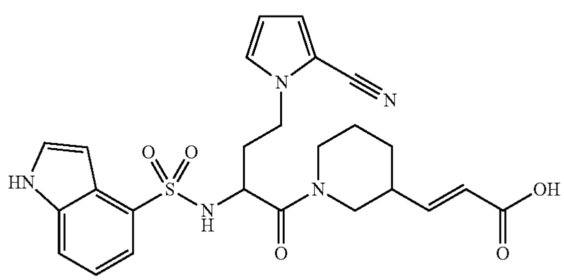 [SMILES: N#Cc1cccn1CCC(NS(=O)(=O)c1cccc2[nH]ccc12)C(=O)N1CCCC(/C=C/C(=O)O)C1] | (2E)-3-(1-{4-(2-cyano-1H-pyrrol-1-yl)-2-[(1H-indol-4-ylsulfonyl)amino]butanoyl}piperidin-3-yl)prop-2-enoic acid |
| 446 | 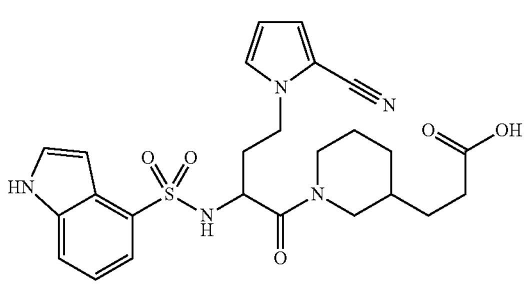 [SMILES: N#Cc1cccn1CCC(NS(=O)(=O)c1cccc2[nH]ccc12)C(=O)N1CCCC(CCC(=O)O)C1] | 3-(1-{4-(2-cyano-1H-pyrrol-1-yl)-2-[(1H-indol-4-ylsulfonyl)amino]butanoyl}piperidin-3-yl)propanoic acid |
| 447 | 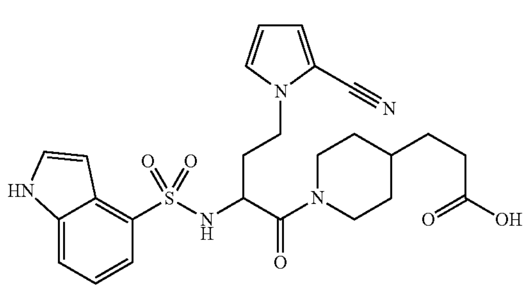 [SMILES: N#Cc1cccn1CCC(NS(=O)(=O)c1cccc2[nH]ccc12)C(=O)N1CCC(CCC(=O)O)CC1] | 3-(1-{4-(2-cyano-1H-pyrrol-1-yl)-2-[(1H-indol-4-ylsulfonyl)amino]butanoyl}piperidin-4-yl)propanoic acid |

| Example | Structure | Name |
| --- | --- | --- |
| 448 | 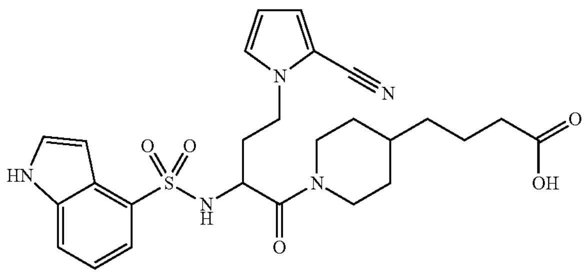 [SMILES: N#Cc1cccn1CCC(NS(=O)(=O)c1cccc2[nH]ccc12)C(=O)N1CCC(CCCC(=O)O)CC1] | 4-(1-{4-(2-cyano-1H-pyrrol-1-yl)-2-[(1H-indol-4-ylsulfonyl)amino]butanoyl}piperidin-4-yl)butanoic acid |
| 449 | 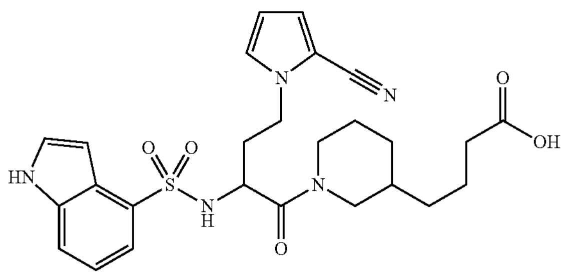 [SMILES: N#Cc1cccn1CCC(NS(=O)(=O)c1cccc2[nH]ccc12)C(=O)N1CCCC(CCCC(=O)O)C1] | 4-(1-{4-(2-cyano-1H-pyrrol-1-yl)-2-[(1H-indol-4-ylsulfonyl)amino]butanoyl}piperidin-3-yl)butanoic acid |
| 450 | 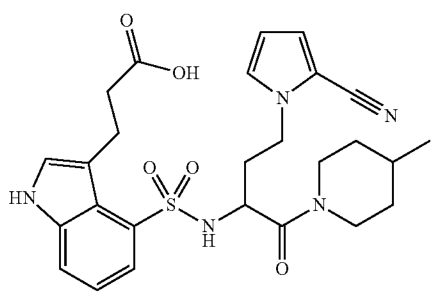 [SMILES: CC1CCN(C(=O)C(CCn2cccc2C#N)NS(=O)(=O)c2cccc3[nH]cc(CCC(=O)O)c23)CC1] | 3-{4-[({3-(2-cyano-1H-pyrrol-1-yl)-1-[(4-methylpiperidin-1-yl)carbonyl]propyl}amino)sulfonyl]-1H-indol-3-yl}propanoic acid |
| 451 | 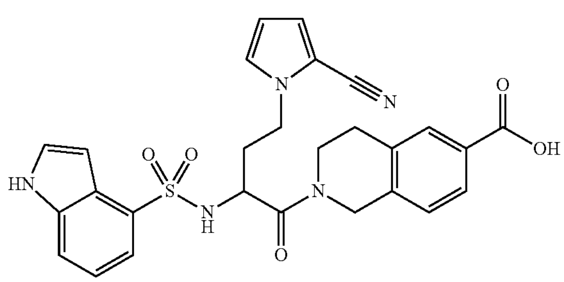 [SMILES: N#Cc1cccn1CCC(NS(=O)(=O)c1cccc2[nH]ccc12)C(=O)N1CCc2cc(C(=O)O)ccc2C1] | 2-{4-(2-cyano-1H-pyrrol-1-yl)-2-[(1H-indol-4-ylsulfonyl)amino]butanoyl}-1,2,3,4-tetrahydroisoquinoline-6-carboxylic acid |
| 452 | 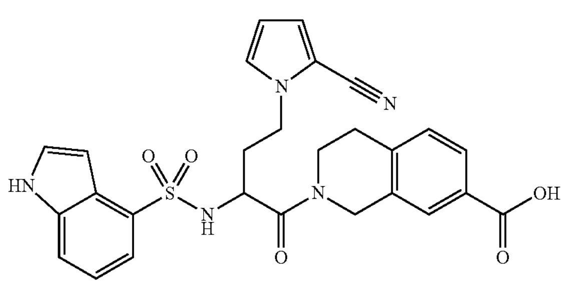 [SMILES: N#Cc1cccn1CCC(NS(=O)(=O)c1cccc2[nH]ccc12)C(=O)N1CCc2ccc(C(=O)O)cc2C1] | 2-{4-(2-cyano-1H-pyrrol-1-yl)-2-[(1H-indol-4-ylsulfonyl)amino]butanoyl}-1,2,3,4-tetrahydroisoquinoline-7-carboxylic acid |

| Example | Structure | Name |
|---|---|---|
| 453 | 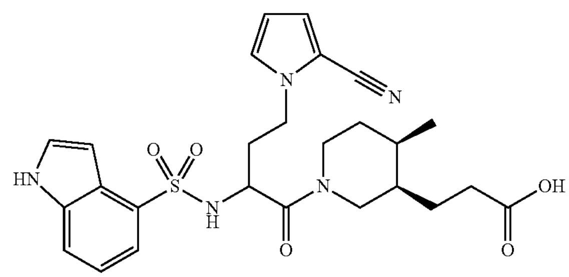 [SMILES: C[C@@H]1CCN(C(=O)C(CCn2cccc2C#N)NS(=O)(=O)c2cccc3[nH]ccc23)C[C@@H]1CCC(=O)O] | 3-[(cis)-1-{4-(2-cyano-1H-pyrrol-1-yl)-2-[(1H-indol-4-ylsulfonyl)amino]butanoyl}-4-methylpiperidin-3-yl]propanoic acid |
| 454 | 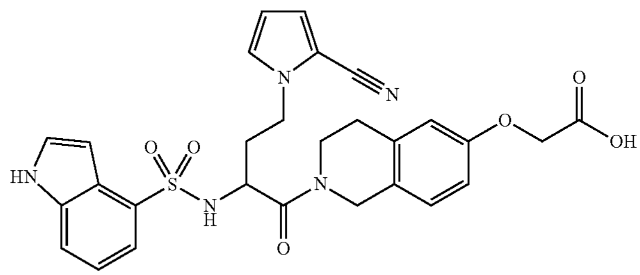 [SMILES: N#Cc1cccn1CCC(NS(=O)(=O)c1cccc2[nH]ccc12)C(=O)N1CCc2cc(OCC(=O)O)ccc2C1] | [(2-{4-(2-cyano-1H-pyrrol-1-yl)-2-[(1H-indol-4-ylsulfonyl)amino]butanoyl}-1,2,3,4-tetrahydroisoquinolin-6-yl)oxy]acetic acid |
| 455 | 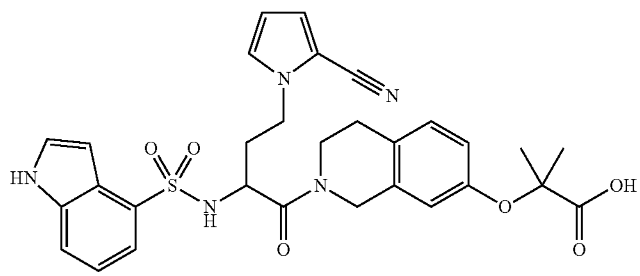 [SMILES: CC(C)(Oc1ccc2c(c1)CN(C(=O)C(CCn1cccc1C#N)NS(=O)(=O)c1cccc3[nH]ccc13)CC2)C(=O)O] | 2-[(2-{4-(2-cyano-1H-pyrrol-1-yl)-2-[(1H-indol-4-ylsulfonyl)amino]butanoyl}-1,2,3,4-tetrahydroisoquinolin-7-yl)oxy]-2-methylpropanoic acid |

In still another embodiment of the invention, there are provided compounds of the formula (I) selected from the group below or a tautomer thereof or a salt thereof:

N-{3-(2-cyano-1H-pyrrol-1-yl)-1-[(4-methylpiperidin-1-yl)carbonyl]propyl}thiophene-3-sulfonamide
N-{3-(2-cyano-1H-pyrrol-1-yl)-1-[(4-methylpiperidin-1-yl)carbonyl]propyl}-2-methylbenzenesulfonamide
N-{3-(2-cyano-1H-pyrrol-1-yl)-1-[(4-methylpiperidin-1-yl)carbonyl]propyl}-3-methylbenzenesulfonamide
N-{3-(2-cyano-1H-pyrrol-1-yl)-1-[(4-methylpiperidin-1-yl)carbonyl]propyl}-4-methylbenzenesulfonamide
N-{1-[(4-methylpiperidin-1-yl)carbonyl]-3-(1H-pyrazol-1-yl)propyl}-1H-indole-4-sulfonamide
N-{3-(2-cyano-1H-pyrrol-1-yl)-1-[(4-methylpiperidin-1-yl)carbonyl]propyl}-2,4-dimethylbenzenesulfonamide
N-{3-(2-cyano-1H-pyrrol-1-yl)-1[(4-methylpiperidin-1-yl)carbonyl]propyl}-2,5-dimethylbenzenesulfonamide
N-{3-(2-cyano-1H-pyrrol-1-yl)-1-[(4-methylpiperidin-1-yl)carbonyl]propyl}-3,5-dimethylbenzenesulfonamide
N-{3-(2-cyano-1H-pyrrol-1-yl)-1-[(4-methylpiperidin-1-yl)carbonyl]propyl}-2-methoxybenzenesulfonamide
N-{3-(2-cyano-1H-pyrrol-1-yl)-1-[(4-methylpiperidin-1-yl)carbonyl]propyl}-3-methoxybenzenesulfonamide
N-{3-(2-cyano-1H-pyrrol-1-yl)-1-[(4-methylpiperidin-1-yl)carbonyl]propyl}-4-methoxybenzenesulfonamide
N-[1-{[4-(hydroxymethyl)piperidin-1-yl]carbonyl}-3-(1H-pyrazol-1-yl)propyl]-1H-indole-4-sulfonamide
N-{3-(2-cyano-1H-pyrrol-1-yl)-1-[(4-methylpiperidin-1-yl)carbonyl]propyl}-1,3,5-trimethyl-1H-pyrazole-4-sulfonamide
N-{3-(2-cyano-1H-pyrrol-1-yl)-1-[(4-methylpiperidin-1-yl)carbonyl]propyl}-4-fluoro-2-methylbenzenesulfonamide
2-chloro-N-{3-(2-cyano-1H-pyrrol-1-yl)-1-[(4-methylpiperidin-1-yl)carbonyl]propyl}benzenesulfonamide
3-chloro-N-{3-(2-cyano-1H-pyrrol-1-yl)-1-[(4-methylpiperidin-1-yl)carbonyl]propyl}benzenesulfonamide
4-chloro-N-{3-(2-cyano-1H-pyrrol-1-yl)-1-[(4-methylpiperidin-1-yl)carbonyl]propyl}benzenesulfonamide
N-{3-(2-cyano-1H-pyrrol-1-yl)-1-[(4-methylpiperidin-1-yl)carbonyl]propyl}-2,5-dimethylthiophene-3-sulfonamide
2-chloro-N-{3-(2-cyano-1H-pyrrol-1-yl)-1-[(4-methylpiperidin-1-yl)carbonyl]propyl}pyridine-3-sulfonamide
N-{3-(2-cyano-1H-pyrrol-1-yl)-1-[(4-methylpiperidin-1-yl)carbonyl]propyl}-1H-indole-3-sulfonamide
2-cyano-N-{3-(2-cyano-1H-pyrrol-1-yl)-1-[(4-methylpiperidin-1-yl)carbonyl]propyl}-5-methylbenzenesulfonamide
N-{3-(2-cyano-1H-pyrrol-1-yl)-1-[(4-methylpiperidin-1-yl)carbonyl]propyl}-1H-indole-4-sulfonamide
N-{3-(2-cyano-1H-pyrrol-1-yl)-1-[(4-methylpiperidin-1-yl)carbonyl]propyl}-1H-indole-6-sulfonamide
N-{3-(2-cyano-1H-pyrrol-1-yl)-1-[(4-methylpiperidin-1-yl)carbonyl]propyl}-1-benzofuran-7-sulfonamide
N-{3-(2-cyano-1H-pyrrol-1-yl)-1-[(4-methylpiperidin-1-yl)carbonyl]propyl}-1H-indazole-4-sulfonamide
N-{3-(2-cyano-1H-pyrrol-1-yl)-1-[(4-methylpiperidin-1-yl)carbonyl]propyl}-1H-indazole-6-sulfonamide
N-{3-(2-cyano-1H-pyrrol-1-yl)-1-[(4-methylpiperidin-1-yl)carbonyl]propyl}-1H-indole-5-sulfonamide N-{3-(3-cyano-1H-pyrazol-1-yl)-1-[(4-methylpiperidin-1-yl)carbonyl]propyl}-1H-indole-4-sulfonamide
N-{3-(5-cyano-1H-pyrazol-1-yl)-1-[(4-methylpiperidin-1-yl)carbonyl]propyl}-1H-indole-4-sulfonamide
N-{3-(2-cyano-1H-pyrrol-1-yl)-1-[(4-methylpiperidin-1-yl)carbonyl]propyl}-2,4,6-trimethylbenzenesulfonamide
3-amino-N-{3-(2-cyano-1H-pyrrol-1-yl)-1-[(4-methylpiperidin-1-yl)carbonyl]propyl}-2,4-dimethylbenzenesulfonamide
N-[3-(2-cyano-1H-pyrrol-1-yl)-1-{[4-(hydroxymethyl)piperidin-1-yl]carbonyl}propyl]-2,5-dimethylbenzenesulfonamide
N-{3-(2-cyano-1H-pyrrol-1-yl)-1-[(4-methylpiperidin-1-yl)carbonyl]propyl}-2-methoxy-4-methylbenzenesulfonamide
N-{3-(2-cyano-1H-pyrrol-1-yl)-1-[(4-methylpiperidin-1-yl)carbonyl]propyl}-2-methoxy-5-methylbenzenesulfonamide
2-chloro-N-{3-(2-cyano-1H-pyrrol-1-yl)-1-[(4-methylpiperidin-1-yl)carbonyl]propyl}-6-methylbenzenesulfonamide
3-chloro-N-{3-(2-cyano-1H-pyrrol-1-yl)-1-[(4-methylpiperidin-1-yl)carbonyl]propyl}-2-methylbenzenesulfonamide
N-{3-(5-chloro-1H-pyrazol-1-yl)-1-[(4-methylpiperidin-1-yl)carbonyl]propyl}-1H-indole-4-sulfonamide
N-{3-(2-cyano-1H-pyrrol-1-yl)-1-[(4-methylpiperidin-1-yl)carbonyl]propyl}naphthalene-1-sulfonamide
N-benzyl-4-(2-cyano-1H-pyrrol-1-yl)-2-{[(2,5-dimethylphenyl)sulfonyl]amino}-N-methylbutanamide
N-{3-(2-cyano-1H-pyrrol-1-yl)-1-[(4-methylpiperidin-1-yl)carbonyl]propyl}isoquinoline-5-sulfonamide
2-chloro-N-{3-(2-cyano-1H-pyrrol-1-yl)-1-[(4-methylpiperidin-1-yl)carbonyl]propyl}-4-fluorobenzenesulfonamide
5-chloro-N-{3-(2-cyano-1H-pyrrol-1-yl)-1-[(4-methylpiperidin-1-yl)carbonyl]propyl}-1,3-dimethyl-1H-pyrazole-4-sulfonamide
N-{3-(2-cyano-1H-pyrrol-1-yl)-1-[(4-methylpiperidin-1-yl)carbonyl]propyl}-1-methyl-1H-indole-4-sulfonamide
N-{3-(2-cyano-1H-pyrrol-1-yl)-1-[(4-methylpiperidin-1-yl)carbonyl]propyl}-1-benzothiophene-3-sulfonamide
N-[3-(5-cyano-1H-pyrazol-1-yl)-1-{[4-(hydroxymethyl)piperidin-1-yl]carbonyl}propyl]-1H-indole-4-sulfonamide
N-[3-(2-cyano-1H-pyrrol-1-yl)-1-{[4-(hydroxymethyl)piperidin-1-yl]carbonyl}propyl]-1H-indazole-4-sulfonamide
methyl 2-[({3-(2-cyano-1H-pyrrol-1-yl)-1-[(4-methylpiperidin-1-yl)carbonyl]propyl}amino)sulfonyl]benzoate
N-{3-(2-cyano-1H-pyrrol-1-yl)-1-[(4-methylpiperidin-1-yl)carbonyl]propyl}-5-ethyl-2-methoxybenzenesulfonamide
N-{1-[(4-methylpiperidin-1-yl)carbonyl]-3-(2-nitro-1H-imidazol-1-yl)propyl}-1H-indole-4-sulfonamide
N-{1-[(4-methylpiperidin-1-yl)carbonyl]-3-(2-nitro-1H-imidazol-1-yl)propyl}-1H-indole-6-sulfonamide
N-{3-(2-cyano-1H-pyrrol-1-yl)-1-[(4-methylpiperidin-1-yl)carbonyl]propyl}-2,5-dimethoxybenzenesulfonamide
N-benzyl-4-(2-cyano-1H-pyrrol-1-yl)-2-[(1H-indol-4-ylsulfonyl)amino]-N-methylbutanamide
2-chloro-N-[3-(2-cyano-1H-pyrrol-1-yl)-1-{[4-(hydroxymethyl)piperidin-1-yl]carbonyl}propyl]-6-methylbenzenesulfonamide
5-chloro-N-{3-(2-cyano-1H-pyrrol-1-yl)-1-[(4-methylpiperidin-1-yl)carbonyl]propyl}-2-methoxybenzenesulfonamide
N-{3-(2-cyano-1H-pyrrol-1-yl)-1-[(4-methylpiperidin-1-yl)carbonyl]propyl}-4-methylnaphthalene-1-sulfonamide
N-[3-(2-cyano-1H-pyrrol-1-yl)-1-{[4-(hydroxymethyl)piperidin-1-yl]carbonyl}propyl]naphthalene-1-sulfonamide
2,3-dichloro-N-{3-(2-cyano-1H-pyrrol-1-yl)-1-[(4-methylpiperidin-1-yl)carbonyl]propyl}benzenesulfonamide
2,5-dichloro-N-{3-(2-cyano-1H-pyrrol-1-yl)-1-[(4-methylpiperidin-1-yl)carbonyl]propyl}benzenesulfonamide
2,6-dichloro-N-{3-(2-cyano-1H-pyrrol-1-yl)-1-[(4-methylpiperidin-1-yl)carbonyl]propyl}benzenesulfonamide
3,5-dichloro-N-{3-(2-cyano-1H-pyrrol-1-yl)-1-[(4-methylpiperidin-1-yl)carbonyl]propyl}benzenesulfonamide
N-{3-(2-cyano-1H-pyrrol-1-yl)-1-[(4-methylpiperidin-1-yl)carbonyl]propyl}-2-(trifluoromethyl)benzenesulfonamide
N-{3-(2-cyano-1H-pyrrol-1-yl)-1-[(trans)-octahydroisoquinolin-2(1H)-ylcarbonyl]propyl}-2,5-dimethylbenzenesulfonamide
2-chloro-N-{3-(2-cyano-1H-pyrrol-1-yl)-1-[(4-methylpiperidin-1-yl)carbonyl]propyl}-4,5-difluorobenzenesulfonamide
N-benzyl-2-{[(2-chloro-6-methylphenyl)sulfonyl]amino}-4-(2-cyano-1H-pyrrol-1-yl)-N-methylbutanamide
5-chloro-N-{3-(2-cyano-1H-pyrrol-1-yl)-1-[(4-methylpiperidin-1-yl)carbonyl]propyl}-3-methyl-1-benzothiophene-2-sulfonamide
N-{4-[({3-(2-cyano-1H-pyrrol-1-yl)-1-[(4-methylpiperidin-1-yl)carbonyl]propyl}amino)sulfonyl]-3-methylphenyl}acetamide
methyl 1-{3-[(1H-indol-4-ylsulfonyl)amino]-4-(4-methylpiperidin-1-yl)-4-oxobutyl}-1H-pyrrole-2-carboxylate
N-{3-(2-cyano-1H-pyrrol-1-yl)-1-[(4-methylpiperidin-1-yl)carbonyl]propyl}-1-methyl-3-(trifluoromethyl)-1H-pyrazole-4-sulfonamide
N-{3-(2-cyano-1H-pyrrol-1-yl)-1-[(4-methylpiperidin-1-yl)carbonyl]propyl}-4-methoxy-2,3,6-trimethylbenzenesulfonamide
N-{3-(2-cyano-1H-pyrrol-1-yl)-1-[(4-methylpiperidin-1-yl)carbonyl]propyl}-5-methyl-2,1,3-benzothiadiazole-4-sulfonamide
2,5-dichloro-N-{3-(2-cyano-1H-pyrrol-1-yl)-1-[(4-methylpiperidin-1-yl)carbonyl]propyl}thiophene-3-sulfonamide
2-bromo-N-[3-(2-cyano-1H-pyrrol-1-yl)-1-(piperidin-1-ylcarbonyl)propyl]-6-methylbenzenesulfonamide
2-bromo-N-{3-(2-cyano-1H-pyrrol-1-yl)-1-[(4-methylpiperidin-1-yl)carbonyl]propyl}benzenesulfonamide
N-{3-(2-cyano-1H-pyrrol-1-yl)-1-[(trans)-octahydroisoquinolin-2(1H)-ylcarbonyl]propyl}-1H-indole-4-sulfonamide
6-chloro-N-{3-(2-cyano-1H-pyrrol-1-yl)-1-[(4-methylpiperidin-1-yl)carbonyl]propyl}imidazo[2,1-b][1,3]thiazole-5-sulfonamide
2,4-dichloro-N-{3-(2-cyano-1H-pyrrol-1-yl)-1-[(4-methylpiperidin-1-yl)carbonyl]propyl}-5-methylbenzenesulfonamide
2,4-dichloro-N-{3-(2-cyano-1H-pyrrol-1-yl)-1-[(4-methylpiperidin-1-yl)carbonyl]propyl}-6-methylbenzenesulfonamide
2-amino-4,6-dichloro-N-{3-(2-cyano-1H-pyrrol-1-yl)-1-[(4-methylpiperidin-1-yl)carbonyl]propyl}benzenesulfonamide
4-amino-2,5-dichloro-N-{3-(2-cyano-1H-pyrrol-1-yl)-1-[(4-methylpiperidin-1-yl)carbonyl]propyl}benzenesulfonamide
4-amino-3,5-dichloro-N-{3-(2-cyano-1H-pyrrol-1-yl)-1-[(4-methylpiperidin-1-yl)carbonyl]propyl}benzenesulfonamide 4-chloro-2,5-dimethyl-N-{1-[(4-methylpiperidin-1-yl)carbonyl]-3-(2-nitro-1H-imidazol-1-yl)propyl}benzenesulfonamide 4-bromo-N-{3-(2-cyano-1H-pyrrol-1-yl)-1-[(4-methylpiperidin-1-yl)carbonyl]propyl}thiophene-3-sulfonamide 2,6-dichloro-N-[3-(2-cyano-1H-pyrrol-1-yl)-1-{[4-(hydroxymethyl)piperidin-1-yl]carbonyl}propyl]benzenesulfonamide 4-amino-3,5-dichloro-N-{3-(2-cyano-1H-imidazol-1-yl)-1-[(4-methylpiperidin-1-yl)carbonyl]propyl}benzenesulfonamide 4-amino-3,5-dichloro-N-{3-(5-cyano-1H-pyrazol-1-yl)-1-[(4-methylpiperidin-1-yl)carbonyl]propyl}benzenesulfonamide 4-chloro-N-{3-(2-cyano-1H-pyrrol-1-yl)-1-[(4-methylpiperidin-1-yl)carbonyl]propyl}naphthalene-1-sulfonamide N-(4-chlorobenzyl)-4-(2-cyano-1H-pyrrol-1-yl)-2-{[(2,5-dimethylphenyl)sulfonyl]amino}-N-methylbutanamide N-{3-(2-cyano-1H-pyrrol-1-yl)-1-[(4-methylpiperidin-1-yl)carbonyl]propyl}-2-(trifluoromethoxy)benzenesulfonamide N-{3-(2-cyano-1H-pyrrol-1-yl)-1-[(4-methylpiperidin-1-yl)carbonyl]propyl}-4-fluoro-2-(trifluoromethyl)benzenesulfonamide 2-chloro-N-{3-(2-cyano-1H-pyrrol-1-yl)-1-[(trans)-octahydroisoquinolin-2(1H)-ylcarbonyl]propyl}-6-methylbenzenesulfonamide methyl 3-[({3-(2-cyano-1H-pyrrol-1-yl)-1-[(4-methylpiperidin-1-yl)carbonyl]propyl}amino)sulfonyl]-4-methoxybenzoate N-benzyl-4-(2-cyano-1H-pyrrol-1-yl)-2-{[(2,6-dichlorophenyl)sulfonyl]amino}-N-methylbutanamide N-{3-(2-cyano-1H-pyrrol-1-yl)-1-[(trans)-octahydroisoquinolin-2(1H)-ylcarbonyl]propyl}naphthalene-1-sulfonamide 2-bromo-N-{3-(2-cyano-1H-pyrrol-1-yl)-1-[(4-methylpiperidin-1-yl)carbonyl]propyl}-6-methylbenzenesulfonamide 4-amino-3,5-dichloro-N-{3-(2-chloro-1H-imidazol-1-yl)-1-[(4-methylpiperidin-1-yl)carbonyl]propyl}benzenesulfonamide N-{3-(5-bromo-1H-pyrazol-1-yl)-1-[(4-methylpiperidin-1-yl)carbonyl]propyl}-1H-indole-4-sulfonamide 2-bromo-N-{3-(2-cyano-1H-pyrrol-1-yl)-1-[(4-methylpiperidin-1-yl)carbonyl]propyl}-4-fluorobenzenesulfonamide 2-acetyl-N-{3-(2-cyano-1H-pyrrol-1-yl)-1-[(4-methylpiperidin-1-yl)carbonyl]propyl}-1,2,3,4-tetrahydroisoquinoline-7-sulfonamide N-{3-(2-cyano-1H-pyrrol-1-yl)-1-[(4-methylpiperidin-1-yl)carbonyl]propyl}-4-(2-methyl-1,3-thiazol-4-yl)benzenesulfonamide 2,4,6-trichloro-N-{3-(2-cyano-1H-pyrrol-1-yl)-1-[(4-methylpiperidin-1-yl)carbonyl]propyl}benzenesulfonamide 2,4-dichloro-6-methyl-N-{1-[(4-methylpiperidin-1-yl)carbonyl]-3-(2-nitro-1H-imidazol-1-yl)propyl}benzenesulfonamide N-{3-(2-cyano-1H-pyrrol-1-yl)-1-[(2-methylpiperidin-1-yl)carbonyl]propyl}-1H-indole-4-sulfonamide 4-amino-3,5-dichloro-N-{1-[(4-methylpiperidin-1-yl)carbonyl]-3-(2-nitro-1H-imidazol-1-yl)propyl}benzenesulfonamide N-(4-chlorobenzyl)-2-{[(2-chloro-6-methylphenyl)sulfonyl]amino}-4-(2-cyano-1H-pyrrol-1-yl)-N-methylbutanamide 2,6-dichloro-N-{3-(2-cyano-1H-pyrrol-1-yl)-1-[(trans)-octahydroisoquinolin-2(1H)-ylcarbonyl]propyl}benzenesulfonamide 5-bromo-N-{3-(2-cyano-1H-pyrrol-1-yl)-1-[(4-methylpiperidin-1-yl)carbonyl]propyl}-2-methoxybenzenesulfonamide N-[3-(5-bromo-1H-pyrazol-1-yl)-1-{[4-(hydroxymethyl)piperidin-1-yl]carbonyl}propyl]-1H-indole-4-sulfonamide 2-bromo-6-methyl-N-{1-[(4-methylpiperidin-1-yl)carbonyl]-3-(2-nitro-1H-imidazol-1-yl)propyl}benzenesulfonamide 2-bromo-N-{3-(2-cyano-1H-pyrrol-1-yl)-1-[(4-methylpiperidin-1-yl)carbonyl]propyl}-4,6-difluorobenzenesulfonamide 2,4,6-trichloro-N-[3-(2-cyano-1H-pyrrol-1-yl)-1-{[4-(hydroxymethyl)piperidin-1-yl]carbonyl}propyl]benzenesulfonamide N-[3-(2-cyano-1H-pyrrol-1-yl)-1-{[4-(hydroxymethyl)piperidin-1-yl]carbonyl}propyl]-1H-indole-6-sulfonamide N-[1-(3,4-dihydroisoquinolin-2(1H)-ylcarbonyl)-3-(2-nitro-1H-imidazol-1-yl)propyl]-4-methylnaphthalene-1-sulfonamide 5-bromo-N-{3-(2-cyano-1H-pyrrol-1-yl)-1-[(4-methylpiperidin-1-yl)carbonyl]propyl}-2,3-dihydro-1-benzofuran-7-sulfonamide N-benzyl-4-(2-cyano-1H-pyrrol-1-yl)-N-methyl-2-{[(2,4,6-trichlorophenyl)sulfonyl]amino}butanamide 4-methyl-N-{3-(2-nitro-1H-imidazol-1-yl)-1-[(trans)-octahydroisoquinolin-2(1H)-ylcarbonyl]propyl}naphthalene-1-sulfonamide 2,6-dichloro-N-{3-(2-nitro-1H-imidazol-1-yl)-1-[(cis)-octahydroisoquinolin-2(1H)-ylcarbonyl]propyl}benzenesulfonamide 2-bromo-N-[3-(2-cyano-1H-pyrrol-1-yl)-1-{[4-(hydroxymethyl)piperidin-1-yl]carbonyl}propyl]-4,6-difluorobenzenesulfonamide 2-amino-4,6-dichloro-N-{3-(2-chloro-1H-imidazol-1-yl)-1-[(cis)-octahydroisoquinolin-2(1H)-ylcarbonyl]propyl}benzenesulfonamide 2-amino-4,6-dichloro-N-{3-(2-chloro-1H-imidazol-1-yl)-1-[(trans)-octahydroisoquinolin-2(1H)-ylcarbonyl]propyl}benzenesulfonamide 4-amino-3,5-dichloro-N-{3-(2-chloro-1H-imidazol-1-yl)-1-[(cis)-octahydroisoquinolin-2(1H)-ylcarbonyl]propyl}benzenesulfonamide 4-amino-3,5-dichloro-N-{3-(2-chloro-1H-imidazol-1-yl)-1-[(trans)-octahydroisoquinolin-2(1H)-ylcarbonyl]propyl}benzenesulfonamide N-benzyl-2-{[(2-bromo-4,6-difluorophenyl)sulfonyl]amino}-4-(2-cyano-1H-pyrrol-1-yl)-N-methylbutanamide N-{3-(2-cyano-1H-pyrrol-1-yl)-1-[(4-methylpiperidin-1-yl)carbonyl]propyl}-2,5-bis(trifluoromethyl)benzenesulfonamide 4-amino-N-{3-(2-bromo-1H-imidazol-1-yl)-1-[(4-methylpiperidin-1-yl)carbonyl]propyl}-3,5-dichlorobenzenesulfonamide 2-amino-4,6-dichloro-N-[1-(3,4-dihydroisoquinolin-2(1H)-ylcarbonyl)-3-(2-nitro-1H-imidazol-1-yl)propyl]benzenesulfonamide 2-{[(4-amino-3,5-dichlorophenyl)sulfonyl]amino}-N-(4-chlorobenzyl)-4-(2-cyano-1H-pyrrol-1-yl)-N-methylbutanamide 2,4,6-trichloro-N-{3-(2-cyano-1H-pyrrol-1-yl)-1-[(trans)-octahydroisoquinolin-2(1H)-ylcarbonyl]propyl}benzenesulfonamide 2-amino-4,6-dichloro-N-{3-(2-nitro-1H-imidazol-1-yl)-1-[(cis)-octahydroisoquinolin-2(1H)-ylcarbonyl]propyl}benzenesulfonamide
2-amino-4,6-dichloro-N-{3-(2-nitro-1H-imidazol-1-yl)-1-[(trans)-octahydroisoquinolin-2(1H)-ylcarbonyl]propyl}benzenesulfonamide
2-bromo-N-{3-(2-cyano-1H-pyrrol-1-yl)-1-[(4-methylpiperidin-1-yl)carbonyl]propyl}-5-(trifluoromethyl)benzenesulfonamide
4-bromo-2,5-dichloro-N-{3-(2-cyano-1H-pyrrol-1-yl)-1-[(4-methylpiperidin-1-yl)carbonyl]propyl}thiophene-3-sulfonamide
tert-butyl 3-[({3-(2-cyano-1H-pyrrol-1-yl)-1-[(4-methylpiperidin-1-yl)carbonyl]propyl}amino)sulfonyl]-2-methyl-1H-indole-1-carboxylate
2-bromo-N-{3-(2-cyano-1H-pyrrol-1-yl)-1-[(trans)-octahydroisoquinolin-2(1H)-ylcarbonyl]propyl}-4,6-difluorobenzenesulfonamide
5-chloro-4-[3-(2-cyano-pyrrol-1-yl)-1-(4-methyl-piperidine-1-carbonyl)-propylsulfamoyl]-indole-1-carboxylic acid tert-butyl ester
4-amino-3,5-dibromo-N-{1-[(4-methylpiperidin-1-yl)carbonyl]-3-(2-nitro-1H-imidazol-1-yl)propyl}benzenesulfonamide
3-chloro-N-{3-(2-cyano-1H-pyrrol-1-yl)-1-[(4-methylpiperidin-1-yl)carbonyl]propyl}-1H-indazole-5-sulfonamide
4-amino-3,5-dichloro-N-{3-(5-chloro-1H-pyrazol-1-yl)-1-[(4-methylpiperidin-1-yl)carbonyl]propyl}benzenesulfonamide
2-amino-4,6-dichloro-N-{3-(2-chloro-1H-imidazol-1-yl)-1-[(4-methylpiperidin-1-yl)carbonyl]propyl}benzenesulfonamide
2-amino-4,6-dichloro-N-{1-[(4-methylpiperidin-1-yl)carbonyl]-3-(2-nitro-1H-imidazol-1-yl)propyl}benzenesulfonamide
N-{3-(2-cyano-1H-pyrrol-1-yl)-1-[(4-methylpiperidin-1-yl)carbonyl]propyl}-1H-pyrrolo[2,3-b]pyridine-4-sulfonamide
3-bromo-N-{3-(2-cyano-1H-pyrrol-1-yl)-1-[(4-methylpiperidin-1-yl)carbonyl]propyl}-1H-pyrrolo[2,3-b]pyridine-4-sulfonamide
2,6-dichloro-N-{3-(2-chloro-1H-imidazol-1-yl)-1-[(4-methylpiperidin-1-yl)carbonyl]propyl}benzenesulfonamide
2,6-dichloro-N-{1-[(4-methylpiperidin-1-yl)carbonyl]-3-(2-nitro-1H-imidazol-1-yl)propyl}benzenesulfonamide
N-{1-[(4-methylpiperidin-1-yl)carbonyl]-3-(2-nitro-1H-imidazol-1-yl)propyl}naphthalene-1-sulfonamide
2,4,6-trimethyl-N-{1-[(4-methylpiperidin-1-yl)carbonyl]-3-(2-nitro-1H-imidazol-1-yl)propyl}benzenesulfonamide
2-chloro-6-methyl-N-{1-[(4-methylpiperidin-1-yl)carbonyl]-3-(2-nitro-1H-imidazol-1-yl)propyl}benzenesulfonamide
4-bromo-2,5-dichloro-N-{1-[(4-methylpiperidin-1-yl)carbonyl]-3-(2-nitro-1H-imidazol-1-yl)propyl}thiophene-3-sulfonamide
4-amino-3,5-dichloro-N-{1-[(4-methylpiperidin-1-yl)carbonyl]-3-(1H-pyrrol-1-yl)propyl}benzenesulfonamide
N-{3-(2-cyano-1H-pyrrol-1-yl)-1-[(4-methyl-3,6-dihydropyridin-1(2H)-yl)carbonyl]propyl}-1H-indole-4-sulfonamide
N-[1-(azepan-1-ylcarbonyl)-3-(2-cyano-1H-pyrrol-1-yl)propyl]-1H-indole-4-sulfonamide
N-[1-(azepan-1-ylcarbonyl)-3-(2-cyano-1H-pyrrol-1-yl)propyl]-1H-indole-6-sulfonamide
N-{3-(2-cyano-1H-pyrrol-1-yl)-1-[(2-methylpiperidin-1-yl)carbonyl]propyl}-1H-indole-6-sulfonamide
N-{3-(2-cyano-1H-pyrrol-1-yl)-1-[(3-methylpiperidin-1-yl)carbonyl]propyl}-1H-indole-4-sulfonamide
N-{3-(2-cyano-1H-pyrrol-1-yl)-1-[(3-methylpiperidin-1-yl)carbonyl]propyl}-1H-indole-6-sulfonamide
N-{3-(2-cyano-1H-pyrrol-1-yl)-1-[(4-oxopiperidin-1-yl)carbonyl]propyl}-1H-indole-4-sulfonamide
N-{3-(2-cyano-1H-pyrrol-1-yl)-1-[(4-methylpiperazin-1-yl)carbonyl]propyl}-1H-indole-4-sulfonamide
N-[3-(2-cyano-1H-pyrrol-1-yl)-1-(1,4-oxazepan-4-ylcarbonyl)propyl]-1H-indole-4-sulfonamide
N-{3-(2-cyano-1H-pyrrol-1-yl)-1-[(3-hydroxypiperidin-1-yl)carbonyl]propyl}-1H-indole-4-sulfonamide
N-{3-(2-cyano-1H-pyrrol-1-yl)-1-[(4-hydroxypiperidin-1-yl)carbonyl]propyl}-1H-indole-4-sulfonamide
N-{3-(2-cyano-1H-pyrrol-1-yl)-1-[(4-fluoropiperidin-1-yl)carbonyl]propyl}-1H-indole-4-sulfonamide
N-[1-(azepan-1-ylcarbonyl)-3-(2-cyano-1H-pyrrol-1-yl)propyl]-2-chloro-6-methylbenzenesulfonamide
2-chloro-N-{3-(2-cyano-1H-pyrrol-1-yl)-1-[(2-methylpiperidin-1-yl)carbonyl]propyl}-6-methylbenzenesulfonamide
2-chloro-N-{3-(2-cyano-1H-pyrrol-1-yl)-1-[(3-methylpiperidin-1-yl)carbonyl]propyl}-6-methylbenzenesulfonamide
N-[1-(6-azaspiro[2.5]oct-6-ylcarbonyl)-3-(2-cyano-1H-pyrrol-1-yl)propyl]-1H-indole-4-sulfonamide
N-[1-(6-azaspiro[2.5]oct-6-ylcarbonyl)-3-(2-cyano-1H-pyrrol-1-yl)propyl]-1H-indole-6-sulfonamide
N-{3-(2-cyano-1H-pyrrol-1-yl)-1-[(5-oxo-1,4-diazepan-1-yl)carbonyl]propyl}-1H-indole-4-sulfonamide
N-[3-(2-cyano-1H-pyrrol-1-yl)-1-{[2-(hydroxymethyl)piperidin-1-yl]carbonyl}propyl]-1H-indole-4-sulfonamide
N-[3-(2-cyano-1H-pyrrol-1-yl)-1-{[3-(hydroxymethyl)piperidin-1-yl]carbonyl}propyl]-1H-indole-4-sulfonamide
N-[3-(2-cyano-1H-pyrrol-1-yl)-1-{[4-(hydroxymethyl)piperidin-1-yl]carbonyl}propyl]-1H-indole-4-sulfonamide
N-[1-(6-azaspiro[2.5]oct-6-ylcarbonyl)-3-(2-cyano-1H-pyrrol-1-yl)propyl]-2-chloro-6-methylbenzenesulfonamide
N-{3-(2-cyano-1H-pyrrol-1-yl)-1-[(4-propylpiperidin-1-yl)carbonyl]propyl}-1H-indole-4-sulfonamide
N-{3-(2-cyano-1H-pyrrol-1-yl)-1-[(4-propylpiperidin-1-yl)carbonyl]propyl}-1H-indole-6-sulfonamide
2,6-dichloro-N-{3-(2-cyano-1H-pyrrol-1-yl)-1-[(3-methylpiperidin-1-yl)carbonyl]propyl}benzenesulfonamide
N-[1-(azepan-1-ylcarbonyl)-3-(2-cyano-1H-pyrrol-1-yl)propyl]-2,6-dichlorobenzenesulfonamide
N-{1-[(4-acetylpiperazin-1-yl)carbonyl]-3-(2-cyano-1H-pyrrol-1-yl)propyl}-1H-indole-4-sulfonamide
N-{3-(2-cyano-1H-pyrrol-1-yl)-1-[(4,4-difluoropiperidin-1-yl)carbonyl]propyl}-1H-indole-4-sulfonamide
N-[3-(2-cyano-1H-pyrrol-1-yl)-1-{[4-(2-hydroxyethyl)piperidin-1-yl]carbonyl}propyl]-1H-indole-4-sulfonamide
N-[3-(2-cyano-1H-pyrrol-1-yl)-1-{[4-(methoxymethyl)piperidin-1-yl]carbonyl}propyl]-1H-indole-4-sulfonamide
N-[3-(2-cyano-1H-pyrrol-1-yl)-1-(3,4-dihydroisoquinolin-2(1H)-ylcarbonyl)propyl]-1H-indole-4-sulfonamide
N-[3-(2-cyano-1H-pyrrol-1-yl)-1-(3,4-dihydroisoquinolin-2(1H)-ylcarbonyl)propyl]-1H-indole-6-sulfonamide
2-chloro-N-{3-(2-cyano-1H-pyrrol-1-yl)-1-[(4-propylpiperidin-1-yl)carbonyl]propyl}-6-methylbenzenesulfonamide
N-{3-(2-cyano-1H-pyrrol-1-yl)-1-[(cis)-octahydroisoquinolin-2(1H)-ylcarbonyl]propyl}-1H-indole-4-sulfonamide
N-{3-(2-cyano-1H-pyrrol-1-yl)-1-[(cis)-octahydroisoquinolin-2(1H)-ylcarbonyl]propyl}-1H-indole-6-sulfonamide
N-[1-(6-azaspiro[2.5]oct-6-ylcarbonyl)-3-(2-cyano-1H-pyrrol-1-yl)propyl]-2,6-dichlorobenzenesulfonamide 2-chloro-N-[3-(2-cyano-1H-pyrrol-1-yl)-1-(3,4-dihydroisoquinolin-2(1H)-ylcarbonyl)propyl]-6-methylbenzenesulfonamide
N-{1-[(4-acetyl-1,4-diazepan-1-yl)carbonyl]-3-(2-cyano-1H-pyrrol-1-yl)propyl}-1H-indole-4-sulfonamide
4-amino-3,5-dichloro-N-{3-(2-cyano-1H-pyrrol-1-yl)-1-[(2-methylpiperidin-1-yl)carbonyl]propyl}benzenesulfonamide
4-amino-3,5-dichloro-N-{3-(2-cyano-1H-pyrrol-1-yl)-1-[(3-methylpiperidin-1-yl)carbonyl]propyl}benzenesulfonamide
4-amino-N-[1-(azepan-1-ylcarbonyl)-3-(2-cyano-1H-pyrrol-1-yl)propyl]-3,5-dichlorobenzenesulfonamide
methyl 1-{4-(2-cyano-1H-pyrrol-1-yl)-2-[(1H-indol-4-ylsulfonyl)amino]butanoyl}piperidine-4-carboxylate
methyl 1-{4-(2-cyano-1H-pyrrol-1-yl)-2-[(1H-indol-6-ylsulfonyl)amino]butanoyl}piperidine-4-carboxylate
N-[3-(2-cyano-1H-pyrrol-1-yl)-1-(1,4-dioxa-8-azaspiro[4.5]dec-8-ylcarbonyl)propyl]-1H-indole-4-sulfonamide
2-{[(2-chloro-6-methylphenyl)sulfonyl]amino}-4-(2-cyano-1H-pyrrol-1-yl)-N-(3-fluorobenzyl)-N-methylbutanamide
2-{[(2-chloro-6-methylphenyl)sulfonyl]amino}-4-(2-cyano-1H-pyrrol-1-yl)-N-(4-fluorobenzyl)-N-methylbutanamide
2-chloro-N-{3-(2-cyano-1H-pyrrol-1-yl)-1-[(cis)-octahydroisoquinolin-2(1H)-ylcarbonyl]propyl}-6-methylbenzenesulfonamide
methyl 1-[2-{[(2-chloro-6-methylphenyl)sulfonyl]amino}-4-(2-cyano-1H-pyrrol-1-yl)butanoyl]piperidine-4-carboxylate
N-[3-(2-cyano-1H-pyrrol-1-yl)-1-{[4-(trifluoromethyl)piperidin-1-yl]carbonyl}propyl]-1H-indole-4-sulfonamide
N-[3-(2-cyano-1H-pyrrol-1-yl)-1-{[4-(trifluoromethyl)piperidin-1-yl]carbonyl}propyl]-1H-indole-6-sulfonamide
4-amino-N-[1-(6-azaspiro[2.5]oct-6-ylcarbonyl)-3-(2-cyano-1H-pyrrol-1-yl)propyl]-3,5-dichlorobenzenesulfonamide
methyl (1-{4-(2-cyano-1H-pyrrol-1-yl)-2-[(1H-indol-4-ylsulfonyl)amino]butanoyl}piperidin-4-ylidene)acetate
2,6-dichloro-N-{3-(2-cyano-1H-pyrrol-1-yl)-1-[(4-propylpiperidin-1-yl)carbonyl]propyl}benzenesulfonamide
methyl (1-{4-(2-cyano-1H-pyrrol-1-yl)-2-[(1H-indol-4-ylsulfonyl)amino]butanoyl}piperidin-2-yl)acetate
methyl (1-{4-(2-cyano-1H-pyrrol-1-yl)-2-[(1H-indol-4-ylsulfonyl)amino]butanoyl}piperidin-3-yl)acetate
methyl (1-{4-(2-cyano-1H-pyrrol-1-yl)-2-[(1H-indol-4-ylsulfonyl)amino]butanoyl}piperidin-4-yl)acetate
3-chloro-N-[3-(2-cyano-1H-pyrrol-1-yl)-1-(5,6-dihydro[1,2,4]triazolo[4,3-a]pyrazin-7(8H)-ylcarbonyl)propyl]-1H-indole-4-sulfonamide
4-amino-3,5-dichloro-N-[3-(2-cyano-1H-pyrrol-1-yl)-1-{[4-(hydroxymethyl)piperidin-1-yl]carbonyl}propyl]benzenesulfonamide
2-{[(2-chloro-6-methylphenyl)sulfonyl]amino}-4-(2-cyano-1H-pyrrol-1-yl)-N-(2-methoxybenzyl)-N-methylbutanamide
2,6-dichloro-N-[3-(2-cyano-1H-pyrrol-1-yl)-1-(3,4-dihydroisoquinolin-2(1H)-ylcarbonyl)propyl]benzenesulfonamide
2-chloro-N-[3-(2-cyano-1H-pyrrol-1-yl)-1-{[4-(trifluoromethyl)piperidin-1-yl]carbonyl}propyl]-6-methylbenzenesulfonamide
N-{3-(2-cyano-1H-pyrrol-1-yl)-1-[(4-phenylpiperazin-1-yl)carbonyl]propyl}-1H-indole-4-sulfonamide
N-{3-(2-cyano-1H-pyrrol-1-yl)-1-[(4-pyrimidin-2-ylpiperazin-1-yl)carbonyl]propyl}-1H-indole-4-sulfonamide
2,6-dichloro-N-{3-(2-cyano-1H-pyrrol-1-yl)-1-[(cis)-octahydroisoquinolin-2(1H)-ylcarbonyl]propyl}benzenesulfonamide
N-[3-(2-cyano-1H-pyrrol-1-yl)-1-{[4-(1,3-thiazol-2-yl)piperazin-1-yl]carbonyl}propyl]-1H-indole-4-sulfonamide
methyl (2E)-3-(1-{4-(2-cyano-1H-pyrrol-1-yl)-2-[(1H-indol-4-ylsulfonyl)amino]butanoyl}piperidin-3-yl)prop-2-enoate
N-[2-(1-{4-(2-cyano-1H-pyrrol-1-yl)-2-[(1H-indol-4-ylsulfonyl)amino]butanoyl}piperidin-4-yl)ethyl]acetamide
4-amino-3,5-dichloro-N-{3-(2-cyano-1H-pyrrol-1-yl)-1-[(4-propylpiperidin-1-yl)carbonyl]propyl}benzenesulfonamide
methyl 3-(1-{4-(2-cyano-1H-pyrrol-1-yl)-2-[(1H-indol-4-ylsulfonyl)amino]butanoyl}piperidin-3-yl)propanoate
methyl 3-(1-{4-(2-cyano-1H-pyrrol-1-yl)-2-[(1H-indol-4-ylsulfonyl)amino]butanoyl}piperidin-4-yl)propanoate
N-[3-(2-cyano-1H-pyrrol-1-yl)-1-(5,6-dihydro[1,2,4]triazolo[4,3-a]pyrazin-7(8H)-ylcarbonyl)propyl]-1H-indole-4-sulfonamide
methyl 1-[4-(2-cyano-1H-pyrrol-1-yl)-2-{[(2,6-dichlorophenyl)sulfonyl]amino}butanoyl]piperidine-4-carboxylate
2-{[(2-chloro-6-methylphenyl)sulfonyl]amino}-4-(2-cyano-1H-pyrrol-1-yl)-N-(2-methoxy-5-methylbenzyl)-N-methylbutanamide
2,6-dichloro-N-[3-(2-cyano-1H-pyrrol-1-yl)-1-{[4-(trifluoromethyl)piperidin-1-yl]carbonyl}propyl]benzenesulfonamide
methyl 4-(1-{4-(2-cyano-1H-pyrrol-1-yl)-2-[(1H-indol-4-ylsulfonyl)amino]butanoyl}piperidin-4-yl)butanoate
methyl 1-[2-{[(4-amino-3,5-dichlorophenyl)sulfonyl]amino}-4-(2-cyano-1H-pyrrol-1-yl)butanoyl]piperidine-4-carboxylate
methyl 2-{4-(2-cyano-1H-pyrrol-1-yl)-2-[(1H-indol-4-ylsulfonyl)amino]butanoyl}-1,2,3,4-tetrahydroisoquinoline-6-carboxylate
2-{4-(2-cyano-1H-pyrrol-1-yl)-2-[(1H-indol-4-ylsulfonyl)amino]butanoyl}-1,2,3,4-tetrahydroisoquinoline-7-carboxylic acid methyl ester
2-{[(2-chloro-6-methylphenyl)sulfonyl]amino}-4-(2-cyano-1H-pyrrol-1-yl)-N-[4-(1H-imidazol-1-yl)benzyl]-N-methylbutanamide
3-[(cis)-1-{4-(2-cyano-1H-pyrrol-1-yl)-2-[(1H-indol-4-ylsulfonyl)amino]butanoyl}-4-methylpiperidin-3-yl]propanoic acid
2-{[(2-chloro-6-methylphenyl)sulfonyl]amino}-4-(2-cyano-1H-pyrrol-1-yl)-N-methyl-N-(3-pyridin-3-ylbenzyl)butanamide
2-{[(2-chloro-6-methylphenyl)sulfonyl]amino}-4-(2-cyano-1H-pyrrol-1-yl)-N-methyl-N-(4-pyrimidin-5-ylbenzyl)butanamide
2-{[(2-chloro-6-methylphenyl)sulfonyl]amino}-4-(2-cyano-1H-pyrrol-1-yl)-N-methyl-N-(3-pyrimidin-5-ylbenzyl)butanamide
2-{[(2-chloro-6-methylphenyl)sulfonyl]amino}-4-(2-cyano-1H-pyrrol-1-yl)-N-methyl-N-[3-(5-methyl-1,2,4-oxadiazol-3-yl)benzyl]butanamide
4-amino-3,5-dichloro-N-{3-(2-nitro-1H-imidazol-1-yl)-1-[(trans)-octahydroisoquinolin-2(1H)-ylcarbonyl]propyl}benzenesulfonamide
N-[3-(2-cyano-1H-pyrrol-1-yl)-1-(3,6-dihydropyridin-1(2H)-ylcarbonyl)propyl]-1H-indole-4-sulfonamide
N-[3-(2-cyano-1H-pyrrol-1-yl)-1-(piperidin-1-ylcarbonyl)propyl]-1H-indole-4-sulfonamide
N-[3-(2-cyano-1H-pyrrol-1-yl)-1-(piperidin-1-ylcarbonyl)propyl]-1H-indole-6-sulfonamide 2-chloro-N-[3-(2-cyano-1H-pyrrol-1-yl)-1-(piperidin-1-yl-carbonyl)propyl]-6-methylbenzenesulfonamide
N-{3-(2-cyano-1H-pyrrol-1-yl)-1-[(4-oxoazepan-1-yl)carbonyl]propyl}-1H-indole-4-sulfonamide
N-[3-(2-cyano-1H-pyrrol-1-yl)-1-{[(trans)-3-hydroxy-4-methylpiperidin-1-yl]carbonyl}propyl]-1H-indole-4-sulfonamide
N-{3-(2-cyano-1H-pyrrol-1-yl)-1-[(3,4-dimethylpiperidin-1-yl)carbonyl]propyl}-1H-indole-4-sulfonamide
N-benzyl-4-(2-cyano-1H-pyrrol-1-yl)-2-[(1H-indol-6-ylsulfonyl)amino]-N-methylbutanamide
N-[3-(2-cyano-1H-pyrrol-1-yl)-1-(5,6-dihydro-imidazo[4,3-a]pyrazin-7(8H)-ylcarbonyl)propyl]-1H-indole-4-sulfonamide
4-amino-3,5-dichloro-N-[3-(2-cyano-1H-pyrrol-1-yl)-1-(piperidin-1-ylcarbonyl)propyl]benzenesulfonamide
N-[3-(2-cyano-1H-pyrrol-1-yl)-1-(6,7-dihydrothieno[3,2-c]pyridin-5(4H)-ylcarbonyl)propyl]-1H-indole-4-sulfonamide
N-{3-(2-cyano-1H-pyrrol-1-yl)-1-[(trans)-octahydroisoquinolin-2(1H)-ylcarbonyl]propyl}-1H-indole-6-sulfonamide
4-amino-3,5-dichloro-N-{3-(2-cyano-1H-pyrrol-1-yl)-1-[(4-methylenepiperidin-1-yl)carbonyl]propyl}benzenesulfonamide
1H-indole-4-sulfonic acid [342-cyano-pyrrol-1-yl)-1-(7-cyano-3,4-dihydro-1H-isoquinoline-2-carbonyl)-propyl]-amide
N-{3-(2-cyano-1H-pyrrol-1-yl)-1-[(4-phenylpiperidin-1-yl)carbonyl]propyl}-1H-indole-4-sulfonamide
2-{[(4-amino-3,5-dichlorophenyl)sulfonyl]amino}-N-benzyl-4-(2-cyano-1H-pyrrol-1-yl)-N-methylbutanamide
ethyl 1-[2-{[(2-chloro-6-methylphenyl)sulfonyl]amino}-4-(2-cyano-1H-pyrrol-1-yl)butanoyl]piperidine-3-carboxylate
N-[3-(2-cyano-1H-pyrrol-1-yl)-1-{[4-(3-methyl-1,2,4-oxadiazol-5-yl)piperidin-1-yl]carbonyl}propyl]-1H-indole-4-sulfonamide
4-amino-3,5-dichloro-N-[3-(2-cyano-1H-pyrrol-1-yl)-1-(3,4-dihydroisoquinolin-2(1H)-ylcarbonyl)propyl]benzenesulfonamide
1H-indole-4-sulfonic acid [3-(2-cyano-pyrrol-1-yl)-1-(7-nitro-3,4-dihydro-1H-isoquinoline-2-carbonyl)-propyl]-amide
4-amino-3,5-dichloro-N-{3-(2-cyano-1H-pyrrol-1-yl)-1-[(cis)-octahydroisoquinolin-2(1H)-ylcarbonyl]propyl}benzenesulfonamide
4-amino-3,5-dichloro-N-{3-(2-cyano-1H-pyrrol-1-yl)-1-[(trans)-octahydroisoquinolin-2(1H)-ylcarbonyl]propyl}benzenesulfonamide
1H-indole-4-sulfonic acid [3-(2-cyano-pyrrol-1-yl)-1-(8-nitro-1,3,4,5-tetrahydro-2-benzazepine-2-carbonyl)-propyl]-amide
4-amino-3,5-dichloro-N-[3-(2-cyano-1H-pyrrol-1-yl)-1-{[4-(trifluoromethyl)piperidin-1-yl]carbonyl}propyl]benzenesulfonamide
2-{4-(2-cyano-1H-pyrrol-1-yl)-2-[(1H-indol-4-ylsulfonyl)amino]butanoyl}-1,2,3,4-tetrahydroisoquinoline-7-sulfonamide
2-{4-(2-cyano-1H-pyrrol-1-yl)-2-[(1H-indol-4-ylsulfonyl)amino]butanoyl}-1,2,3,4-tetrahydroisoquinoline-7-sulfonic acid
2-{4-(2-cyano-1H-pyrrol-1-yl)-2-[(1H-indol-4-ylsulfonyl)amino]butanoyl}-N-methyl-1,2,3,4-tetrahydroisoquinoline-7-sulfonamide
2-{4-(2-cyano-1H-pyrrol-1-yl)-2-[(1H-indol-4-ylsulfonyl)amino]butanoyl}-N,N-dimethyl-1,2,3,4-tetrahydroisoquinoline-7-sulfonamide
2-{4-(2-cyano-1H-pyrrol-1-yl)-2-[(1H-indol-4-ylsulfonyl)amino]butanoyl}-N-methyl-1,2,3,4-tetrahydroisoquinoline-7-carboxamide
2-{4-(2-cyano-1H-pyrrol-1-yl)-2-[(1H-indol-4-ylsulfonyl)amino]butanoyl}-N,N-dimethyl-1,2,3,4-tetrahydroisoquinoline-7-carboxamide
N-[3-(2-cyano-1H-pyrrol-1-yl)-1-{[7-(morpholin-4-ylcarbonyl)-3,4-dihydroisoquinolin-2(1H)-yl]carbonyl}propyl]-1H-indole-4-sulfonamide
4-amino-3,5-dichloro-N-{3-(2-cyano-1H-pyrrol-1-yl)-1-[(4-methylcyclohexyl)carbonyl]propyl}benzenesulfonamide
N-[3-(2-cyano-1H-pyrrol-1-yl)-1-({4-[(E/Z)-(methoxyimino)methyl]piperidin-1-yl}carbonyl)propyl]-1H-indole-4-sulfonamide
1-acetyl-N-{3-(2-cyano-1H-pyrrol-1-yl)-1-[(4-methylpiperidin-1-yl)carbonyl]propyl}-1H-indole-4-sulfonamide
tert-butyl 4-[({3-(2-cyano-1H-pyrrol-1-yl)-1-[(4-methylpiperidin-1-yl)carbonyl]propyl}amino)sulfonyl]-1H-indole-1-carboxylate
N-{3-(2-cyano-1H-pyrrol-1-yl)-1-[(4-methylpiperidin-1-yl)carbonyl]propyl}-N-methyl-1H-indole-4-sulfonamide
4-{4-(2-cyano-1H-pyrrol-1-yl)-2-[(1H-indol-4-ylsulfonyl)amino]butanoyl}-1,4-diazepane-1-carboxamide
N-{3-(2-cyano-1H-pyrrol-1-yl)-1-[(4-glycoloyl-1,4-diazepan-1-yl)carbonyl]propyl}-1H-indole-4-sulfonamide
2-chloro-N-{3-(2-cyano-1H-pyrrol-1-yl)-1-[(4-methylpiperidin-1-yl)carbonyl]propyl}-4-(1H-tetrazol-5-yl)benzenesulfonamide
4-amino-3,5-dichloro-N-{3-(2-chloro-1H-pyrrol-1-yl)-1-[(4-methylpiperidin-1-yl)carbonyl]propyl}benzenesulfonamide
3-bromo-N-{3-(2-cyano-1H-pyrrol-1-yl)-1-[(4-methylpiperidin-1-yl)carbonyl]propyl}-1H-indole-4-sulfonamide
3-cyano-N-{3-(2-cyano-1H-pyrrol-1-yl)-1-[(4-methylpiperidin-1-yl)carbonyl]propyl}-1H-indole-4-sulfonamide
N-{3-(2-cyano-1H-pyrrol-1-yl)-1-[(4-methylpiperidin-1-yl)carbonyl]propyl}-2-oxoindoline-4-sulfonamide
N-{3-(3-bromo-2-cyano-1H-pyrrol-1-yl)-1-[(4-methylpiperidin-1-yl)carbonyl]propyl}-2-oxoindoline-4-sulfonamide
N-{3-(2-cyano-1H-pyrrol-1-yl)-1-[(4-methylpiperidin-1-yl)carbonyl]propyl}-3-formyl-1H-indole-4-sulfonamide
N-{3-(2-cyano-1H-pyrrol-1-yl)-1-[(4-methylpiperidin-1-yl)carbonyl]propyl}-1H-indole-7-sulfonamide
N-{3-(2-cyano-1H-pyrrol-1-yl)-1-[(4-methylpiperidin-1-yl)carbonyl]propyl}-2-methyl-1H-indole-3-sulfonamide
N-{3-(2-cyano-1H-pyrrol-1-yl)-1-[(4-methylpiperidin-1-yl)carbonyl]propyl}-5-fluoro-1H-indole-4-sulfonamide
N-{3-(2-cyano-1H-pyrrol-1-yl)-1-[(4-methylpiperidin-1-yl)carbonyl]propyl}-5-fluoro-1H-indole-6-sulfonamide
5-chloro-N-{3-(2-cyano-1H-pyrrol-1-yl)-1-[(4-methylpiperidin-1-yl)carbonyl]propyl}-1H-indole-4-sulfonamide
5-chloro-N-{3-(2-cyano-1H-pyrrol-1-yl)-1-[(4-methylpiperidin-1-yl)carbonyl]propyl}-1H-indole-6-sulfonamide
5-chloro-1H-indole-6-sulfonic acid [3-(2-cyano-pyrrol-1-yl)-1-(5,6-dihydro-8H-[1,2,4]triazolo[4,3-a]pyrazine-7-carbonyl)-propyl]-amide
ethyl 3-{4-[({3-(2-cyano-1H-pyrrol-1-yl)-1-[(4-methylpiperidin-1-yl)carbonyl]propyl}amino)sulfonyl]-1H-indol-3-yl}propanoate
N-{3-(2-cyano-1H-pyrrol-1-yl)-1-[(4-methylpiperidin-1-yl)carbonyl]propyl}-5-methyl-2,3-dihydro-1-benzofuran-7-sulfonamide 3-chloro-N-{3-(2-cyano-1H-pyrrol-1-yl)-1-[(4-methylpip-eridin-1-yl)carbonyl]propyl}-1H-indole-6-sulfonamide
3-chloro-N-{3-(2-cyano-1H-pyrrol-1-yl)-1-[(4-methylpip-eridin-1-yl)carbonyl]propyl}-1H-indole-4-sulfonamide
3-chloro-N-{3-(5-cyano-1H-pyrazol-1-yl)-1-[(4-methylpip-eridin-1-yl)carbonyl]propyl}-1H-indole-4-sulfonamide
methyl 1-[2-{[(3-chloro-1H-indol-4-yl)sulfonyl]amino}-4-(2-cyano-1H-pyrrol-1-yl)butanoyl]piperidine-4-carboxylate
3-chloro-N-[3-(2-cyano-1H-pyrrol-1-yl)-1-{[4-(hydroxymethyl)piperidin-1-yl]carbonyl}propyl]-1H-indole-4-sulfonamide
(2E)-3-(1-[4-(2-cyano-1H-pyrrol-1-yl)-2-[(1H-indol-4-yl-sulfonyl)amino]butanoyl]piperidin-3-yl)prop-2-enoic acid
3-(1-[4-(2-cyano-1H-pyrrol-1-yl)-2-[(1H-indol-4-ylsulfo-nyl)amino]butanoyl]piperidin-3-yl)propanoic acid
4-(1-[4-(2-cyano-1H-pyrrol-1-yl)-2-[(1H-indol-4-ylsulfo-nyl)amino]butanoyl]piperidin-4-yl)butanoic acid
4-(1-[4-(2-cyano-1H-pyrrol-1-yl)-2-[(1H-indol-4-ylsulfo-nyl)amino]butanoyl]piperidin-3-yl)butanoic acid
2-[4-(2-cyano-1H-pyrrol-1-yl)-2-[(1H-indol-4-ylsulfonyl)amino]butanoyl]-1,2,3,4-tetrahydroisoquinoline-6-car-boxylic acid
2-[4-(2-cyano-1H-pyrrol-1-yl)-2-[(1H-indol-4-ylsulfonyl)amino]butanoyl]-1,2,3,4-tetrahydroisoquinoline-7-car-boxylic acid
3-[(cis)-1-{4-(2-cyano-1H-pyrrol-1-yl)-2-[(1H-indol-4-yl-sulfonyl)amino]butanoyl}-4-methylpiperidin-3-yl]pro-panoic acid
2-[(2-{4-(2-cyano-1H-pyrrol-1-yl)-2-[(1H-indol-4-ylsulfo-nyl)amino]butanoyl}-1,2,3,4-tetrahydroisoquinolin-7-yl)oxy]-2-methylpropanoic acid In all the compounds disclosed in this application, in the event the nomenclature is in conflict with the structure, it shall be understood that the compound is defined by the structure.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-6}$ alkoxy" is a $C_{1-4}$alkyl that contain an oxygen atom, such as methoxy, ethoxy, propoxy, or butoxy.

The term "$C_{1-10}$-alkyl" (including those which are part of other groups) refers to branched and unbranched alkyl groups with 1 to 10 carbon atoms, by the term "$C_{1-6}$-alkyl" accordingly means branched and unbranched alkyl groups with 1 to 6 carbon atoms. "$C_{1-4}$-alkyl" accordingly denotes branched and unbranched alkyl groups with 1 to 4 carbon atoms. Alkyl groups with 1 to 4 carbon atoms are preferred. Examples include: methyl, ethyl, n-propyl, iso-propyl, n-butyl, iso-butyl, sec-butyl, tert-butyl, n-pentyl, iso-pentyl, neo-pentyl or hexyl. Optionally the abbreviations Me, Et, n-Pr, i-Pr, n-Bu, i-Bu, t-Bu, etc. may also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{2-6}$-alkenyl" (including those which are part of other groups) refers to branched and unbranched alkenyl groups with 2 to 6 carbon atoms and by the term "$C_{2-4}$-alkenyl" refers to branched and unbranched alkenyl groups with 2 to 4 carbon atoms, provided that they have at least one double bond. Alkenyl groups with 2 to 4 carbon atoms are preferred. Examples include: ethenyl or vinyl, propenyl, butenyl, pentenyl, or hexenyl. Unless stated otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkynyl" (including those which are part of other groups) refers to branched and unbranched alkynyl groups with 2 to 6 carbon atoms and by the term "$C_{2-4}$-alkynyl" refers to branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl or hexynyl. Unless stated otherwise, the definitions propynyl, butynyl, pentynyl and hexynyl include all the possible isomeric forms of the groups in question. Thus for example propynyl includes 1-propynyl and 2-propynyl, butynyl includes 1,2- and 3-butynyl, 1-methyl-1-propynyl, 1-methyl-2-propynyl etc.

The term "cycloalkyl" shall be understood to mean an aliphatic hydrocarbon radical containing from three to twelve carbon atoms. Cycloalkyls include hydrocarbon rings containing from three to ten carbon atoms. These cycloalkyls may be either aromatic or non-aromatic ring systems. The non-aromatic ring systems may be mono- or polyunsaturated. Preferred cycloalkyls include, but are not limited to, cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl, and benzocycloheptenyl. Certain terms for cycloalkyl, such as cyclobutanyl and cyclobutyl, shall be used interchangeably.

The term "heterocycle" refers to a stable, nonaromatic, 4-8 membered (but preferably 5 or 6 membered) monocyclic or nonaromatic, 8-11 membered, bicyclic heterocycle radical that may be either saturated or unsaturated. Each heterocycle consists of carbon atoms and at least one, i.e., 1-4, heteroatoms chosen from, e.g., nitrogen, oxygen, or sulfur. The heterocycle may be attached by any atom of the cycle that results in the creation of a stable structure. Unless otherwise stated, heterocycles include, but are not limited to, for example, aziridinyl, azetidinyl, pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, 1-oxo-lambda-4-thiomorpholinyl, 13-oxa-11-aza-tricyclo[7.3.1.0-2,7]trideca-2,4,6-triene, tetrahydropyranyl, 2-oxo-2H-pyranyl, tetrahydrofuranyl, 1,3-dioxolanone, 1,3-dioxanone, 1,4-dioxanyl, 8-oxa-3-aza-bicyclo[3.2.1]octanyl, 2-oxa-5-aza-bicyclo[2.2.1]heptanyl, 2-thia-5-aza-bicyclo[2.2.1]heptanyl, piperidinonyl, tetrahydropyrimidonyl, pentamethylene sulfide, pentamethylene sulfoxide, pentamethylene sulfone, tetramethylene sulfide, tetramethylene sulfoxide, and tetramethylene sulfone.

The term "heteroaryl" shall be understood to mean an aromatic 5-8 membered monocyclic or 8-11 membered bicyclic ring containing 1-4 heteroatoms, such as N, O, and S. Unless otherwise stated, such heteroaryls include thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl, and imidazo[4,5-b]pyridinyl.

In all alkyl groups or carbon chains, one or more carbon atoms can be optionally replaced by heteroatoms, such as O, S, or N. It shall be understood that, if N is not substituted, then it is NH. It shall also be understood that heteroatoms may replace either terminal carbon atoms or internal carbon atoms within a branched or unbranched carbon chain. Such groups can be substituted as herein above described by groups, such as oxo, to result in definitions, such as, but not limited to, alkoxycarbonyl, acyl, amido, and thioxo.

The term "aryl" shall be understood to mean aromatic cycloalkyl or heteroaryl as defined herein. Each aryl unless otherwise specified includes it's partially or fully hydrogenated derivative. For example, quinolinyl may include decahydroquinolinyl and tetrahydroquinolinyl, and naphthyl may include its hydrogenated derivatives, such as tetrahydranaphthyl. Other partially or fully hydrogenated derivatives of the aryl compounds described herein will be apparent to one of ordinary skill in the art.

Terms that are analogs of the above cyclic moieties, such as aryloxy or heteroaryl amine, shall be understood to mean an aryl, heteroaryl, and/or heterocycle as defined above attached to its respective group.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used herein shall be understood to mean bromine, chlorine, fluorine or iodine. The definitions "partially or fully halogenated" and "substituted by one or more halogen atoms" include, for example, mono-, di-, or tri-halo derivatives on one or more carbon atoms. For alkyl, non-limiting examples would be —$CH_2CHF_2$, —$CF_3$, etc.

The term "ureido" means the general formula of either $C(O)NR^xR^y$ or $NHC(O)R^x$.

The term "carbamoyl" means the general formula $C(O)NR^xR^y$ or $NHC(O)R^x$.

The compounds of the invention are only those which are contemplated to be chemically stable as will be appreciated by those skilled in the art. For example, a compound that would have a dangling valency or carbanion is not a compound contemplated by the present invention.

The invention includes pharmaceutically acceptable derivatives of compounds of formula (I). A "pharmaceutically acceptable derivative" refers to any pharmaceutically acceptable salt or ester, or any other compound that, upon administration to a patient, is capable of providing (directly or indirectly) a compound useful for the invention, or a pharmacologically active metabolite, or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric, and benzenesulfonic acids. Other acids, such as oxalic acid, while not themselves pharmaceutically acceptable per se, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium, and N—(C1-C4 alkyl)4+ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation, and reduction. Specifically, when a prodrug is administered to a patient, the prodrug may be transformed into a compound disclosed hereinabove, thereby imparting the desired pharmacological effect.

General Synthetic Methods

The invention additionally provides for methods for making the compounds of the formula (I). The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Reaction progress may be monitored by conventional methods such as thin layer chromatography (TLC) or mass spectrometry (MS). Intermediates and products may be purified by methods known in the art, including column chromatography, HPLC, or recrystallization.

Compounds of formula (I) having $R^3$=—$NR^5R^6$ may be prepared as illustrated in Scheme 1. Aminobutyrolactone II is treated with HBr in HOAc to provide the HBr salt of the bromo amino acid III. Esterification, for example by treatment with MeOH and acetyl chloride, thionyl chloride or HCl gas, followed by protection of the amine with a suitable protecting group such as the Boc group shown provides the protected amino ester IV. Treatment with the salt of a desired heterocycle in a suitable solvent such as DMF provides V. Removal of the amine protecting group, for example by treatment with HCl or TFA for the Boc-protecting group, provides amino ester VI. Treatment with a sulfonyl chloride bearing the desired $R^1$ in the presence of a suitable base such as triethylamine or 1-methylmorpholine provides sulfonamide VII. Hydrolysis of the ester, for example with aqueous base, followed by treatment of the resulting acid with a suitable coupling agent such as a dialkylcarbodimide with HOBt, or HATU with a suitable base such as i-Pr$_2$NEt and the desired amine HN$R^5R^6$ provides the desired compound of formula (I) ($R^3$=—$NR^5R^6$).

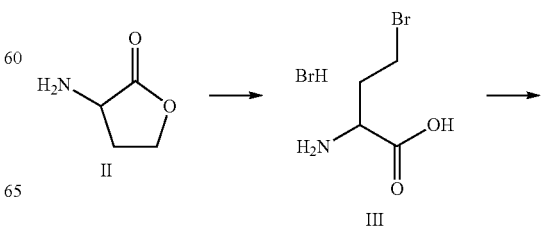

Scheme 1

199

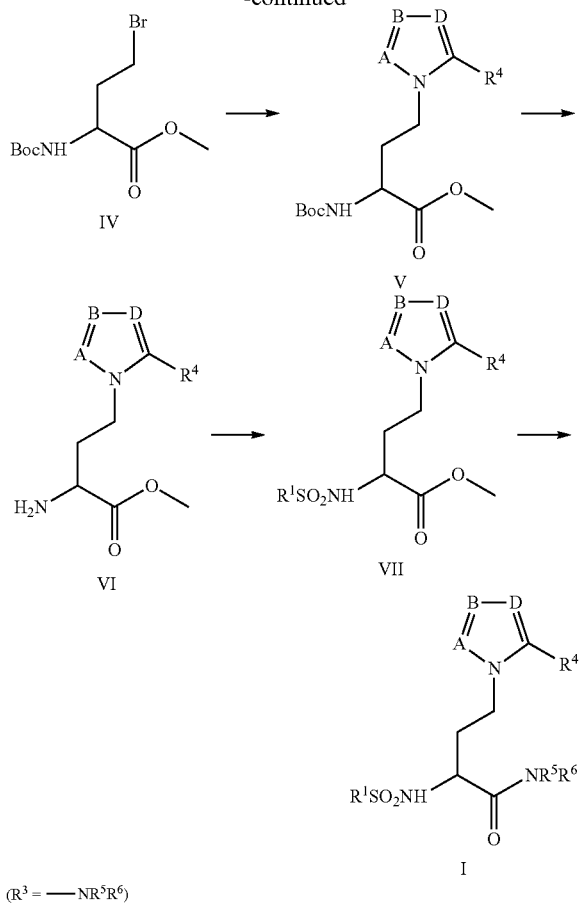

A variation of the above method is illustrated in Scheme 2. The protected amino ester V may be first hydrolyzed to the carboxylic acid VIII, for example by treatment with aqueous base, followed by the coupling reaction with the desired amine as described above to provide IX. This may then be followed by removal of the protected amine as described above and reaction with the desired sulfonyl chloride to provide the desired compound of formula (I) ($R^3$=—$NR^5R^6$).

200

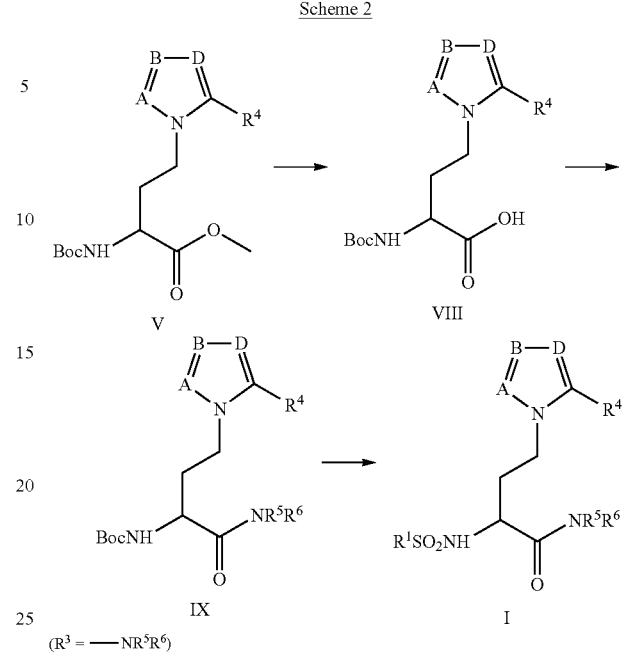

An alternative method to obtain compounds of formula (I) ($R^3$=$NR^5R^6$) is illustrated in Scheme 3 Aminobutyrolactone may be first protected with an amine protecting group such a Boc group as described above, followed by treatment with the desired amine $HNR^5R^6$ while heating to provide the amide X. Intermediate X may be treated with a chlorinating agent such as PS—PPh$_3$ in CCl$_4$ to provide XI, followed by treatment with the salt of the desired heterocycle in a suitable solvent such as DMF to provide XII. Alternatively, XII may be formed directly by treatment of X with DEAD, PPh$_3$, a suitable amine such as Et$_3$N and the desired heterocycle. The Boc protecting group may then be removed from XII as described above, followed by reaction of the resulting amine with a sulfonyl chloride bearing $R_1$ as described above to provide the desired compound of formula (I) ($R^3$=—$NR^5R^6$).

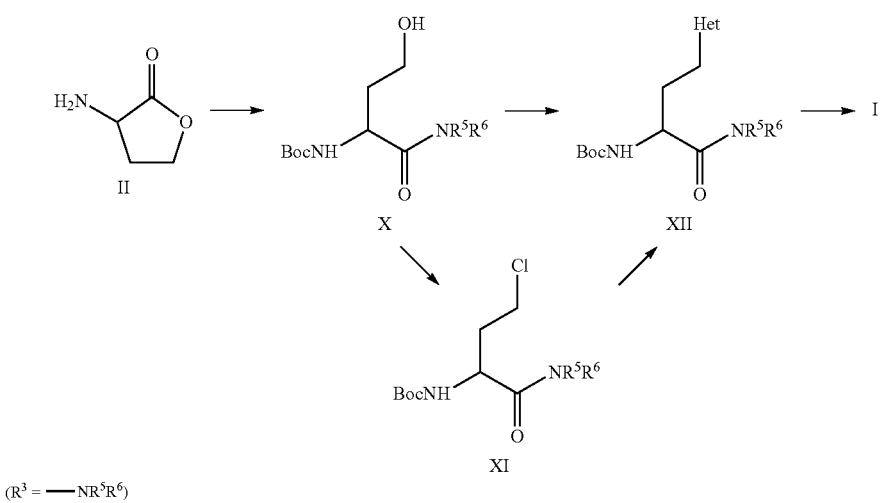

The R¹SO₂Cl intermediates used in the above schemes may be prepared by methods known in the art, for example by treatment of R₁ with chlorosulfonic acid, by treatment of R¹Br with t-BuLi followed by SO₂ and N-chlorosuccinimide or SO₂Cl₂, or by treatment of R¹NH₂ with NaNO2 followed by CuCl or CuCl₂ and so2 or SO₃H₂ in acetic acid.

A method to prepare compounds of formula (I) (R³=cycloalkyl) is illustrated in Scheme 4. Intermediate XIII may be prepared from Intermediate VIII by the coupling reaction with the N-methyl methoxylamine as described above to provide Intermediate XIII Intermediate XIII may be treated with a cycloalkyl Grignard reagent to provide the desired compound of formula (I) (R³=cycloalkyl).

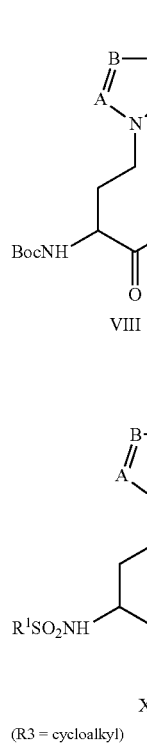

Scheme 4

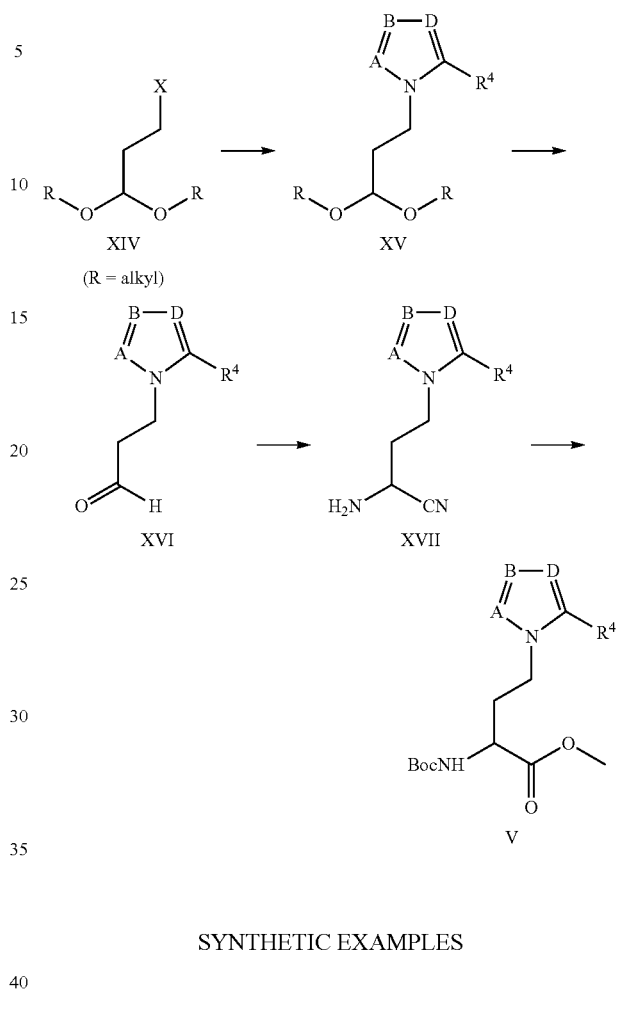

Scheme 5

An additional method that may be used to prepare compounds of formula (I) is illustrated in Scheme 5. Treatment of a 3-halopropionaldehyde dialkylacetal (XIV) with a salt of the desired heterocycle bearing R⁴, in a suitable solvent such as DMF provides XV. Alternatively, XV may be formed by reaction of XIV with the desired heterocycle in the presence of DEAD, PPh₃, and a suitable amine such as triethylamine. If R⁴ is H, it may be converted to a halogen by treatment with an alkyl lithium reagent such as n-BuLi, followed by treatment with an electrophilic halogenating agent such as hexachloroethane or bromine The acetal may be removed with aqueous acid to provide XVI, which may in turn undergo a Strecker reaction to provide XVII, for example, by treatment with TMSCN, ZnI₂, and ammonia. Compound V may then be prepared by hydrolysis of the nitrile of XVII, for example in 6 N HCl, followed by esterification, for example with EDC, HOBt, and MeOH, and then by treatment with Boc₂O. Intermediate V may be used to prepare compounds of formula (I) as illustrated in Scheme 1.

SYNTHETIC EXAMPLES

| Abbreviations: | |
|---|---|
| Boc | tert-butyloxycarbonyl |
| dba | dibenzylideneacetone |
| DCE | dichloroethane |
| DMAP | 4-(dimethylamino)pyridine |
| DMA | dimethylacetamide |
| DMF | dimethylformamide |
| dppf | 1,1'-bisdiphenylphosphinoferrocene |
| EDC | 1-(3-dimethylaminopropyl)-3-ethylcarbodiimide hydrochloride |
| HATU | O-(-7-azabenzotriazol-1-yl)-N,N,N',N'-tetramethyluronium hexafluorophosphate |
| HOBt | 1-hydroxybenzotriazole |
| MeCN | acetonitrile |
| MP- | macroporous polystyrene support |
| NBS | N-bromosuccinimide |
| NCS | N-chlorosuccinimide |
| NMM | N-methyl morpholine |
| PS- | gel-form polystyrene support |
| rt | room temperature |
| TFA | trifluoroacetic acid |
| TMS | trimethylsilyl |

I-001: 4-amino-3,5-dichlorosulfonyl chloride

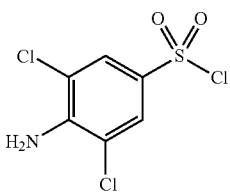 [SMILES: Nc1c(Cl)cc(S(=O)(=O)Cl)cc1Cl]

To 43 mL of stirring chlorosulfonic acid (640 mmol) at 20° C. is added 26 g (160 mmol) of 2,6-dichloroaniline at such a rate that the reaction temperature does not exceed 40° C. When the addition is complete, the mixture is heated at 120° C. for 1 hour, and then cooled to rt. The viscous liquid is poured slowly into 200 mL of stirring ice water immersed in an ice/water bath. The resulting solid is filtered, sucked dry, and then is washed with ice-cold water and cold hexanes. The mixture is dried in an oven overnight to provide I-001 as a light-gray powder.

I-002: 3-amino-2,4-dimethylsulfonyl chloride is prepared from 2,6-dimethylaniline in the same manner as I-001, with purification by flash chromatography (0-75% EtOAc in hexanes).

I-003: 2-oxo-2,3-dihydro-1H-indole-5-sulfonyl chloride

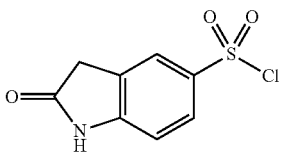 [SMILES: O=C1Cc2cc(S(=O)(=O)Cl)ccc2N1]

Oxindole (2.0 g, 15 mmol) is added slowly to 5.0 mL (75 mmol) of chlorosulfonic acid at 0° C. The mixture is stirred at 0° C. until gas evolution slows. The mixture is warmed first to rt, then to 50° C. until the gas evolution stops (40 min). The mixture is cooled to rt, then poured over chipped ice. The resulting precipitate is filtered and washed with cold water and hexanes, and then dried to provide 3.0 g (86%) of I-003.

I-004: 3-chloro-1H-indazole-5-sulfonyl chloride and I-005: 3-chloro-1H-indazole-7-sulfonyl chloride

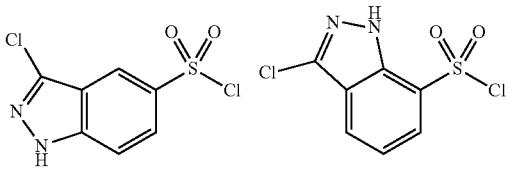

3-Chloroindazole (0.50 g, 3.3 mmol) is added slowly to 1.1 mL (16 mmol) of chlorosulfonic acid at 0° C. The mixture is stirred at 0° C. until gas evolution slows. The mixture is warmed first to rt, then to 50° C. for 2 h. The mixture is cooled to rt, then poured over chipped ice. The resulting mixture is extracted twice with 5% MeCN in $CH_2Cl_2$, and the combined extracts are washed with water and brine, dried over $Na_2SO_4$, filtered and concentrated to provide 640 mg (77%) of a 1:1 mixture of I-004 and I-005.

I-006: 2,5,6-trimethyl-3H-benzimidazole-4-sulfonyl chloride

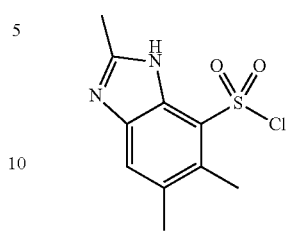

2,5,6-Trimethylbenzimidazole (0.5 g, 3.1 mmol) is added slowly to 1.0 mL (15 mmol) of chlorosulfonic acid at 0° C. The mixture is stirred at 0° C. until the gas evolution slows. The mixture is warmed first to rt, then to 50° C. for 2 h. The mixture is cooled to rt, then poured into $CH_2Cl_2$. Ice water is slowly added, and the phases are separated. The aqueous phase is washed with $CH_2Cl_2$, and the combined extracts are washed with water and brine, dried over $Na_2SO_4$, filtered, and concentrated to provide 68 mg of a gray solid containing 53% I-006, and 47% of a non-reactive unknown by-product (5% yield).

I-007: 1H-indole-6-sulfonyl chloride

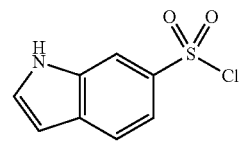 [SMILES: O=S(=O)(Cl)c1ccc2cc[nH]c2c1]

To a solution of 2.4 g (12 mmol) of 6-bromoindole in 20 mL of THF and 20 mL of $Et_2O$ at 0° C. is added 500 mg (12 mmol) of 60% NaH in mineral oil. After stirring for 15 min, the mixture is cooled to −78° C., and 14 mL (24 mmol) of 1.7 M t-BuLi in pentane is added slowly. After 30 min, 8.0 mL (24 mmol) of a 19% solution of $SO_2$ in THF is slowly added. The mixture is then allowed to warm to rt overnight. To the resulting solid is added 30 mL of $Et_2O$ and 0.76 mL (13 mmol) of glacial acetic acid. The mixture is stirred for 30 min at 0° C., and then is filtered and quickly washed with $Et_2O$. The solids are then suspended in 30 mL of $Et_2O$, chilled to 0° C., and 1.7 g (12 mmol) of NCS is carefully added. The resulting suspension is stirred rapidly for 30 min, and then is filtered and washed with $Et_2O$. The filtrate and washes are concentrated to provide 1.8 g (70%) of I-007 as a brown crystalline solid.

I-008: 1H-indole-4-sulfonyl chloride is prepared from 4-bromoindole in the same manner as I-007.

I-009: 7-methyl-1H-indole-4-sulfonyl chloride is prepared from 4-bromo-7-methylindole in the same manner as I-007.

I-010: 2-dimethylcarbamoyl-1H-indole-4-sulfonyl chloride is prepared from 4-bromo-1H-indole-2-carboxylic acid dimethylamide in the same manner as I-007

I-011: 4-bromo-5-chloro-indole-1-carboxylic acid tert-butyl ester and I-012: 6-bromo-5-chloro-indole-1-carboxylic acid tert-butyl ester

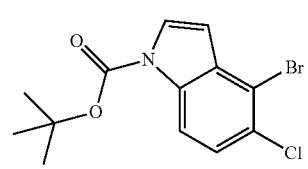

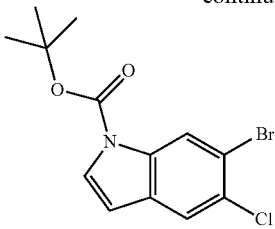

A 1.0 M solution of vinylmagnesium bromide in THF (0.13 L, 130 mmol) is added slowly to 10 g (43 mmol) of 3-bromo-4-chloro-nitrobenzene in 140 mL of THF at −40° C. The mixture is stirred at −40 C for an additional hour when aqueous NH$_4$Cl is added. The mixture is allowed to warm to rt, and then is extracted with EtOAc. The extract is washed with brine, dried over MgSO$_4$, filtered, concentrated, and purified twice by chromatography (33% EtOAc in hexanes) to provide 0.95 g (9.7%) of 4-bromo-5-chloro-1H-indole and 0.77 g (7.9%) of 6-bromo-5-chloro-1H-indole. Each of the indole products is separately treated with 1.1 equivalents of Boc$_2$O and 0.2 equivalents of DMAP in MeCN. The mixtures are concentrated and the residues chromatographed (10% EtOAc in hexanes) to provide I-011 (32%) and I-012 (48%).

I-013: 4-bromo-5-fluoro-indole-1-carboxylic acid tert-butyl ester and I-014: 5-bromo-6-fluoro-indole-1-carboxylic acid tert-butyl ester are prepared from 3-bromo-4-fluoro-nitrobenzene in the same manner as I-011.

I-015: 7-bromo-indole-1-carboxylic acid tert-butyl ester

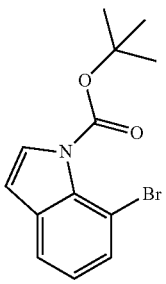 [SMILES: CC(C)(C)OC(=O)n1ccc2cccc(Br)c21]

A solution of 0.35 g (1.8 mmol) of 7-bromoindole, 0.43 g (2.0 mmol) of Boc$_2$O, and 44 mg (0.36 mmol) of DMAP in 4 mL of MeCN is stirred for 1 h, and then EtOAc is added. The mixture is washed with water and brine, dried over MgSO$_4$, filtered, concentrated, and purified by flash chromatography (10% EtOAc in hexanes) to provide 0.20 g (38%) of I-015.

I-016: indol-5-yl sulfonyl chloride

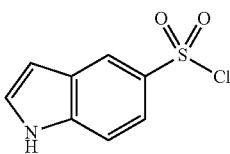 [SMILES: O=S(=O)(Cl)c1ccc2[nH]ccc2c1]

To a solution of 5-bromoindole in 5 ml of Et$_2$O at −78° C. is added 2.2 mL of 1.7 M t-BuLi (3.7 mmol). After stirring for 40 min, the reaction is warmed to 0° C. for 5 min then cooled to −78° C. Sulfur dioxide is bubbled through the solution for 5 min, and then the mixture is allowed to warm to rt and stirred overnight. To this is added 0.64 g (4.8 mmol) of NCS. After stirring for 1.5 h, the mixture is filtered and the precipitate is washed with Et$_2$O. The filtrate is concentrated to provide 0.27 mg (78%) of I-016.

I-017: 7-chlorosulfonyl-indole-1-carboxylic acid tert-butyl ester is prepared from I-015 in the same manner as I-016.

I-018: 1-triisopropylsilanyl-1H-indole-3-sulfonyl chloride is prepared from 3-bromo-1-triisopropylsilanyl-1H-indole in the same manner as I-016.

I-019: 3-chlorosulfonyl-2-methyl-indole-1-carboxylic acid tert-butyl ester is prepared from 3-bromo-2-methyl-indole-1-carboxylic acid tert-butyl ester (SynChem) in the same manner as I-016.

I-020:1 H-indazole-4-sulfonyl chloride is prepared from 4-bromo-1H-indazole in the same manner as I-016 with purification by flash chromatography.

I-021: 4-chlorosulfonyl-5-fluoro-indole-1-carboxylic acid tert-butyl ester is prepared from I-013 in the same manner as I-016, but is used in situ without isolation.

I-022: 6-chlorosulfonyl-5-fluoro-indole-1-carboxylic acid tert-butyl ester is prepared from I-014 in the same manner as I-016, but is used in situ without isolation.

I-023: 5-chloro-4-chlorosulfonyl-indole-1-carboxylic acid tert-butyl ester is prepared from I-011 in the same manner as I-016, but is used in situ without isolation.

I-024: 5-chloro-6-chlorosulfonyl-indole-1-carboxylic acid tert-butyl ester is prepared from I-012 in the same manner as I-016, but is used in situ without isolation.

I-025: 1H-indazole-6-sulfonyl chloride

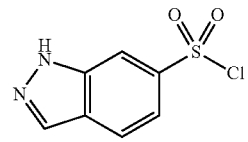 [SMILES: O=S(=O)(Cl)c1ccc2cn[nH]c2c1]

A solution of 3.8 g (55 mmol) of NaNO$_2$ in 5 mL of water is added to 6.7 g (50 mmol) of 6-aminoindazole in 15 mL of concentrated HCl and 5 mL of glacial acetic acid at −10° C. is added at such a rate that the temperature does not exceed −5° C. After stirring for 30 min, a solution of 1.2 g (13 mmol) of CuCl in 50 mL of saturated SO$_2$ in acetic acid is added over 10 minutes. The mixture is warmed to rt and stirred until N$_2$ evolution ceases. The mixture is poured onto ice and the resulting precipitate is filtered, and then is suspended in EtOAc (150 mL) and washed with NaHCO$_3$ and brine, dried over MgSO$_4$, filtered, and concentrated to provide 2.5 g (23%) of I-025 as a yellow solid.

I-026: 7-azaindol-4-yl sulfonyl chloride and I-027: 3-bromo-7-azaindol-4-yl sulfonyl chloride

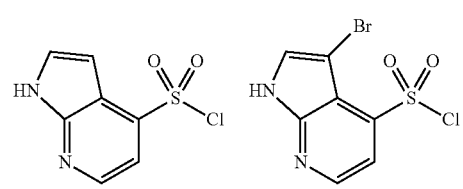 [SMILES: O=S(=O)(Cl)c1ccnc2[nH]ccc12 ; O=S(=O)(Cl)c1ccnc2[nH]cc(Br)c12]

Methanesulfonic acid anhydride (13 g, 73 mmol) is added to 6.1 g (37 mmol) of 7-azaindole-7-oxide (*J. Org. Chem.*, 1980, 45, 4045) oxide and 8.5 g (55 mmol) of Me$_4$NBr in 50 mL of DMF at 0° C. The suspension is allowed to warm as it stirs for 12 h. The mixture is poured into water and 50% NaOH solution is added to bring the pH to 7. The solution is chilled to 0° C. for 30 minutes, and the precipitate filtered, washed with cold water, and dissolved in $CH_2Cl_2$/MeOH (10:1). This solution is dried over $MgSO_4$, filtered and concentrated to provide 2.4 g of a mixture of 4-bromo-7-azaindole and 3,4-dibromo-7-azaindole. This mixture is treated with t-BuLi, $SO_2$, and NCS just as in the synthesis of I-016 to access a mixture of I-026 and I-027.

I-028: 4-chlorosulfonyl-1-(2-trimethylsilanyl-ethoxymethyl)-1H-indole-7-carboxylic acid

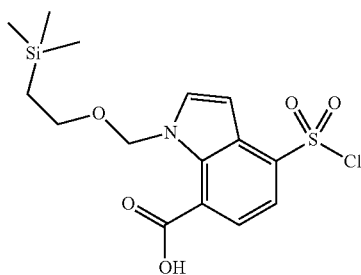 [SMILES: C[Si](C)(C)CCOCn1ccc2c(S(=O)(=O)Cl)ccc(C(=O)O)c21]

To a solution of 0.54 g (1.0 mmol) of 4,7-dibromo-1-(2-trimethylsilanyl-ethoxymethyl)-1H-indole (Li, L. et al. *Tetrahedron Lett.*, 2003, 44, 5987) in 5 mL of THF at −78° C. is added 1.4 mL (2.3 mmol) of 1.7 M t-BuLi in hexanes. After stirring for 20 min, 0.088 g (2.0 mmol) of solid $CO_2$ is added. After stirring for 1 h, excess $CO_2$ is removed in vacuo and then 1.3 mL (2.2 mmol) of t-BuLi is added at −78° C. After stirring for 15 min, $SO_2$ is bubbled through the solution for 10 min. The mixture is warmed to 0° C. over 2 h and 0.64 (4.8 mmol) of NCS is added and the mixture is stirred for 12 h. Both EtOAc and water are added, followed by enough saturated $Na_2SO_3$ solution to bring the pH to 5. The layers are separated, and the aqueous phase is extracted three times with EtOAc. The combined extracts are dried over $MgSO_4$, filtered, and concentrated to provide 0.38 g (12%) of I-028 as a black solid.

I-029: 2-bromo-6-methylbenzenesulfonyl chloride

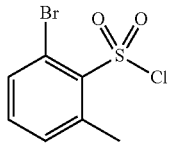

To a solution of 0.20 g (1.1 mmol) of 2-bromo-6-methylaniline in 2 mL of acetic acid is added 0.20 mL of concentrated HCl. A solution of 74 mg (1.1 mmol) of $NaNO_2$ in 0.20 mL of water is added at 0° C. After stirring for 1 h, 0.5 mL of acetic acid, 0.35 mL of sulfurous acid, and 31 mg (0.32 mmol) of CuCl are added. The mixture is stirred overnight, and then is poured onto ice-water. The mixture is extracted with EtOAc, washed with brine, dried over $MgSO_4$, filtered, and concentrated to provide 81 mg (28%) of I-029.

I-030: 1,2,3,4-tetrahydro-isoquinoline-7-sulfonic acid hydrochloride

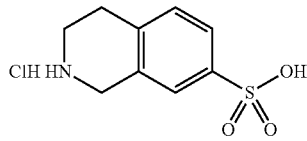

A solution of 1.2 g (4.4 mmol) of 2-acetyl-7-chlorosulphonyl-1,2,3,4-tetrahydroiso-quinoline (Pendelton, R. G., et al. *J. Pharmacol. Exp. Ther.*, 1979, 208, 24) in 20 mL of EtOH is stirred at rt for 2 days, then concentrated. The residue is stirred in 15 mL of 10% HCl at 100° C. in a pressure tube for 12 h, then cooled and concentrated. The residue is azeotroped to dryness with EtOH, and then recrystallized from EtOH to provide 0.63 g (58%) of I-030 as white crystals.

I-031: 3-((cis)-4-methyl-piperidin-3-yl)-propionic acid ethyl ester

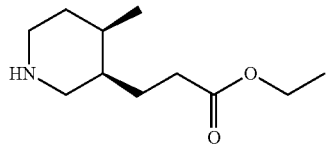

A mixture of 2.0 g (12 mmol) of 3-bromo-4-methylpyridine, 2.5 mL of $CH_3CN$, 3.2 mL (23 mmol) of $Et_3N$, 5.8 g (58 mmol) of ethyl acrylate, and 0.095 g (0.12 mmol) of $PdCl_2$ (dppf).$CH_2Cl_2$ is stirred in an evacuated and sealed pressure tube at 125° C. for 1 h. The mixture is concentrated and purified by flash chromatography (5-60% EtOAc in hexanes) to provide 1.0 g (47%) of (E)-3-(4-methyl-pyridin-3-yl)-acrylic acid ethyl ester as a dark oil. This material is stirred in 2 mL of toluene with 0.70 mL (6.0 mmol) of benzyl bromide at 60° C. overnight. The resulting precipitate is filtered and washed with toluene to provide 1.4 g (4.0 mmol) of the benzyl pyridinium bromide as a white powder. To this material in 20 mL of EtOH at 0° C. is added 0.30 g (8.0 mmol) of $NaBH_4$ in portions over 30 minutes. The mixture is stirred for 90 min, concentrated by half, dissolved in $CH_2Cl_2$, washed twice with water and once with brine, dried over $Na_2SO_4$, filtered, and concentrated. Flash chromatography (5-50% EtOAc in hexanes) provides 0.42 g (1.5 mmol) of (E)-3-(1-benzyl-4-methyl-1,2,5,6-tetrahydro-pyridin-3-yl)-acrylic acid ethyl ester as a yellow oil. This material is stirred in 3 mL of EtOH with 42 mg of Pd/C under an $H_2$ atmosphere overnight. The vessel is evacuated with $N_2$, filtered through diatomaceous earth, and concentrated to provide 208 mg of I-031 as a yellow oil.

I-032: (E)-3-piperidin-3-yl-acrylic acid methyl ester hydrochloride

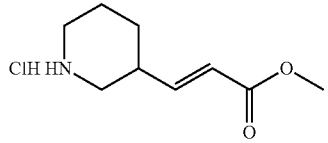

Diethyl[1-(methoxycarbonyl)methyl]phosphonate (1.8 mL, 9.8 mmol) is added to 0.38 g (9.4 mmol) of 60% NaH in mineral oil stirring in 36 mL of toluene at 0° C. After 1 h, 1.0 g (4.7 mmol) of N-Boc-piperidine-3-carbaldehyde is added. After stirring for 1 h at 0° C., aqueous saturated $NH_4Cl$ is added, and the mixture is extracted with ether. The extract is dried over MgSO₄, filtered, and concentrated. Chromatography (10-70% EtOAc in hexanes) provides 0.75 g of a colorless oil. This material (0.25 g, 0.93 mmol) is stirred in 0.5 mL of 4M HCl in 1,4-dioxane for 1 h. The mixture is concentrated to provide 0.16 g (83%) of I-032.

I-033: 4-methyl-1,2,3,6-tetrahydro-pyridine hydrochloride

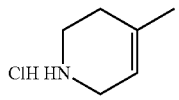

A mixture of 0.10 g (0.53 mmol) of 1-benzyl-4-methyl-1,2,3,6-tetrahydro-pyridine (Bonin, M. et al. *J. Org. Chem.*, 1984, 49, 2392) and 0.061 mL (0.053 mmol) of 1-chloroethyl chloroformate in 0.5 mL of dichloroethane is stirred at 80° C. overnight. The mixture is concentrated and taken up in 1 mL of MeOH. The mixture is heated at 60° C. for 6 h, and then cooled. This material is dissolved in aqueous HCl, extracted twice with Et₂O, and lypholized to provide I-033 as an orange foam.

I-034: (trans)-3-hydroxy-4-methyl-piperidine hydrochloride

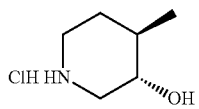

To a solution of 0.10 g (0.49 mmol) of trans-4-methyl-1-(phenylmethyl)-3-piperidinol (Brown Ripin, D. H., et al. *Tetrahedron Lett.* 2000, 5817) in 1 mL of DCE at 0° C. is added 0.12 mL (1.1 mmol) of 2-chloroethyl-chloroformate. The mixture is warmed to 80° C. and stirred for 12 h. The mixture is concentrated, and then dissolved in 2 mL of MeOH and heated to 60° C. for 6 h. The mixture is dissolved in 1 mL of 1N HCl and extracted twice with Et₂O. The aqueous phase is then lyophilized to provide 40 mg of an orange oil composed of I-034 and unreacted benzylamine in a 1:1 ratio.

I-035: 1,2,3,4-tetrahydro-isoquinoline-7-carboxylic acid methylamide trifluoroacetate

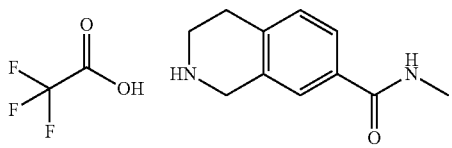

A solution of 0.20 g (0.72 mmol) of N-Boc-1,2,3,4-tetrahydro-isoquinoline-7-carboxylic acid (ASW MedChem), 0.28 g (1.4 mmol) of EDC, and 0.19 (1.4 mmol) of HOBt hydrate is stirred in 2 mL of DMF for 30 min when 3.6 mL (7.2 mmol) of methylamine (2.0 M in THF) is added. The mixture is stirred at 80° C. for 5 h, and then is diluted with EtOAc and washed twice with water and twice with brine. The extract is dried over Na₂SO₄, filtered, and concentrated. This material is stirred in 1.5 mL of 33% TFA in CH₂Cl₂ for 2 h, and then concentrated to provide I-035.

I-036: 1,2,3,4-tetrahydro-isoquinoline-7-carboxylic acid dimethylamide is prepared from N-Boc-1,2,3,4-tetrahydro-isoquinoline-7-carboxylic acid and dimethylamine hydrochloride (with 5 equivalents of Et₃N) in the same manner as I-035.

I-037: morpholin-4-yl-(1,2,3,4-tetrahydro-isoquinolin-7-yl)-methanone is prepared from N-Boc-1,2,3,4-tetrahydro-isoquinoline-7-carboxylic acid and morpholine in the same manner as I-035.

I-038: (1,2,3,4-tetrahydro-isoquinolin-6-yloxy)-acetic acid methyl ester

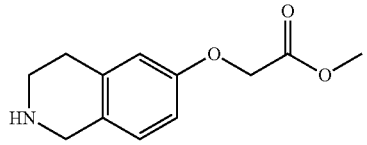 [SMILES: COC(=O)COc1ccc2c(c1)CCNC2]

A mixture of 0.45 g (2.0 mmol) of 6-hydroxyl-1,2,3,4-tetrahydroisoquinoline hydrobromide and 0.92 mL (6.5 mmol) of Et₃N in 5 mL of MeOH is treated with 0.71 (3.3 mmol) of Boc₂O. After stirring for 1 h, the mixture is concentrated, dissolved in EtOAc, and washed with water, 1N HCl, NaHCO₃, and brine. The solution is dried over MgSO₄, filtered, concentrated, and purified by flash chromatography (10-50% EtOAc in hexanes) to provide 0.40 g (83%) of a colorless oil. This material (0.14 g, 0.55 mmol), 0.13 (0.82 mmol) of methyl bromoacetate, and 0.11 g (0.82 mmol) of K₂CO₃ are stirred in 0.5 mL of DMF for 12 h. Water is added, and the mixture is extracted twice with EtOAc. The extracts are dried over MgSO4, filtered, concentrated, and purified by flash chromatography (40% EtOAc in hexanes) to provide 0.12 g (67%) of a yellow oil. This material is stirred in 2 mL of 4N HCl in 1,4-dioxane for 3 h, then concentrated. The residue is dissolved NaHCO₃ and extracted twice with EtOAc. The extracts are washed with brine, dried over MgSO₄, filtered, and concentrated to provide 68 mg (90%) of I-038.

I-039: 2-methyl-2-(1,2,3,4-tetrahydro-isoquinolin-7-yloxy)-propionic acid ethyl ester

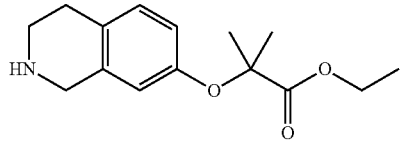 [SMILES: CCOC(=O)C(C)(C)Oc1ccc2c(c1)CNCC2]

A mixture of 1.0 g (6.8 mmol) of 7-hydroxyisoquinoline, 6.0 g (30 mmol) of ethyl bromoisobutyrate, and 4.2 g (30 mmol) of K₂CO₃ in 14 mL of DMF is heated to 95° C. under N₂ for 18 hrs. The reaction is diluted with water and extracted twice with EtOAc. The extracts are dried over MgSO₄, filtered, and concentrated. Chromatography (40% EtOAc in hexanes) provides 1.8 g (>99%) of a yellow oil. This material (0.47 g, 1.8 mmol) is stirred over 21 mg of Pt₂O.H₂O in 10 mL of HOAc under 50 psi of H₂ for 18 h. The mixture is filtered, and the filtrate is dissolved in EtOAc and extracted with NaOH. The basic wash is extracted twice with EtOAc and the combined extracts are washed with brine, dried over MgSO₄, filtered, and concentrated to provide 0.48 (99%) of I-039.

I-040: [3-hydroxy-1-(4-methyl-piperidine-1-carbonyl)-propyl]-carbamic acid tert-butyl ester

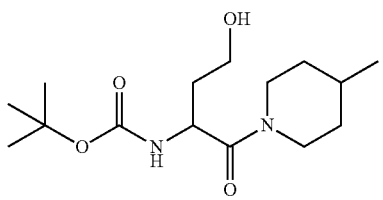 [SMILES: CC1CCN(C(=O)C(CCO)NC(=O)OC(C)(C)C)CC1]

To 25.6 g (141 mmol) of 2-amino-γ-butyrolactone in 200 mL of CH₂Cl₂ is added 32.2 g (157 mmol) of Boc₂O. Triethylamine (40 mL, 290 mmol) is then added in two portions, and the mixture is stirred for 48 h. The mixture is washed with water, 1 M NaHSO₄, and brine, and then dried with Na₂SO₄, filtered, and concentrated to provide 26.8 g (95%) of (2-oxo-tetrahydro-furan-3-yl)-carbamic acid tert-butyl ester as a white solid. This material (14.6 g, 72.6 mmol), 17.5 mL of 4-methylpiperidine, and 17.5 mL of 1,4-dioxane are sealed in a pressure tube and heated to 120° C. for 30 min. After cooling, the mixture is dissolved in EtOAc and washed with water, 1 M NaHSO₄, and brine, and then it is dried with Na₂SO₄, filtered, and concentrated to provide a white solid. Recrystallization from hexanes provides 21.3 g (98%) of I-040.

I-041: [3-chloro-1-(4-methyl-piperidine-1-carbonyl)-propyl]-carbamic acid tert-butyl ester

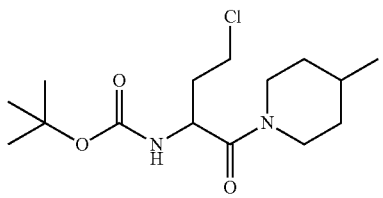

To 300 mg (1.0 mmol) I-040 in 5.0 mL of CCl₄ and 5.0 mL of CH₂Cl₂ is added 1.0 g (3.0 mmol) of PS—PPh₃. The mixture is shaken overnight, and then the resin is filtered and washed with CH₂Cl₂. The filtrate is concentrated, and the resulting residue is dissolved in EtOAc, filtered, and concentrated to provide 284 mg of I-041.

I-042: 4-bromo-2-tert-butoxycarbonylamino-butyric acid methyl ester

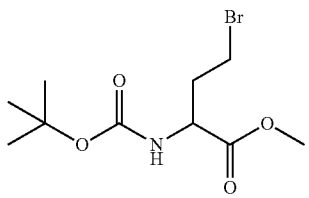 [SMILES: COC(=O)C(CCBr)NC(=O)OC(C)(C)C]

A suspension of α-amino-γ-butyrolactone hydrobromide in 30% HBr in HOAc is heated at 100° C. in a sealed tube for 5 days. The mixture is concentrated to give a white solid that is washed with ether to provide 23.1 g (64%) of 2-amino-4-bromo-butyric acid hydrobromide. Acetyl chloride (61 mL, 860 mmol) is added dropwise to 200 mL of MeOH at 0° C. The mixture is stirred at rt for 30 min before 22.5 g (124 mmol) of 2-amino-4-bromo-butyric acid hydrobromide is added. The mixture is stirred overnight and concentrated. The residue is washed with ether to provide 23.5 g (82%) of methyl 4-bromo-2-amino-butyrate hydrochloride. A solution of 27.7 g (330 mmol) of NaHCO₃ in 100 mL of water is slowly added to 19.2 g (82.5 mmol) of this material along with 21.6 g (99.0 mmol) of Boc₂O in 140 mL of 1,4-dioxane at 0° C. The mixture is warmed to rt and stirred overnight. N,N-dimethyl propane-1,3-diamine (5 mL) is added to the mixture, and it is stirred for 20 min. The mixture is diluted with water then extracted twice with EtOAc. The extracts are washed with water, 1M NaHSO₄, and brine, and then combined, dried with Na₂SO₄, filtered, and concentrated to provide 21.5 g (88%) of I-042 as a white solid.

I-043: 2-tert-butoxycarbonylamino-4-(2-chloro-imidazol-1-yl)-butyric acid methyl ester

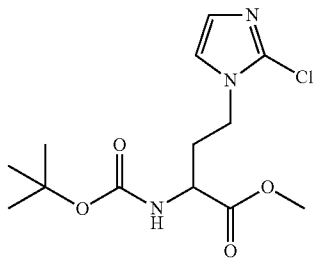 [SMILES: COC(=O)C(CCn1ccnc1Cl)NC(=O)OC(C)(C)C]

To a solution of 0.87 g (8.4 mmol) of 2-chloroimidazole in 14 mL of DMF is added 0.40 g (10 mmol) of 60% NaH in mineral oil. After 20 min of stirring, 2.5 g (8.4 mmol) of I-042 in 5 mL of DMF is added. The reaction mixture is heated to 80° C. for 1 h. The mixture is diluted with EtOAc (150 mL), washed with water, brine, dried over MgSO₄, filtered, and concentrated. The residue is purified by flash chromatography (0-5% MeOH in CH₂Cl₂) to provide 2.1 g (78%) of I-043.

I-044: 2-tert-butoxycarbonylamino-4-(2-cyano-pyrrol-1-yl)-butyric acid methyl ester is prepared from pyrrole-2-carbonitrile and I-042 in the same manner as I-043.

I-045: 2-tert-butoxycarbonylamino-4-(2-nitro-imidazol-1-yl)-butyric acid methyl ester is prepared from 2-nitroimidazole and I-042 in the same manner as I-043.

I-046: 2-tert-butoxycarbonylamino-4-1,2,3-triazol-2-yl-butyric acid methyl ester is prepared from 1,2,3-triazole and I-042 in the same manner as I-043, with chromatographic separation from the 1-triazolyl isomer.

I-047: 2-tert-butoxycarbonylamino-4-pyrazol-1-yl-butyric acid methyl ester is prepared from pyrazole and I-042 in the same manner as I-043.

I-048: 2-tert-butoxycarbonylamino-4-(2-chloro-imidazol-1-yl)-butyric acid

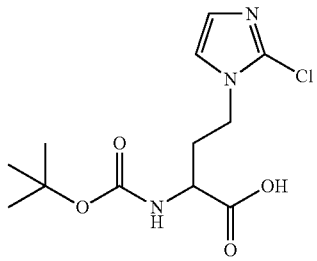 [SMILES: CC(C)(C)OC(=O)NC(CCn1ccnc1Cl)C(=O)O]

A mixture of 0.50 g (1.6 mmol) of I-043 in 12 mL of MeOH and 3.1 mL (6.2 mmol) of 2 M aq. NaOH is stirred for 60 min, and then concentrated by ⅓ and diluted with saturated aqueous NH₄Cl. After adjusting the pH to 4 with HCl, the mixture is extracted with CH₂Cl₂ (3×) and the extracts are washed with brine, then dried with Na₂SO₄, filtered, and concentrated to provide 0.42 g (87%) of I-048 as a white solid.

I-049: 2-tert-butoxycarbonylamino-4-pyrazol-1-yl-butyric acid is prepared from I-047 in the same manner as I-048.

I-050: 2-tert-butoxycarbonylamino-4-(2-cyano-pyrrol-1-yl)-butyric acid is prepared from I-044 in the same manner as I-048.

I-051: 2-tert-butoxycarbonylamino-4-(2-nitro-imidazol-1-yl)-butyric acid is prepared from I-045 in the same manner as I-048.

I-052: 2-tert-butoxycarbonylamino-4-1,2,3-triazol-2-yl-butyric acid is prepared from I-046 in the same manner as I-048.

I-053: 1-(3,3-dimethoxy-propyl)-1H-pyrazole

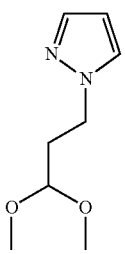

To a solution of 1.7 g (25 mmol) of pyrazole in 15 mL of DMF is added 0.98 g (25 mmol) of 60% NaH in mineral oil. After stirring for 15 min, 5.0 g (25 mmol) of 3-bromopropionaldehyde dimethylacetal is added. The mixture is heated to 160° C. for 3 h, then cooled and diluted 20 mL of EtOAc. The mixture is washed with water and brine, dried over MgSO₄, filtered, and concentrated. Flash chromatography (0-5% MeOH in CH₂Cl₂) provides 3.2 g (72%) of I-053 as a colorless oil.

I-054: 4-(5-chloro-pyrazol-1-yl)-2-tert-butoxycarbonylamino-butyric acid

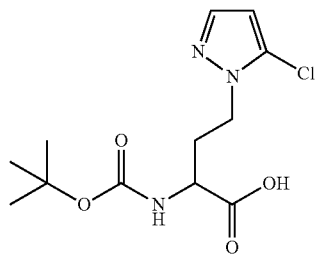 [SMILES: CC(C)(C)OC(=O)NC(CCn1nccc1Cl)C(=O)O]

A 2.5 M solution of BuLi (4.2 mL, 11 mmol) is added slowly to a stirring solution of 1.5 g (8.8 mmol) of I-053 in 50 mL of THF at −78° C. The mixture is stirred for 30 min, and then hexachloroethane (2.3 g, 9.7 mmol) is slowly added. The mixture allowed to come to rt and stirred overnight. Saturated Na₂CO₃ (50 mL) is added, and the mixture is extracted with EtOAc. The extract is washed with water and brine, dried over MgSO₄, filtered, and concentrated. Flash chromatography (0-75% EtOAc in hexanes) provides 1.0 g (55%) of 5-chloro-1-(3,3-dimethoxy-propyl)-1H-pyrazole. To 1.9 g (9.5 mmol) of this material in 10 mL of THF at 0° C. is added a solution of 6.0 mL (16 mmol) of 70% HClO₄ in 15 mL of THF. Water (5 ml) is subsequently added, and the mixture is stirred for 1 h. The mixture is poured into saturated NaHCO₃ and extracted with EtOAc. The extract is washed with brine, dried over MgSO₄, filtered, and concentrated to provide 1.4 g (93%) of 3-(5-chloro-pyrazol-1-yl)-propionaldehyde. To a mixture of 1.4 g (8.8 mmol) of this material and 1.5 mL (11 mmol) of TMSCN in 4 ml of THF is added ~1 mg of ZnI₂. After stirring for 15 min, a solution of 7M NH₃ in MeOH (8 ml) is added. The mixture is sealed in a pressure tube and heated to 40° C. for 2 h. The mixture is cooled and concentrated to provide 1.3 g (81%) of crude 2-amino-4-(5-chloro-pyrazol-1-yl)-butyronitrile. A mixture of 1.2 g (6.5 mmol) of this material in 4 mL of concentrated HCl is heated to reflux for 12 h. The mixture is cooled and neutralized with saturated NaHCO₃. After adding 50 ml of water and 50 ml dioxane, 7.1 g (33 mmol) of Boc₂O is added. The mixture is stirred overnight and extracted with EtOAc. The aqueous phase is acidified to pH 4 with 1N HCl, and extracted with EtOAc. This extract is washed with brine, dried over MgSO₄, filtered, and concentrated to provide 1.7 g (86%) of I-054.

I-055: 4-(5-bromo-pyrazol-1-yl)-2-tert-butoxycarbonylamino-butyric acid is prepared from I-053 in the same manner as I-054 by substituting Br₂ for hexachloroethane.

I-056: 2-tert-butoxycarbonylamino-4-(5-carbamoyl-pyrazol-1-yl)-butyric acid

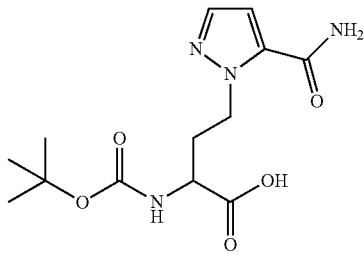 [SMILES: CC(C)(C)OC(=O)NC(CCn1nccc1C(N)=O)C(=O)O]

A mixture of 0.78 g (2.2 mmol) of I-055, 0.52 g (2.7 mmol) of EDC, 0.36 g (2.7 mmol) of HOBt, and 5 mg of DMAP in 3 mL of DMF is stirred for 5 min, and then 86 mg of MeOH is added. The mixture is stirred for 4 h, then diluted with EtOAc, washed with water and brine, dried over MgSO₄, filtered, and concentrated. Preparative HPLC provides 0.58 g (71%) of 2-tert-butoxycarbonylamino-4-(5-bromo-pyrazol-1-yl)-butyric acid methyl ester. A mixture of 0.35 g (0.97 mmol) of this material, 35 mg (0.038 mmol) of Pd₂(dba)₃, 43 mg (0.077 mmol) of dppf, 110 mg (0.97 mmol) of Zn(CN)₂, and 15 mg (0.23 mmol) of Zn powder in 2 mL of DMA is heated to 120° C. for 5 h in a pressure tube. The mixture is cooled, filtered, and purified directly on preparative HPLC to provide 0.13 g (44%) of 2-tert-butoxycarbonylamino-4-(5-cyano-pyrazol-1-yl)-butyric acid methyl ester. This material is dissolved in 2.5 mL of MeOH and 2.5 mL of 1M NaOH is added. After stirring for 3 h, the mixture is neutralized with 6N HCl and extracted with EtOAc (3×15 mL). The extracts are washed with water and brine, dried over MgSO₄, filtered, and concentrated to provide a small amount of product. Lyophilization of the aqueous washes provides 110 mg (84%) of I-056 contaminated with NaCl.

I-057: 2-amino-1-(4-methyl-piperidin-1-yl)-4-(2-nitro-imidazol-1-yl)-butan-1-one hydrochloride

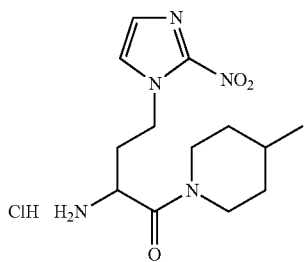 [SMILES: Cl ; CC1CCN(C(=O)C(N)CCn2ccnc2[N+](=O)[O-])CC1]

A mixture of 320 mg (1.0 mmol) of I-051 and 290 mg (2.1 mmol) of HOBt is dissolved in 1 mL of DMF, and then 0.32 g (1.6 mmol) of EDC is added. After stirring for 20 min, 0.36 mL (3.0 mmol) of 4-methylpiperidine is added. The mixture is stirred overnight, diluted with EtOAc, and washed twice with water and once with brine. It is then dried with $Na_2SO_4$, filtered, and concentrated. Flash chromatography (2-5% MeOH in $CH_2Cl_2$) provides 400 mg (75%) of [1-(4-methyl-piperidine-1-carbonyl)-3-(2-nitro-imidazol-1-yl)-propyl]-carbamic acid tert-butyl ester as a pale yellow oil. A solution of 0.37 g (0.94 mmol) of this material in 10 mL of 4 M HCl in 1,4-dioxane is stirred for 10 min, and then is concentrated to provide 0.27 g (98%) of I-057 as a yellow solid.

I-058-I-082 are prepared in the same manner as I-057.

I-058: 2-amino-1-piperidin-1-yl-4-pyrazol-1-yl-butan-1-one dihydrochloride from I-049 and piperidine.

I-059: 2-amino-1-(4-hydroxymethyl-piperidin-1-yl)-4-pyrazol-1-yl-butan-1-one dihydrochloride from I-049 and 4-hydroxymethylpiperidine.

I-060: 2-amino-1-(3,4-dihydro-1H-isoquinolin-2-yl)-4-(2-nitro-imidazol-1-yl)-butan-1-one hydrochloride from I-051 and tetrahydroisoquinoline.

I-061: 2-amino-4-(2-nitro-imidazol-1-yl)-1-(trans)-octahydro-isoquinolin-2-yl-butan-1-one hydrochloride from I-051 and trans-decahydroisoquinoline.

I-062: 2-amino-4-(2-nitro-imidazol-1-yl)-1-(cis)-octahydro-isoquinolin-2-yl-butan-1-one hydrochloride from I-051 and cis-decahydroisoquinoline.

I-063: 2-amino-4-(2-nitro-imidazol-1-yl)-1-(4-trifluoromethyl-piperidin-1-yl)-butan-1-one hydrochloride from I-051 and 4-trifluoromethylpiperidine.

I-064: 2-amino-1-(cis)-octahydroisoquinolin-2-yl-4-1,2,3-triazol-2-yl-butan-1-one hydrochloride from I-052 and cis-decahydroisoquinoline.

I-065: 2-amino-1-(4-methyl-piperidin-1-yl)-4-1,2,3-triazol-2-yl-butan-1-one hydrochloride from I-052 and 4-methylpiperidine.

I-066: 2-amino-4-(2-chloro-imidazol-1-yl)-1-(4-methyl-piperidin-1-yl)-butan-1-one hydrochloride from I-048 and 4-methylpiperidine.

I-067: 2-amino-4-(2-chloro-imidazol-1-yl)-1-(cis)-octahydro-isoquinolin-2-yl-butan-1-one hydrochloride from I-048 and cis-decahydroisoquinoline.

I-068: 2-amino-4-(2-chloro-imidazol-1-yl)-1-(trans)-octahydro-isoquinolin-2-yl-butan-1-one hydrochloride from I-048 and trans-decahydroisoquinoline.

I-069: 2-amino-4-(2-chloro-imidazol-1-yl)-1-(3,4-dihydro-1H-isoquinolin-2-yl)-butan-1-one hydrochloride from I-048 and tetrahydroisoquinoline.

I-070: 2-amino-4-(2-chloro-imidazol-1-yl)-1-(4-trifluoromethyl-piperidin-1-yl)-butan-1-one hydrochloride from I-048 and 4-trifluoromethylpiperidine.

I-071: 2-amino-N-(4-chloro-benzyl)-4-(2-cyano-pyrrol-1-yl)-N-methyl-butyramide hydrochloride from I-050 and N-methyl 4-chlorobenzylamine.

I-072: 2-amino-N-benzyl-4-(2-cyano-pyrrol-1-yl)-N-methyl-butyramide hydrochloride from I-050 and N-methyl benzylamine.

I-073: 1-(3-amino-4-oxo-4-piperidin-1-yl-butyl)-1H-pyrrole-2-carbonitrile hydrochloride from I-050 and piperidine.

I-074: 1-[3-amino-4-oxo-4-(4-phenyl-piperazin-1-yl)-butyl]-1H-pyrrole-2-carbonitrile dihydrochloride from I-050 and 4-phenylpiperazine.

I-075: 1-[3-amino-4-(4-hydroxymethyl-piperidin-1-yl)-4-oxo-butyl]-1H-pyrrole-2-carbonitrile hydrochloride from I-050 and 4-hydroxymethylpiperidine.

I-076: 1-(trans-3-amino-4-octahydro-isoquinolin-2-yl-4-oxo-butyl)-1H-pyrrole-2-carbonitrile hydrochloride from I-050 and trans-decahydroisoquinoline.

I-077: 1-[3-amino-4-(5,6-dihydro-8H-1,2,4-triazolo[4,3-a]pyrazin-7-yl)-4-oxo-butyl]-1H-pyrrole-2-carbonitrile hydrochloride from I-050 and 5,6,7,8-tetrahydro-1,2,4-triazolo[4,3-a]pyrazine.

I-078: 2-amino-4-(2-cyano-pyrrol-1-yl)-N-methyl-N—((R)-1-phenyl-ethyl)-butyramide hydrochloride from I-050 and (R)-1-phenylethylamine.

I-079: 2-[3-amino-4-(4-methyl-piperidin-1-yl)-4-oxo-butyl]-2H-pyrazole-3-carboxylic acid amide hydrochloride from I-056 and 4-methylpiperidine.

I-080: 2-amino-4-(5-bromo-pyrazol-1-yl)-1-(4-methyl-piperidin-1-yl)-butan-1-one hydrochloride from I-055 and 4-methylpiperidine.

I-081: 2-amino-4-(5-bromo-pyrazol-1-yl)-1-(4-hydroxymethyl-piperidin-1-yl)-butan-1-one hydrochloride from I-055 and 4-hydroxymethylpiperidine.

I-082: 2-amino-4-(5-chloro-pyrazol-1-yl)-1-(4-methyl-piperidin-1-yl)-butan-1-one hydrochloride from I-054 and 4-methylpiperidine.

I-065a: 2-amino-1-(4-methyl-piperidin-1-yl)-4-1,2,3-triazol-2-yl-butan-1-one

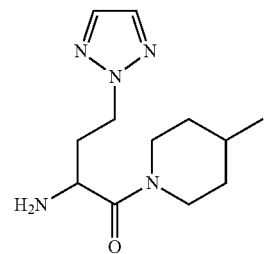 [SMILES: CC1CCN(C(=O)C(N)CCn2nccn2)CC1]

1,2,3-Triazole (0.20 mL, 3.4 mmol) is added to a suspension of 150 g (3.8 mmol) of 60% NaH in mineral oil stirring in 10 mL of DMF at rt. After 15 min, a solution of 1.0 g (3.4 mmol) of I-041 in 5 mL of DMF is added. The solution is heated to 80° C. for 2 h, and then is cooled and dissolved in EtOAc. The mixture is washed twice with water and once with brine, dried with $Na_2SO_4$, filtered, and concentrated. Flash chromatography (0-5% MeOH in $CH_2Cl_2$) separates 620 g (57%) of [1-(4-methyl-piperidine-1-carbonyl)-3-1,2,3-triazol-2-yl-propyl]-carbamic acid tert-butyl ester from the [1-(4-methyl-piperidine-1-carbonyl)-3-1,2,3-triazol-1-yl-propyl]-carbamic acid tert-butyl ester isomer. A 4M solution of HCl in 1,4-dioxane (3.7 mL, 15 mmol) is added to 620 mg (1.8 mmol) of [1-(4-methyl-piperidine-1-carbonyl)-3-1,2,3-triazol-2-yl-propyl]-carbamic acid tert-butyl ester in 2 mL of dioxane, and the mixture is stirred overnight. The mixture is concentrated, and the residue is dissolved in 0.2 M HCl and washed with EtOAc. The pH of the aqueous layer is adjusted to 8 with NaHCO₃, and the mixture is extracted twice with EtOAc, twice with CH₂Cl₂, and twice with 20% iPrOH in CHCl₃. The extracts are combined, dried with Na₂SO₄, filtered, and concentrated to provide 420 mg (81%) of I-065a as a pale yellow oil.

I-083: 1-[3-amino-4-(4-methyl-piperidin-1-yl)-4-oxo-butyl]-1H-imidazole-2-carbonitrile hydrochloride is prepared from 2-cyanoimidazole and I-041 in the same manner as I-065a with the omission of the aqueous workup.

I-084: 2-amino-4-(2-bromo-imidazol-1-yl)-1-(4-methyl-piperidin-1-yl)-butan-1-one hydrochloride is prepared from 2-bromoimidazole and I-041 in the same manner as I-065a with the omission of the aqueous workup.

I-085: 1-[3-amino-4-(4-methyl-piperidin-1-yl)-4-oxo-butyl]-1H-imidazole-2-carbonitrile hydrochloride is prepared from pyrazole and I-041 in the same manner as as I-065a with the omission of the aqueous workup.

I-086: 1-[3-amino-4-(4-methyl-piperidin-1-yl)-4-oxo-butyl]-1H-pyrazole-3-carbonitrile hydrochloride is prepared in a 2:1 mixture with its isomer I-091 from 3-cyanopyrazole and I-041 in the same manner as I-065a with the omission of the aqueous workup.

I-087: 2-amino-4-(4-chloro-pyrazol-1-yl)-1-(4-methyl-piperidin-1-yl)-butan-1-one hydrochloride is prepared in a 2:1 mixture with its isomer I-082 from 3-chloropyrazole and I-041 in the same manner as I-065a with the omission of the aqueous workup.

I-057: 2-amino-1-(4-methyl-piperidin-1-yl)-4-(2-nitro-imidazol-1-yl)-butan-1-one hydrochloride is prepared from 2-nitroimidazole and I-041 in the same manner as I-065a with the omission of the aqueous workup.

I-088: 2-amino-1-(4-methyl-piperidin-1-yl)-4-pyrrolo[2,3-b]pyridin-1-yl-butan-1-one hydrochloride is prepared from 7-azaindole and I-041 in the same manner as I-065a with the omission of the aqueous workup.

I-089: 1-[3-amino-4-(4-methyl-piperidin-1-yl)-4-oxo-butyl]-1H-pyrrole-2-carbonitrile hydrochloride

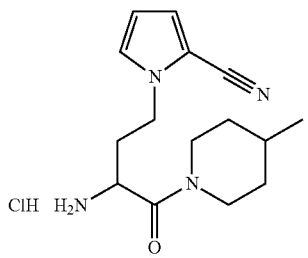 [SMILES: Cl ; CC1CCN(C(=O)C(N)CCn2cccc2C#N)CC1]

To 6.0 g (20 mmol) of I-040 in 100 mL of THF is added 2.8 g (30 mmol) of pyrrole-2-carbonitrile, 7.9 g (30 mmol) of PPh₃, and 4.7 mL (30 mmol) of diethyl azodicarboxylate. The mixture is stirred overnight, concentrated, and purified by flash chromatography (5-50% EtOAc in hexanes) to provide 7.5 g (quantitative yield) of [3-(2-cyano-pyrrol-1-yl)-1-(4-methyl-piperidine-1-carbonyl)-propyl]-carbamic acid tert-butyl ester. This material (4.0 g, 11 mmol) is dissolved in 11 mL of 4M HCl in dioxane along with enough MeOH to complete dissolution. The mixture is stirred until a precipitate forms. The precipitate is filtered to provide 3.0 g (89%) of I-089 as a white solid.

I-090: 1-[3-amino-4-(4-methyl-piperidin-1-yl)-4-oxo-butyl]-1H-pyrrole-2-carboxylic acid methyl ester trifluoroacetate

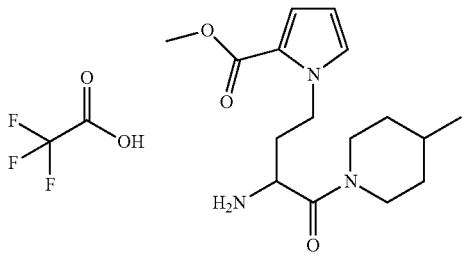

To a solution of 87 mg (0.21 mmol) of 1-[3-tert-butoxycarbonylamino-4-(4-methyl-piperidin-1-yl)-4-oxo-butyl]-1H-pyrrole-2-carboxylic acid methyl ester (prepared from methylpyrrole-2-carboxylate and I-040 in the same manner as [3-(2-cyano-pyrrol-1-yl)-1-(4-methyl-piperidine-1-carbonyl)-propyl]-carbamic acid tert-butyl ester (see I-089)) in 1 mL of CH₂Cl₂ is added 0.08 mL of TFA. After stirring for 1 h, the mixture is concentrated to provide 65 mg of I-090.

I-091: 2-[3-amino-4-(4-methyl-piperidin-1-yl)-4-oxo-butyl]-2H-pyrazole-3-carbonitrile hydrochloride

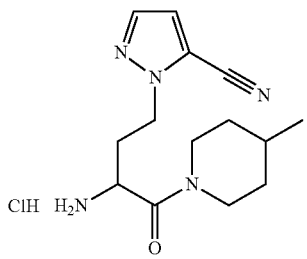 [SMILES: Cl ; CC1CCN(C(=O)C(N)CCn2nccc2C#N)CC1]

A mixture of 0.34 g (0.79 mmol) of [3-(5-bromo-pyrazol-1-yl)-1-(4-methyl-piperidine-1-carbonyl)-propyl]-carbamic acid tert-butyl ester (prepared in the synthesis of I-080), 31 mg (0.034 mmol) of Pd₂(dba)₃, 38 mg (0.069 mmol) of dppf, 96 mg (0.83 mmol) of Zn(CN)₂, and 13 mg (0.20 mmol) of Zn powder in 2 mL of DMA is heated to 120° C. for 3 h in a pressure tube. The mixture is cooled, filtered, and purified directly on preparative HPLC to provide 0.22 g (74%) of [3-(5-cyano-pyrazol-1-yl)-1-(4-methyl-piperidine-1-carbonyl)-propyl]-carbamic acid tert-butyl ester. This material is then stirred in 2.5 mL of 4 M HCl in 1,4-dioxane for 1 h, and then concentrated to provide I-091.

I-092: 2-[3-amino-4-(4-hydroxymethyl-piperidin-1-yl)-4-oxo-butyl]-2H-pyrazole-3-carbonitrile hydrochloride is prepared from [3-(5-bromo-pyrazol-1-yl)-1-(4-hydroxymethyl-piperidine-1-carbonyl)-propyl]-carbamic acid tert-butyl ester (from the synthesis of I-081) in the same manner as I-091.

I-093: 2-(4-amino-3,5-dichloro-benzenesulfonylamino)-4-(2-nitro-imidazol-1-yl)-butyric acid methyl ester and I-094: 2-(4-amino-3,5-dichloro-benzenesulfonylamino)-4-(2-chloro-imidazol-1-yl)-butyric acid methyl ester

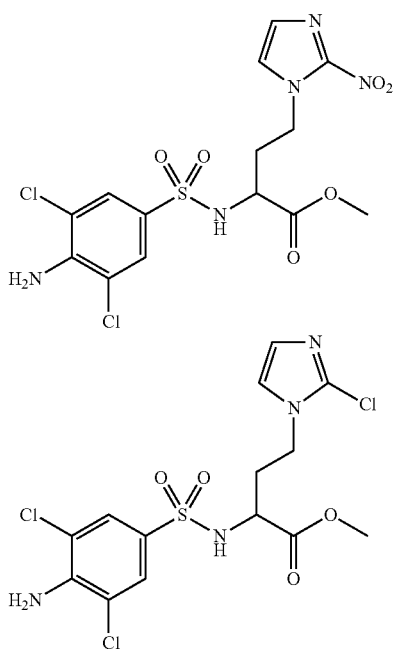

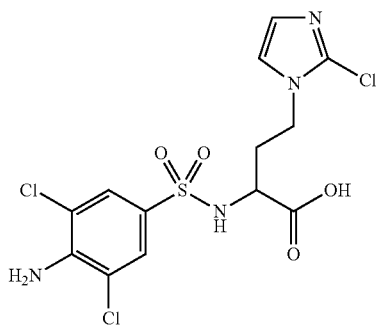 [SMILES: Nc1c(Cl)cc(S(=O)(=O)NC(CCn2ccnc2Cl)C(=O)O)cc1Cl]

To 4.1 g (12 mmol) of I-045 is added 31 mL (120 mmol) of 4M HCl in dioxane. After stirring for 15 min, the solution is concentrated to provide a mixture of 2-amino-4-(2-nitro-imidazol-1-yl)-butyric acid methyl ester hydrochloride and 2-amino-4-(2-nitro-imidazol-1-yl)-butyric acid methyl ester. To this mixture is added 30 ml of DMF followed by 3.4 mL (25 mmol) of $Et_3N$ and 3.2 g (12 mmol) of 4-amino-3,5-dichlorosulfonyl chloride. After stirring for 4 h, the mixture is diluted with EtOAc and washed three times with water and once with brine, and then dried with $MgSO_4$, filtered, and concentrated. Flash chromatography (1-2% MeOH in $CH_2Cl_2$) provides 2.1 g (38%) of I-093 and 0.70 g (13%) of I-094.

I-095: 2-(4-amino-3,5-dichloro-benzenesulfonylamino)-4-(2-chloro-imidazol-1-yl)-butyric acid A solution of 530 mg (1.2 mmol) of I-094 in 5 mL of MeOH and 2.8 mL of 2 M NaOH and 1 mL of additional water is stirred overnight. The mixture is concentrated, and the pH adjusted to 6 with $NH_4Cl$ and HCl. The resulting mixture is extracted twice with 20% MeOH in $CH_2Cl_2$. The extracts are combined and concentrated. The residue is dissolved in MeOH and concentrated again to provide 0.15 g mg (28%) of I-095.

I-096: 2-(4-Amino-3,5-dichloro-benzenesulfonylamino)-4-(2-nitro-imidazol-1-yl)-butyric acid

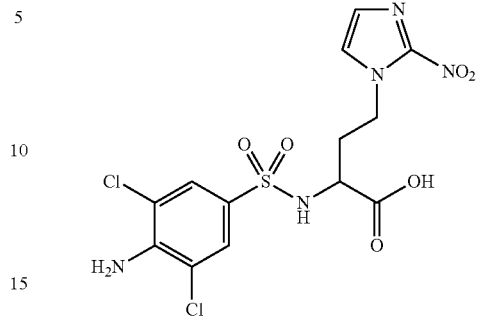

A solution of 1.1 g (2.4 mmol) of I-093 in 20 mL of conc. HCl is stirred for 3 h at 65° C. The mixture is concentrated, and the residue is washed with $Et_2O$ to provide 0.88 g (85%) of I-096 as a yellow solid.

I-097: 2-(4-Amino-3,5-dichloro-benzenesulfonylamino)-4-1,2,3-triazol-2-yl-butyric acid

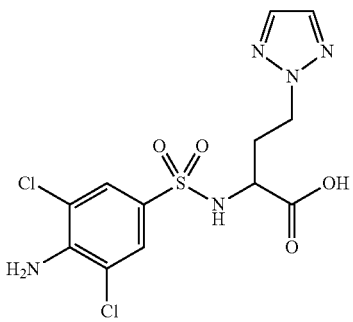 [SMILES: Nc1c(Cl)cc(S(=O)(=O)NC(CCn2nccn2)C(=O)O)cc1Cl]

A mixture of 1.0 g (3.6 mmol) of I-046 in 4.5 mL of 4M HCl in 1,4-dioxane is stirred for 1 h, and then is concentrated. The residue is dissolved in MeOH and $CH_2Cl_2$ and concentrated again. The residue is dissolved in 10 mL of DMF, and 0.94 g (3.6 mmol) I-001 and 1.3 mL (7.2 mmol) of $iPr_2NEt$ are added. After stirring for 3 h, the mixture is diluted with EtOAc (150 mL), washed with water (30 mL×3) and brine, dried over $MgSO_4$, filtered, and concentrated. Flash chromatography (2-5% MeOH in $CH_2Cl_2$) provides 1.2 g (85%) of 2-(4-amino-3,5-dichloro-benzenesulfonylamino)-4-1,2,3-triazol-2-yl-butyric acid methyl ester as a white solid. A mixture of 1.1 g (2.7 mmol) of this material in 20 mL of conc. HCl is heated to 65° C. for 3 h. The reaction mixture is concentrated to provide 1.0 g (93%) of I-097.

I-098: 2-(4-Amino-3,5-dichloro-benzenesulfonylamino)-4-(2-cyano-pyrrol-1-yl)-butyric acid

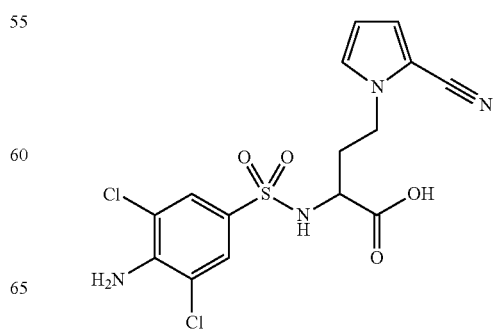

A mixture of 1.8 g (5.7 mmol) of I-044 in 10 mL of 4N HCl in 1,4-dioxane is stirred for 1 h. The mixture is concentrated, and the residue dissolved in 10 mL of DMF. To this is added 16 mL (110 mmol) of Et₃N, and 1.5 g (5.7 mmol) of I-001. After stirring overnight, the mixture is diluted with EtOAc and washed three times with water, once with 1N HCl, and once with brine. The solution is dried with MgSO₄, filtered, and concentrated. Flash chromatography (2-5% MeOH in CH₂Cl₂) provides 1.7 g (69%) of 2-(4-amino-3,5-dichloro-benzenesulfonylamino)-4-(2-cyano-pyrrol-1-yl)-butyric acid methyl ester. To this material in 15 mL of dioxane is added 3.3 mL (9.9 mmol) of a 3M NaOH. After stirring for 3 h, 2N HCl is added until the pH is 3. The mixture is extracted with EtOAc, and the extract is washed with brine, dried over Na₂SO₄, filtered, and concentrated to provide 1.4 g (85%) of I-098 as a yellow oil.

I-099: 2-(2-Chloro-6-methyl-benzenesulfonylamino)-4-(2-cyano-pyrrol-1-yl)-butyric acid is prepared from I-044 and 2-chloro-6-methylbenzenesulfonyl chloride in the same manner as I-098.

I-100: 2-(2,6-Dichlorobenzenesulfonylamino)-4-(2-cyano-pyrrol-1-yl)-butyric acid is prepared from I-044 and 2,6-dichlorobenzenesulfonyl chloride in the same manner as I-098.

I-101: 4-(2-Cyano-pyrrol-1-yl)-2-(1H-indole-6-sulfonylamino)-butyric acid is prepared from I-044 and indol-6-ylsulfonyl chloride in the same manner as I-098.

I-102: 4-(2-Cyano-pyrrol-1-yl)-2-(1H-indole-4-sulfonylamino)-butyric acid is prepared from I-044 and indol-4-ylsulfonyl chloride in the same manner as I-098.

I-103: 2-(3-Chloro-1H-indole-4-sulfonylamino)-4-(2-cyano-pyrrol-1-yl)-butyric acid

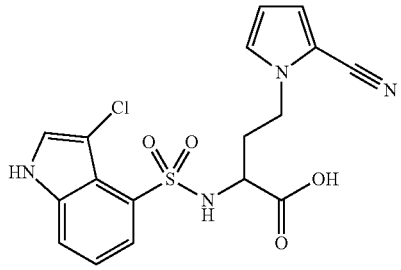 [SMILES: N#Cc1cccn1CCC(NS(=O)(=O)c1cccc2[nH]cc(Cl)c12)C(=O)O]

A solution of 0.20 g (0.52 mmol) of 4-(2-cyano-pyrrol-1-yl)-2-(1H-indole-4-sulfonylamino)-butyric acid methyl ester (from the synthesis of I-102) and 0.070 g (0.52 mmol) of NCS in 1 mL of DMF is stirred overnight, and then diluted with MeCN and purified by preparative HPLC to provide 0.15 g (0.36 mmol; 69%) of 2-(3-chloro-1H-indole-4-sulfonylamino)-4-(2-cyano-pyrrol-1-yl)-butyric acid methyl ester. This material is stirred in 1.4 mL of THF with 1.4 mL of 1M NaOH for 3 h, and then 2N HCl is added until the pH is 3. The mixture is extracted with EtOAc, and the extract washed with brine, dried over Na₂SO₄, filtered, and concentrated to provide 0.12 g (85%) of I-103 as a tan powder.

I-104: 2-(4-Amino-3,5-dichloro-benzenesulfonylamino)-4-(2-cyano-pyrrol-1-yl)-N-methoxy-N-methyl-butyramide

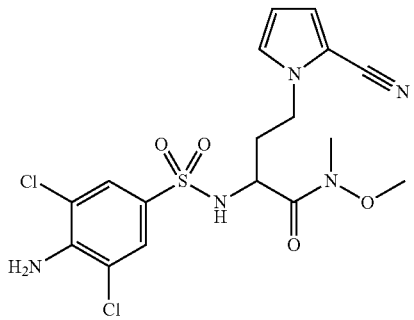 [SMILES: CON(C)C(=O)C(CCn1cccc1C#N)NS(=O)(=O)c1cc(Cl)c(N)c(Cl)c1]

To 300 mg (0.72 mmol) of I-098, 280 mg (1.4 mmol) of EDC, 200 mg (1.4 mmol) of HOBt, and 18 mg (0.14 mmol) of DMAP is added 2 ml of DMF. The reaction mixture is stirred for 1 hour, and then 110 mg (1.1 mmol) of N-methylmethoxylamine hydrochloride and 0.25 mL (1.4 mmol) of iPr₂NEt are added. The mixture is stirred overnight, then diluted with EtOAc and washed with water, 1N HCl, and brine. The organic layer is dried over MgSO₄, filtered, and concentrated. Flash chromatography provides 210 mg of I-104.

I-105: 2-(4-Amino-3,5-dichloro-benzenesulfonylamino)-N-methoxy-N-methyl-4-1,2,3-triazol-2-yl-butyramide

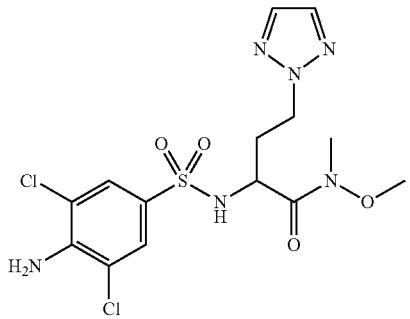 [SMILES: CON(C)C(=O)C(CCn1nccn1)NS(=O)(=O)c1cc(Cl)c(N)c(Cl)c1]

To 500 mg (1.3 mmol) of I-097, 500 mg (2.5 mmol) of EDC, and 350 mg (2.5 mmol) of HOBt and 32 mg (0.25 mmol) of DMAP is added 15 ml of DMF. The reaction mixture is stirred for 20 minutes, and then 190 mg (1.9 mmol) of N-methylmethoxylamine hydrochloride and 0.35 mL (2.5 mmol) of Et₃N are added. The mixture is stirred overnight, then diluted with EtOAc and washed with water, 1N HCl, and brine. The organic layer is dried over MgSO₄, filtered, and concentrated. Flash chromatography provides 330 mg of I-105 as a yellow oil.

EXAMPLES

General Method A (Sulfonamide Formation)

A mixture of 1 equivalent of amine or its salt, ≥1 equivalent of sulfonyl chloride, and ≥1 equivalent of an acid scavenger (≥2 equivalents in cases where amine salts are used) is stirred or shaken in the listed solvent for 2 to 24 h. Purification by preparative HPLC or flash chromatography provides Examples 1-210.

Example 1

N-{3-(2-cyano-1H-pyrrol-1-yl)-1-[(4-methylpiperidin-1-yl)carbonyl]propyl}benzenesulfonamide is prepared by reacting I-089 with benzenesulfonyl chloride in DCE with NMM as acid scavenger. ESI MS: Calc: 414.2. Found: 415.2 (M+H)$^+$.

Example 2

N-[1-(piperidin-1-ylcarbonyl)-3-(1H-pyrazol-1-yl)propyl]-1H-indole-4-sulfonamide is prepared by reacting I-058 with I-008 in CH$_2$Cl$_2$ with iPr$_2$NEt as acid scavenger. ESI MS: Calc: 415.2. Found: 416.1 (M+H)$^+$.

Example 3

N-{3-(2-cyano-1H-pyrrol-1-yl)-1-[(4-methylpiperidin-1-yl)carbonyl]propyl}thiophene-3-sulfonamide is prepared by reacting I-089 with thiophene-3-sulfonyl chloride in DCE with NMM as acid scavenger. ESI MS: Calc: 420.1. Found: 421.1 (M+H)$^+$.

Example 4

N-{3-(2-cyano-1H-pyrrol-1-yl)-1-[(4-methylpiperidin-1-yl)carbonyl]propyl}-2-methylbenzenesulfonamide is prepared by reacting I-089 with 2-methylbenzene sulfonyl chloride in DMF with Et$_3$N as acid scavenger. ESI MS: Calc: 428.2. Found: 430.1 (M+H)$^+$.

Example 5

N-{3-(2-cyano-1H-pyrrol-1-yl)-1-[(4-methylpiperidin-1-yl)carbonyl]propyl}-3-methylbenzenesulfonamide is prepared by reacting I-089 with 3-methylbenzenesulfonyl chloride in DCE with NMM as acid scavenger. ESI MS: Calc: 428.2. Found: 429.2 (M+H)$^+$.

Example 6

N-{3-(2-cyano-1H-pyrrol-1-yl)-1-[(4-methylpiperidin-1-yl)carbonyl]propyl}-4-methylbenzenesulfonamide is prepared by reacting I-089 with 4-toluenesulfonyl chloride in DMF with Et$_3$N as acid scavenger. ESI MS: Calc: 428.2. Found: 429.8 (M+H)$^+$.

Example 7

N-{1-[(4-methylpiperidin-1-yl)carbonyl]-3-(1H-pyrazol-1-yl)propyl}-1H-indole-4-sulfonamide is prepared by reacting I-085 with I-008 in DMF with NMM as acid scavenger. ESI MS: Calc: 429.2. Found: 430.5 (M+H)$^+$.

Example 8

N-{1-[(4-methylpiperidin-1-yl)carbonyl]-3-(1H-pyrazol-1-yl)propyl}-1H-indole-6-sulfonamide is prepared by reacting I-085 with I-007 DMF with NMM as acid scavenger. ESI MS: Calc: 429.2. Found: 430.5 (M+H)$^+$.

Example 9

N-{1-[(4-methylpiperidin-1-yl)carbonyl]-3-(2H-1,2,3-triazol-2-yl)propyl}-1H-indole-4-sulfonamide is prepared by reacting I-065 with I-008 in DMF with NMM as acid scavenger. ESI MS: Calc: 430.2. Found: 431.5 (M+H)$^+$.

Example 10

N-{3-(2-cyano-1H-pyrrol-1-yl)-1-[(4-methylpiperidin-1-yl)carbonyl]propyl}-3,5-dimethylisoxazole-4-sulfonamide is prepared by reacting I-089 with 3,5-dimethylisoxazole-4-sulfonyl chloride in DCE with NMM as acid scavenger. ESI MS: Calc: 433.2. Found: 434.3 (M+H)$^+$.

Example 11

2-cyano-N-{3-(2-cyano-1H-pyrrol-1-yl)-1-[(4-methylpiperidin-1-yl) carbonyl]propyl}benzenesulfonamide is prepared by reacting I-089 with 2-cyanobenzenesulfonyl chloride in DCE with NMM as acid scavenger. ESI MS: Calc: 439.2. Found: 440.2 (M+H)$^+$.

Example 12

3-cyano-N-{3-(2-cyano-1H-pyrrol-1-yl)-1-[(4-methylpiperidin-1-yl) carbonyl]propyl}benzenesulfonamide is prepared by reacting I-089 with 3-cyanobenzenesulfonyl chloride in DCE with NMM as acid scavenger. ESI MS: Calc: 439.2. Found: 440.2 (M+H)$^+$.

Example 13

N-{3-(2-cyano-1H-pyrrol-1-yl)-1-[(4-methylpiperidin-1-yl)carbonyl]propyl}-2,4-dimethylbenzenesulfonamide is prepared by reacting I-089 with 2,4-dimethyl benzenesulfonyl chloride in DCE with NMM as acid scavenger. ESI MS: Calc: 442.2. Found: 443.3 (M+H)$^+$.

Example 14

N-{3-(2-cyano-1H-pyrrol-1-yl)-1-[(4-methylpiperidin-1-yl)carbonyl]propyl}-2,5-dimethylbenzenesulfonamide is prepared by reacting I-089 with 2,5-dimethyl benzenesulfonyl chloride in DCE with NMM as acid scavenger. ESI MS: Calc: 442.2. Found: 443.3 (M+H)$^+$.

Example 15

N-{3-(2-cyano-1H-pyrrol-1-yl)-1-[(4-methylpiperidin-1-yl)carbonyl]propyl}-3,5-dimethylbenzenesulfonamide is prepared by reacting I-089 with 3,5-dimethylbenzenesulfonyl chloride in DCE with NMM as acid scavenger. ESI MS: Calc: 442.2. Found: 443.3 (M+H)$^+$.

Example 16

N-{3-(2-cyano-1H-pyrrol-1-yl)-1-[(4-methylpiperidin-1-yl)carbonyl]propyl}-2-methoxybenzenesulfonamide is prepared by reacting I-089 with 2-methoxy benzenesulfonyl chloride in DCE with NMM as acid scavenger. ESI MS: Calc: 444.2. Found: 445.3 (M+H)$^+$.

Example 17

N-{3-(2-cyano-1H-pyrrol-1-yl)-1-[(4-methylpiperidin-1-yl)carbonyl]propyl}-3-methoxybenzenesulfonamide is prepared by reacting I-089 with 3-methoxy benzenesulfonyl chloride in DCE with NMM as acid scavenger. ESI MS: Calc: 444.2. Found: 445.2 (M+H)$^+$.

Example 18

N-{3-(2-cyano-1H-pyrrol-1-yl)-1-[(4-methylpiperidin-1-yl)carbonyl]propyl}-4-methoxybenzenesulfonamide is prepared by reacting I-089 with 4-methoxy benzenesulfonyl chloride in DCE with NMM as acid scavenger. ESI MS: Calc: 444.2. Found: 445.2 (M+H)$^+$.

Example 19

N-[1-{[4-(hydroxymethyl)piperidin-1-yl]carbonyl}-3-(1H-pyrazol-1-yl) propyl]-1H-indole-4-sulfonamide is prepared by reacting I-059 with I-008 in CH$_2$Cl$_2$ with iPr$_2$NEt as acid scavenger. ESI MS: Calc: 445.2. Found: 446.3 (M+H)$^+$.

Example 20

N-{3-(2-cyano-1H-pyrrol-1-yl)-1-[(4-methylpiperidin-1-yl)carbonyl]propyl}-1,3,5-trimethyl-1H-pyrazole-4-sulfonamide is prepared by reacting I-089 with 1,3,5-trimethyl-1H-pyrazole-4-sulfonyl chloride in DCE with NMM as acid scavenger. ESI MS: Calc: 446.2. Found: 447.3 (M+H)$^+$.

Example 21

N-{3-(2-cyano-1H-pyrrol-1-yl)-1-[(4-methylpiperidin-1-yl)carbonyl]propyl}-4-fluoro-2-methylbenzenesulfonamide is prepared by reacting I-089 with 4-fluoro-2-methylbenzenesulfonyl chloride in DCE with NMM as acid scavenger. ESI MS: Calc: 446.2. Found: 447.3 (M+H)$^+$.

Example 22

2-chloro-N-{3-(2-cyano-1H-pyrrol-1-yl)-1-[(4-methylpiperidin-1-yl) carbonyl]propyl}benzenesulfonamide is prepared by reacting I-089 with 2-chlorobenzenesulfonyl chloride in DCE with NMM as acid scavenger. ESI MS: Calc: 448.1. Found: 449.3 (M+H)$^+$.

Example 23

3-chloro-N-{3-(2-cyano-1H-pyrrol-1-yl)-1-[(4-methylpiperidin-1-yl) carbonyl]propyl}benzenesulfonamide is prepared by reacting I-089 with 3-chlorobenzenesulfonyl chloride in DCE with NMM as acid scavenger. ESI MS: Calc: 448.1. Found: 449.2 (M+H)$^+$.

Example 24

4-chloro-N-{3-(2-cyano-1H-pyrrol-1-yl)-1-[(4-methylpiperidin-1-yl) carbonyl]propyl}benzenesulfonamide is prepared by reacting I-089 with 4-chlorobenzenesulfonyl chloride in DCE with NMM as acid scavenger. ESI MS: Calc: 448.1. Found: 449.1 (M+H)$^+$.

Example 25

N-{3-(2-cyano-1H-pyrrol-1-yl)-1-[(4-methylpiperidin-1-yl)carbonyl]propyl}-2,5-dimethylthiophene-3-sulfonamide is prepared by reacting I-089 with 2,5-dimethylthiophene-3-sulfonyl chloride in DCE with NMM as acid scavenger. ESI MS: Calc: 448.2. Found: 449.2 (M+H)$^+$.

Example 26

2-chloro-N-{3-(2-cyano-1H-pyrrol-1-yl)-1-[(4-methylpiperidin-1-yl) carbonyl]propyl}pyridine-3-sulfonamide is prepared by reacting I-089 with 2-chloropyridine-3-sulfonyl chloride in DCE with NMM as acid scavenger. ESI MS: Calc: 449.1. Found: 450.1 (M+H)$^+$.

Example 27

N-{3-(2-cyano-1H-pyrrol-1-yl)-1-[(4-methylpiperidin-1-yl)carbonyl]propyl}-2,4-dimethyl-1,3-thiazole-5-sulfonamide is prepared by reacting I-089 with 2,4-dimethyl-1,3-thiazole-5-sulfonyl chloride in DCE with NMM as acid scavenger. ESI MS: Calc: 449.2. Found: 450.2 (M+H)$^+$.

Example 28

N-{3-(2-cyano-1H-pyrrol-1-yl)-1-[(4-methylpiperidin-1-yl)carbonyl]propyl}-1H-indole-3-sulfonamide is prepared by reacting I-089 with I-018 in DMF with Et$_3$N as acid scavenger, and with subsequent treatment with 1 equivalent of TBAF in THF. ESI MS: Calc: 453.2. Found: 454.3 (M+H)$^+$.

Example 29

2-cyano-N-{3-(2-cyano-1H-pyrrol-1-yl)-1-[(4-methylpiperidin-1-yl) carbonyl]propyl}-5-methylbenzenesulfonamide is prepared by reacting I-089 with 2-cyano-5-methylbenzenesulfonyl chloride in DCE with NMM as acid scavenger. ESI MS: Calc: 453.2. Found: 454.2 (M+H)$^+$.

Example 30

N-{3-(2-cyano-1H-pyrrol-1-yl)-1-[(4-methylpiperidin-1-yl)carbonyl]propyl}-1H-indole-4-sulfonamide is prepared by reacting I-089 with I-008 in DMF with NMM as acid scavenger. ESI MS: Calc: 453.2. Found: 454.5 (M+H)$^+$.

Example 31

N-{3-(2-cyano-1H-pyrrol-1-yl)-1-[(4-methylpiperidin-1-yl)carbonyl]propyl}-1H-indole-6-sulfonamide is prepared by reacting I-089 with I-007 in DMF with NMM as acid scavenger. ESI MS: Calc: 453.2. Found: 454.9 (M+H)$^+$.

Example 32

N-{3-(2-cyano-1H-pyrrol-1-yl)-1-[(4-methylpiperidin-1-yl)carbonyl]propyl}-1-benzofuran-7-sulfonamide is prepared by reacting I-089 with benzofuran-7-sulfonyl chloride in DMF with NMM as acid scavenger. ESI MS: Calc: 454.2. Found: 455.3 (M+H)$^+$.

Example 33

N-{3-(2-cyano-1H-pyrrol-1-yl)-1-[(4-methylpiperidin-1-yl)carbonyl]propyl}-1H-indazole-4-sulfonamide is prepared by reacting I-089 with I-020 in DMF with Et$_3$N as acid scavenger. ESI MS: Calc: 454.2. Found: 455.2 (M+H)$^+$.

Example 34

N-{3-(2-cyano-1H-pyrrol-1-yl)-1-[(4-methylpiperidin-1-yl)carbonyl]propyl}-1H-indazole-6-sulfonamide is prepared by reacting I-089 with I-025 in DMF with Et$_3$N as acid scavenger. ESI MS: Calc: 454.2. Found: 455.4 (M+H)$^+$.

Example 35

N-{3-(2-cyano-1H-pyrrol-1-yl)-1-[(4-methylpiperidin-1-yl)carbonyl]propyl}-1H-indole-5-sulfonamide is prepared by reacting I-089 with I-016 in DMF with NMM as acid scavenger. ESI MS: Calc: 453.2. Found: 454.9 (M+H)$^+$.

Example 36

N-{3-(3-cyano-1H-pyrazol-1-yl)-1-[(4-methylpiperidin-1-yl)carbonyl]propyl}-1H-indole-4-sulfonamide is prepared by reacting a 2:1 mixture of I-086 and I-091 with I-008 in 4:1 CH$_2$Cl$_2$/DMF with Et$_3$N as acid scavenger. Preparative HPLC provides pure Example 36. ESI MS: Calc: 454.2. Found: 455.4 (M+H)$^+$.

Example 37

N-{3-(5-cyano-1H-pyrazol-1-yl)-1-[(4-methylpiperidin-1-yl)carbonyl]propyl}-1H-indole-4-sulfonamide is prepared by reacting I-091 with I-008 in DMF with Et$_3$N as acid scavenger. ESI MS: Calc: 454.2. Found: 455.5 (M+H)$^+$.

Example 38

3-acetyl-N-{3-(2-cyano-1H-pyrrol-1-yl)-1-[(4-methylpiperidin-1-yl) carbonyl]propyl}benzenesulfonamide is prepared by reacting I-089 with 3-acetylbenzenesulfonyl chloride in DCE with NMM as acid scavenger. ESI MS: Calc: 456.2. Found: 457.2 (M+H)$^+$.

Example 39

4-acetyl-N-{3-(2-cyano-1H-pyrrol-1-yl)-1-[(4-methylpiperidin-1-yl) carbonyl]propyl}benzenesulfonamide is prepared by reacting I-089 with 4-acetylbenzenesulfonyl chloride in DCE with NMM as acid scavenger. ESI MS: Calc: 456.2. Found: 457.2 (M+H)$^+$.

Example 40

N-{3-(2-cyano-1H-pyrrol-1-yl)-1-[(4-methylpiperidin-1-yl)carbonyl]propyl}-2,4,6-trimethylbenzenesulfonamide is prepared by reacting I-089 with 2,4,6-trimethyl benzenesulfonyl chloride in DCE with NMM as acid scavenger. ESI MS: Calc: 456.2. Found: 457.3 (M+H)$^+$.

Example 41

3-amino-N-{3-(2-cyano-1H-pyrrol-1-yl)-1-[(4-methylpiperidin-1-yl) carbonyl]propyl}-2,4-dimethylbenzenesulfonamide is prepared by reacting I-089 with I-002 in DMF with Et$_3$N as acid scavenger. ESI MS: Calc: 457.2. Found: 459.9 (M+H)$^+$.

Example 42

N-[3-(2-cyano-1H-pyrrol-1-yl)-1-{[4-(hydroxymethyl) piperidin-1-yl]carbonyl]propyl}-2,5-dimethylbenzenesulfonamide is prepared by reacting I-075 with 2,5-trichlorobenzenesulfonyl chloride in DCE with NMM as acid scavenger. ESI MS: Calc: 458.2. Found: 459.2 (M+H)$^+$.

Example 43

N-{3-(2-cyano-1H-pyrrol-1-yl)-1-[(4-methylpiperidin-1-yl)carbonyl]propyl}-2-methoxy-4-methylbenzenesulfonamide is prepared by reacting I-089 with 2-methoxy-4-methylbenzenesulfonyl chloride in DCE with NMM as acid scavenger. ESI MS: Calc: 458.2. Found: 459.3 (M+H)$^+$.

Example 44

N-{3-(2-cyano-1H-pyrrol-1-yl)-1-[(4-methylpiperidin-1-yl)carbonyl]propyl}-2-methoxy-5-methylbenzenesulfonamide is prepared by reacting I-089 with 2-methoxy-5-methylbenzenesulfonyl chloride in DCE with NMM as acid scavenger. ESI MS: Calc: 458.2. Found: 459.3 (M+H)$^+$.

Example 45

2-chloro-N-{3-(2-cyano-1H-pyrrol-1-yl)-1-[(4-methylpiperidin-1-yl) carbonyl]propyl}-6-methylbenzenesulfonamide is prepared by reacting I-089 with 2-chloro-6-methylbenzenesulfonyl chloride in DMF with Et$_3$N as acid scavenger. ESI MS: Calc: 462.2. Found: 463.4 (M+H)$^+$.

Example 46

3-chloro-N-{3-(2-cyano-1H-pyrrol-1-yl)-1-[(4-methylpiperidin-1-yl) carbonyl]propyl}-2-methylbenzenesulfonamide is prepared by reacting I-089 with 3-chloro-2-methyl benzenesulfonyl chloride in DCE with NMM as acid scavenger. ESI MS: Calc: 462.2. Found: 463.2 (M+H)$^+$.

Example 47

N-{3-(5-chloro-1H-pyrazol-1-yl)-1-[(4-methylpiperidin-1-yl)carbonyl]propyl}-1H-indole-4-sulfonamide is prepared by reacting I-082 with I-008 in DMF with iPr$_2$NEt as acid scavenger. ESI MS: Calc: 463.1. Found: 464.4 (M+H)$^+$.

Example 48

N-{3-(5-chloro-1H-pyrazol-1-yl)-1-[(4-methylpiperidin-1-yl)carbonyl]propyl}-1H-indole-6-sulfonamide is prepared by reacting I-082 with I-007 in MeCN with NMM as acid scavenger. ESI MS: Calc: 463.1. Found: 464.5 (M+H)$^+$.

Example 49

N-{3-(2-cyano-1H-pyrrol-1-yl)-1-[(4-methylpiperidin-1-yl)carbonyl]propyl}naphthalene-1-sulfonamide is prepared by reacting I-089 with naphthalene-1-sulfonyl chloride in DCE with NMM as acid scavenger. ESI MS: Calc: 464.2. Found: 465.3 (M+H)$^+$.

Example 50

N-benzyl-4-(2-cyano-1H-pyrrol-1-yl)-2-{[(2,5-dimethylphenyl) sulfonyl]amino}-N-methylbutanamide is prepared by reacting I-072 with 2,5-dimethylbenzenesulfonyl chloride in DCE with NMM as acid scavenger. ESI MS: Calc: 464.2. Found: 465.2 (M+H)$^+$.

Example 51

N-{3-(2-cyano-1H-pyrrol-1-yl)-1-[(4-methylpiperidin-1-yl)carbonyl]propyl}isoquinoline-5-sulfonamide is prepared by reacting I-089 with isoquinoline-5-sulfonyl chloride in DCE with NMM as acid scavenger. ESI MS: Calc: 465.2. Found: 466.3 (M+H)$^+$.

Example 52

2-chloro-N-{3-(2-cyano-1H-pyrrol-1-yl)-1-[(4-methylpiperidin-1-yl) carbonyl]propyl}-4-fluorobenzenesulfonamide is prepared by reacting I-089 with 2-chloro-4,5-difluorobenzensulfonyl chloride in DCE with NMM as acid scavenger. ESI MS: Calc: 466.1. Found: 467.2 (M+H)$^+$.

Example 53

5-chloro-N-{3-(2-cyano-1H-pyrrol-1-yl)-1-[(4-methylpiperidin-1-yl) carbonyl]propyl}-1,3-dimethyl-1H-pyrazole-4-sulfonamide is prepared by reacting I-089 with 5-chloro-1,3-dimethyl-1H-pyrazole-4-sulfonyl chloride in DCE with NMM as acid scavenger. ESI MS: Calc: 466.2. Found: 467.2 (M+H)$^+$.

Example 54

N-{3-(2-cyano-1H-pyrrol-1-yl)-1-[(4-methylpiperidin-1-yl)carbonyl]propyl}-1-methyl-1H-indole-4-sulfonamide is prepared by reacting I-089 with 1-methylindole-4-sulfonyl chloride in DMF with iPr$_2$NEt as acid scavenger. ESI MS: Calc: 467.2. Found: 468.3 (M+H)$^+$.

Example 55

N-{3-(2-cyano-1H-pyrrol-1-yl)-1-[(4-methylpiperidin-1-yl)carbonyl]propyl}-7-methyl-1H-indole-4-sulfonamide is prepared by reaction I-089 with I-009 in DMF with iPr$_2$NEt as acid scavenger. ESI MS: Calc: 467.2. Found: 468.2 (M+H)$^+$.

Example 56

N-{3-(2-cyano-1H-pyrrol-1-yl)-1-[(4-methylpiperidin-1-yl)carbonyl]propyl}-2-oxoindoline-5-sulfonamide is prepared by reacting I-089 with I-003 in DMF with NMM as acid scavenger. ESI MS: Calc: 469.2. Found: 470.9 (M+H)$^+$.

Example 57

N-{3-(2-cyano-1H-pyrrol-1-yl)-1-[(4-methylpiperidin-1-yl)carbonyl]propyl}-1-benzothiophene-3-sulfonamide is prepared by reacting I-089 with benzothiophene-3-sulfonyl chloride in DCE with NMM as acid scavenger. ESI MS: Calc: 470.1. Found: 471.1 (M+H)$^+$.

Example 58

N-[3-(5-cyano-1H-pyrazol-1-yl)-1-{[4-(hydroxymethyl)piperidin-1-yl]carbonyl}propyl]-1H-indole-4-sulfonamide is prepared by reacting I-092 with I-008 in DMF with Et$_3$N as acid scavenger. ESI MS: Calc: 470.2. Found: 471.3 (M+H)$^+$.

Example 59

N-[3-(2-cyano-1H-pyrrol-1-yl)-1-{[1-(hydroxymethyl)piperidin-1-yl]carbonyl}propyl]-1H-indazole-4-sulfonamide is prepared by reacting I-075 with I-020 in CH$_2$Cl$_2$ with iPr$_2$NEt as acid scavenger. ESI MS: Calc: 470.2. Found: 471.3 (M+H)$^+$.

Example 60

N-{3-[({3-(2-cyano-1H-pyrrol-1-yl)-1-[(4-methylpiperidin-1-yl)carbonyl]propyl}amino)sulfonyl]phenyl}acetamide is prepared by reacting I-089 with 3-acetylamino-benzenesulfonyl chloride in DCE with NMM as acid scavenger. ESI MS: Calc: 471.2. Found: 472.2 (M+H)$^+$.

Example 61

N-{4-[({3-(2-cyano-1H-pyrrol-1-yl)-1-[(4-methylpiperidin-1-yl)carbonyl]propyl}amino)sulfonyl]phenyl}acetamide is prepared by reacting I-089 with 4-acetylamino-benzenesulfonyl chloride in DCE with NMM as acid scavenger. ESI MS: Calc: 471.2. Found: 472.2 (M+H)$^+$.

Example 62

N-{3-(2-cyano-1H-pyrrol-1-yl)-1-[(4-methylpiperidin-1-yl)carbonyl]propyl}-2,1,3-benzothiadiazole-4-sulfonamide is prepared by reacting I-089 with 2,1,3-benzothiadiazole-4-sulfonyl chloride in DMF with NMM as acid scavenger. ESI MS: Calc: 472.1. Found: 473.2 (M+H)$^+$.

Example 63

2-chloro-N-{3-(5-chloro-1H-pyrazol-1-yl)-1-[(4-methylpiperidin-1-yl) carbonyl]propyl}-6-methylbenzenesulfonamide is prepared by reacting I-082 with 2-chloro-6-methylbenzenesulfonyl chloride in DMF with Et$_3$N as acid scavenger. ESI MS: Calc: 472.1. Found: 473.4 (M+H)$^+$.

Example 64

1-{3-[(1H-indol-4-ylsulfonyl)amino]-4-(4-methylpiperidin-1-yl)-4-oxobutyl}-1H-pyrazole-5-carboxamide is prepared by reacting I-079 with I-001 in DMF with Et$_3$N as acid scavenger. ESI MS: Calc: 472.2. Found: 473.5 (M+H)$^+$.

Example 65

4-(carbamoylamino)-N-{3-(2-cyano-1H-pyrrol-1-yl)-1-[(4-methyl piperidin-1-yl)carbonyl]propyl} benzenesulfonamide is prepared by reacting I-089 with 4-(carbamoylamino) benzenesulfonyl chloride in DCE with NMM as acid scavenger. ESI MS: Calc: 472.2. Found: 473.3 (M+H)$^+$.

Example 66 methyl 2-[({3-(2-cyano-1H-pyrrol-1-yl)-1-[(4-methylpiperidin-1-yl) carbonyl]propyl}amino)sulfonyl]benzoate is prepared by reacting I-089 with 2-carbomethoxy benzenesulfonyl chloride in DMF with NMM as acid scavenger. ESI MS: Calc: 472.2. Found: 473.6 (M+H)$^+$.

Example 67 methyl 4-[({3-(2-cyano-1H-pyrrol-1-yl)-1-[(4-methylpiperidin-1-yl) carbonyl]propyl}amino)sulfonyl]benzoate is prepared by reacting I-089 with methyl 4-chlorosulfonylbenzoate in DCE with NMM as acid scavenger. ESI MS: Calc: 472.2. Found: 473.2 (M+H)$^+$.

Example 68

N-{3-(2-cyano-1H-pyrrol-1-yl)-1-[(4-methylpiperidin-1-yl)carbonyl]propyl}-5-ethyl-2-methoxybenzenesulfonamide is prepared by reacting I-089 with 5-ethyl-2-methoxy benzenesulfonyl chloride in DCE with NMM as acid scavenger. ESI MS: Calc: 472.2. Found: 473.3 (M+H)$^+$.

Example 69

2-chloro-4-cyano-N-{3-(2-cyano-1H-pyrrol-1-yl)-1-[(4-methylpiperidin-1-yl)carbonyl]propyl}benzenesulfonamide is prepared by reacting I-089 with 2-chloro-4-cyano benzenesulfonyl chloride in DCE with NMM as acid scavenger. ESI MS: Calc: 473.1. Found: 474.3 (M+H)$^+$.

Example 70

4-amino-3,5-dichloro-N-{1-[(4-methylpiperidin-1-yl)carbonyl]-3-(1H-pyrazol-1-yl)propyl}benzenesulfonamide is prepared by reacting I-085 with I-001 in CH$_2$Cl$_2$ with iPr$_2$NEt as acid scavenger. ESI MS: Calc: 473.1. Found: 474.0 (M+H)$^+$.

Example 71

2-amino-4,6-dichloro-N-{1-[(4-methylpiperidin-1-yl)carbonyl]-3-(2H-1,2,3-triazol-2-yl)propyl}benzenesulfonamide is prepared by reacting I-065 with 2-amino-4,6-dichlorobenznesulfonyl chloride in DCE with Et$_3$N as acid scavenger. ESI MS: Calc: 474.1. Found: 475.2 (M+H)$^+$.

Example 72

4-amino-3,5-dichloro-N-{1-[(4-methylpiperidin-1-yl)carbonyl]-3-(2H-1,2,3-triazol-2-yl)propyl}benzenesulfonamide is prepared by reacting I-065 with I-001 in CH$_2$Cl$_2$ with PS-NMM as acid scavenger. ESI MS: Calc: 474.1. Found: 475.1 (M+H)$^+$.

Example 73

N-{1-[(4-methylpiperidin-1-yl)carbonyl]-3-(2-nitro-1H-imidazol-1-yl)propyl}-1H-indole-4-sulfonamide is prepared by reacting I-057a with I-008 in DMF with NMM as acid scavenger. ESI MS: Calc: 474.2. Found: 475.5 (M+H)$^+$.

Example 74

N-{1-[(4-methylpiperidin-1-yl)carbonyl]-3-(2-nitro-1H-imidazol-1-yl)propyl}-1H-indole-6-sulfonamide is prepared by reacting I-057a with I-008 in DMF with NMM as acid scavenger. ESI MS: Calc: 474.2. Found: 475.5 (M+H)$^+$.

Example 75

N-{3-(2-cyano-1H-pyrrol-1-yl)-1-[(4-methylpiperidin-1-yl)carbonyl]propyl}-2,5-dimethoxybenzenesulfonamide is prepared by reacting I-089 with 2,5-dimethoxy benzenesulfonyl chloride in DCE with NMM as acid scavenger. ESI MS: Calc: 474.2. Found: 475.3 (M+H)$^+$.

Example 76

N-benzyl-4-(2-cyano-1H-pyrrol-1-yl)-2-[(1H-indol-4-ylsulfonyl)amino]-N-methylbutanamide is prepared by reacting I-072 with I-008 in 4:1 CH$_2$Cl$_2$/DMF with Et$_3$N as acid scavenger. ESI MS: Calc: 475.2. Found: 476.3 (M+H)$^+$.

Example 77

2-chloro-N-[3-(2-cyano-1H-pyrrol-1-yl)-1-{[4-(hydroxymethyl)piperidin-1-yl]carbonyl}propyl]-6-methylbenzenesulfonamide is prepared by reacting I-075 with 2-chloro-6-methylbenzensulfonyl chloride in DCE with NMM as acid scavenger. ESI MS: Calc: 478.1. Found: 479.1 (M+H)$^+$.

Example 78

5-chloro-N-{3-(2-cyano-1H-pyrrol-1-yl)-1-[(4-methylpiperidin-1-yl) carbonyl]propyl}-2-methoxybenzenesulfonamide is prepared by reacting I-089 with 5-chloro-2-methoxy benzenesulfonyl chloride in DCE with NMM as acid scavenger. ESI MS: Calc: 478.1. Found: 479.2 (M+H)$^+$.

Example 79

3-Amino-2,4-dimethyl-N-{1-[(4-methylpiperidin-1-yl)carbonyl]-3-(2-nitro-1H-imidazol-1-yl)propyl}benzenesulfonamide is prepared by reacting I-057 with I-002 in CH$_2$Cl$_2$ with iPr$_2$NEt as acid scavenger. ESI MS: Calc: 478.2. Found: 479.3 (M+H)$^+$.

Example 80

4-(2-cyano-1H-pyrrol-1-yl)-2-{[(2,5-dimethylphenyl)sulfonyl]amino}-N-methyl-N-[(1R)-1-phenylethyl]butanamide is prepared by reacting I-078 with 2,6-dichlorobenzenesulfonyl chloride in DCE with NMM as acid scavenger. ESI MS: Calc: 478.2. Found: 479.2 (M+H)$^+$.

Example 81

N-{3-(2-cyano-1H-pyrrol-1-yl)-1-[(4-methylpiperidin-1-yl)carbonyl]propyl}-4-methylnaphthalene-1-sulfonamide is prepared by reacting I-089 with 4-methyl-naphthalene-1-sulfonyl chloride in DMF with Et$_3$N as acid scavenger. ESI MS: Calc: 478.2. Found: 479.7 (M+H)$^+$.

Example 82

N-[3-(2-cyano-1H-pyrrol-1-yl)-1-{[4-(hydroxymethyl)piperidin-1-yl]carbonyl}propyl]naphthalene-1-sulfonamide is prepared by reacting I-075 with naphthalene-1-sulfonyl chloride in DCE with NMM as acid scavenger. ESI MS: Calc: 480.2. Found: 481.2 (M+H)$^+$.

Example 83

N-{1-[(4-methylpiperidin-1-yl)carbonyl]-3-(2H-1,2,3-triazol-2-yl)propyl}-2,4-dinitrobenzenesulfonamide is prepared by reacting I-065a with 2,4-dinitro benzenesulfonyl chloride in DMF with NMM as acid scavenger. ESI MS: Calc: 481.1. Found: 482.3 (M+H)$^+$.

Example 84

2,3-dichloro-N-{3-(2-cyano-1H-pyrrol-1-yl)-1-[(4-methylpiperidin-1-yl) carbonyl]propyl}benzenesulfonamide is prepared by reacting I-089 with 2,3-dichloro-benzenesulfonyl chloride in DCE with NMM as acid scavenger. ESI MS: Calc: 482.1. Found: 483.2 (M+H)$^+$.

Example 85

2,5-dichloro-N-{3-(2-cyano-1H-pyrrol-1-yl)-1-[(4-methylpiperidin-1-yl) carbonyl]propyl}benzenesulfonamide is prepared by reacting I-089 with 2,5-dichloro benzenesulfonyl chloride in DCE with NMM as acid scavenger. ESI MS: Calc: 482.1. Found: 483.1 (M+H)$^+$.

Example 86

2,6-dichloro-N-{3-(2-cyano-1H-pyrrol-1-yl)-1-[(4-methylpiperidin-1-yl) carbonyl]propyl}benzenesulfonamide is prepared by reacting I-089 with 2,6-dichloro benzenesulfonyl chloride in DMF with $Et_3N$ as acid scavenger. ESI MS: Calc: 482.1. Found: 483.3 $(M+H)^+$.

Example 87

3,5-dichloro-N-{3-(2-cyano-1H-pyrrol-1-yl)-1-[(4-methylpiperidin-1-yl) carbonyl]propyl}benzenesulfonamide is prepared by reacting I-089 with 3,5-dichloro benzenesulfonyl chloride in DCE with NMM as acid scavenger. ESI MS: Calc: 482.1. Found: 483.1 $(M+H)^+$.

Example 88

N-{3-(2-cyano-1H-pyrrol-1-yl)-1-[(4-methylpiperidin-1-yl)carbonyl]propyl}-2-(trifluoromethyl)benzenesulfonamide is prepared by reacting I-089 with 2-(trifluoromethyl)benzenesulfonyl chloride in DCE with NMM as acid scavenger. ESI MS: Calc: 482.2. Found: 483.3 $(M+H)^+$.

Example 89

N-{3-(2-cyano-1H-pyrrol-1-yl)-1-[(4-methylpiperidin-1-yl)carbonyl]propyl}-3-(trifluoromethyl)benzenesulfonamide is prepared by reacting I-089 with 3-(trifluoromethyl)benzenesulfonyl chloride in DCE with NMM as acid scavenger. ESI MS: Calc: 482.2. Found: 483.2 $(M+H)^+$.

Example 90

N-{3-(2-cyano-1H-pyrrol-1-yl)-1-[trans-octahydroisoquinolin-2(1H)-yl carbonyl]propyl}-2,5-dimethylbenzenesulfonamide is prepared by reacting I-076 with 2,5-dimethylbenzenesulfonyl chloride in DCE with NMM as acid scavenger. ESI MS: Calc: 482.2. Found: 483.2 $(M+H)^+$.

Example 91

2-chloro-N-{3-(2-cyano-1H-pyrrol-1-yl)-1-[(4-methylpiperidin-1-yl)carbonyl]propyl}-4,5-difluorobenzenesulfonamide is prepared by reacting I-089 with 2-chloro-4,5-difluorobenzensulfonyl chloride in DCE with NMM as acid scavenger. ESI MS: Calc: 484.1. Found: 485.2 $(M+H)^+$.

Example 92

N-benzyl-2-{[(2-chloro-6-methylphenyl)sulfonyl]amino}-4-(2-cyano-1H-pyrrol-1-yl)-N-methylbutanamide is prepared by reacting I-072 with 2-chloro-6-methylbenzenesulfonyl chloride in DCE with NMM as acid scavenger. ESI MS: Calc: 484.1. Found: 485.1 $(M+H)^+$.

Example 93

5-chloro-N-{3-(2-cyano-1H-pyrrol-1-yl)-1-[(4-methylpiperidin-1-yl)carbonyl]propyl}-3-methyl-1-benzothiophene-2-sulfonamide is prepared by reacting I-089 with 5-chloro-3-methyl-1-benzothiophene-2-sulfonyl chloride in DCE with NMM as acid scavenger. ESI MS: Calc: 518.1. Found: 519.2 $(M+H)^+$.

Example 94

N-{4-[({3-(2-cyano-1H-pyrrol-1-yl)-1-[(4-methylpiperidin-1-yl)carbonyl]propyl}amino)sulfonyl]-3-methylphenyl}acetamide is prepared by reacting I-089 with 4-acetylamino-2-methyl-benzenesulfonyl chloride in DCE with NMM as acid scavenger. ESI MS: Calc: 485.2. Found: 486.3 $(M+H)^+$.

Example 95 methyl 1-{3-[(1H-indol-4-ylsulfonyl)amino]-4-(4-methylpiperidin-1-yl)-4-oxobutyl}-1H-pyrrole-2-carboxylate is prepared by reacting I-090 with I-008 in $CH_2Cl_2$ with $iPr_2NEt$ as acid scavenger. ESI MS: Calc: 486.2. Found: 487.5 $(M+H)^+$.

Example 96

N-{3-(2-cyano-1H-pyrrol-1-yl)-1-[(4-methylpiperidin-1-yl)carbonyl]propyl}-1-methyl-3-(trifluoromethyl)-1H-pyrazole-4-sulfonamide is prepared by reacting I-089 with 1-methyl-3-(trifluoromethyl)-1H-pyrazole-4-sulfonyl chloride in DCE with NMM as acid scavenger. ESI MS: Calc: 486.2. Found: 487.3 $(M+H)^+$.

Example 97

N-{3-(2-cyano-1H-pyrrol-1-yl)-1-[(4-methylpiperidin-1-yl)carbonyl]propyl}-4-methoxy-2,3,6-trimethylbenzenesulfonamide is prepared by reacting I-089 with 4-methoxy-2,3,5-trimethylbenzenesulfonyl chloride in DCE with NMM as acid scavenger. ESI MS: Calc: 486.2. Found: 487.3 $(M+H)^+$.

Example 98

N-{3-(2-cyano-1H-pyrrol-1-yl)-1-[(4-methylpiperidin-1-yl)carbonyl]-propyl}-5-methyl-2,1,3-benzothiadiazole-4-sulfonamide is prepared by reacting I-089 with 5-methyl-2,1,3-benzothiadiazole-4-sulfonyl chloride in DMF with NMM as acid scavenger. ESI MS: Calc: 486.2. Found: 487.1 $(M+H)^+$.

Example 99

2,5-dichloro-N-{3-(2-cyano-1H-pyrrol-1-yl)-1-[(4-methylpiperidin-1-yl) carbonyl]propyl}thiophene-3-sulfonamide is prepared by reacting I-089 with 2,5-dichlorothiophene-3-sulfonyl chloride in DCE with NMM as acid scavenger. ESI MS: Calc: 488.1. Found: 489.1 $(M+H)^+$.

Example 100

N-{3-(2-chloro-1H-imidazol-1-yl)-1-[(4-methylpiperidin-1-yl)carbonyl]propyl}-4-methylnaphthalene-1-sulfonamide is prepared by reacting I-066 with 4-methyl-naphthalene-1-sulfonyl chloride in DCE with $Et_3N$ as acid scavenger. ESI MS: Calc: 488.2. Found: 489.2 $(M+H)^+$.

Example 101

2-bromo-N-[3-(2-cyano-1H-pyrrol-1-yl)-1-(piperidin-1-ylcarbonyl) propyl]-6-methylbenzenesulfonamide is prepared by reacting I-073 with I-029 in $CH_2Cl_2$ with $iPr_2NEt$ as acid scavenger. ESI MS: Calc: 492.1. Found: 493.2 $(M+H)^+$.

Example 102

2-bromo-N-{3-(2-cyano-1H-pyrrol-1-yl)-1-[(4-methylpiperidin-1-yl) carbonyl]propyl}benzenesulfonamide is prepared by reacting I-089 with 2-bromobenzenesulfonyl chloride in DCE with NMM as acid scavenger. ESI MS: Calc: 492.1. Found: 493.2 (M+H)$^+$.

Example 103

N-{3-(2-cyano-1H-pyrrol-1-yl)-1-[trans-octahydroisoquinolin-2(1H)-yl carbonyl]propyl}-1H-indole-4-sulfonamide is prepared by reacting I-089 with I-076 in 4:1 CH$_2$Cl$_2$/DMF with iPr$_2$NEt as acid scavenger. ESI MS: Calc: 493.2. Found: 494.4 (M+H)$^+$.

Example 104

6-chloro-N-{3-(2-cyano-1H-pyrrol-1-yl)-1-[(4-methylpiperidin-1-yl) carbonyl]propyl}imidazo[2,1-b][1,3]thiazole-5-sulfonamide is prepared by reacting I-089 with 6-imidazo[2,1-b][1,3]thiazole-5-sulfonyl chloride in DCE with NMM as acid scavenger. ESI MS: Calc: 494.1. Found: 495.2 (M+H)$^+$.

Example 105

N-{3-(2-cyano-1H-pyrrol-1-yl)-1-[(4-methylpiperidin-1-yl)carbonyl]propyl}-5-methyl-3-phenylisoxazole-4-sulfonamide is prepared by reacting I-089 with 5-methyl-3-phenylisoxazole-4-sulfonyl chloride in DCE with NMM as acid scavenger. ESI MS: Calc: 495.2. Found: 496.3 (M+H)$^+$.

Example 106

2,4-dichloro-N-{3-(2-cyano-1H-pyrrol-1-yl)-1-[(4-methylpiperidin-1-yl) carbonyl]propyl}-5-methylbenzenesulfonamide is prepared by reacting I-089 with 2,4-dichloro-5-methylbenzenesulfonyl chloride in DCE with NMM as acid scavenger. ESI MS: Calc: 496.1. Found: 497.2 (M+H)$^+$.

Example 107

2,4-dichloro-N-{3-(2-cyano-1H-pyrrol-1-yl)-1-[(4-methylpiperidin-1-yl) carbonyl]propyl}-6-methylbenzenesulfonamide is prepared by reacting I-089 with 2,4-dichloro-6-methyl-benzenesulfonyl chloride in DCE with NMM as acid scavenger. ESI MS: Calc: 496.1. Found: 497.2 (M+H)$^+$.

Example 108

N-{3-(2-cyano-1H-pyrrol-1-yl)-1-[(4-methylpiperidin-1-yl)carbonyl]propyl}-2,5,6-trimethyl-1H-benzimidazole-7-sulfonamide is prepared by reacting I-089 with I-006 in DMF with NMM as acid scavenger. ESI MS: Calc: 496.2. Found: 497.8 (M+H)$^+$.

Example 109

2-amino-4,6-dichloro-N-{3-(2-cyano-1H-pyrrol-1-yl)-1-[(4-methyl piperidin-1-yl)carbonyl]propyl} benzenesulfonamide is prepared by reacting I-089 with 2-amino-4,6-dichlorobenzensulfonyl chloride in DMF with NMM as acid scavenger. ESI MS: Calc: 497.1. Found: 498.6 (M+H)$^+$.

Example 110

4-amino-2,5-dichloro-N-{3-(2-cyano-1H-pyrrol-1-yl)-1-[(4-methyl piperidin-1-yl)carbonyl]propyl} benzenesulfonamide is prepared by reacting I-089 with 4-amino-2,5-dichlorobenzenesulfonyl chloride in DCE with NMM as acid scavenger. ESI MS: Calc: 497.1. Found: 498.2 (M+H)$^+$.

Example 111

4-amino-3,5-dichloro-N-{3-(2-cyano-1H-pyrrol-1-yl)-1-[(4-methyl piperidin-1-yl)carbonyl]propyl} benzenesulfonamide is prepared by reacting I-089 with I-001 in CH$_2$Cl$_2$ with iPr$_2$NEt as acid scavenger. ESI MS: Calc: 497.1. Found: 498.2 (M+H)$^+$.

Example 112

4-chloro-2,5-dimethyl-N-{1-[(4-methylpiperidin-1-yl)carbonyl]-3-(2-nitro-1H-imidazol-1-yl)propyl}benzenesulfonamide is prepared by reacting I-057 with 4-chloro-2,5-dimethylbenzenesulfonyl chloride in CH$_2$Cl$_2$ with Et$_3$N as acid scavenger. ESI MS: Calc: 497.2. Found: 497.9 (M+H)$^+$.

Example 113

4-bromo-N-{3-(2-cyano-1H-pyrrol-1-yl)-1-[(4-methylpiperidin-1-yl) carbonyl]propyl}thiophene-3-sulfonamide is prepared by reacting I-089 with 4-bromothiophene-3-sulfonyl chloride in DCE with NMM as acid scavenger. ESI MS: Calc: 498.0. Found: 499.1 (M+H)$^+$.

Example 114

2,6-dichloro-N-[3-(2-cyano-1H-pyrrol-1-yl)-1-{[4-(hydroxymethyl)piperidin-1-yl]carbonyl}propyl]benzenesulfonamide is prepared by reacting I-075 with 2,6-dichlorobenzenesulfonyl chloride in DCE with NMM as acid scavenger. ESI MS: Calc: 498.1. Found: 499.1 (M+H)$^+$.

Example 115

4-amino-3,5-dichloro-N-{3-(2-cyano-1H-imidazol-1-yl)-1-[(4-methyl piperidin-1-yl)carbonyl]propyl} benzenesulfonamide is prepared by reacting I-083 with I-001 in CH$_2$Cl$_2$ with iPr$_2$NEt as acid scavenger. ESI MS: Calc: 498.1. Found: 499.2 (M+H)$^+$.

Example 116

4-amino-3,5-dichloro-N-{3-(5-cyano-1H-pyrazol-1-yl)-1-[(4-methyl piperidin-1-yl)carbonyl]propyl} benzenesulfonamide is prepared by reacting I-091 with I-001 in DMF with Et$_3$N as acid scavenger. ESI MS: Calc: 498.1. Found: 499.2 (M+H)$^+$.

Example 117

4-chloro-N-{3-(2-cyano-1H-pyrrol-1-yl)-1-[(4-methylpiperidin-1-yl) carbonyl]propyl}naphthalene-1-sulfonamide is prepared by reacting I-089 with 4-chloronaphthalene-1-sulfonyl chloride in DCE with NMM as acid scavenger. ESI MS: Calc: 498.2. Found: 499.3 (M+H)$^+$.

Example 118

N-(4-chlorobenzyl)-4-(2-cyano-1H-pyrrol-1-yl)-2-{[(2,5-dimethyl phenyl)sulfonyl]amino}-N-methylbutanamide is prepared by reacting I-071 with 2,5-dimethylbenzenesulfonyl chloride in DCE with NMM as acid scavenger. ESI MS: Calc: 498.2. Found: 499.2 (M+H)$^+$.

Example 119

N-{3-(2-cyano-1H-pyrrol-1-yl)-1-[(4-methylpiperidin-1-yl)carbonyl]propyl}-2-(trifluoromethoxy)benzenesulfonamide is prepared by reacting I-089 with 2-(trifluoromethoxy)benzenesulfonyl chloride in DCE with NMM as acid scavenger. ESI MS: Calc: 498.2. Found: 499.3 (M+H)$^+$.

Example 120

N-{3-(2-cyano-1H-pyrrol-1-yl)-1-[(4-methylpiperidin-1-yl)carbonyl]propyl}-4-fluoro-2-(trifluoromethyl)benzenesulfonamide is prepared by reacting I-089 with 2-trifluoromethyl-4-fluorobenzene-sulfonyl chloride in DMF with NMM as acid scavenger. ESI MS: Calc: 500.2. Found: 501.7 (M+H)$^+$.

Example 121

2-chloro-N-{3-(2-cyano-1H-pyrrol-1-yl)-1-[trans-octahydroisoquinolin-2(1H)-ylcarbonyl]propyl}-6-methylbenzenesulfonamide is prepared by reacting I-076 with 2-chloro-6-methylbenzensulfonyl chloride in DCE with NMM as acid scavenger. ESI MS: Calc: 502.2. Found: 503.2 (M+H)$^+$.

Example 122 methyl 3-[({3-(2-cyano-1H-pyrrol-1-yl)-1-[(4-methylpiperidin-1-yl) carbonyl]propyl}amino)sulfonyl]-4-methoxybenzoate is prepared by reacting I-089 with 3-chlorosulfonyl-4-methoxybenzoate in DCE with NMM as acid scavenger. ESI MS: Calc: 502.2. Found: 503.2 (M+H)$^+$.

Example 123

N-benzyl-4-(2-cyano-1H-pyrrol-1-yl)-2-{[(2,6-dichlorophenyl)sulfonyl]amino}-N-methylbutanamide is prepared by reacting I-072 with 2,6-dichloro-benzenesulfonyl chloride in DCE with NMM as acid scavenger. ESI MS: Calc: 504.1. Found: 505.0 (M+H)$^+$.

Example 124

N-{3-(2-cyano-1H-pyrrol-1-yl)-1-[trans-octahydroisoquinolin-2(1H)-yl carbonyl]propyl}naphthalene-1-sulfonamide is prepared by reacting I-076 with naphthalene-1-sulfonyl chloride in DCE with NMM as acid scavenger. ESI MS: Calc: 504.2. Found: 505.2 (M+H)$^+$.

Example 125

N-{2-chloro-4-[({3-(2-cyano-1H-pyrrol-1-yl)-1-[(4-methylpiperidin-1-yl) carbonyl]propyl}amino)sulfonyl]phenyl}acetamide is prepared by reacting I-089 with 3-chloro-4-acetamidobenzene-sulfonyl chloride in DMF with NMM as acid scavenger. ESI MS: Calc: 505.2. Found: 506.6 (M+H)$^+$.

Example 126

2-bromo-N-{3-(2-cyano-1H-pyrrol-1-yl)-1-[(4-methylpiperidin-1-yl) carbonyl]propyl}-6-methylbenzenesulfonamide is prepared by reacting I-089 with I-029 in DMF with Et$_3$N as acid scavenger. ESI MS: Calc: 506.1. Found: 506.9 (M+H)$^+$.

Example 127

N-{3-(2-cyano-1H-pyrrol-1-yl)-1-[(4-methylpiperidin-1-yl)carbonyl]propyl}-3-(2-methylpyrimidin-4-yl)benzenesulfonamide is prepared by reacting I-089 with 3-(2-methylpyrimidin-4-yl)benzenesulfonyl chloride in DCE with NMM as acid scavenger. ESI MS: Calc: 506.2. Found: (M+H)$^+$.

Example 128

N-{3-(2-cyano-1H-pyrrol-1-yl)-1-[(4-methylpiperidin-1-yl)carbonyl]propyl}-4-phenoxybenzenesulfonamide is prepared by reacting I-089 with 4-phenoxy benzenesulfonyl chloride in DCE with NMM as acid scavenger. ESI MS: Calc: 506.2. Found: 507.3 (M+H)$^+$.

Example 129

4-amino-3,5-dichloro-N-{3-(2-chloro-1H-imidazol-1-yl)-1-[(4-methyl piperidin-1-yl)carbonyl]propyl} benzenesulfonamide is prepared by reacting I-066 with I-001 in CH$_2$Cl$_2$ with iPr$_2$NEt as acid scavenger. ESI MS: Calc: 507.1. Found: 508.2 (M+H)$^+$.

Example 130

N-{3-(5-bromo-1H-pyrazol-1-yl)-1-[(4-methylpiperidin-1-yl)carbonyl]propyl}-1H-indole-4-sulfonamide is prepared by reacting I-080 with I-008 in DMF with iPr$_2$NEt as acid scavenger. ESI MS: Calc: 507.1. Found: 508.4 (M+H)$^+$.

Example 131

2-bromo-N-{3-(2-cyano-1H-pyrrol-1-yl)-1-[(4-methylpiperidin-1-yl) carbonyl]propyl}-4-fluorobenzenesulfonamide is prepared by reacting I-089 with 2-bromo-4-fluorobenzensulfonyl chloride in DCE with NMM as acid scavenger. ESI MS: Calc: 510.1. Found: 511.2 (M+H)$^+$.

Example 132

2-acetyl-N-{3-(2-cyano-1H-pyrrol-1-yl)-1-[(4-methylpiperidin-1-yl) carbonyl]propyl}-1,2,3,4-tetrahydroisoquinoline-7-sulfonamide is prepared by reaction I-089 with 2-acetyl-7-chlorosulphonyl-1,2,3,4-tetrahydroiso-quinoline (Pendelton, R. G., et al. *J. Pharmacol. Exp. Ther.*, 1979, 208, 24) in DCE with NMM as acid scavenger. ESI MS: Calc: 511.2. Found: 512.3 (M+H)$^+$.

Example 133

N-{3-(2-cyano-1H-pyrrol-1-yl)-1-[(4-methylpiperidin-1-yl)carbonyl]propyl}-4-(2-methyl-1,3-thiazol-4-yl)benzenesulfonamide is prepared by reacting I-089 with 4-(2-methyl-1,3-thiazol-4-yl)benzenesulfonyl chloride in DCE with NMM as acid scavenger. ESI MS: Calc: 511.2. Found: 512.2 (M+H)$^+$.

Example 134

N-{3-(2-cyano-1H-pyrrol-1-yl)-1-[(4-methylpiperidin-1-yl)carbonyl]propyl}-2-methoxy-5-(trifluoromethyl)benzenesulfonamide is prepared by reacting I-089 with 2-methoxy-5-(trifluoromethyl)benzenesulfonyl chloride in DCE with NMM as acid scavenger. ESI MS: Calc: 512.2. Found: 513.2 (M+H)$^+$.

Example 135

2-bromo-N-{1-[(4-methylpiperidin-1-yl)carbonyl]-3-(2-nitro-1H-imidazol-1-yl)propyl}benzenesulfonamide is prepared by reacting I-057 with 2-(trifluoromethyl)benzenesulfonyl chloride in $CH_2Cl_2$ with $Et_3N$ as acid scavenger. ESI MS: Calc: 513.1. Found: 514.4 (M+H)$^+$.

Example 136

2-amino-4,6-dichloro-N-{1-[cis-octahydroisoquinolin-2(1H)-ylcarbonyl]-3-(2H-1,2,3-triazol-2-yl)propyl}benzenesulfonamide is prepared by reacting I-064 with 2-amino-4,6-dichlorobenznesulfonyl chloride in DCE with $Et_3N$ as acid scavenger. ESI MS: Calc: 514.1. Found: 515.1 (M+H)$^+$.

Example 137

2,4,6-trichloro-N-{3-(2-cyano-1H-pyrrol-1-yl)-1-[(4-methylpiperidin-1-yl)carbonyl]propyl}benzenesulfonamide is prepared by reacting I-089 with 2,4,6-trichloro benzenesulfonyl chloride in DCE with NMM as acid scavenger. ESI MS: Calc: 516.1. Found: 517.2 (M+H)$^+$.

Example 138

2-chloro-N-{3-(5-bromo-1H-pyrazol-1-yl)-1-[(4-methylpiperidin-1-yl) carbonyl]propyl}-6-methylbenzenesulfonamide is prepared by reacting I-080 with 2-chloro-6-methylbenzenesulfonyl chloride in DMF with $Et_3N$ as acid scavenger. ESI MS: Calc: 516.1. Found: 517.2 (M+H)$^+$.

Example 139

2,4-dichloro-6-methyl-N-{1-[(4-methylpiperidin-1-yl)carbonyl]-3-(2-nitro-1H-imidazol-1-yl)propyl}benzenesulfonamide is prepared by reacting I-057 with 2,4-dichloro-6-methyl-benzenesulfonyl chloride in $CH_2Cl_2$ with $Et_3N$ as acid scavenger. ESI MS: Calc: 517.1. Found: 518.4 (M+H)$^+$.

Example 140

4-(2-cyano-1H-pyrrol-1-yl)-2-{[(2,6-dichlorophenyl)sulfonyl]amino}-N-methyl-N-[(1R)-1-phenylethyl]butanamide is prepared by reacting I-078 with 2,6-dichlorobenzenesulfonyl chloride in DCE with NMM as acid scavenger. ESI MS: Calc: 518.1. Found: 519.1 (M+H)$^+$.

Example 141

4-amino-3,5-dichloro-N-{1-[(4-methylpiperidiN-1-yl)carbonyl]-3-(2-nitro-1H-imidazol-1-yl)propyl}benzenesulfonamide is prepared by reacting I-057 with I-001 in $CH_2Cl_2$ with $Et_3N$ as acid scavenger. ESI MS: Calc: 518.1. Found: 519.0 (M+H)$^+$.

Example 142

N-(4-chlorobenzyl)-2-{[(2-chloro-6-methylphenyl)sulfonyl]amino}-4-(2-cyano-1H-pyrrol-1-yl)-N-methylbutanamide is prepared by reacting I-071 with 2-chloro-6-methyl-benzenesulfonyl chloride in DCE with NMM as acid scavenger. ESI MS: Calc: 518.1. Found: 519.1 (M+H)$^+$.

Example 143

2,6-dichloro-N-{3-(2-cyano-1H-pyrrol-1-yl)-1-[trans-octahydro isoquinolin-2(1H)-ylcarbonyl]propyl} benzenesulfonamide is prepared by reacting I-076 with 2,6-dichlorobenzenesulfonyl chloride in DCE with NMM as acid scavenger. ESI MS: Calc: 522.1. Found: 523.1 (M+H)$^+$.

Example 144

5-bromo-N-{3-(2-cyano-1H-pyrrol-1-yl)-1-[(4-methylpiperidin-1-yl) carbonyl]propyl}-2-methoxybenzenesulfonamide is prepared by reacting I-089 with 5-bromo-2-methoxy benzenesulfonyl chloride in DCE with NMM as acid scavenger. ESI MS: Calc: 522.1. Found: 523.1 (M+H)$^+$.

Example 145

N-[3-(2-chloro-1H-imidazol-1-yl)-1-(3,4-dihydroisoquinolin-2(1H)-yl carbonyl)propyl]-4-methylnaphthalene-1-sulfonamide is prepared by reacting I-069 with 4-methyl-naphthalene-1-sulfonyl chloride in DCE with $Et_3N$ as acid scavenger. ESI MS: Calc: 522.2. Found: 523.3 (M+H)$^+$.

Example 146

4-amino-3,5-dichloro-N-{1-[(4-methylpiperidin-1-yl)carbonyl]-3-(1H-pyrrolo[2,3-b]pyridin-1-yl)propyl}benzenesulfonamide is prepared by reacting I-088 with I-001 in DMF with $Et_3N$ as acid scavenger. ESI MS: Calc: 523.1. Found: 524.0 (M+H)$^+$.

Example 147

N-[3-(5-bromo-1H-pyrazol-1-yl)-1-{[4-(hydroxymethyl)piperidin-1-yl]carbonyl}propyl]-1H-indole-4-sulfonamide is prepared by reacting I-081 with I-008 in DMF with $iPr_2NEt$ as acid scavenger. ESI MS: Calc: 523.1. Found: 378.1 (M-$C_4H_3BrN$)$^+$.

Example 148

4-({3-(2-cyano-1H-pyrrol-1-yl)-1-[(4-methylpiperidin-1-yl)carbonyl]-propyl}sulfamoyl)-N,N-dimethyl-1H-indole-2-carboxamide is prepared by reaction I-089 with I-010 in DMF with $iPr_2NEt$ as acid scavenger. ESI MS: Calc: 524.2. Found: 525.7 (M+H)$^+$.

Example 149

2-chloro-N-{3-(2-cyano-1H-pyrrol-1-yl)-1-[(4-phenylpiperazin-1-yl) carbonyl]propyl}-6-methylbenzenesulfonamide is prepared by reacting I-074 with 2-methyl-6-chlorobenzenesulfonyl chloride in DMF with NMM as acid scavenger. ESI MS: Calc: 525.2. Found: 526.4 (M+H)$^+$.

Example 150

2,4,6-trichloro-N-{3-(2-chloro-1H-imidazol-1-yl)-1-[(4-methylpiperidin-1-yl)carbonyl]propyl}benzenesulfonamide is prepared by reacting I-066 with 2,4,6-trichloro benzenesulfonyl chloride in DCE with $Et_3N$ as acid scavenger. ESI MS: Calc: 526.0. Found: 527.1 $(M+H)^+$.

Example 151

2-bromo-6-methyl-N-{1-[(4-methylpiperidin-1-yl)carbonyl]-3-(2-nitro-1H-imidazol-1-yl)propyl}benzenesulfonamide is prepared by reacting I-057 with I-029 in $CH_2Cl_2$ with $iPr_2NEt$ as acid scavenger. ESI MS: Calc: 527.1. Found: 528.2 $(M+H)^+$.

Example 152

2-bromo-N-{3-(2-cyano-1H-pyrrol-1-yl)-1-[(4-methylpiperidin-1-yl) carbonyl]propyl}-4,6-difluorobenzenesulfonamide is prepared by reacting I-089 with 2-bromo-4,6-difluorobenzensulfonyl chloride in DCE with NMM as acid scavenger. ESI MS: Calc: 528.1. Found: 529.2 $(M+H)^+$.

Example 153

N-{3-(2-chloro-1H-imidazol-1-yl)-1-[cis-octahydroisoquinolin-2(1H)-yl carbonyl]propyl}-4-methylnaphthalene-1-sulfonamide is prepared by reacting I-067 with 4-methyl-naphthalene-1-sulfonyl chloride in DCE with $Et_3N$ as acid scavenger. ESI MS: Calc: 528.2. Found: 529.3 $(M+H)^+$.

Example 154

N-{3-(2-chloro-1H-imidazol-1-yl)-1-[trans-octahydroisoquinolin-2(1H)-ylcarbonyl]propyl}-4-methylnaphthalene-1-sulfonamide is prepared by reacting I-068 with 4-methyl-naphthalene-1-sulfonyl chloride in DCE with $Et_3N$ as acid scavenger. ESI MS: Calc: 528.2. Found: 529.3 $(M+H)^+$.

Example 155

2,4,6-trichloro-N-[3-(2-cyano-1H-pyrrol-1-yl)-1-{[4-(hydroxymethyl)piperidin-1-yl]carbonyl}propyl]benzenesulfonamide is prepared by reacting I-075 with 2,4,6-trichlorobenzenesulfonyl chloride in DCE with NMM as acid scavenger. ESI MS: Calc: 532.1. Found: 533.0 $(M+H)^+$.

Example 156

2,6-dichloro-N-[3-(2-chloro-1H-imidazol-1-yl)-1-(3,4-dihydro isoquinolin-2(1H)-ylcarbonyl)propyl]benzenesulfonamide is prepared by reacting I-069 with 2,6-dichloro benznesulfonyl chloride in DCE with $Et_3N$ as acid scavenger. ESI MS: Calc: 526.0. Found: 527.1 $(M+H)^+$.

Example 157

2,6-dichloro-N-{3-(2-chloro-1H-imidazol-1-yl)-1-[cis-octahydro isoquinolin-2(1H)-ylcarbonyl]propyl}benzenesulfonamide is prepared by reacting I-067 with 2,6-dichloro benznesulfonyl chloride in DCE with $Et_3N$ as acid scavenger. ESI MS: Calc: 532.1. Found: 533.1 $(M+H)^+$.

Example 158

2,6-dichloro-N-{3-(2-chloro-1H-imidazol-1-yl)-1-[trans-octahydro isoquinolin-2(1H)-ylcarbonyl]propyl} benzenesulfonamide is prepared by reacting I-068 with 2,6-dichloro benznesulfonyl chloride in DCE with $Et_3N$ as acid scavenger. ESI MS: Calc: 532.1. Found: 533.1 $(M+H)^+$.

Example 159

2-{[(4-amino-3,5-dichlorophenyl)sulfonyl]amino}-4-(2-cyano-1H-pyrrol-1-yl)-N-methyl-N-[(1R)-1-phenylethyl]butanamide is prepared by reacting I-078 TFA with I-001 in DMF with NMM as acid scavenger. ESI MS: Calc: 533.1. Found: 534.3 $(M+H)^+$.

Example 160

N-[1-(3,4-dihydroisoquinolin-2(1H)-ylcarbonyl)-3-(2-nitro-1H-imidazol-1-yl)propyl]-4-methylnaphthalene-1-sulfonamide is prepared by reacting I-060 with 4-methyl-naphthalene-1-sulfonyl chloride in DCE with $Et_3N$ as acid scavenger. ESI MS: Calc: 533.2. Found: 534.3 $(M+H)^+$.

Example 161

5-bromo-N-{3-(2-cyano-1H-pyrrol-1-yl)-1-[(4-methylpiperidin-1-yl) carbonyl]propyl}-2,3-dihydro-1-benzofuran-7-sulfonamide is prepared by reacting I-089 with 5-bromo-2,3-dihydro-1-benzofuran-7-sulfonyl chloride in DCE with NMM as acid scavenger. ESI MS: Calc: 534.1. Found: 535.2 $(M+H)^+$.

Example 162

2,6-dichloro-N-[1-(3,4-dihydroisoquinolin-2(1H)-ylcarbonyl)-3-(2-nitro-1H-imidazol-1-yl)propyl]benzenesulfonamide is prepared by reacting I-060 with 2,6-dichloro benzenesulfonyl chloride in DCE with $Et_3N$ as acid scavenger. ESI MS: Calc: 537.1. Found: 538.1 $(M+H)^+$.

Example 163

N-(4-chlorobenzyl)-4-(2-cyano-1H-pyrrol-1-yl)-2-{[(2,6-dichlorophenyl) sulfonyl]amino}-N-methylbutanamide is prepared by reacting I-071 with 2,6-dichlorobenzenesulfonyl chloride in DCE with NMM as acid scavenger. ESI MS: Calc: 538.0. Found: 539.1 $(M+H)^+$.

Example 164

N-benzyl-4-(2-cyano-1H-pyrrol-1-yl)-N-methyl-2-{[(2,4,6-trichloro phenyl) sulfonyl]amino}butanamide is prepared by reacting I-072 with 2,4,6-trichlorobenzenesulfonyl chloride in DCE with NMM as acid scavenger. ESI MS: Calc: 538.0. Found: 538.9 $(M+H)^+$.

Example 165

4-methyl-N-{3-(2-nitro-1H-imidazol-1-yl)-1-[cis-octahydroisoquinolin-2(1H)-ylcarbonyl]propyl}naphthalene-1-sulfonamide is prepared by reacting I-062 with 4-methyl-naphthalene-1-sulfonyl chloride in DCE with $Et_3N$ as acid scavenger. ESI MS: Calc: 539.2. Found: 540.3 $(M+H)^+$.

Example 166

4-methyl-N-{3-(2-nitro-1H-imidazol-1-yl)-1-[trans-octahydro isoquinolin-2(1H)-ylcarbonyl]propyl}naphthalene-1-sulfonamide is prepared by reacting I-061 with 4-methyl-naphthalene-1-sulfonyl chloride in DCE with $Et_3N$ as acid scavenger. ESI MS: Calc: 539.2. Found: 540.3 $(M+H)^+$.

Example 167

2-amino-4,6-dichloro-N-[3-(2-chloro-1H-imidazol-1-yl)-1-(3,4-dihydro isoquinolin-2(1H)-ylcarbonyl)propyl]benzenesulfonamide is prepared by reacting I-069 with 2-amino-4,6-dichlorobenznesulfonyl chloride in DCE with $Et_3N$ as acid scavenger. ESI MS: Calc: 541.1. Found: 542.1 $(M+H)^+$.

Example 168

4-amino-3,5-dichloro-N-[3-(2-chloro-1H-imidazol-1-yl)-1-(3,4-dihydro isoquinolin-2(1H)-ylcarbonyl)propyl]benzenesulfonamide is prepared by reacting I-069 with 4-amino-2,6-dichlorobenznesulfonyl chloride in DCE with $Et_3N$ as acid scavenger. ESI MS: Calc: 541.1. Found: 542.1 $(M+H)^+$.

Example 169

2,6-dichloro-N-{3-(2-nitro-1H-imidazol-1-yl)-1-[cis-octahydro isoquinolin-2(1H)-ylcarbonyl]propyl} benzenesulfonamide is prepared by reacting I-062 with 2,6-dichloro benzenesulfonyl chloride in DCE with $Et_3N$ as acid scavenger. ESI MS: Calc: 543.1. Found: 544.2 $(M+H)^+$.

Example 170

2,6-dichloro-N-{3-(2-nitro-1H-imidazol-1-yl)-1-[trans-octahydro isoquinolin-2(1H)-ylcarbonyl]propyl} benzenesulfonamide is prepared by reacting I-061 with 2,6-dichloro benzenesulfonyl chloride in DCE with $Et_3N$ as acid scavenger. ESI MS: Calc: 543.1. Found: 544.2 $(M+H)^+$.

Example 171

2-bromo-N-[3-(2-cyano-1H-pyrrol-1-yl)-1-{[4-(hydroxymethyl)piperidin-1-yl]carbonyl]propyl}-4,6-difluorobenzenesulfonamide is prepared by reacting I-075 with 2-bromo-4,6-difluorobenzenesulfonyl chloride in DCE with NMM as acid scavenger. ESI MS: Calc: 544.1. Found: 545.1 $(M+H)^+$.

Example 172

2-amino-4,6-dichloro-N-{3-(2-chloro-1H-imidazol-1-yl)-1-[cis-octahydro isoquinolin-2(1H)-ylcarbonyl]propyl} benzenesulfonamide is prepared by reacting I-067 with 2-amino-4,6-dichlorobenzenesulfonyl chloride in DCE with $Et_3N$ as acid scavenger. ESI MS: Calc: 547.1. Found: 548.1 $(M+H)^+$.

Example 173

2-amino-4,6-dichloro-N-{3-(2-chloro-1H-imidazol-1-yl)-1-[trans-octa hydroisoquinolin-2(1H)-ylcarbonyl]propyl} benzenesulfonamide is prepared by reacting I-068 with 2-amino-4,6-dichlorobenznesulfonyl chloride in DCE with $Et_3N$ as acid scavenger. ESI MS: Calc: 547.1. Found: 548.1 $(M+H)^+$.

Example 174

4-amino-3,5-dichloro-N-{3-(2-chloro-1H-imidazol-1-yl)-1-[cis-octahydro isoquinolin-2(1H)-ylcarbonyl]propyl} benzenesulfonamide is prepared by reacting I-067 with 4-amino-2,6-dichlorobenznesulfonyl chloride in DCE with $Et_3N$ as acid scavenger. ESI MS: Calc: 547.1. Found: 548.1 $(M+H)^+$.

Example 175

4-amino-3,5-dichloro-N-{3-(2-chloro-1H-imidazol-1-yl)-1-[trans-octa hydroisoquinolin-2(1H)-ylcarbonyl]propyl} benzenesulfonamide is prepared by reacting I-068 with 4-amino-2,6-dichlorobenznesulfonyl chloride in DCE with $Et_3N$ as acid scavenger. ESI MS: Calc: 547.1. Found: 548.1 $(M+H)^+$.

Example 176

N-benzyl-2-{[(2-bromo-4,6-difluorophenyl)sulfonyl]amino}-4-(2-cyano-1H-pyrrol-1-yl)-N-methylbutanamide is prepared by reacting I-072 with 2-bromo-4,6-difluorobenzenesulfonyl chloride in DEC with NMM as acid scavenger. ESI MS: Calc: 550.1. Found: 551.0 $(M+H)^+$.

Example 177

N-{3-(2-cyano-1H-pyrrol-1-yl)-1-[(4-methylpiperidin-1-yl)carbonyl]propyl}-2,5-bis(trifluoromethyl)benzenesulfonamide is prepared by reacting I-089 with 2,5-bis(trifluoromethyl)benzenesulfonyl chloride in DCE with NMM as acid scavenger. ESI MS: Calc: 550.2. Found: 551.2 $(M+H)^+$.

Example 178

4-amino-N-{3-(2-bromo-1H-imidazol-1-yl)-1-[(4-methylpiperidin-1-yl) carbonyl]propyl}-3,5-dichlorobenzenesulfonamide is prepared by reacting I-084 with I-001 in $CH_2Cl_2$ with $iPr_2NEt$ as acid scavenger. ESI MS: Calc: 551.0. Found: 552.1 $(M+H)^+$.

Example 179

2-amino-4,6-dichloro-N-[1-(3,4-dihydroisoquinolin-2(1H)-ylcarbonyl)-3-(2-nitro-1H-imidazol-1-yl)propyl]benzenesulfonamide is prepared by reacting I-060 with 2-amino-4,6-dichlorobenzenesulfonyl chloride in DCE with $Et_3N$ as acid scavenger. ESI MS: Calc: 552.1. Found: 553.1 $(M+H)^+$.

Example 180

2-{[(4-amino-3,5-dichlorophenyl)sulfonyl]amino}-N-(4-chlorobenzyl)-4-(2-cyano-1H-pyrrol-1-yl)-N-methylbutanamide is prepared by reacting I-071 TFA with I-001 in DMF with NMM as acid scavenger. ESI MS: Calc: 553.1. Found: 554.2 $(M+H)^+$.

Example 181

7-[3-(2-cyano-pyrrol-1-yl)-1-(4-methyl-piperidine-1-carbonyl)-propylsulfamoyl]-indole-1-carboxylic acid tert-butyl ester is prepared by reaction I-089 with I-017 in THF with iPr$_2$NEt as acid scavenger. ESI MS: Calc: 553.2. Found: 554.3 (M+H)$^+$.

Example 182

2,4,6-trichloro-N-{3-(2-cyano-1H-pyrrol-1-yl)-1-[trans-octahydro isoquinolin-2(1H)-ylcarbonyl]propyl} benzenesulfonamide is prepared by reacting I-076 with 2,4,6-trichloro benzenesulfonyl chloride in DCE with NMM as acid scavenger. ESI MS: Calc: 556.1. Found: 557.0 (M+H)$^+$.

Example 183

2-amino-4,6-dichloro-N-{3-(2-nitro-1H-imidazol-1-yl)-1-[cis-octahydro isoquinolin-2(1H)-ylcarbonyl]propyl} benzenesulfonamide is prepared by reacting I-062 with 2-amino-4,6-dichlorobenzenesulfonyl chloride in DCE with Et$_3$N as acid scavenger. ESI MS: Calc: 558.1. Found: 559.2 (M+H)$^+$.

Example 184

2-amino-4,6-dichloro-N-{3-(2-nitro-1H-imidazol-1-yl)-1-[trans-octa hydroisoquinolin-2(1H)-ylcarbonyl]propyl} benzenesulfonamide is prepared by reacting I-061 with 2-amino-4,6-dichlorobenzenesulfonyl chloride in DCE with Et$_3$N as acid scavenger. ESI MS: Calc: 558.1. Found: 559.2 (M+H)$^+$.

Example 185

2-bromo-N-{3-(2-cyano-1H-pyrrol-1-yl)-1-[(4-methylpiperidin-1-yl) carbonyl]propyl}-5-(trifluoromethyl)benzenesulfonamide is prepared by reacting I-089 with 2-bromo-5-(trifluoromethyl)-benzenesulfonyl chloride in DCE with NMM as acid scavenger. ESI MS: Calc: 560.1. Found: 561.1 (M+H)$^+$.

Example 186

2-amino-4,6-dichloro-N-{3-(2-chloro-1H-imidazol-1-yl)-1-{[4-(trifluoromethyl)piperidin-1-yl]carbonyl}propyl}benzenesulfonamide is prepared by reacting I-070 with 2-amino-4,6-dichlorobenzenesulfonyl chloride in DCE with Et$_3$N as acid scavenger. ESI MS: Calc: 561.0. Found: 562.0 (M+H)$^+$.

Example 187

2-{[(2-bromo-4,6-difluorophenyl)sulfonyl]amino}-4-(2-cyano-1H-pyrrol-1-yl)-N-methyl-N-[(1R)-1-phenylethyl] butanamide is prepared by reacting I-078 with 2-bromo-4,6-difluorobenzenesulfonyl chloride in DCE with NMM as acid scavenger. ESI MS: Calc: 564.1. Found: 565.1 (M+H)$^+$.

Example 188

4-bromo-2,5-dichloro-N-{3-(2-cyano-1H-pyrrol-1-yl)-1-[(4-methyl piperidin-1-yl)carbonyl]propyl}thiophene-3-sulfonamide is prepared by reacting I-089 with 4-bromo-2,5-dichloro-thiophene-3-sulfonyl chloride in DMF with Et$_3$N as acid scavenger. ESI MS: Calc: 566.0. Found: 567.0 (M+H)$^+$.

Example 189

2,4,6-trichloro-N-{3-(2-chloro-1H-imidazol-1-yl)-1-[(cis)-octahydro isoquinolin-2(1H)-ylcarbonyl]propyl}benzenesulfonamide is prepared by reacting I-066 with 2,4,6-trichloro benzenesulfonyl chloride in DCE with Et$_3$N as acid scavenger. ESI MS: Calc: 566.1. Found: 567.1 (M+H)$^+$.

Example 190

2,4,6-trichloro-N-{3-(2-chloro-1H-imidazol-1-yl)-1-[(trans)-octahydro isoquinolin-2(1H)-ylcarbonyl]propyl}benzenesulfonamide is prepared by reacting I-068 with 2,4,6-trichloro benznesulfonyl chloride in DCE with Et$_3$N as acid scavenger. ESI MS: Calc: 566.1. Found: 567.1 (M+H)$^+$.

Example 191 tert-butyl 3-[({3-(2-cyano-1H-pyrrol-1-yl)-1-[(4-methylpiperidin-1-yl) carbonyl]propyl}amino)sulfonyl]-2-methyl-1H-indole-1-carboxylate is prepared by reacting I-089 with I-019 in DMF with Et$_3$N as acid scavenger. ESI MS: Calc: 567.3. Found: 568.3 (M+H)$^+$.

Example 192

2-bromo-N-{3-(2-cyano-1H-pyrrol-1-yl)-1-[(trans)-octahydroisoquinolin-2(1H)-ylcarbonyl]propyl}-4,6-difluorobenzenesulfonamide is prepared by reacting I-076 with 2-bromo-4,6-difluorobenzenesulfonyl chloride in DCE with NMM as acid scavenger. ESI MS: Calc: 568.1. Found: 569.1 (M+H)$^+$.

Example 193

2,4,6-trichloro-N-[1-(3,4-dihydroisoquinolin-2(1H)-ylcarbonyl)-3-(2-nitro-1H-imidazol-1-yl)propyl]benzenesulfonamide is prepared by reacting I-060 with 2,4,6-trichloro benzenesulfonyl chloride in DCE with Et$_3$N as acid scavenger. ESI MS: Calc: 571.0. Found: 572.1 (M+H)$^+$.

Example 194

4-[3-(2-cyano-pyrrol-1-yl)-1-(4-methyl-piperidine-1-carbonyl)-propylsulfamoyl]-5-fluoro-indole-1-carboxylic acid tert-butyl ester is prepared by reaction I-089 with I-021 in THF with iPr$_2$NEt as acid scavenger. ESI MS: Calc: 571.1. Found: 572.3 (M+H)$^+$.

Example 195

6-[3-(2-cyano-pyrrol-1-yl)-1-(4-methyl-piperidine-1-carbonyl)-propylsulfamoyl]-5-fluoro-indole-1-carboxylic acid tert-butyl ester is prepared by reacting I-089 with I-022 in THF with iPr$_2$NEt as acid scavenger. ESI MS: Calc: 571.1. Found: 572.3 (M+H)$^+$.

Example 196

2-amino-4,6-dichloro-N-{3-(2-nitro-1H-imidazol-1-yl)-1-{[4-(trifluoromethyl)piperidin-1-yl]carbonyl}propyl}benzenesulfonamide is prepared by reacting I-063 with 2-amino-4,6-dichlorobenzenesulfonyl chloride in DCE with Et$_3$N as acid scavenger. ESI MS: Calc: 572.1. Found: 573.1 (M+H)$^+$.

Example 197

2,4,6-trichloro-N-{3-(2-nitro-1H-imidazol-1-yl)-1-[(cis)-octahydro isoquinolin-2(1H)-ylcarbonyl]propyl} benzenesulfonamide is prepared by reacting I-062 with 2,4,6-trichloro benzenesulfonyl chloride in DCE with Et$_3$N as acid scavenger. ESI MS: Calc: 577.1. Found: 578.1 (M+H)$^+$.

Example 198

2,4,6-trichloro-N-{3-(2-nitro-1H-imidazol-1-yl)-1-[(trans)-octahydro isoquinolin-2(1H)-ylcarbonyl]propyl}benzenesulfonamide is prepared by reacting I-061 with 2,4,6-trichloro benzenesulfonyl chloride in DCE with Et$_3$N as acid scavenger. ESI MS: Calc: 577.1. Found: 578.1 (M+H)$^+$.

Example 199

4-bromo-2,6-dichloro-N-{1-[(4-methylpiperidin-1-yl)carbonyl]-3-(2-nitro-1H-imidazol-1-yl)propyl}benzenesulfonamide is prepared by reacting I-057 with 4-bromo-2,6-dichlorobenzenesulfonyl chloride in CH$_2$Cl$_2$ with Et$_3$N as acid scavenger. ESI MS: Calc: 581.0. Found: 582.2 (M+H)$^+$.

Example 200

2-{[(2-bromo-4,6-difluorophenyl)sulfonyl]amino}-N-(4-chlorobenzyl)-4-(2-cyano-1H-pyrrol-1-yl)-N-methylbutanamide is prepared by reacting I-071 with 2-bromo-4,6-difluorobenzenesulfonyl chloride in DCE with NMM as acid scavenger. ESI MS: Calc: 584.0. Found: 585.0 (M+H)$^+$.

Example 201

5-chloro-4-[3-(2-cyano-pyrrol-1-yl)-1-(4-methyl-piperidine-1-carbonyl)-propylsulfamoyl]-indole-1-carboxylic acid tert-butyl ester is prepared by reacting I-089 with I-023 in THF with iPr$_2$NEt as acid scavenger. ESI MS: Calc: 587.2. Found: 588.8 (M+H)$^+$.

Example 202

5-chloro-6-[3-(2-cyano-pyrrol-1-yl)-1-(4-methyl-piperidine-1-carbonyl)-propylsulfamoyl]-indole-1-carboxylic acid tert-butyl ester is prepared by reacting I-089 with I-024 in THF with iPr$_2$NEt as acid scavenger. ESI MS: Calc: 587.2. Found: 588.3 (M+H)$^+$.

Example 203

4-amino-3,5-dibromo-N-{1-[(4-methylpiperidin-1-yl)carbonyl]-3-(2-nitro-1H-imidazol-1-yl)propyl}benzenesulfonamide is prepared by reacting I-057 with 4-amino-3,5-dibromo benzenesulfonyl chloride in CH$_2$Cl$_2$ with iPr$_2$NEt as acid scavenger. ESI MS: Calc: 606.0. Found: 607.2 (M+H)$^+$.

Example 204

5-chloro-4-[3-(2-cyano-pyrrol-1-yl)-1-(5,6-dihydro-8H-1,2,4-triazolo[4,3-a]pyrazine-7-carbonyl)-propylsulfamoyl]-indole-1-carboxylic acid tert-butyl ester is prepared by reaction I-077 with I-023 in THF with iPr$_2$NEt as acid scavenger. ESI MS: Calc: 612.2. Found: 613.3 (M+H)$^+$.

Example 205

5-chloro-6-[3-(2-cyano-pyrrol-1-yl)-1-(5,6-dihydro-8H-1,2,4-triazolo[4,3-a]pyrazine-7-carbonyl)-propylsulfamoyl]-indole-1-carboxylic acid tert-butyl ester is prepared by reacting I-077 with I-024 in THF with iPr$_2$NEt as acid scavenger.

Example 206

4-[3-(2-cyano-pyrrol-1-yl)-1-(4-methyl-piperidine-1-carbonyl)-propylsulfamoyl]-1-(2-trimethylsilanyl-ethoxymethyl)-1H-indole-7-carboxylic acid is prepared by reaction I-089 with I-028 in DMF with Et$_3$N as acid scavenger. ESI MS: Calc: 627.3. Found: 628.2 (M+H)$^+$.

Example 207

3-chloro-N-{3-(2-cyano-1H-pyrrol-1-yl)-1-[(4-methylpiperidin-1-yl)carbonyl]propyl}-1H-indazole-5-sulfonamide and Example 208: 3-chloro-N-{3-(2-cyano-1H-pyrrol-1-yl)-1-[(4-methylpiperidin-1-yl)carbonyl]propyl}-1H-indazole-7-sulfonamide are prepared by reacting I-089 with 1:1 mixture of I-004 and I-005 in DMF with NMM as acid scavenger. Example 207: ESI MS: Calc: 488.1. Found: 489.2. Example 208: ESI MS. Calc. 488.1. Found 489.6 (M+H)$^+$.

Example 209

4-amino-3,5-dichloro-N-{3-(3-chloro-1H-pyrazol-1-yl)-1-[(4-methylpiperidin-1-yl)carbonyl]propyl}benzenesulfonamide and Example 210: 4-amino-3,5-dichloro-N-{3-(5-chloro-1H-pyrazol-1-yl)-1-[(4-methylpiperidin-1-yl)carbonyl]propyl}benzenesulfonamide are prepared by reacting I-087 and I-082 with I-001 in CH$_2$Cl$_2$ with iPr$_2$NEt as acid scavenger. Example 209: ESI MS: Calc: 507.1. Found: 508.2. Example 210: ESI MS. Calc: 507.1. Found: 508.2 (M+H)$^+$.

Example 211

2-amino-4,6-dichloro-N-{3-(2-chloro-1H-imidazol-1-yl)-1-[(4-methylpiperidin-1-yl)carbonyl]propyl}benzenesulfonamide and Example 212: 2-amino-4,6-dichloro-N-{1-[(4-methylpiperidin-1-yl)carbonyl]-3-(2-nitro-1H-imidazol-1-yl)propyl}benzenesulfonamide

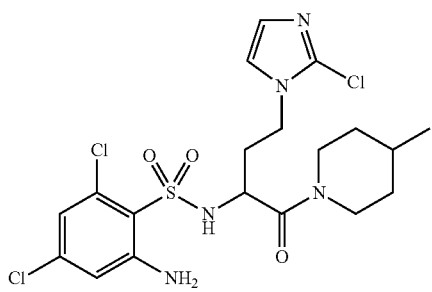

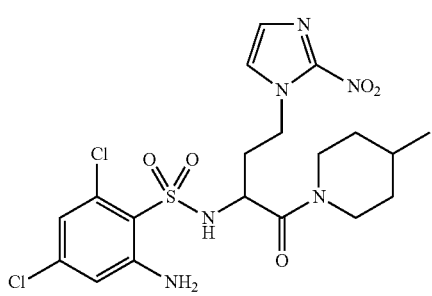

A mixture of 120 mg (0.31 mmol) of [1-(4-methyl-piperidine-1-carbonyl)-3-(2-nitro-imidazol-1-yl)-propyl]-carbamic acid tert-butyl ester (prepared in the synthesis of I-057) in 5 mL of 4 M HCl in 1,4-dioxane is stirred for 1 h, and then concentrated. This residue is suspended in 5 mL of CH$_2$Cl$_2$, and 88 mg (0.34 mmol) of I-001 and 0.16 mL (0.92 mmol) of iPr$_2$NEt are added. After 16 h, the mixture is washed with 1 M KHSO$_4$, dried with MgSO$_4$, filtered, and evaporated. The mixture is purified by preparative HPLC to provide 13 mg (8.3%) of Example 211 and 110 mg (67%) of Example 212. Example 211: ESI MS: Calc: 507.1. Found: 508.0 (M+H)$^+$. Example 212: ESI MS. Calc: 518.1. Found: 519.1 (M+H)$^+$.

Example 213

N-{3-(2-cyano-1H-pyrrol-1-yl)-1-[(4-methylpiperidin-1-yl)carbonyl]propyl}-1H-pyrrolo[2,3-b]pyridine-4-sulfonamide and Example 214: 3-bromo-N-{3-(2-cyano-1H-pyrrol-1-yl)-1-[(4-methylpiperidin-1-yl)carbonyl]propyl}-1H-pyrrolo[2,3-b]pyridine-4-sulfonamide

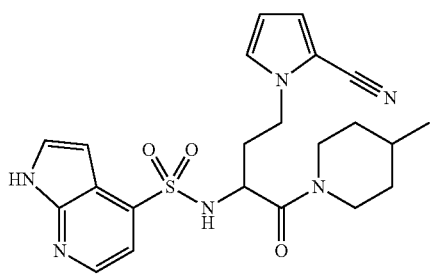

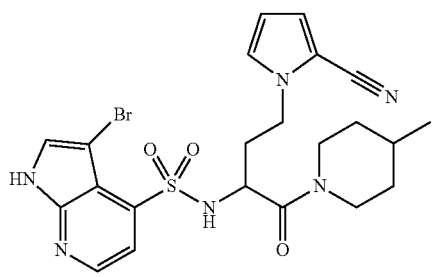

To a stirring mixture of 50 mg (0.16 mmol) of I-089 in 2.0 mL of DMF is added 0.080 mL (0.57 mmol) of Et$_3$N and 42 mg of a mixture of I-026 and I-027. The mixture is stirred overnight and purified directly by preparative HPLC to provide 2 mg (3%) of Example 213 and 3 mg (5%) of Example 214. Example 213: ESI MS: Calc: 454.2. Found: 455.6 (M+H)$^+$. Example 214: ESI MS. Calc: 532.1. Found: 533.5 (M+H)$^+$.

Example 215

2,6-dichloro-N-{3-(2-chloro-1H-imidazol-1-yl)-1-[(4-methylpiperidin-1-yl)carbonyl]propyl}benzenesulfonamide and Example 216: 2,6-dichloro-N-{1-[(4-methylpiperidin-1-yl)carbonyl]-3-(2-nitro-1H-imidazol-1-yl)propyl}benzenesulfonamide

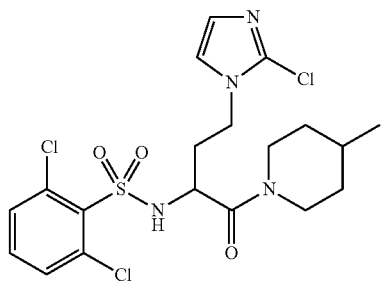

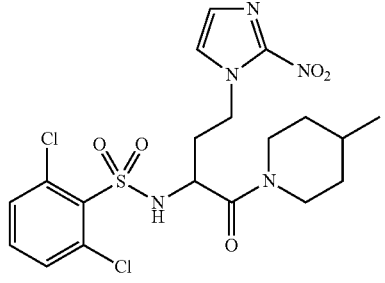

A mixture of 120 mg (0.31 mmol) of [1-(4-methyl-piperidine-1-carbonyl)-3-(2-nitro-imidazol-1-yl)-propyl]-carbamic acid tert-butyl ester (from the synthesis of I-057) in 5 mL of 4 M HCl in 1,4-dioxane is stirred for 1 h and then is concentrated. This residue is suspended in 5 mL of CH$_2$Cl$_2$, and 83 mg (0.34 mmol) of 2,6-dichlorobenzenesulfonyl chloride and 0.16 mL (0.93 mmol) of iPr$_2$NEt are added. After 16 h, the mixture is washed with 1 M KHSO$_4$, and dried with MgSO$_4$, filtered, and evaporated. The mixture is purified by preparative HPLC to provide 13 mg (8.5%) of Example 215 and 130 mg (81%) of Example 216. Example 215: ESI MS: Calc: 492.1. Found: 493.0 (M+H)$^+$. Example 216: ESI MS: Calc: 503.1. Found: 504.4 (M+H)$^+$.

General Method B (Sulfonamide Formation)

To 20 mg (0.068 mmol) of I-057 in 1 mL of DCE is added 0.019 mL of Et$_3$N (0.14 mmol) and a solution of 0.1 mmol of a sulfonyl chloride in 0.5 mL of DCE. After shaking for 45 min, 0.11 g (7 equiv) of PS-trisamine and 0.17 g (7 equiv) of MP-carbonate are added, and the mixture is shaken for 24 h. The mixture is filtered, and the filtrate concentrated to provide product. Flash chromatography (1-5% MeOH/CH$_2$Cl$_2$) is used when necessary. Examples 217-234 are prepared from the indicated sulfonyl chlorides via this method.

Example 217

2,5-dimethoxy-N-{1-[(4-methylpiperidin-1-yl)carbonyl]-3-(2-nitro-1H-imidazol-1-yl)propyl}benzenesulfonamide from 2,5-dimethoxybenzenesulfonyl chloride. ESI MS. Calc: 495.2. Found: 496.3 (M+H)$^+$.

Example 218

2-methoxy-4-methyl-N-{1-[(4-methylpiperidin-1-yl)carbonyl]-3-(2-nitro-1H-imidazol-1-yl)propyl}benzenesulfonamide from 2-methoxy-4-methylbenzene-sulphonyl chloride. ESI MS. Calc: 478.2. Found: 479.5 (M+H)$^+$.

Example 219

N-{1-[(4-methylpiperidin-1-yl)carbonyl]-3-(2-nitro-1H-imidazol-1-yl) propyl}naphthalene-1-sulfonamide from 1-napthalenesulfonyl chloride. ESI MS. Calc: 485.2. Found: 485.6 (M+H)$^+$.

Example 220

2,3,4-trichloro-N-{1-[(4-methylpiperidin-1-yl)carbonyl]-3-(2-nitro-1H-imidazol-1-yl)propyl}benzenesulfonamide from 2,3,4-trichlorobenzenesulfonyl chloride. ESI MS. Calc: 537.0. Found: 538.2 (M+H)$^+$.

Example 221

2,3-dichloro-N-{1-[(4-methylpiperidin-1-yl)carbonyl]-3-(2-nitro-1H-imidazol-1-yl)propyl}benzenesulfonamide from 2,3-dichlorobenzenesulfonyl chloride. ESI MS. Calc: 503.1. Found: 504.4 (M+H)$^+$.

Example 222

2,4,6-trichloro-N-{1-[(4-methylpiperidin-1-yl)carbonyl]-3-(2-nitro-1H-imidazol-1-yl)propyl}benzenesulfonamide from 2,4,6-trichlorobenzenesulfonyl chloride. ESI MS. Calc: 537.0. Found: 538.2 (M+H)$^+$.

Example 223

2,4,6-trimethyl-N-{1-[(4-methylpiperidin-1-yl)carbonyl]-3-(2-nitro-1H-imidazol-1-yl)propyl}benzenesulfonamide from 2-mesitylenesulfonyl chloride. ESI MS. Calc: 477.2. Found: 477.6 (M+H)$^+$.

Example 224

2,4-dichloro-5-methyl-N-{1-[(4-methylpiperidin-1-yl)carbonyl]-3-(2-nitro-1H-imidazol-1-yl)propyl}benzenesulfonamide from 2,4-dichloro-5-methyl-benzene-1-sulfonyl chloride. ESI MS. Calc: 517.1. Found: 518.4 (M+H)$^+$.

Example 225

2-trifluoromethyl-N-{1-[(4-methylpiperidin-1-yl)carbonyl]-3-(2-nitro-1H-imidazol-1-yl)propyl}benzenesulfonamide from 2-(trifluoromethyl)-benzenesulfonyl chloride.

Example 226

2-chloro-6-methyl-N-{1-[(4-methylpiperidin-1-yl)carbonyl]-3-(2-nitro-1H-imidazol-1-yl)propyl}benzenesulfonamide from 2-chloro-6-methylbenzenesulfonyl chloride. ESI MS. Calc: 483.1. Found: 483.9 (M+H)$^+$.

Example 227

2-methoxy-5-methyl-N-{1-[(4-methylpiperidin-1-yl)carbonyl]-3-(2-nitro-1H-imidazol-1-yl)propyl}benzenesulfonamide from 6-methoxy-m-toluenesulfonyl chloride. ESI MS. Calc: 479.2. Found: 479.5 (M+H)$^+$.

Example 228

3-bromo-5-chloro-N-{1-[(4-methylpiperidin-1-yl)carbonyl]-3-(2-nitro-1H-imidazol-1-yl)propyl}thiophene-2-sulfonamide from 3-bromo-5-chlorothiophene-2-sulfonyl chloride. ESI MS. Calc: 553.0. Found: 554.2 (M+H)$^+$.

Example 229

3-chloro-2-methyl-N-{1-[(4-methylpiperidin-1-yl)carbonyl]-3-(2-nitro-1H-imidazol-1-yl)propyl}benzenesulfonamide from 3-chloro-2-methylbenzenesulfonyl chloride. ESI MS. Calc: 483.1. Found: 483.9 (M+H)$^+$.

Example 230

4-bromo-2,5-dichloro-N-{1-[(4-methylpiperidin-1-yl)carbonyl]-3-(2-nitro-1H-imidazol-1-yl)propyl}thiophene-3-sulfonamide from 4-bromo-2,5-dichlorothiophene-3-sulfonyl chloride. ESI MS. Calc: 587.0. Found: 588.1 (M+H)$^+$.

Example 231

4-methoxy-2,3,6-trimethyl-N-{1-[(4-methylpiperidin-1-yl)carbonyl]-3-(2-nitro-1H-imidazol-1-yl)propyl}benzenesulfonamide from 4-methoxy-2,3,6-trimethyl-benzenesulphonyl chloride. ESI MS. Calc: 507.2. Found: 508.4 (M+H)$^+$.

Example 232

4-methyl-N-{1-[(4-methylpiperidin-1-yl)carbonyl]-3-(2-nitro-1H-imidazol-1-yl)propyl}naphthalene-1-sulfonamide from 4-methyl-1-naphthalenesulfonyl chloride. ESI MS. Calc: 499.2. Found: 500.3 (M+H)⁺.

Example 234

5-bromo-2-methoxy-N-{1-[(4-methylpiperidin-1-yl)carbonyl]-3-(2-nitro-1H-imidazol-1-yl)propyl}benzenesulfonamide from 5-bromo-2-methoxybenzenesulfonyl chloride. ESI MS. Calc: 543.1. Found: 544.4 (M+H)⁺.

Example 235

4-amino-3,5-dichloro-N-{1-[(4-methylpiperidin-1-yl)carbonyl]-3-(1H-pyrrol-1-yl)propyl}benzenesulfonamide

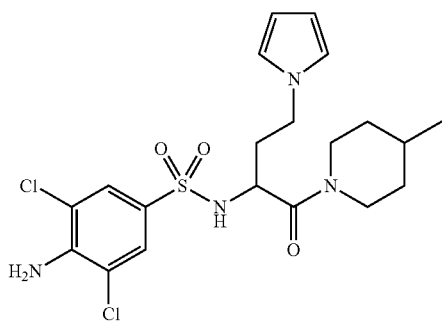

A mixture of 1 g (3.4 mmol) of I-042 and 330 mg (5.0 mmol) of NaN₃ in 4 mL of DMF and 0.4 mL of water is stirred for 3 days. The mixture is diluted with EtOAc and washed twice with water and once with brine, and then dried with Na₂SO₄, filtered, and concentrated to provide 860 mg (99%) of 4-azido-2-tert-butoxycarbonylamino-butyric acid methyl ester. To this compound (500 mg, 1.9 mmol) in 2 mL of 50% 1,4-dioxane in water is added 160 mg (3.9 mmol) of NaOH. After stirring for 30 min, the mixture is diluted with 3M HCl and extracted three times with EtOAc. The extracts are combined, washed twice with water and once with brine, and then dried over Na₂SO₄, filtered, and concentrated to provide 470 mg of 4-azido-2-tert-butoxycarbonylamino-butyric acid. To 190 mg (0.77 mmol) of this material, 160 mg (0.85 mmol) of EDC, 120 mg (0.85 mmol) of HOBt, and a crystal of DMAP in 1 mL of DMF, is added 0.089 mL (0.77 mmol) of 4-methylpiperidine. The mixture is stirred for 30 min, and then is diluted with EtOAc and washed twice with water, and once with brine. The organic layer is dried over Na₂SO₄, filtered, and concentrated. Flash chromatography provides 180 mg (73%) of [3-azido-1-(4-methyl-piperidine-1-carbonyl)-propyl]-carbamic acid tert-butyl ester as a colorless oil. To a solution of 180 mg (0.56 mmol) of this material in 1 mL of CH₂Cl₂ is added 0.13 mL (1.7 mmol) of TFA. The mixture is stirred for 3 h, concentrated, and dissolved in 1 mL of DMF. Triethylamine (0.54 mL, 3.9 mL) and I-001 (280 mg, 1.1 mmol) are added, and the mixture is stirred for 4 h. The mixture is diluted with water and extracted three times with EtOAc. The combined extracts are washed twice with water, and three times with brine, then dried over Na₂SO₄, filtered, and concentrated. Flash chromatography provides 4-amino-N-[3-azido-1-(4-methyl-piperidine-1-carbonyl)-propyl]-3,5-dichloro-benzenesulfonamide as a colorless oil. To a solution of 100 mg (0.22 mmol) of the above azide is added 1.5 mL of 1:1 THF/H₂O and 0.25 mL (0.25 mmol) of a 1.0 M solution of PMe₃ in toluene. The mixture is stirred overnight, and then concentrated. The residue is diluted with EtOAc and washed three times with water, once with brine, and then dried over MgSO₄, filtered, and concentrated to provide 77 mg (81%) of 4-amino-N-[3-amino-1-(4-methyl-piperidine-1-carbonyl)-propyl]-3,5-dichloro-benzenesulfonamide. To this material (200 mg from multiple experiments, 0.48 mmol) in 2.0 mL of acetic acid at 75° C. is added dropwise 0.064 mL (0.62 mmol) of 2,5-dimethoxytetrahydrofuran. After stirring for 3 h, the mixture is diluted with water and is purified by preparative HPLC to provide 56 mg (25%) of Example 235 as a light yellow solid. ESI MS: Calc: 472.1. Found: 473.3 (M+H)⁺.

General Method C (Amide Formation)

A mixture of 0.1 mmol of carboxylic acid and 0.15 mmol of HATU in 1 mL of DMF is added to a mixture of 0.12 mmol of secondary amine and 0.044 mL (0.4 mmol) of tertiary amine base. The mixtures is shaken overnight, concentrated, and purified by preparative HPLC to provide Examples 236-361.

Example 236

N-[3-(2-cyano-1H-pyrrol-1-yl)-1-(morpholin-4-ylcarbonyl)propyl]-1H-indole-4-sulfonamide from I-102 and morpholine with NMM as base. ESI MS Calc.: 441.2. Found: 442.1 (M+H)⁺.

Example 237

N-{3-(2-cyano-1H-pyrrol-1-yl)-1-[(4-methyl-3,6-dihydropyridin-1(2H)-yl)carbonyl]propyl}-1H-indole-4-sulfonamide from I-102 and I-033 with Et₃N as base. ESI MS Calc.: 451.2. Found: 452.2 (M+H)⁺.

Example 238

N-[1-(azepan-1-ylcarbonyl)-3-(2-cyano-1H-pyrrol-1-yl)propyl]-1H-indole-4-sulfonamide from I-102 and azepane with NMM as base. ESI MS Calc.: 453.2. Found: 454.1 (M+H)⁺.

Example 239

N-[1-(azepan-1-ylcarbonyl)-3-(2-cyano-1H-pyrrol-1-yl)propyl]-1H-indole-6-sulfonamide from I-101 and azepane with NMM as base. ESI MS Calc.: 453.2. Found: 454.2 (M+H)⁺.

Example 240

N-{3-(2-cyano-1H-pyrrol-1-yl)-1-[(2-methylpiperidin-1-yl)carbonyl]propyl}-1H-indole-4-sulfonamide from I-102 and 2-methylpiperidine with NMM as base. ESI MS Calc.: 453.2. Found: 454.1 (M+H)⁺.

Example 241

N-{3-(2-cyano-1H-pyrrol-1-yl)-1-[(2-methylpiperidin-1-yl)carbonyl]propyl}-1H-indole-6-sulfonamide from I-101 and 2-methylpiperidine with NMM as base. ESI MS Calc.: 453.2. Found: 454.2 (M+H)⁺.

Example 242

N-{3-(2-cyano-1H-pyrrol-1-yl)-1-[(3-methylpiperidin-1-yl)carbonyl]propyl}-1H-indole-4-sulfonamide from I-102 and 3-methylpiperidine with NMM as base. ESI MS Calc.: 453.2. Found: 454.1 (M+H)$^+$.

Example 243

N-{3-(2-cyano-1H-pyrrol-1-yl)-1-[(3-methylpiperidin-1-yl)carbonyl]propyl}-1H-indole-6-sulfonamide from I-101 and 3-methylpiperidine with NMM as base. ESI MS Calc.: 453.2. Found: 454.2 (M+H)$^+$.

Example 244

N-{3-(2-cyano-1H-pyrrol-1-yl)-1-[(4-oxopiperidin-1-yl)carbonyl]propyl}-1H-indole-4-sulfonamide from I-102 and 4-oxopiperidine hydrate with NMM as base. ESI MS Calc.: 453.2. Found: 454.1 (M+H)$^+$.

Example 245

N-{3-(2-cyano-1H-pyrrol-1-yl)-1-[(4-methylpiperazin-1-yl)carbonyl]propyl}-1H-indole-4-sulfonamide from I-102 and 4-methylpiperazine with NMM as base. ESI MS Calc.: 454.2. Found: 455.2 (M+H)$^+$.

Example 246

N-[3-(2-cyano-1H-pyrrol-1-yl)-1-(1,4-oxazepan-4-ylcarbonyl)propyl]-1H-indole-4-sulfonamide from I-102 and homomorpholine with NMM as base. ESI MS Calc.: 455.2. Found: 456.2 (M+H)$^+$.

Example 247

N-{3-(2-cyano-1H-pyrrol-1-yl)-1-[(3-hydroxypiperidin-1-yl)carbonyl]propyl}-1H-indole-4-sulfonamide from I-102 and 3-hydroxypiperidine with NMM as base. ESI MS Calc.: 455.2. Found: 456.2 (M+H)$^+$.

Example 248

N-{3-(2-cyano-1H-pyrrol-1-yl)-1-[(4-hydroxypiperidin-1-yl)carbonyl]propyl}-1H-indole-4-sulfonamide from I-102 and 4-hydroxypiperidine with NMM as base. ESI MS Calc.: 455.2. Found: 456.2 (M+H)$^+$.

Example 249

N-{3-(2-cyano-1H-pyrrol-1-yl)-1-[(4-fluoropiperidin-1-yl)carbonyl]propyl}-1H-indole-4-sulfonamide from I-102 and 4-fluoropiperidine with NMM as base. ESI MS Calc.: 457.2. Found: 458.2 (M+H)$^+$.

Example 250

N-[1-(azepan-1-ylcarbonyl)-3-(2-cyano-1H-pyrrol-1-yl)propyl]-2-chloro-6-methylbenzenesulfonamide from I-099 and azepane with NMM as base. ESI MS Calc.: 462.1. Found: 463.2 (M+H)$^+$.

Example 251

2-chloro-N-{3-(2-cyano-1H-pyrrol-1-yl)-1-[(2-methylpiperidin-1-yl) carbonyl]propyl}-6-methylbenzenesulfonamide from I-099 and 2-methylpiperidine with NMM as base. ESI MS Calc.: 462.2. Found: 463.1 (M+H)$^+$.

Example 252

2-chloro-N-{3-(2-cyano-1H-pyrrol-1-yl)-1-[(3-methylpiperidin-1-yl) carbonyl]propyl}-6-methylbenzenesulfonamide from I-099 and 3-methylpiperidine with NMM as base. ESI MS Calc.: 462.2. Found: 463.1 (M+H)$^+$.

Example 253

N-[1-(6-azaspiro[2.5]oct-6-ylcarbonyl)-3-(2-cyano-1H-pyrrol-1-yl) propyl]-1H-indole-4-sulfonamide from I-102 and 6-azaspiro[2.5]octane with NMM as base. ESI MS Calc.: 465.2. Found: 466.2 (M+H)$^+$.

Example 254

N-[1-(6-azaspiro[2.5]oct-6-ylcarbonyl)-3-(2-cyano-1H-pyrrol-1-yl) propyl]-1H-indole-6-sulfonamide from I-101 and 6-azaspiro[2.5]octane with NMM as base. ESI MS Calc.: 465.2. Found: 466.2 (M+H)$^+$.

Example 255

N-{3-(2-cyano-1H-pyrrol-1-yl)-1-[(4-methyl-1,4-diazepan-1-yl) carbonyl]propyl}-1H-indole-4-sulfonamide from I-102 and 4-methyl-1,4-diazepane with NMM as base. ESI MS Calc.: 468.2. Found: 469.2 (M+H)$^+$.

Example 256

N-{3-(2-cyano-1H-pyrrol-1-yl)-1-[(5-oxo-1,4-diazepan-1-yl)carbonyl]propyl}-1H-indole-4-sulfonamide from I-102 and 5-oxo-1,4-diazepane with NMM as base. ESI MS Calc.: 468.2. Found: 469.2 (M+H)$^+$.

Example 257

N-[3-(2-cyano-1H-pyrrol-1-yl)-1-{[2-(hydroxymethyl)piperidin-1-yl]carbonyl]propyl}-1H-indole-4-sulfonamide from I-102 and 2-hydroxymethyl-piperidine with NMM as base. ESI MS Calc.: 469.2. Found: 470.2 (M+H)$^+$.

Example 258

N-[3-(2-cyano-1H-pyrrol-1-yl)-1-{[3-(hydroxymethyl)piperidin-1-yl]carbonyl]propyl}-1H-indole-4-sulfonamide from I-102 and 3-hydroxymethyl-piperidine with NMM as base. ESI MS Calc.: 469.2. Found: 470.2 (M+H)$^+$.

Example 259

N-[3-(2-cyano-1H-pyrrol-1-yl)-1-{[4-(hydroxymethyl)piperidin-1-yl]carbonyl]propyl}-1H-indole-4-sulfonamide from I-102 and 4-hydroxymethyl-piperidine with NMM as base. ESI MS Calc.: 469.2. Found: 470.1 (M+H)$^+$.

Example 260

N-[3-(2-cyano-1H-pyrrol-1-yl)-1-{[4-(hydroxymethyl)piperidin-1-yl]carbonyl]propyl}-1H-indole-6-sulfonamide from I-101 and 4-hydroxymethyl-piperidine with NMM as base. ESI MS Calc.: 469.2. Found: 470.2 (M+H)$^+$.

Example 261

N-[1-(6-azaspiro[2.5]oct-6-ylcarbonyl)-3-(2-cyano-1H-pyrrol-1-yl) propyl]-2-chloro-6-methylbenzenesulfonamide from I-099 and 6-azaspiro-[2.5]octane with NMM as base. ESI MS Calc.: 474.2. Found: 475.2 (M+H)$^+$.

Example 262

2-{[(2-chloro-6-methylphenyl)sulfonyl]amino}-4-(2-cyano-1H-pyrrol-1-yl)-N-cyclohexyl-N-methylbutanamide from I-099 and cyclohexyl-N-methyl-amine with NMM as base. ESI MS Calc.: 476.2. Found: 477.2 (M+H)$^+$.

Example 263

N-{3-(2-cyano-1H-pyrrol-1-yl)-1-[(4-propylpiperidin-1-yl)carbonyl]propyl}-1H-indole-4-sulfonamide from I-102 and 4-propylpiperidine with NMM as base. ESI MS Calc.: 481.2. Found: 482.1 (M+H)$^+$.

Example 264

N-{3-(2-cyano-1H-pyrrol-1-yl)-1-[(4-propylpiperidin-1-yl)carbonyl]propyl}-1H-indole-6-sulfonamide from I-101 and 4-propylpiperidine with NMM as base. ESI MS Calc.: 481.2. Found: 482.2 (M+H)$^+$.

Example 265

2,6-dichloro-N-{3-(2-cyano-1H-pyrrol-1-yl)-1-[(3-methylpiperidin-1-yl) carbonyl]propyl}benzenesulfonamide from I-100 and 3-methylpiperidine with NMM as base. ESI MS Calc.: 482.1. Found: 483.1 (M+H)$^+$.

Example 266

N-[1-(azepan-1-ylcarbonyl)-3-(2-cyano-1H-pyrrol-1-yl) propyl]-2,6-dichlorobenzenesulfonamide from I-100 and azepane with NMM as base. ESI MS Calc.: 482.1. Found: 483.1 (M+H)$^+$.

Example 267

N-{1-[(4-acetylpiperazin-1-yl)carbonyl]-3-(2-cyano-1H-pyrrol-1-yl) propyl}-1H-indole-4-sulfonamide from I-102 and 4-acetylpiperazine with NMM as base. ESI MS Calc.: 482.2. Found: 483.2 (M+H)$^+$.

Example 268

N-{3-(2-cyano-1H-pyrrol-1-yl)-1-[(4,4-difluoropiperidin-1-yl)carbonyl]propyl}-1H-indole-4-sulfonamide from I-102 and 4,4-difluoropiperidine with NMM as base. ESI MS Calc.: 482.2. Found: 483.2 (M+H)$^+$.

Example 269

N-[3-(2-cyano-1H-pyrrol-1-yl)-1-{[4-(2-hydroxyethyl)piperidin-1-yl]carbonyl]propyl}-1H-indole-4-sulfonamide from I-102 and 4-(2-hydroxyethyl)-piperidine with NMM as base. ESI MS Calc.: 483.2. Found: 484.2 (M+H)$^+$.

Example 270

N-[3-(2-cyano-1H-pyrrol-1-yl)-1-{[4-(methoxymethyl)piperidin-1-yl]carbonyl]propyl}-1H-indole-4-sulfonamide from I-102 and 4-(methoxymethyl)-piperidine with NMM as base. ESI MS Calc.: 483.2. Found: 484.2 (M+H)$^+$.

Example 271

N-[3-(2-cyano-1H-pyrrol-1-yl)-1-{[4-(2-hydroxyethyl)piperazin-1-yl]carbonyl]propyl}-1H-indole-4-sulfonamide from I-102 and 4-(2-hydroxyethyl)-piperazine with NMM as base. ESI MS Calc.: 484.2. Found: 485.2 (M+H)$^+$.

Example 272

2-{[(2-chloro-6-methylphenyl)sulfonyl]amino}-4-(2-cyano-1H-pyrrol-1-yl)-N-methyl-N-(pyridin-2-ylmethyl)butanamide from I-099 and pyridine-2-yl-methyl-amine with NMM as base. ESI MS Calc.: 485.1. Found: 486.2 (M+H)$^+$.

Example 273

2-{[(2-chloro-6-methylphenyl)sulfonyl]amino}-4-(2-cyano-1H-pyrrol-1-yl)-N-methyl-N-(pyridin-3-ylmethyl)butanamide from I-099 and pyridine-3-yl-methyl-amine with NMM as base. ESI MS Calc.: 485.1. Found: 486.1 (M+H)$^+$.

Example 274

N-[3-(2-cyano-1H-pyrrol-1-yl)-1-(3,4-dihydroisoquinolin-2(1H)-ylcarbonyl)propyl]-1H-indole-4-sulfonamide from I-102 and 3,4-tetrahydro-isoquinoline with NMM as base. ESI MS Calc.: 487.2. Found: 488.1 (M+H)$^+$.

Example 275

N-[3-(2-cyano-1H-pyrrol-1-yl)-1-(3,4-dihydroisoquinolin-2(1H)-yl carbonyl)propyl]-1H-indole-6-sulfonamide from I-101 and tetrahydroisoquinoline with NMM as base. ESI MS Calc.: 487.2. Found: 488.2 (M+H)$^+$.

Example 276

2-chloro-N-{3-(2-cyano-1H-pyrrol-1-yl)-1-[(4-propylpiperidin-1-yl) carbonyl]propyl}-6-methylbenzenesulfonamide from I-099 and 4-propyl-piperidine with NMM as base. ESI MS Calc.: 490.2. Found: 491.2 (M+H)$^+$.

Example 277

N-[3-(2-cyano-1H-pyrrol-1-yl)-1-(3-methyl-5,6-dihydro[1,2,4]triazole[4,3-a]pyrazin-7(8H)-ylcarbonyl)propyl]-1H-indole-4-sulfonamide from I-102 and 3-methyl-5,6,7,8-tetrahydro-1,2,4-triazolo[4,3-a]pyrazine hydrochloride with Et$_3$N as base. ESI MS Calc.: 492.2. Found: 493.3 (M+H)$^+$.

Example 278

N-{3-(2-cyano-1H-pyrrol-1-yl)-1-[(cis)-octahydroisoquinolin-2(1H)-yl carbonyl]propyl}-1H-indole-4-sulfonamide from I-102 and cis-decahydroisoquinoline with NMM as base. ESI MS Calc.: 493.2. Found: 494.2 (M+H)$^+$.

Example 279

N-{3-(2-cyano-1H-pyrrol-1-yl)-1-[(cis)-octahydroisoquinolin-2(1H)-yl carbonyl]propyl}-1H-indole-6-sulfonamide from I-100 and cis-ocatahydroisoquinoline with NMM as base. ESI MS Calc.: 493.2. Found: 494.3 (M+H)$^+$.

Example 280

N-[1-(6-azaspiro[2.5]oct-6-ylcarbonyl)-3-(2-cyano-1H-pyrrol-1-yl) propyl]-2,6-dichlorobenzenesulfonamide from I-100 and 6-azaspiro[2.5]octane with NMM as base. ESI MS Calc.: 494.1. Found: 495.1 (M+H)$^+$.

Example 281

N-[3-(2-cyano-1H-pyrrol-1-yl)-1-(octahydro-2H-pyrido[1,2-a]pyrazin-2-ylcarbonyl)propyl]-1H-indole-4-sulfona-

Example 282

2-chloro-N-[3-(2-cyano-1H-pyrrol-1-yl)-1-(3,4-dihydroisoquinolin-2(1H)-ylcarbonyl)propyl]-6-methylbenzenesulfonamide from I-099 and 3,4-tetrahydroisoquinoline with NMM as base. ESI MS Calc.: 496.1. Found: 497.2 (M+H)$^+$.

mide from I-102 and octahydro-2H-pyrido[1,2-a]pyrazine with NMM as base. ESI MS Calc.: 494.2. Found: 495.2 (M+H)$^+$.

Example 283

N-{1-[(4-acetyl-1,4-diazepan-1-yl)carbonyl]-3-(2-cyano-1H-pyrrol-1-yl) propyl}-1H-indole-4-sulfonamide from I-102 and 4-acetyl-1,4-diazepane with NMM as base. ESI MS Calc.: 496.2. Found: 497.2 (M+H)$^+$.

Example 284

4-amino-3,5-dichloro-N-{3-(2-cyano-1H-pyrrol-1-yl)-1-[(2-methyl-piperidin-1-yl)carbonyl] propyl}benzenesulfonamide from I-098 and 2-methyl-piperidine with NMM as base. ESI MS Calc.: 497.1. Found: 498.1 (M+H)$^+$.

Example 285

4-amino-3,5-dichloro-N-{3-(2-cyano-1H-pyrrol-1-yl)-1-[(3-methyl-piperidin-1-yl)carbonyl] propyl}benzenesulfonamide from I-098 and 3-methyl-piperidine with NMM as base. ESI MS Calc.: 497.1. Found: 498.1 (M+H)$^+$.

Example 286

4-amino-N-[1-(azepan-1-ylcarbonyl)-3-(2-cyano-1H-pyrrol-1-yl)propyl]-3,5-dichlorobenzenesulfonamide from I-098 and azepane with NMM as base. ESI MS Calc.: 497.1. Found: 498.1 (M+H)$^+$.

Example 287 methyl 1-{4-(2-cyano-1H-pyrrol-1-yl)-2-[(1H-indol-4-ylsulfonyl)amino]butanoyl}piperidine-4-carboxylate from I-102 and methyl piperidine-4-carboxylate with NMM as base. ESI MS Calc.: 497.2. Found: 498.1 (M+H)$^+$.

Example 288 methyl 1-{4-(2-cyano-1H-pyrrol-1-yl)-2-[(1H-indol-6-ylsulfonyl)amino]butanoyl}piperidine-4-carboxylate from I-100 and 4-propylpiperidine with NMM as base. ESI MS Calc.: 497.2. Found: 498.2 (M+H)$^+$.

Example 289

N-[3-(2-cyano-1H-pyrrol-1-yl)-1-(1,4-dioxa-8-azaspiro[4.5]dec-8-yl carbonyl)propyl]-1H-indole-4-sulfonamide from I-102 and 1,4-dioxa-8-aza-spiro-[4.5]decane with NMM as base. ESI MS Calc.: 497.2. Found: 498.2 (M+H)$^+$.

Example 290

N-[3-(2-cyano-1H-pyrrol-1-yl)-1-{[4-(1-hydroxy-1-methylethyl)piperidin-1-yl]carbonyl]propyl}-1H-indole-4-sulfonamide from I-102 and 4-(1-hydroxy-1-methylethyl)piperidine with NMM as base. ESI MS Calc.: 497.2. Found: 498.3 (M+H)$^+$.

Example 291

2-{[(2-chloro-6-methylphenyl)sulfonyl]amino}-4-(2-cyano-1H-pyrrol-1-yl)-N-methyl-N-(3-methylbenzyl)butanamide from I-099 and (3-methylbenzyl)-methyl-amine with NMM as base. ESI MS Calc.: 498.2. Found: 499.1 (M+H)$^+$.

Example 292

2-{[(2-chloro-6-methylphenyl)sulfonyl]amino}-4-(2-cyano-1H-pyrrol-1-yl)-N-methyl-N-(4-methylbenzyl)butanamide from I-099 and 4-methylbenzyl-methyl-amine with NMM as base. ESI MS Calc.: 498.2. Found: 499.1 (M+H)$^+$.

Example 293

2-{[(2-chloro-6-methylphenyl)sulfonyl]amino}-4-(2-cyano-1H-pyrrol-1-yl)-N-methyl-N-[(1S)-1-phenylethyl]butanamide from I-099 and methyl-(1S)-1-phenethylamine with NMM as base. ESI MS Calc.: 498.2. Found: 499.1 (M+H)$^+$.

Example 294

2-{[(2-chloro-6-methylphenyl)sulfonyl]amino}-4-(2-cyano-1H-pyrrol-1-yl)-N-(2-fluorobenzyl)-N-methylbutanamide from I-099 and (2-fluorobenzyl)-methyl-amine with NMM as base. ESI MS Calc.: 502.1. Found: 503.0 (M+H)$^+$.

Example 295

2-{[(2-chloro-6-methylphenyl)sulfonyl]amino}-4-(2-cyano-1H-pyrrol-1-yl)-N-(3-fluorobenzyl)-N-methylbutanamide from I-099 and (3-fluorobenzyl)-methyl-amine with NMM as base. ESI MS Calc.: 502.1. Found: 503.1 (M+H)$^+$.

Example 296

2-{[(2-chloro-6-methylphenyl)sulfonyl]amino}-4-(2-cyano-1H-pyrrol-1-yl)-N-(4-fluorobenzyl)-N-methylbutanamide from I-099 and (4-fluorobenzyl)-methyl-amine with NMM as base. ESI MS Calc.: 502.1. Found: 503.1 (M+H)$^+$.

Example 297

2-chloro-N-{3-(2-cyano-1H-pyrrol-1-yl)-1-[(cis)-octahydroisoquinolin-2(1H)-ylcarbonyl]propyl}-6-methylbenzenesulfonamide from I-099 and cis-decahydroisoquinoline with NMM as base. ESI MS Calc.: 502.2. Found: 503.2 (M+H)$^+$.

Example 298 methyl 1-[2-{[(2-chloro-6-methylphenyl)sulfonyl]amino}-4-(2-cyano-1H-pyrrol-1-yl)butanoyl]piperidine-4-carboxylate from I-099 and methyl piperidine-4-carboxylate with NMM as base. ESI MS Calc.: 506.1. Found: 507.2 (M+H)$^+$.

Example 299

N-[3-(2-cyano-1H-pyrrol-1-yl)-1-{[4-(trifluoromethyl)piperidin-1-yl]carbonyl]propyl}-1H-indole-4-sulfonamide

Example 300

N-[3-(2-cyano-1H-pyrrol-1-yl)-1-{[4-(trifluoromethyl)piperidin-1-yl]carbonyl]propyl}-1H-indole-6-sulfonamide from I-101 and 4-(trifluoromethyl)-piperidine with NMM as base. ESI MS Calc.: 507.2. Found: 508.2 (M+H)$^+$.

Example 301

4-amino-N-[1-(6-azaspiro[2.5]oct-6-ylcarbonyl)-3-(2-cyano-1H-pyrrol-1-yl)propyl]-3,5-dichlorobenzenesulfonamide from I-098 and aza-spiro[2.5]octane with NMM as base. ESI MS Calc.: 509.1. Found: 510.1 (M+H)$^+$.

Example 302 methyl (1-{4-(2-cyano-1H-pyrrol-1-yl)-2-[(1H-indol-4-ylsulfonyl)amino]butanoyl}piperidin-4-ylidene)acetate from I-102 and piperidin-4-ylidene-acetic acid methyl ester with NMM as base. ESI MS Calc.: 509.2. Found: 510.2 (M+H)$^+$.

Example 303

2,6-dichloro-N-{3-(2-cyano-1H-pyrrol-1-yl)-1-[(4-propylpiperidin-1-yl) carbonyl]propyl}benzenesulfonamide from I-100 and 4-propylpiperidine with NMM as base. ESI MS Calc.: 510.1. Found: 511.1 (M+H)$^+$.

Example 304

3-(1-{4-(2-cyano-1H-pyrrol-1-yl)-2-[(1H-indol-4-ylsulfonyl)amino]butanoyl}piperidin-4-yl)propanamide from I-102 and 3-(piperidine-4-yl)-propanamide with NMM as base. ESI MS Calc.: 510.2. Found: 511.2 (M+H)$^+$.

Example 305 methyl (1-{4-(2-cyano-1H-pyrrol-1-yl)-2-[(1H-indol-4-ylsulfonyl)amino]butanoyl}piperidin-2-yl)acetate from I-102 and piperidin-2-yl-acetic acid methyl ester with NMM as base. ESI MS Calc.: 511.2. Found: 512.2 (M+H)$^+$.

Example 306 methyl (1-{4-(2-cyano-1H-pyrrol-1-yl)-2-[(1H-indol-4-ylsulfonyl)amino]butanoyl}piperidin-3-yl)acetate from I-102 and piperidin-3-yl-acetic acid methyl ester with NMM as base. ESI MS Calc.: 511.2. Found: 512.2 (M+H)$^+$.

Example 307 methyl (1-{4-(2-cyano-1H-pyrrol-1-yl)-2-[(1H-indol-4-ylsulfonyl)amino]butanoyl}piperidin-4-yl)acetate from I-102 and piperidin-4-yl-acetic acid methyl ester with NMM as base. ESI MS Calc.: 511.2. Found: 512.2 (M+H)$^+$.

Example 308

3-chloro-N-[3-(2-cyano-1H-pyrrol-1-yl)-1-(5,6-dihydro[1,2,4]triazolo[4,3-a]pyrazin-7(8H)-ylcarbonyl)propyl]-1H-indole-4-sulfonamide from I-103 and 5,6,7,8-tetrahydro-1,2,4-triazolo[4,3-c]pyrazine with Et$_3$N as base. ESI MS Calc.: 512.1. Found: 513.2 (M+H)$^+$.

Example 309

4-amino-3,5-dichloro-N-[3-(2-cyano-1H-pyrrol-1-yl)-1-{[4-(hydroxy-methyl)piperidin-1-yl]carbonyl}propyl]benzenesulfonamide from I-098 and 4-hydroxymethylpiperidine with NMM as base. ESI MS Calc.: 513.1. Found: 514.1 (M+H)$^+$.

Example 310

2-{[(2-chloro-6-methylphenyl)sulfonyl]amino}-4-(2-cyano-1H-pyrrol-1-yl)-N-(2-methoxybenzyl)-N-methylbutanamide from I-099 and (2-methoxy-benzyl)-methyl-amine with NMM as base. ESI MS Calc.: 514.1. Found: 515.1 (M+H)$^+$.

Example 311

2-{[(2-chloro-6-methylphenyl)sulfonyl]amino}-4-(2-cyano-1H-pyrrol-1-yl)-N-(3-methoxybenzyl)-N-methylbutanamide from I-099 and (3-methoxy-benzyl)-methyl-amine with NMM as base. ESI MS Calc.: 514.1. Found: 515.1 (M+H)$^+$.

Example 312

2-{[(2-chloro-6-methylphenyl)sulfonyl]amino}-4-(2-cyano-1H-pyrrol-1-yl)-N-(4-methoxybenzyl)-N-methylbutanamide from I-099 and (2-methoxy-benzyl)-methyl-amine with NMM as base. ESI MS Calc.: 514.1. Found: 515.2 (M+H)$^+$.

Example 313

2,6-dichloro-N-[3-(2-cyano-1H-pyrrol-1-yl)-1-(3,4-dihydroisoquinolin-2(1H)-ylcarbonyl)propyl]benzenesulfonamide from I-100 and tetrahydro-isoquinoline with NMM as base. ESI MS Calc.: 516.1. Found: 517.1 (M+H)$^+$.

Example 314

2-chloro-N-[3-(2-cyano-1H-pyrrol-1-yl)-1-{[4-(trifluoromethyl)piperidin-1-yl]carbonyl}propyl]-6-methylbenzenesulfonamide from I-099 and 4-(trifluoromethyl)piperidine with NMM as base. ESI MS Calc.: 516.1. Found: 517.1 (M+H)$^+$.

Example 315

N-{3-(2-cyano-1H-pyrrol-1-yl)-1-[(4-phenylpiperazin-1-yl)carbonyl]propyl}-1H-indole-4-sulfonamide from I-102 and 4-phenylpiperazine with NMM as base. ESI MS Calc.: 516.2. Found: 517.3 (M+H)$^+$.

Example 316

N-[3-(2-cyano-1H-pyrrol-1-yl)-1-{[4-(methylsulfonyl)piperidin-1-yl]carbonyl}propyl]-1H-indole-4-sulfonamide from I-102 and 4-methanesulfonyl-piperidine (US2003/100567A1) with Et$_3$N as base. ESI MS Calc.: 517.2. Found: 518.2 (M+H)$^+$.

Example 317

N-(2-chlorobenzyl)-2-{[(2-chloro-6-methylphenyl)sulfonyl]amino}-4-(2-cyano-1H-pyrrol-1-yl)-N-methylbutanamide from I-099 and (2-chlorobenzyl)-methyl-amine with NMM as base. ESI MS Calc.: 518.1. Found: 519.1 (M+H)$^+$.

Example 318

N-(3-chlorobenzyl)-2-{[(2-chloro-6-methylphenyl)sulfonyl]amino}-4-(2-cyano-1H-pyrrol-1-yl)-N-methylbutanamide from I-099 and (3-chlorobenzyl)-methyl-amine with NMM as base. ESI MS Calc.: 518.1. Found: 519.0 (M+H)$^+$.

Example 319

N-{3-(2-cyano-1H-pyrrol-1-yl)-1-[(4-pyrimidin-2-ylpiperazin-1-yl) carbonyl]propyl}-1H-indole-4-sulfonamide from I-102 and 4-pyrimidin-2-yl-piperiazine with NMM as base. ESI MS Calc.: 518.2. Found: 518.2 (M+H)$^+$.

Example 320

2,6-dichloro-N-{3-(2-cyano-1H-pyrrol-1-yl)-1-[(cis)-octahydro-isoquinolin-2(1H)-ylcarbonyl]propyl}benzenesulfonamide from I-100 and cis-decahydroisoquinoline with NMM as base. ESI MS Calc.: 522.1. Found: 523.2 (M+H)$^+$.

Example 321

N-[3-(2-cyano-1H-pyrrol-1-yl)-1-{[4-(1,3-thiazol-2-yl)piperazin-1-yl]carbonyl}propyl]-1H-indole-4-sulfonamide from I-102 and 4-(1,3-thiazol-2-yl)-piperazine with NMM as base. ESI MS Calc.: 523.2. Found: 524.2 (M+H)$^+$.

Example 322 methyl (2E)-3-(1-{4-(2-cyano-1H-pyrrol-1-yl)-2-[(1H-indol-4-ylsulfonyl)amino]butanoyl}piperidin-3-yl)prop-2-enoate from I-102 and I-032 with Et$_3$N as base. ESI MS Calc.: 523.2. Found: 524.2 (M+H)$^+$.

Example 323

N-[2-(1-{4-(2-cyano-1H-pyrrol-1-yl)-2-[(1H-indol-4-ylsulfonyl)amino]butanoyl}piperidin-2-yl)ethyl]acetamide from I-102 and N-[2-(piperidine-2-yl)ethyl]acetamide with NMM as base. ESI MS Calc.: 524.2. Found: 525.2 (M+H)$^+$.

Example 324

N-[2-(1-{4-(2-cyano-1H-pyrrol-1-yl)-2-[(1H-indol-4-ylsulfonyl)amino]butanoyl}piperidin-4-yl)ethyl]acetamide from I-102 and N-[2-(piperidine-4-yl)ethyl]acetamide with NMM as base. ESI MS Calc.: 524.2. Found: 525.2 (M+H)$^+$.

Example 325

4-amino-3,5-dichloro-N-{3-(2-cyano-1H-pyrrol-1-yl)-1-[(4-propylpiperidin-1-yl)carbonyl]propyl}benzenesulfonamide from I-098 and 4-propylpiperidine with NMM as base. ESI MS Calc.: 525.1. Found: 526.1 (M+H)$^+$.

Example 326 methyl 3-(1-{4-(2-cyano-1H-pyrrol-1-yl)-2-[(1H-indol-4-ylsulfonyl)amino]butanoyl}piperidin-3-yl)propanoate from I-102 and piperidin-3-yl-propionic acid methyl ester with NMM as base. ESI MS Calc.: 525.2. Found: 526.3 (M+H)$^+$.

Example 327 methyl 3-(1-{4-(2-cyano-1H-pyrrol-1-yl)-2-[(1H-indol-4-ylsulfonyl)amino]butanoyl}piperidin-4-yl)propanoate from I-102 and piperidin-4-yl-propionic acid methyl ester with NMM as base. ESI MS Calc.: 525.2. Found: 526.3 (M+H)$^+$.

Example 328

N-[3-(2-cyano-1H-pyrrol-1-yl)-1-(5,6-dihydro[1,2,4]triazolo[4,3-a]pyrazin-7(8H)-ylcarbonyl)propyl]-1H-indole-4-sulfonamide from I-102 and 5,6,7,8-tetrahydro-1,2,4-triazolo[4,3-a]pyrazine with Et$_3$N as base. ESI MS Calc.: 478.2. Found: 479.2 (M+H)$^+$.

Example 329 methyl 1-[4-(2-cyano-1H-pyrrol-1-yl)-2-{[(2,6-dichlorophenyl)sulfonyl]amino}butanoyl]piperidine-4-carboxylate from I-100 and methyl piperidine-4-carboxylate with NMM as base. ESI MS Calc.: 526.1. Found: 527.1 (M+H)$^+$.

Example 330

2-{[(2-chloro-6-methylphenyl)sulfonyl]amino}-4-(2-cyano-1H-pyrrol-1-yl)-N-(2-methoxy-5-methylbenzyl)-N-methylbutanamide from I-099 and (2-methoxy-5-methylbenzyl)-methyl-amine with NMM as base. ESI MS Calc.: 528.2. Found: 529.2 (M+H)$^+$.

Example 331

2-{[(2-chloro-6-methylphenyl)sulfonyl]amino}-4-(2-cyano-1H-pyrrol-1-yl)-N-methyl-N-(2-naphthylmethyl)butanamide from I-099 and methyl-naphthalene-2-ylmethyl-amine with NMM as base. ESI MS Calc.: 534.2. Found: 535.1 (M+H)$^+$.

Example 332

2-{[(2-chloro-6-methylphenyl)sulfonyl]amino}-4-(2-cyano-1H-pyrrol-1-yl)-N-methyl-N-(1-naphthylmethyl)butanamide from I-099 and methyl-naphthalene-1-ylmethyl-amine with NMM as base. ESI MS Calc.: 534.3. Found: 535.2 (M+H)$^+$.

Example 333

2,6-dichloro-N-[3-(2-cyano-1H-pyrrol-1-yl)-1-{[4-(trifluoromethyl)piperidin-1-yl]carbonyl}propyl]benzenesulfonamide from I-100 and (4-trifluoro-methyl)piperidine with NMM as base. ESI MS Calc.: 536.1. Found: 537.1 (M+H)$^+$.

Example 334 methyl 4-(1-{4-(2-cyano-1H-pyrrol-1-yl)-2-[(1H-indol-4-ylsulfonyl)amino]butanoyl}piperidin-4-yl)butanoate from I-102 and methyl piperidine-4-butanoate with NMM as base. ESI MS Calc.: 539.2. Found: 540.1 (M+H)⁺.

Example 335 methyl 4-(1-{4-(2-cyano-1H-pyrrol-1-yl)-2-[(1H-indol-4-ylsulfonyl)amino]butanoyl}piperidin-3-yl)butanoate from I-102 and methyl piperidine-3-butanoate with NMM as base. ESI MS Calc.: 539.2. Found: 540.1 (M+H)⁺.

Example 336

1-[2-{[(4-amino-3,5-dichlorophenyl)sulfonyl]amino}-4-(2-cyano-1H-pyrrol-1-yl)butanoyl]-N-methylpiperidine-4-carboxamide from I-098 and N-methyl piperidine-4-carboxamide with NMM as base. ESI MS Calc.: 540.1. Found: 541.1 (M+H)⁺.

Example 337 methyl 1-[2-{[(4-amino-3,5-dichlorophenyl)sulfonyl]amino}-4-(2-cyano-1H-pyrrol-1-yl)butanoyl]piperidine-4-carboxylate from I-098 and methyl piperidine-4-carboxylate with NMM as base. ESI MS Calc.: 541.1. Found: 542.1 (M+H)⁺.

Example 338

2-{[(2-chloro-6-methylphenyl)sulfonyl]amino}-4-(2-cyano-1H-pyrrol-1-yl)-N-(3,4-dimethoxybenzyl)-N-methylbutanamide from I-099 and (3,4-dimethoxybenzyl)-methyl-amine with NMM as base. ESI MS Calc.: 544.2. Found: 545.2 (M+H)⁺.

Example 339

N-{1-[(4-benzyl-1,4-diazepan-1-yl)carbonyl]-3-(2-cyano-1H-pyrrol-1-yl) propyl}-1H-indole-4-sulfonamide from I-102 and 4-benzyl-1,4-diazepane with NMM as base. ESI MS Calc.: 544.2. Found: 545.3 (M+H)⁺.

Example 340 methyl 2-{4-(2-cyano-1H-pyrrol-1-yl)-2-[(1H-indol-4-ylsulfonyl)amino]butanoyl}-1,2,3,4-tetrahydroisoquinoline-6-carboxylate from I-102 and 1,2,3,4-tetrahydro-isoquinoline-6-carboxylic acid methyl ester with iPr₂NEt as base. ESI MS Calc.: 545.2. Found: 546.3 (M+H)⁺.

Example 341

2-{4-(2-cyano-1H-pyrrol-1-yl)-2-[(1H-indol-4-ylsulfonyl)amino]butanoyl}-1,2,3,4-tetrahydroisoquinoline-7-carboxylic acid methyl ester from I-102 and 1,2,3,4-Tetrahydroisoquinoline-7-carboxylic acid methyl ester with iPr₂NEt as base. ESI MS Calc.: 545.2. Found: 546.2 (M+H)⁺.

Example 342

2-{[(2-chloro-6-methylphenyl)sulfonyl]amino}-4-(2-cyano-1H-pyrrol-1-yl)-N-[4-(1H-imidazol-1-yl)benzyl]-N-methylbutanamide from I-099 and [4-(1H-imidazol-1-yl)benzyl]-methyl-amine with NMM as base. ESI MS Calc.: 550.2. Found: 551.2 (M+H)⁺.

Example 343

2-{[(2-chloro-6-methylphenyl)sulfonyl]amino}-4-(2-cyano-1H-pyrrol-1-yl)-N-methyl-N-[4-(1H-pyrazol-1-yl)benzyl]butanamide from I-099 and methyl-(4-pyrazol-1-yl-benzyl)amine with NMM as base. ESI MS Calc.: 550.2. Found: 551.2 (M+H)⁺.

Example 344

2-{[(2-chloro-6-methylphenyl)sulfonyl]amino}-4-(2-cyano-1H-pyrrol-1-yl)-N-methyl-N-[3-(trifluoromethyl)benzyl]butanamide from I-099 and 3-(trifluoromethyl)benzyl-methyl-amine with NMM as base. ESI MS Calc.: 552.1. Found: 553.1 (M+H)⁺.

Example 345

2-{[(2-chloro-6-methylphenyl)sulfonyl]amino}-4-(2-cyano-1H-pyrrol-1-yl)-N-methyl-N-[4-(trifluoromethyl)benzyl]butanamide from I-099 and 4(-trifluoromethyl)benzyl-methyl-amine with NMM as base. ESI MS Calc.: 552.1. Found: 553.1 (M+H)⁺.

Example 346

2-{[(2-chloro-6-methylphenyl)sulfonyl]amino}-4-(2-cyano-1H-pyrrol-1-yl)-N-methyl-N-[(1-methyl-1,2,3,4-tetrahydroquinolin-6-yl)methyl]butanamide from I-099 and (1-methyl-1,2,3,4-tetrahydroquinolin-6-yl)methyl-amine with NMM as base. ESI MS Calc.: 553.2. Found: 554.2 (M+H)⁺.

Example 347

3-[(cis)-1-{4-(2-cyano-1H-pyrrol-1-yl)-2-[(1H-indol-4-ylsulfonyl)amino]butanoyl}-4-methylpiperidin-3-yl]propanoic acid from I-102 and I-031 with Et₃N as base. ESI MS Calc.: 553.2. Found: 554.3 (M+H)⁺.

Example 348

2-{[(2-chloro-6-methylphenyl)sulfonyl]amino}-4-(2-cyano-1H-pyrrol-1-yl)-N-methyl-N-(3-pyridin-3-ylbenzyl)butanamide from I-099 and 3-(pyridin-3-yl)benzyl-methyl-amine with NMM as base. ESI MS Calc.: 561.2. Found: 562.2 (M+H)⁺.

Example 349

2-{[(2-chloro-6-methylphenyl)sulfonyl]amino}-4-(2-cyano-1H-pyrrol-1-yl)-N-methyl-N-(4-pyridin-4-ylbenzyl)butanamide from I-099 and (4-pyridine-4-yl)benzyl-methyl-amine with NMM as base. ESI MS Calc.: 561.2. Found: 562.2 (M+H)⁺.

Example 350

2-{[(2-chloro-6-methylphenyl)sulfonyl]amino}-4-(2-cyano-1H-pyrrol-1-yl)-N-methyl-N-(4-pyrimidin-5-ylbenzyl)butanamide from I-099 and (4-pyrimidin-4-yl)-methylamine with NMM as base. ESI MS Calc.: 562.0. Found: 563.2 (M+H)⁺.

Example 351

N-(2-bromobenzyl)-2-{[(2-chloro-6-methylphenyl)sulfonyl]amino}-4-(2-cyano-1H-pyrrol-1-yl)-N-methylbutanamide from I-099 and methyl-(2-bromobenzyl)amine with NMM as base. ESI MS Calc.: 562.0. Found: 563.0 (M+H)⁺.

Example 352

N-(3-bromobenzyl)-2-{[(2-chloro-6-methylphenyl)sulfonyl]amino}-4-(2-cyano-1H-pyrrol-1-yl)-N-methylbutanamide from I-099 and (3-bromobenzyl)-methyl-amine with NMM as base. ESI MS Calc.: 562.0. Found: 563.0 (M+H)⁺.

Example 353

N-(4-bromobenzyl)-2-{[(2-chloro-6-methylphenyl)sulfonyl]amino}-4-(2-cyano-1H-pyrrol-1-yl)-N-methylbutanamide from I-099 and (4-bromobenzyl)-methyl-amine with NMM as base. ESI MS Calc.: 562.0. Found: 563.0 (M+H)⁺.

Example 354

2-{[(2-chloro-6-methylphenyl)sulfonyl]amino}-4-(2-cyano-1H-pyrrol-1-yl)-N-methyl-N-(3-pyrimidin-5-ylbenzyl)butanamide from I-099 and (3-pyrimidin-3-yl)benzyl-methyl-amine with NMM as base. ESI MS Calc.: 562.2. Found: 563.2 (M+H)⁺.

Example 355

2-{[(2-chloro-6-methylphenyl)sulfonyl]amino}-4-(2-cyano-1H-pyrrol-1-yl)-N-methyl-N-[3-(5-methyl-1,2,4-oxadiazol-3-yl)benzyl]butanamide from I-099 and 3-(5-methyl-1,2,4-oxadiazol-3-yl)benzyl-methylamine with NMM as base. ESI MS Calc.: 566.2. Found: 567.1 (M+H)⁺.

Example 356

2-{[(2-chloro-6-methylphenyl)sulfonyl]amino}-4-(2-cyano-1H-pyrrol-1-yl)-N-methyl-N-[4-(5-methyl-1,2,4-oxadiazol-3-yl)benzyl]butanamide from I-099 and methyl-[4-(5-methyl-1,2,4-oxadiazol-3-yl)-benzyl]amine with NMM as base. ESI MS Calc.: 566.2. Found: 567.1 (M+H)⁺.

Example 357

2-{[(2-chloro-6-methylphenyl)sulfonyl]amino}-4-(2-cyano-1H-pyrrol-1-yl)-N-methyl-N-(3-piperidin-1-ylbenzyl)butanamide from I-099 and 3-(piperidin-1-yl)benzyl-methylamine with NMM as base. ESI MS Calc.: 567.2. Found: 568.2 (M+H)⁺.

Example 358

2-{[(2-chloro-6-methylphenyl)sulfonyl]amino}-4-(2-cyano-1H-pyrrol-1-yl)-N-methyl-N-(3-morpholin-4-ylbenzyl)butanamide from I-099 and (3-morpholin-4-ylbenzyl)-methyl-amine with NMM as base. ESI MS Calc.: 569.2. Found: 570.2 (M+H)⁺.

Example 359

2-{[(2-chloro-6-methylphenyl)sulfonyl]amino}-4-(2-cyano-1H-pyrrol-1-yl)-N-methyl-N-[3-(morpholin-4-ylmethyl)benzyl]butanamide from I-099 and 3-(morpholin-4-ylmethyl)benzyl-methyl-amine with NMM as base. ESI MS Calc.: 583.2. Found: 584.2 (M+H)⁺.

Example 360

N-[3-(2-cyano-1H-pyrrol-1-yl)-1-{[4-(3-pyrazin-2-yl-1,2,4-oxadiazol-5-yl)piperidin-1-yl]carbonyl}propyl]-1H-indole-4-sulfonamide from I-102 and 4-(3-pyrazine-2-yl-1,2,4-oxadiazol-5-yl)piperidine with NMM as base. ESI MS Calc.: 585.2. Found: 586.2 (M+H)⁺.

Example 361 ethyl 2-[(2-{4-(2-cyano-1H-pyrrol-1-yl)-2-[(1H-indol-4-ylsulfonyl)amino]butanoyl}-1,2,3,4-tetrahydroisoquinolin-7-yl)oxy]-2-methylpropanoate from I-102 and I-039 with Et₃N as base. ESI MS Calc.: 617.2. Found: 618.3 (M+H)⁺.

Example 362

4-amino-3,5-dichloro-N-[1-(3,4-dihydroisoquinolin-2(1H)-ylcarbonyl)-3-(2-nitro-1H-imidazol-1-yl)propyl]benzenesulfonamide

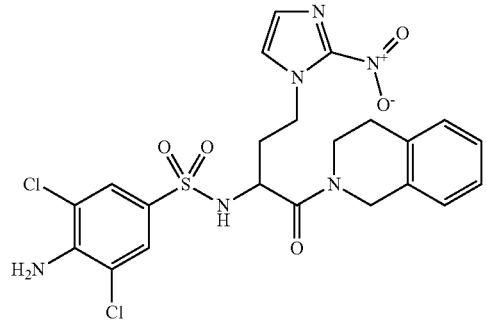 [SMILES: Nc1c(Cl)cc(S(=O)(=O)NC(CCn2ccnc2[N+](=O)[O-])C(=O)N2CCc3ccccc3C2)cc1Cl]

To 25 mg (0.057 mmol) of I-096 in 1.25 mL of 40% DMF in DCE is added 58 mg (0.092 mmol) of PS-carbodimide and 0.25 mL of a 0.32 M solution of HOBt in 50% DMF/DCE. The mixture is shaken for 30 min, and then 0.1 mL of a 0.51 M solution of 1,2,3,4-tetrahydroisoquinoline (0.051 mmol) in DMF is added. The mixture is stirred for 36 h, and then 0.10 g of PS-trisamine (0.42 mmol) and 0.13 g of MP-carbonate (0.42 mmol) are added. The mixture is shaken for an additional 24 h, and then filtered. The filtrate is evaporated to provide Example 362. ESI MS. Calc: 552.1. Found: 553.4 (M+H)⁺.

General Method D (Amide Formation)

A mixture of 1 equivalent of a carboxylic acid, ≥1.2 equivalents of EDC, and ≥1.2 equivalents of HOBt is stirred in DMF for 20 min. Then, ≥1.2 equivalents of secondary amine are added, and the mixture is heated for 10 min at 70° C. in a microwave reactor. The mixture is then diluted with $CH_2Cl_2$ and washed with saturated $NaHCO_3$ and water. The organic layer is dried over $Na_2SO_4$, filtered, and concentrated. Purification by flash chromatography or preparative HPLC provides Examples 363-367.

Example 363

4-amino-3,5-dichloro-N-[3-(2-nitro-1H-imidazol-1-yl)-1-{[4-(trifluoro-methyl)piperidin-1-yl]carbonyl]propyl}benzenesulfonamide from I-096 and 4-trifluoromethylpiperidine. ESI MS. Calc: 572.1. Found: 573.4 $(M+H)^+$.

Example 364

4-amino-3,5-dichloro-N-{1-[(4,4-dimethylpiperidin-1-yl)carbonyl]-3-(2-nitro-1H-imidazol-1-yl)propyl}benzenesulfonamide from I-096 and 4,4-dimethylpiperidine. ESI MS. Calc: 532.1. Found: 533.4 $(M+H)^+$.

Example 365

4-amino-3,5-dichloro-N-{3-(2-nitro-1H-imidazol-1-yl)-1-[(cis)-octahydroisoquinolin-2(1H)-ylcarbonyl]propyl}benzenesulfonamide from I-096 and cis-decahydroisoquinoline. ESI MS. Calc: 558.1. Found: 559.5 $(M+H)^+$.

Example 366

4-amino-3,5-dichloro-N-{3-(2-nitro-1H-imidazol-1-yl)-1-[(trans)-octahydroisoquinolin-2(1H)-ylcarbonyl]propyl}benzenesulfonamide from I-096 and trans-decahydroisoquinoline. ESI MS. Calc: 558.1. Found: 559.5 $(M+H)^+$.

Example 367

4-amino-3,5-dichloro-N-[1-{[4-(hydroxymethyl)piperidin-1-yl]carbonyl}-3-(2-nitro-1H-imidazol-1-yl)propyl]benzenesulfonamide from I-096 and 4-(hydroxymethyl)piperidine. ESI MS. Calc: 534.1. Found: 535.4 $(M+H)^+$.

General Method E (Amide Formation)

A mixture of 1 equivalent of a carboxylic acid, ≥1.2 equivalents of EDC, and ≥1.2 equivalents of HOBt is stirred in DMF for 20 min when ≥1.2 equivalents secondary amine is added, and the mixture is stirred for 2-24 h. The mixture is purified directly by preparative HPLC, or is subjected to an aqueous workup (water, $NaHCO_3$, and brine) before being purified by flash chromatography or preparative HPLC to access Examples 368-401.

Example 368

2-{[(2-chloro-6-methylphenyl)sulfonyl]amino}-4-(2-cyano-1H-pyrrol-1-yl)-N-methyl-N-[2-(trifluoromethyl)benzyl]butanamide from I-099 and methyl-(2-trifluoromethyl-benzyl)-amine with the addition of 0.2 equivalents of DMAP. ESI MS. Calc: 552.1. Found: 553.3 $(M+H)^+$.

Example 369

N-[3-(2-cyano-1H-pyrrol-1-yl)-1-(3,6-dihydropyridin-1(2H)-ylcarbonyl) propyl]-1H-indole-4-sulfonamide from I-102 and 1,2,3,6-tetrahydropyridine. ESI MS Calc.: 437.2. Found: 438.2 $(M+H)^+$.

Example 370

N-[3-(2-cyano-1H-pyrrol-1-yl)-1-(piperidin-1-ylcarbonyl)propyl]-1H-indole-4-sulfonamide from I-102 and piperidine. ESI MS Calc.: 439.2. Found: 440.1 $(M+H)^+$.

Example 371

N-[3-(2-cyano-1H-pyrrol-1-yl)-1-(piperidin-1-ylcarbonyl)propyl]-1H-indole-6-sulfonamide from I-101 and piperidine. ESI MS Calc.: 439.2. Found: 440.3 $(M+H)^+$.

Example 372

2-chloro-N-[3-(2-cyano-1H-pyrrol-1-yl)-1-(piperidin-1-ylcarbonyl) propyl]-6-methylbenzenesulfonamide from I-099 and piperidine with the addition of 0.2 equivalents of DMAP. ESI MS Calc.: 448.1. Found: 449.3 $(M+H)^+$.

Example 373

N-{3-(2-cyano-1H-pyrrol-1-yl)-1-[(4-oxoazepan-1-yl)carbonyl]propyl}-1H-indole-4-sulfonamide from I-102 and 4-perhydroazepanone hydrochloride (Magical Scientific). ESI MS Calc.: 467.2. Found: 468.3 $(M+H)^+$.

Example 374

N-[3-(2-cyano-1H-pyrrol-1-yl)-1-{[(trans)-3-hydroxy-4-methyl-piperidin-1-yl]carbonyl]propyl}-1H-indole-4-sulfonamide from I-102 and I-034 (50% pure). ESI MS Calc.: 469.2. Found: 470.3 $(M+H)^+$.

Example 375

N-{3-(2-cyano-1H-pyrrol-1-yl)-1-[(3,4-dimethylpiperidin-1-yl) carbonyl]propyl}-1H-indole-4-sulfonamide from I-102 and 3,4-dimethylpiperidine. ESI MS Calc.: 467.2. Found: 468.3 $(M+H)^+$.

Example 376

N-benzyl-4-(2-cyano-1H-pyrrol-1-yl)-2-[(1H-indol-6-ylsulfonyl)amino]-N-methylbutanamide from I-101 and N-methylbenzylamine ESI MS Calc.: 475.2. Found: 476.5 $(M+H)^+$.

Example 377

N-[3-(2-cyano-1H-pyrrol-1-yl)-1-(5,6-dihydro-imidazo[4,3-a]pyrazin-7(8H)-ylcarbonyl)propyl]-1H-indole-4-sulfonamide from I-102 and 5,6,7,8-tetrahydro-imidazo[1,2-a]pyrazine. ESI MS Calc.: 477.2. Found: 478.4 $(M+H)^+$.

Example 378

4-amino-3,5-dichloro-N-[3-(2-cyano-1H-pyrrol-1-yl)-1-(piperidin-1-yl-carbonyl)propyl]benzenesulfonamide from I-098 and piperidine with the addition of 0.2 equivalents of DMAP. ESI MS Calc.: 483.1. Found: 484.1 $(M+H)^+$.

Example 379

N-{3-(2-cyano-1H-pyrrol-1-yl)-1-[(1,1-dioxidothiomorpholin-4-yl) carbonyl]propyl}-1H-indole-4-sulfonamide from I-102 and 1,1-dioxothio-morpholine with the addition of 0.2 equivalents of DMAP. ESI MS Calc.: 489.1. Found: 490.2 (M+H)$^+$.

Example 380

N-[3-(2-cyano-1H-pyrrol-1-yl)-1-(6,7-dihydrothieno[3,2-c]pyridin-5(4H)-ylcarbonyl)propyl]-1H-indole-4-sulfonamide from I-102 and 4,5,6,7-tetrahydro-thieno[3,2-c]pyridine with the addition of 0.2 equivalents of DMAP. ESI MS Calc.: 493.1. Found: 494.2 (M+H)$^+$.

Example 381

N-{3-(2-cyano-1H-pyrrol-1-yl)-1-[(trans)-octahydroisoquinolin-2(1H)-ylcarbonyl]propyl}-1H-indole-6-sulfonamide from I-101 and trans-decahydro-sioquinoline. ESI MS Calc.: 493.2. Found: 494.5 (M+H)$^+$.

Example 382

4-amino-3,5-dichloro-N-{3-(2-cyano-1H-pyrrol-1-yl)-1-[(4-methylenepiperidin-1-yl)carbonyl]propyl}benzenesulfonamide from I-098 and 4-methylenepiperidine with the addition of 0.2 equivalents of DMAP. ESI MS Calc.: 495.1. Found: 496.3 (M+H)$^+$.

Example 383

N-{1-[(2-amino-6,7-dihydro[1,3]thiazolo[5,4-c]pyridin-5(4H)-yl) carbonyl]-3-(2-cyano-1H-pyrrol-1-yl)propyl}-1H-indole-4-sulfonamide from I-102 and 4,5,6,7-tetrahydro-thiazolo[5,4-c]pyridin-2-ylamine (Wallace, T. A. et al. Bioorg. Med. Chem. Lett., 2005, 15, 2253). ESI MS Calc.: 509.1. Found: 510.2 (M+H)$^+$.

Example 384

1H-indole-4-sulfonic acid [3-(2-cyano-pyrrol-1-yl)-1-(7-cyano-3,4-dihydro-1H-isoquinoline-2-carbonyl)-propyl]-amide from I-102 and 7-cyano-1,2,3,4-tetrahydroisoquinoline (Gruenewald, G. L. et al. J. Med. Chem., 1997, 40, 3997). ESI MS Calc.: 512.2. Found: 513.4 (M+H)$^+$.

Example 385

N-{3-(2-cyano-1H-pyrrol-1-yl)-1-[(4-phenylpiperidin-1-yl)carbonyl]propyl}-1H-indole-4-sulfonamide from I-102 and 4-phenylpiperidine with the addition of 0.2 equivalents of DMAP. ESI MS Calc.: 515.2. Found: 516.4 (M+H)$^+$.

Example 386

2-{[(4-amino-3,5-dichlorophenyl)sulfonyl]amino}-N-benzyl-4-(2-cyano-1H-pyrrol-1-yl)-N-methylbutanamide from I-098 and N-methyl-benzylamine with the addition of 0.2 equivalents of DMAP. ESI MS Calc.: 519.1. Found: 520.1 (M+H)$^+$.

Example 387 ethyl 1-[2-{[(2-chloro-6-methylphenyl)sulfonyl]amino}-4-(2-cyano-1H-pyrrol-1-yl)butanoyl]piperidine-3-carboxylate from I-099 and ethyl piperidine-3-carboxylate with the addition of 0.2 equivalents of DMAP. ESI MS Calc.: 520.2. Found: 521.2 (M+H)$^+$.

Example 388 methyl 1-[2-{[(2-chloro-6-methylphenyl)sulfonyl]amino}-4-(2-cyano-1H-pyrrol-1-yl)butanoyl]-4-methylpiperidine-4-carboxylate from I-099 and ethyl 4-methylpiperidine-4-carboxylate with the addition of 2 equivalents of iPr$_2$NEt. ESI MS Calc.: 520.2. Found: 521.2 (M+H)$^+$.

Example 389

N-[3-(2-cyano-1H-pyrrol-1-yl)-1-{[4-(3-methyl-1,2,4-oxadiazol-5-yl)piperidin-1-yl]carbonyl}propyl]-1H-indole-4-sulfonamide from I-102 and 4-(3-methyl-1,2,4-oxadiazol-5-yl)-piperidine with the addition of 0.2 equivalents of DMAP. ESI MS Calc.: 521.2. Found: 522.4 (M+H)$^+$.

Example 390

4-amino-3,5-dichloro-N-[3-(2-cyano-1H-pyrrol-1-yl)-1-(3,4-dihydroisoquinolin-2(1H)-ylcarbonyl)propyl]benzenesulfonamide from I-098 and tetrahydroisoquinoline with the addition of 0.2 equivalents of DMAP. ESI MS Calc.: 531.1. Found: 532.1 (M+H)$^+$.

Example 391

1H-indole-4-sulfonic acid [3-(2-cyano-pyrrol-1-yl)-1-(7-nitro-3,4-dihydro-1H-isoquinoline-2-carbonyl)-propyl]-amide from I-102 and 7-nitro-1,2,3,4-tetrahydroisoquinoline (Zhu, Z. et al. J. Med. Chem., 2003, 46, 831). ESI MS Calc.: 532.2. Found: 533.4 (M+H)$^+$.

Example 392

4-amino-3,5-dichloro-N-{3-(2-cyano-1H-pyrrol-1-yl)-1-[(cis)-octahydro-isoquinolin-2(1H)-ylcarbonyl]propyl}benzenesulfonamide from I-098 and cis-decahydroisoquinoline with the addition of 0.2 equivalents of DMAP. ESI MS Calc.: 537.1. Found: 538.2 (M+H)$^+$.

Example 393

4-amino-3,5-dichloro-N-{3-(2-cyano-1H-pyrrol-1-yl)-1-[(trans)-octahydroisoquinolin-2(1H)-ylcarbonyl]propyl}benzenesulfonamide from I-098 and trans-decahydroisoquinoline with the addition of 0.2 equivalents of DMAP. ESI MS Calc.: 537.1. Found: 538.2 (M+H)$^+$.

Example 394

1H-indole-4-sulfonic acid [3-(2-cyano-pyrrol-1-yl)-1-(8-nitro-1,3,4,5-tetrahydro-2-benzazepine-2-carbonyl)-propyl]-amide from I-102 and 8-nitro-2,3,4,5-tetrahydro-1H-2-benzazepine (prepared by nitration of 2,3,4,5-tetrahydro-1H-2-benzazepine as in Zhu, Z. et al. J. Med. Chem., 2003, 46, 831). ESI MS Calc.: 546.2. Found: 547.4 (M+H)$^+$.

Example 395

4-amino-3,5-dichloro-N-[3-(2-cyano-1H-pyrrol-1-yl)-1-{[4-(trifluoro-methyl)piperidin-1-yl]carbonyl]propyl}benzenesulfonamide from I-098 and 4-(trifluoromethyl)piperidine hydrochloride with the addition of 2 equivalents of iPr₂NEt. ESI MS Calc.: 551.1. Found: 552.2 (M+H)⁺.

Example 396

4-[4-(2-Cyano-pyrrol-1-yl)-2-(1H-indole-4-sulfonylamino)-butyryl]-perhydro-1,4-diazepine-1-carboxylic acid tert-butyl ester from I-102 and perhydro-1,4-diazepine-1-carboxylic acid tert-butyl ester. ESI MS Calc.: 554.2. Found: 555.4 (M+H)⁺.

Example 397

2-{4-(2-cyano-1H-pyrrol-1-yl)-2-[(1H-indol-4-ylsulfonyl)amino]butanoyl}-1,2,3,4-tetrahydroisoquinoline-7-sulfonamide from I-102 and 1,2,3,4-tetrahydro-isoquinoline-7-sulfonic acid amide hydrochloride (Pendelton, R. G., et al. *J. Pharmacol. Exp. Ther.*, 1979, 208, 24) with the addition of 3 equivalents of NMM. ESI MS Calc.: 566.1. Found: 567.2 (M+H)⁺.

Example 398

2-{4-(2-cyano-1H-pyrrol-1-yl)-2-[(1H-indol-4-ylsulfonyl)amino]butanoyl}-1,2,3,4-tetrahydroisoquinoline-7-sulfonic acid from I-102 and I-030 and with the addition of 3 equivalents of NMM. ESI MS Calc.: 567.2. Found: 568.3 (M+H)⁺.

Example 399 methyl[(2-{4-(2-cyano-1H-pyrrol-1-yl)-2-[(1H-indol-4-ylsulfonyl)amino]butanoyl}-1,2,3,4-tetrahydroisoquinolin-6-yl)oxy]acetate from I-102 and I-038. ESI MS Calc.: 575.2. Found: 576.2 (M+H)⁺.

Example 400

2-{4-(2-cyano-1H-pyrrol-1-yl)-2-[(1H-indol-4-ylsulfonyl)amino]butanoyl}-N-methyl-1,2,3,4-tetrahydroisoquinoline-7-sulfonamide from I-102 and N-methyl-1,2,3,4-tetrahydroisoquinoline-7-sulfonamide (WO 2006/67587 A2). ESI MS Calc.: 580.2. Found: 581.3 (M+H)⁺.

Example 401

2-{4-(2-cyano-1H-pyrrol-1-yl)-2-[(1H-indol-4-ylsulfonyl)amino]butanoyl}-N,N-dimethyl-1,2,3,4-tetrahydroisoquinoline-7-sulfonamide from I-102 and 1,2,3,4-tetrahydroisoquinoline-7-sulfonic acid dimethylamide (U.S. Pat. No. 6,414,149). ESI MS Calc.: 594.2. Found: 595.3 (M+H)⁺.

General Method F (Amide Formation)

A mixture of 1 equivalent of a carboxylic acid and 1 equivalent of (1-chloro-2-methyl-propenyl)-dimethyl-amine in CH₂Cl₂ is stirred for 2 h when >1 equivalent of a secondary amine is added and the mixture is stirred for 2-24 h. The mixture is concentrated and purified by preparative HPLC, or is subjected to an aqueous workup (water, NaHCO₃, and brine) before being purified by flash chromatography or preparative HPLC to provide Examples 402-405.

Example 402

N-[3-(2-cyano-1H-pyrrol-1-yl)-1-(3,4-dihydroquinolin-1(2H)-ylcarbonyl)propyl]-1H-indole-4-sulfonamide is prepared from I-102 and 1,2,3,4-tetrahydroquinoline. ESI MS Calc.: 487.2. Found: 488.3 (M+H)⁺.

Example 403

2-{4-(2-cyano-1H-pyrrol-1-yl)-2-[(1H-indol-4-ylsulfonyl)amino]butanoyl}-N-methyl-1,2,3,4-tetrahydroisoquinoline-7-carboxamide is prepared from I-102 and I-035. ESI MS Calc.: 544.2. Found: 545.3 (M+H)⁺.

Example 404

2-{4-(2-cyano-1H-pyrrol-1-yl)-2-[(1H-indol-4-ylsulfonyl)amino]butanoyl}-N,N-dimethyl-1,2,3,4-tetrahydroisoquinoline-7-carboxamide is prepared from I-102 and I-036. ESI MS Calc.: 558.2. Found: 559.4 (M+H)⁺.

Example 405

N-[3-(2-cyano-1H-pyrrol-1-yl)-1-{[7-(morpholin-4-ylcarbonyl)-3,4-dihydroisoquinolin-2(1H)-yl]carbonyl}propyl]-1H-indole-4-sulfonamide is prepared from I-102 and I-037. ESI MS Calc.: 600.2. Found: 601.3 (M+H)⁺.

Example 406

4-amino-3,5-dichloro-N-{1-[(4-methylcyclohexyl)carbonyl]-3-(2H-1,2,3-triazol-2-yl)propyl}benzenesulfonamide

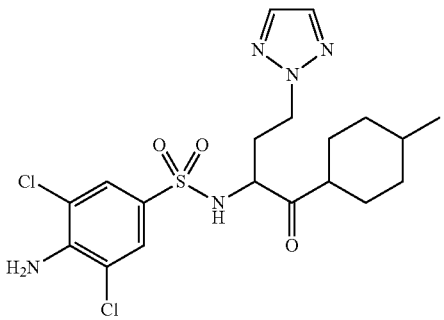 [SMILES: CC1CCC(C(=O)C(CCn2nccn2)NS(=O)(=O)c2cc(Cl)c(N)c(Cl)c2)CC1]

A solution of 1.4 mL (10 mmol) of bromo-4-methylcyclohexane in 5 mL of THF is added slowly to 290 mg (12 mmol) of Mg turnings stirring in 5 mL of THF under N₂ at a rate that maintains a gentle reflux. The mixture is cooled to rt to provide a ~1 M solution of 4-methylcyclohexanemagnesium bromide. To a solution of 110 mg (0.25 mmol) of I-105 in 2 mL of THF is added 5 mL of 1M 4-methylcyclohexanemagnesium bromide in THF (5.0 mmol). After stirring for 2.5 days, saturated aqueous NH₄Cl is added. The mixture is extracted with EtOAc, and the extract is washed with water and brine, and then dried with MgSO₄, filtered, and concentrated. Purification first by flash chromatography, and then by preparative HPLC provides 18 mg (16%) of Example 406 as a white solid. ESI MS. Calc: 473.1. Found: 474.0 (M+H)⁺.

Example 407

4-amino-3,5-dichloro-N-{3-(2-cyano-1H-pyrrol-1-yl)-1-[(4-methyl-cyclohexyl)carbonyl]propyl}benzenesulfonamide is prepared from I-104 in the same manner as Example 406. ESI MS. Calc: 496.1. Found: 497.1 (M+H)+.

Example 408

N-[3-(2-cyano-1H-pyrrol-1-yl)-1-({4-[(E/Z)-(methoxy-imino)methyl]piperidin-1-yl}carbonyl)propyl]-1H-indole-4-sulfonamide

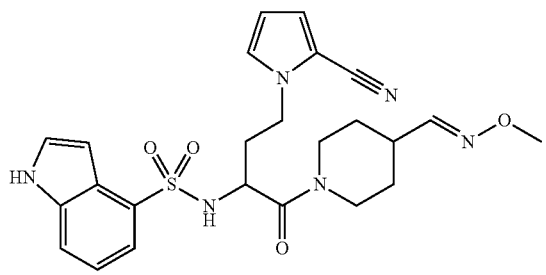

To a stirring solution of 0.020 mL (0.23 mmol) of oxalyl chloride in 1 mL of CH$_2$Cl$_2$ at −78° C. is added 0.033 mL (0.46 mmol) of DMSO. After stirring for 30 min, a solution of 0.072 g (0.15 mmol) of Example 259 is added. After stirring for 2 h at −78° C., 0.11 mL (0.77 mmol) of Et$_3$N is slowly added. The mixture is allowed to warm to rt as it is stirred overnight, and then water is added. The mixture is extracted twice with CH$_2$Cl$_2$, and the combined extracts are washed with brine, dried over MgSO$_4$, filtered, and concentrated to provide the aldehyde as a dark solid. A solution of 29 mg (0.062 mmol) of this aldehyde in 1 mL of pyridine and 15 mg (0.19 mmol) of N-methoxyamine hydrochloride is stirred overnight, and then is concentrated. Purification of the residue by preparative HPLC provides 11 mg (36%) of Example 408 as a 4:1 mixture of E/Z isomers. ESI MS: Calc: 496.2. Found: 497.2 (M+H)+.

Example 409

1-acetyl-N-{3-(2-cyano-1H-pyrrol-1-yl)-1-[(4-methylpiperidin-1-yl)carbonyl]propyl}-1H-indole-4-sulfonamide

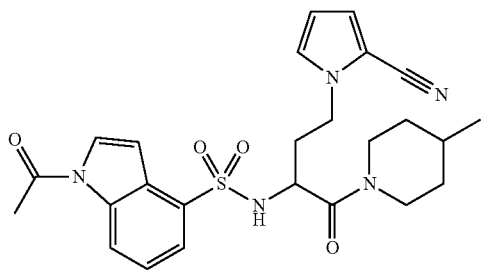 [SMILES: CC(=O)n1ccc2c(S(=O)(=O)NC(CCn3cccc3C#N)C(=O)N3CCC(C)CC3)cccc21]

Example 30 (30 mg, 0.066 mmol) is stirred with 6.9 μL (0.073 mmol) of acetic anhydride and 0.8 mg of DMAP in 2 mL of CH$_2$Cl$_2$ for 3 h. An additional 0.04 mL of acetic anhydride and 1 mg of DMAP is added and the mixture is stirred overnight. The mixture is concentrated and purified by flash chromatography (1:1 EtOAc/hexanes) to provide 25 mg (76%) of Example 409 as a white foam. ESI MS: Calc: 495.2. Found: 496.2 (M+H)+.

Example 410 tert-butyl 4-[({3-(2-cyano-1H-pyrrol-1-yl)-1-[(4-methylpiperidin-1-yl)carbonyl]propyl}amino)sulfonyl]-1H-indole-1-carboxylate

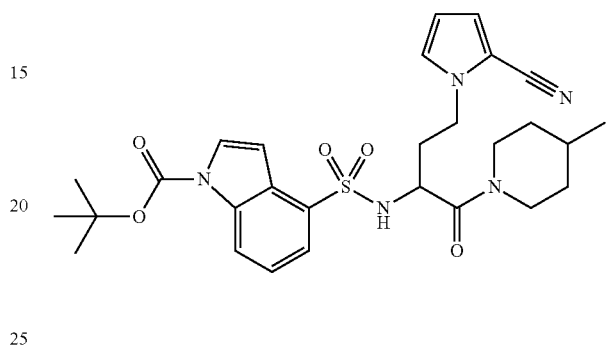

To a stirring solution of 45 mg (0.10 mmol) of Example 30 in 1 mL of CH$_2$Cl$_2$ is added a solution of 24 mg (0.11 mmol) of Boc$_2$O and 2.4 mg (0.020 mmol) of DMAP in 1 mL of CH$_2$Cl$_2$. After stirring for 1 h, the mixture is concentrated and purified by flash chromatography (2:1 hexanes/EtOAc) to provide 46 mg (84%) of Example 410 as a white foam. ESI MS: Calc. 553.2. Found: 554.4 (M+H)+.

Example 411

N-{3-(2-cyano-1H-pyrrol-1-yl)-1-[(4-methylpiperidin-1-yl)carbonyl]propyl}-N-methyl-1H-indole-4-sulfonamide

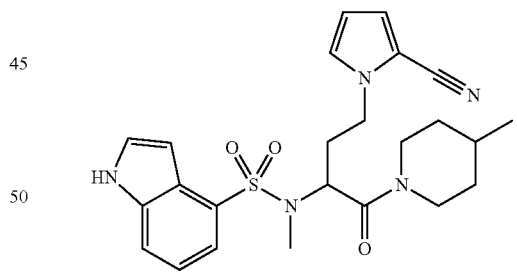

A solution of 0.11 g (0.19 mmol) of Example 410, 40 mg (0.29 mmol) of K$_2$CO$_3$, and 24 μL (0.39 mmol) of MeI is stirred in 1 mL of DMF for 1 h. EtOAc is added, and the mixture is washed twice with water and once with brine, dried over MgSO$_4$, filtered, and concentrated. This residue is stirred in 1.3 mL of 25% TFA in CH$_2$Cl$_2$ for 12 h. The mixture is concentrated and purified by preparative HPLC to provide 74 mg (84%) of Example 411. ESI MS: Calc. 467.2. Found: 468.4 (M+H)+.

Example 412

1H-Indole-4-sulfonic acid [3-(2-cyano-pyrrol-1-yl)-1-(perhydro-1,4-diazepine-1-carbonyl)-propyl]-amide

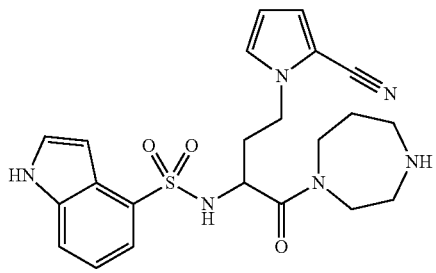 [SMILES: N#Cc1cccn1CCC(NS(=O)(=O)c1cccc2[nH]ccc12)C(=O)N1CCCNCC1]

A solution of 0.65 g (1.1 mmol) of Example 396 in 6 mL of 4 M HCl in 1,4-dioxane is stirred overnight, concentrated, and then is dissolved in 2 mL of 10% MeOH/CH$_2$Cl$_2$. Hydrochloric acid (2 mL of 4M in 1,4-dioxane) is added. The mixture is stirred overnight, and then is dissolved in 1 M NaHSO$_4$ and extracted with EtOAc. The aqueous phase is basified with solid NaOH until the pH is 8. This mixture is extracted twice with EtOAc and the extracts are washed with brine, dried over Na$_2$SO$_4$, filtered, and concentrated to provide 0.46 g (86%) of Example 412. ESI MS: Calc. 454.2. Found: 455.3 (M+H)$^+$.

Example 413

4-{4-(2-cyano-1H-pyrrol-1-yl)-2-[(1H-indol-4-ylsulfonyl)amino]butanoyl}-1,4-diazepane-1-carboxamide.

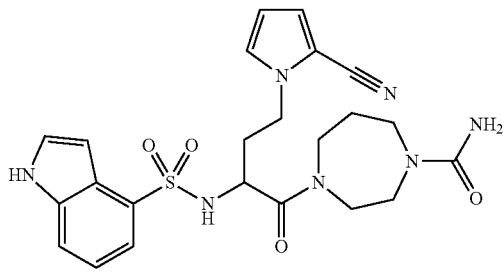 [SMILES: N#Cc1cccn1CCC(NS(=O)(=O)c1cccc2[nH]ccc12)C(=O)N1CCCN(C(N)=O)CC1]

A mixture of 0.040 g (0.088 mmol) of Example 412 and 0.023 mL of trimethylsilylisocyanate (0.17 mmol) is stirred in 0.5 mL of MeCN overnight. The mixture is purified directly by preparative HPLC to provide 19 mg (42%) of Example 413 as a white foam. ESI MS: Calc. 497.2. Found: 498.2 (M+H)$^+$.

Example 414

N-{3-(2-cyano-1H-pyrrol-1-yl)-1-[(4-glycoloyl-1,4-diazepan-1-yl)carbonyl]propyl}-1H-indole-4-sulfonamide

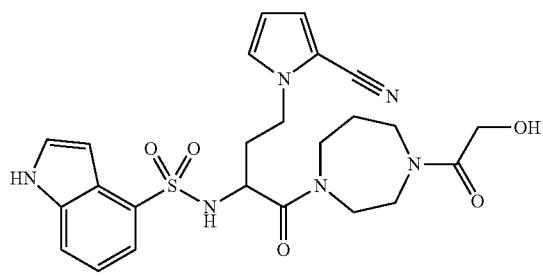 [SMILES: N#Cc1cccn1CCC(NS(=O)(=O)c1cccc2[nH]ccc12)C(=O)N1CCCN(C(=O)CO)CC1]

A mixture of 0.050 g (0.11 mmol) of Example 412 and 0.024 mL (0.22 mmol) of acetoxyacetyl chloride is stirred with 0.17 g (0.34 mmol) of PS-NMM in 2 mL of THF. After 4 h, 0.039 g (0.060 mmol) of PS-Isocyanate and 0.046 g (0.17 mmol) of PS-trisamine are added, and the mixture is agitated for 30 min. The solvent is filtered, and the resins are washed with CH$_2$Cl$_2$ and EtOAc. The combined washes are concentrated, and the residue is taken up in 2 mL of 1.65 M HCl in MeOH and agitated overnight. The mixture is concentrated and purified by preparative HPLC to provide 38 mg (67%) of Example 414 as a white foam. ESI MS: Calc. 512.2. Found: 513.2 (M+H)$^±$

Example 415

N-{3-(2-cyano-1H-pyrrol-1-yl)-1-[(4-propionyl-1,4-diazepan-1-yl)carbonyl]propyl}-1H-indole-4-sulfonamide

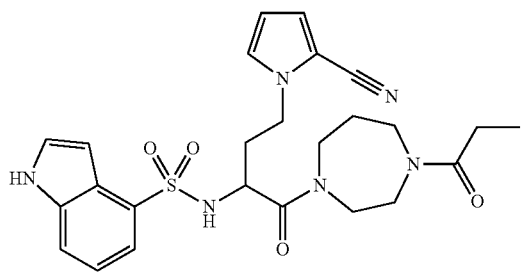 [SMILES: CCC(=O)N1CCCN(C(=O)C(CCn2cccc2C#N)NS(=O)(=O)c2cccc3[nH]ccc23)CC1]

A mixture of 0.048 g (0.11 mmol) of Example 412 and 0.024 mL (0.21 mmol) of propionyl chloride is stirred with 0.15 g (0.31 mmol) of PS-NMM in 2 mL of THF. After 4 h, 0.035 g (0.054 mmol) of PS-Isocyanate and 0.044 g (0.16 mmol) of PS-trisamine are added, and the mixture is agitated for 30 min. The solvent is filtered, and the resins are washed with CH$_2$Cl$_2$ and EtOAc. The filtrate is concentrated and purified by preparative HPLC to provide 27 mg (51%) of Example 415 as a white foam. ESI MS: Calc. 510.2. Found: 511.2 (M+H)$^+$.

Example 416

N-[3-(2-cyano-1H-pyrrol-1-yl)-1-{[4-(methylsulfonyl)-1,4-diazepan-1-yl]carbonyl}propyl]-1H-indole-4-sulfonamide

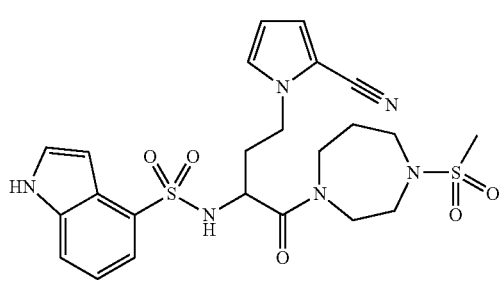 [SMILES: CS(=O)(=O)N1CCCN(C(=O)C(CCn2cccc2C#N)NS(=O)(=O)c2cccc3[nH]ccc23)CC1]

A mixture of 0.050 g (0.11 mmol) of Example 412 and 0.017 mL (0.22 mmol) of methanesulfonyl chloride is stirred with 0.17 g (0.34 mmol) of PS-NMM in 2 mL of THF. After 4 h, 0.039 g (0.060 mmol) of PS-Isocyanate and 0.046 g (0.17 mmol) of PS-trisamine are added, and the mixture is agitated for 30 min. The solvent is filtered, and the resins are washed with $CH_2Cl_2$ and EtOAc. The combined washes are concentrated and purified by preparative HPLC to provide 38 mg (65%) of Example 416 as a white foam. ESI MS: Calc. 532.2. Found: 533.2 (M+H)+.

Example 417

2-chloro-N-{3-(2-cyano-1H-pyrrol-1-yl)-1-[(4-methylpiperidin-1-yl)carbonyl]propyl}-4-(1H-tetrazol-5-yl)benzenesulfonamide

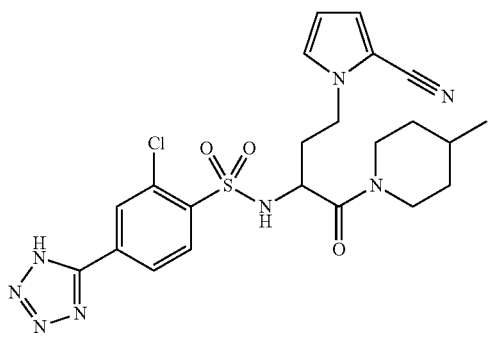 [SMILES: CC1CCN(C(=O)C(CCn2cccc2C#N)NS(=O)(=O)c2ccc(-c3nnn[nH]3)cc2Cl)CC1]

To a solution of 100 mg (0.21 mmol) of Example 69 in 1.0 mL of NMP is added 41 mg (0.63 mmol) of $NaN_3$ and 87 mg (0.63 mmol) of $Et_3N \cdot HCl$. The reaction is stirred at 140° C. in a pressure tube for 15 min. The mixture is cooled and diluted with 50 mL of water. The pH is brought to 4 with addition of 1N HCl. The solution is extracted with EtOAc (3×100 mL), and the combined extracts washed with brine (50 mL), dried over $Na_2SO_4$, filtered, and concentrated. Preparative HPLC provides 52 mg (48%) of Example 417 as a white powder. ESI MS: Calc. 516.2. Found: 517.5 (M+H)+.

Example 418

2-chloro-N-{3-(5-cyano-1H-pyrazol-1-yl)-1-[(4-methylpiperidin-1-yl)carbonyl]propyl}-6-methylbenzenesulfonamide

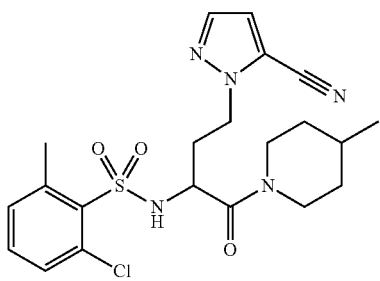

Example 138 (38 mg, 0.073 mmol) is dissolved in 1 mL of DMA and 3 mg (0.003 mmol) of $Pd_2(dba)_3$, 3 mg (0.006 mmol) of dppf, 8.6 mg (0.073 mmol) of $Zn(CN)_2$, and 1.2 mg (0.018 mmol) of Zn powder are added. The mixture is heated in the microwave for 30 min at 120° C. The reaction mixture is cooled and filtered, and then concentrated and purified by preparative HPLC to provide 11 mg (32%) of Example 418 as a colorless oil. ESI MS: Calc. 463.1. Found: 464.3 (M+H)+.

Example 419

4-amino-3,5-dichloro-N-{3-(2-chloro-1H-pyrrol-1-yl)-1-[(4-methylpiperidin-1-yl)carbonyl]propyl}benzenesulfonamide

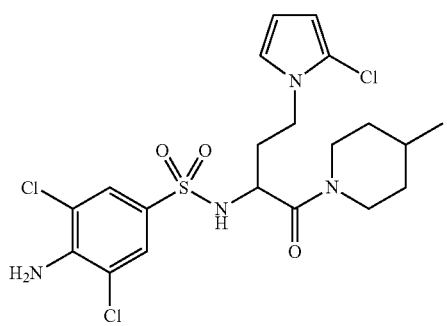

To a solution of 57 mg (0.12 mmol) of Example 235 in 1.0 mL of DMF is added 16 mg (0.12 mmol) of NCS and the mixture is stirred for 2 days. Preparative HPLC provides 14 mg (23%) of Example 419. ESI MS: Calc: 506.1. Found: 507.0 (M+H)+.

Example 420

3-bromo-N-{3-(2-cyano-1H-pyrrol-1-yl)-1-[(4-methylpiperidin-1-yl)carbonyl]propyl}-1H-indole-4-sulfonamide

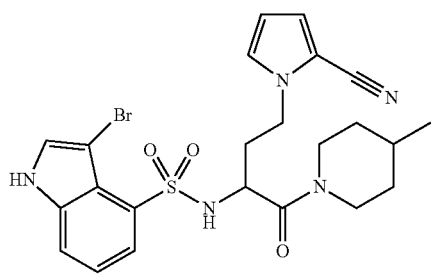

To 110 mg (0.24 mmol) of Example 30 in 1 mL of DMF is added 42 mg (0.24 mmol) of NBS. After stirring for 24 h, the mixture is purified directly by preparative HPLC to provide 17 mg (14%) of Example 420 as a white solid. ESI MS: Calc: 531.1. Found: 532.5 (M+H)+.

Example 421

3-cyano-N-{3-(2-cyano-1H-pyrrol-1-yl)-1-[(4-methylpiperidin-1-yl) carbonyl]propyl}-1H-indole-4-sulfonamide

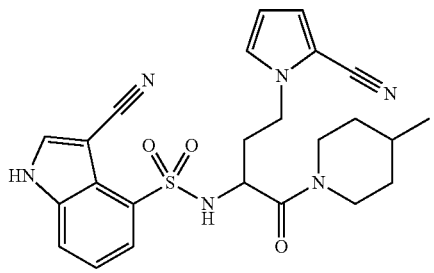

To compound Example 30 (0.18 g, 0.41 mmol) in 1 mL of MeCN at 0° C. is added 0.035 mL (0.41 mmol) of chlorosulphonyl isocyanate. After stirring for 30 min, 0.037 mL (0.49 mmol) of DMF is added. Two hours later, the mixture is directly purified first by preparative HPLC, and then by flash chromatography to provide 110 mg (55%) of Example 421. ESI MS: Calc: 478.2. Found: 479.5 (M+H)⁺.

Example 422

4-[({3-(2-cyano-1H-pyrrol-1-yl)-1-[(4-methylpiperidin-1-yl)carbonyl]propyl}amino)sulfonyl]-1H-indole-3-carboxamide

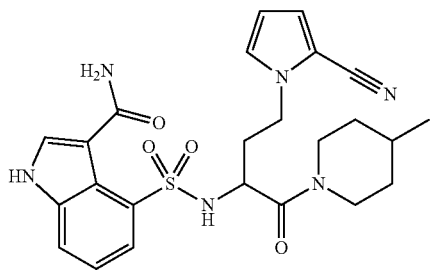 [SMILES: CC1CCN(C(=O)C(CCn2cccc2C#N)NS(=O)(=O)c2cccc3[nH]cc(C(N)=O)c23)CC1]

To compound Example 30 (0.030 g, 0.066 mmol) in 1 mL of MeCN at 0° C. is added 0.006 mL (0.07 mmol) of chlorosulfonyl isocyanate. Two hours later, the mixture is directly purified by preparative HPLC to provide 5.2 mg (16%) of Example 422. ESI MS: Calc: 496.2. Found: 497.4 (M+H)⁺.

Example 423

N-{3-(2-cyano-1H-pyrrol-1-yl)-1-[(4-methylpiperidin-1-yl)carbonyl]propyl}-2-oxoindoline-4-sulfonamide and Example 424: N-{3-(3-bromo-2-cyano-1H-pyrrol-1-yl)-1-[(4-methylpiperidin-1-yl)carbonyl]propyl}-2-oxoindoline-4-sulfonamide

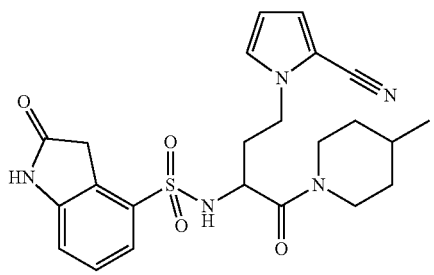

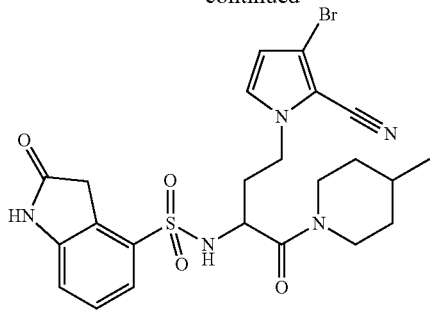

To a solution of 0.055 g (0.12 mmol) of Example 30 in 1.0 mL of t-butanol is added 0.13 g (0.36 mmol) pyridine bromide perbromide. After stirring for 2 h, the solution is concentrated and 1.0 mL of glacial acetic acid and 0.079 g (1.2 mmol) of Zn powder is added. After stirring for 30 min, EtOAc is added, and the mixture is washed with saturated NaHCO₃, water, and brine, and then is dried over MgSO₄, filtered, and concentrated. The residue is purified by preparative HPLC to provide 1.3 mg (2.3%) of Example 423 and 15 mg (23%) of Example 424. Example 423: ESI MS: Calc: 469.2. Found: 470.3; Example 424: ESI MS: Calc: 547.1. Found: 548.2.

Example 425

N-{3-(2-cyano-1H-pyrrol-1-yl)-1-[(4-methylpiperidin-1-yl)carbonyl]propyl}-3-formyl-1H-indole-4-sulfonamide

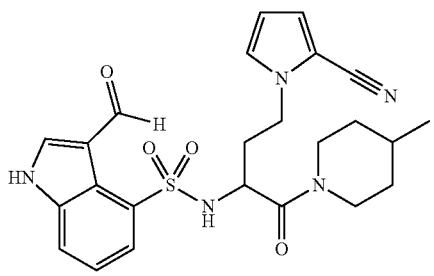 [SMILES: CC1CCN(C(=O)C(CCn2cccc2C#N)NS(=O)(=O)c2cccc3[nH]cc(C=O)c23)CC1]

To 1.5 mL of DMF at 0° C. is added 0.033 mL (0.36 mmol) of POCl₃. After stirring for 20 min, 0.15 g (0.33 mmol) of Example 30 in 0.5 mL of DMF is added dropwise. The mixture is stirred at 35° C. overnight. Crushed ice is added, followed by 1.6 mL (1.6 mmol) of 1N NaOH, and the resulting mixture is stirred for 5 h. The mixture is extracted twice with EtOAc, and the extracts are washed with brine, dried over MgSO₄, filtered, and concentrated. Flash chromatography provides 71 mg (45%) of Example 425. ESI MS: Calc: 481.2. Found: 482.4 (M+H)⁺.

Example 426

N-{3-(2-cyano-1H-pyrrol-1-yl)-1-[(4-methylpiperidin-1-yl)carbonyl]propyl}-3-(hydroxymethyl)-1H-indole-4-sulfonamide

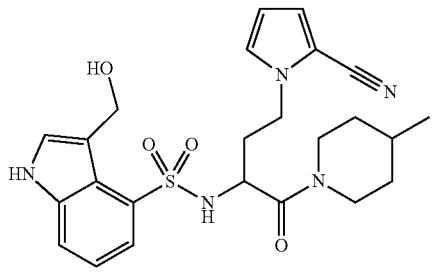

To a stirring solution of 0.030 g (0.062 mmol) of Example 425 in 1.0 mL of MeOH at 0° C. is added 4.7 mg (0.13 mmol) of NaBH$_4$. After stirring for 2 h, the mixture is diluted with MeCN—H$_2$O, filtered, and purified by preparative HPLC to provide 16 mg (53%) of Example 426 as a red solid. ESI MS: Calc: 483.2. Found: 466.2 (M-OH)$^-$.

General Method G (Deprotection of N-Boc Indoles)

An N-Boc-indole is stirred in 20-50% TFA in CH$_2$Cl$_2$ for 3-12 h, and then is concentrated. If necessary, purification by flash chromatography or preparative HPLC provides Examples 427-434.

Example 427

N-{3-(2-cyano-1H-pyrrol-1-yl)-1-[(4-methylpiperidin-1-yl)carbonyl]propyl}-1H-indole-7-sulfonamide from Example 181. ESI MS: Calc. 453.2. Found: 454.7 (M+H)$^+$.

Example 428

N-{3-(2-cyano-1H-pyrrol-1-yl)-1-[(4-methylpiperidin-1-yl)carbonyl]propyl}-2-methyl-1H-indole-3-sulfonamide from Example 191. ESI MS: Calc. 467.2. Found: 468.2 (M+H)$^+$.

Example 429

N-{3-(2-cyano-1H-pyrrol-1-yl)-1-[(4-methylpiperidin-1-yl)carbonyl]propyl}-5-fluoro-1H-indole-4-sulfonamide from Example 194. ESI MS: Calc. 471.2. Found: 472.7 (M+H)$^+$.

Example 430

N-{3-(2-cyano-1H-pyrrol-1-yl)-1-[(4-methylpiperidin-1-yl)carbonyl]propyl}-5-fluoro-1H-indole-6-sulfonamide from Example 195. ESI MS: Calc. 471.2. Found: 472.7 (M+H)$^+$.

Example 431

5-chloro-N-{3-(2-cyano-1H-pyrrol-1-yl)-1-[(4-methylpiperidin-1-yl)carbonyl]propyl}-1H-indole-4-sulfonamide from Example 201. ESI MS: Calc: 487.1. Found: 488.7 (M+H)$^+$.

Example 432

5-chloro-N-{3-(2-cyano-1H-pyrrol-1-yl)-1-[(4-methylpiperidin-1-yl)carbonyl]propyl}-1H-indole-6-sulfonamide from Example 202. ESI MS: Calc: 487.1. Found: 488.7 (M+H)$^+$.

Example 433

N-[3-(2-cyano-1H-pyrrol-1-yl)-1-(5,6-dihydro[1,2,4]triazolo[4,3-a]pyrazin-7(8H)-ylcarbonyl)propyl]-5-chloro-1H-indole-4-sulfonamide from Example 204. ESI MS: ESI MS: Calc: 512.1. Found: 513.7 (M+H)$^+$.

Example 434

5-chloro-1H-indole-6-sulfonic acid [3-(2-cyano-pyrrol-1-yl)-1-(5,6-dihydro-8H-[1,2,4]triazolo[4,3-a]pyrazine-7-carbonyl)-propyl]-amide from Example 205. ESI MS: Calc: 512.1. Found: 513.7 (M+H)$^+$.

Example 435

4-({3-(2-cyano-1H-pyrrol-1-yl)-1-[(4-methylpiperidin-1-yl)carbonyl]-propyl}sulfamoyl)-1H-indole-7-carboxylic acid

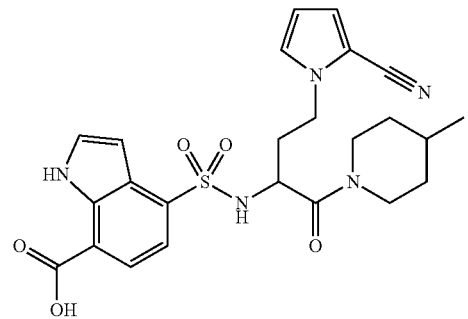 [SMILES: CC1CCN(C(=O)C(CCn2cccc2C#N)NS(=O)(=O)c2ccc(C(=O)O)c3[nH]ccc23)CC1]

A mixture of 9.0 mg (0.014 mmol) of Example 206, 0.085 mL (0.085 mmol) of 1M TBAF in THF, 1.0 mL of DMF, and 0.1 mL of ethylenediamine is stirred at 80° C. for 48 h. Direct purification by preparative HPLC provided 3.2 mg of Example 435. ESI MS: 497.2. Found: 498.2 (M+H)$^+$.

Example 436 ethyl 3-{4-[({3-(2-cyano-1H-pyrrol-1-yl)-1-[(4-methylpiperidin-1-yl) carbonyl]propyl}amino)sulfonyl]-1H-indol-3-yl}propanoate

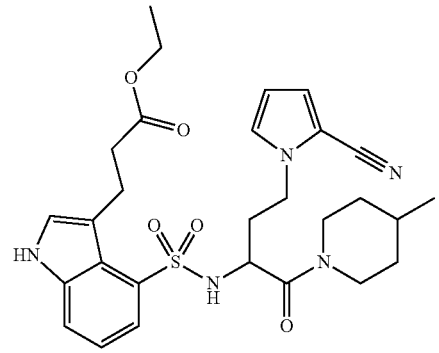 [SMILES: CCOC(=O)CCc1c[nH]c2cccc(S(=O)(=O)NC(CCn3cccc3C#N)C(=O)N3CCC(C)CC3)c12]

To a stirring mixture of 61 mg (1.5 mmol) of 60% NaH in mineral oil in 5 mL of THF at 0° C. is slowly added a solution of 0.28 mL (1.4 mmol) of triethyl phosphonoacetate in 5 mL of THF. The mixture is allowed to warm to rt as it is stirred for 2 h. A solution of 0.23 g (0.48 mmol) of Example 425 in 2 mL of THF is added, and the resulting solution is stirred overnight at 60° C. Aqueous NH$_4$Cl is added, and the mixture is extracted with EtOAc. The extract is washed with brine, dried over MgSO$_4$, filtered, and concentrated, and then the resulting residue is purified by flash chromatography (50-100% EtOAc in hexanes) to provide 63 mg (23%) of the enoate product. This material, 20 mg of Pd/C, and 25 mL of MeOH is stirred under 50 psi of H$_2$ for 3 h. After filtration through diatomaceous earth, the filtrate is concentrated. The resulting residue is purified by flash chromatography (50% EtOAc in hexanes) to provide 23 mg (38%) of Example 436 as a colorless oil. ESI MS: Calc: 553.2. Found: 554. ESI MS: Calc: 553.2. Found: 554.5 (M+H)$^+$.

Example 437

N-{3-(2-cyano-1H-pyrrol-1-yl)-1-[(4-methylpiperidin-1-yl)carbonyl]propyl}-5-methyl-2,3-dihydro-1-benzofuran-7-sulfonamide

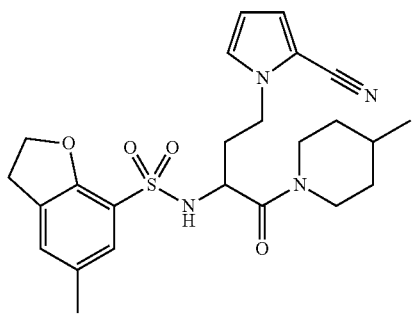 [SMILES: Cc1cc2c(c(S(=O)(=O)NC(CCn3cccc3C#N)C(=O)N3CCC(C)CC3)c1)OCC2]

To 0.025 g (0.047 mmol) of Example 161 in 1 mL of DMF is added 2.5 mg (3 mg, 0.003 mmol) of Pd$_2$(dba)$_3$, 2 mg (0.006 mmol) of P(o-tolyl)$_3$, and 0.013 mL (0.094 mmol) of PhMe$_3$Sn. The mixture is stirred at 80° C. for 3 h, and then is filtered. The filtrate is concentrated and the residue is purified by preparative HPLC to provide 32 mg (7%) as a beige solid. ESI MS: Calc. 470.2. Found: 471.5 (M+H)$^+$.

General Method H (Indole Chlorination)

Indole is stirred in DMF at rt along with 1 equivalent of NCS for 12 to 72 h. The mixture is diluted with EtOAc and washed with aqueous NaSO$_3$, water, and brine, then dried with Na$_2$SO$_4$, filtered, and concentrated. The resulting residue is purified by preparative HPLC to provide Examples 438-443.

Example 438

3-chloro-N-{3-(2-cyano-1H-pyrrol-1-yl)-1-[(4-methylpiperidin-1-yl) carbonyl]propyl}-1H-indole-6-sulfonamide is prepared from Example 31. ESI MS: Calc: 488.1. Found: 489.2 (M+H)$^+$.

Example 439

3-chloro-N-{3-(2-cyano-1H-pyrrol-1-yl)-1-[(4-methylpiperidin-1-yl) carbonyl]propyl}-1H-indole-4-sulfonamide is prepared from Example 30. ESI MS: Calc: 487.1. Found: 488.5 (M+H)$^+$.

Example 440

3-chloro-N-{3-(5-cyano-1H-pyrazol-1-yl)-1-[(4-methylpiperidin-1-yl) carbonyl]propyl}-1H-indole-4-sulfonamide is prepared from Example 37. ESI MS: Calc: 488.1. Found: 489.5 (M+H)$^+$.

Example 441 methyl 1-[2-{[(3-chloro-1H-indol-4-yl)sulfonyl]amino}-4-(2-cyano-1H-pyrrol-1-yl)butanoyl]piperidine-4-carboxylate is prepared from Example 287. ESI MS: Calc: 531.1. Found: 532.4 (M+H)$^+$.

Example 442

3-chloro-N-[3-(2-cyano-1H-pyrrol-1-yl)-1-{[4-(hydroxymethyl)piperidin-1-yl]carbonyl]propyl}-1H-indole-4-sulfonamide is prepared from Example 259. ESI MS: Calc: 503.1. Found: 504.4 (M+H)$^+$.

Example 443

3,5-dichloro-1H-indole-4-sulfonic acid [3-(2-cyano-pyrrol-1-yl)-1-(4-methyl-piperidine-1-carbonyl)-propyl]-amide is prepared from Example 431. ESI MS: Calc: 521.1. Found: 522.7 (M+H)$^+$.

General Method I (Saponification)

To an ester in 1,4-dioxane is added 1 M NaOH (4-8 equiv.). After stirring for 4-12 h, the mixture is concentrated and dissolved in water, and then aq. HCl is added to bring the pH to between 1 and 3. Either the resulting precipitate is filtered and washed with water, then dried to provide the product, or the mixture is extracted with EtOAc, and the extracts are washed with brine, dried over Na$_2$SO$_4$, filtered, and concentrated to provide Examples 444-455.

Example 444

(1-{4-(2-cyano-1H-pyrrol-1-yl)-2-[(1H-indol-4-ylsulfonyl)amino]butanoyl}piperidin-3-yl)acetic acid from Example 306. ESI MS: Calc: 497.2. Found: 498.1 (M+H)$^+$.

Example 445

(2E)-3-(1-{4-(2-cyano-1H-pyrrol-1-yl)-2-[(1H-indol-4-ylsulfonyl)amino]butanoyl}piperidin-3-yl)prop-2-enoic acid from Example 322. ESI MS: Calc: 509.2. Found: 510.2 (M+H)$^+$.

Example 446

3-(1-{4-(2-cyano-1H-pyrrol-1-yl)-2-[(1H-indol-4-ylsulfonyl)amino]butanoyl}piperidin-3-yl)propanoic acid from Example 326. ESI MS: Calc: 511.2. Found: 512.1 (M+H)$^+$.

Example 447

3-(1-{4-(2-cyano-1H-pyrrol-1-yl)-2-[(1H-indol-4-ylsulfonyl)amino]butanoyl}piperidin-4-yl)propanoic acid from Example 327. ESI MS: Calc: 511.1. Found: 512.1 $(M+H)^+$.

Example 448

4-(1-{4-(2-cyano-1H-pyrrol-1-yl)-2-[(1H-indol-4-ylsulfonyl)amino]butanoyl}piperidin-4-yl)butanoic acid from Example 334. ESI MS: Calc: 525.2. Found: 526.1 $(M+H)^+$.

Example 449

4-(1-{4-(2-cyano-1H-pyrrol-1-yl)-2-[(1H-indol-4-ylsulfonyl)amino]butanoyl}piperidin-3-yl)butanoic acid from Example 335. ESI MS: Calc: 525.2. Found: 526.1 $(M+H)^+$.

Example 450

3-{4-[({3-(2-cyano-1H-pyrrol-1-yl)-1-[(4-methylpiperidin-1-yl)carbonyl]propyl}amino)sulfonyl]-1H-indol-3-yl}propanoic acid from Example 436. ESI MS: Calc: 525.2. Found: 526.2 $(M+H)^+$.

Example 451

2-{4-(2-cyano-1H-pyrrol-1-yl)-2-[(1H-indol-4-ylsulfonyl)amino]butanoyl}-1,2,3,4-tetrahydroisoquinoline-6-carboxylic acid from Example 340. ESI MS: Calc: 531.2. Found: 532.2 $(M+H)^+$.

Example 452

2-{4-(2-cyano-1H-pyrrol-1-yl)-2-[(1H-indol-4-ylsulfonyl)amino]butanoyl}-1,2,3,4-tetrahydroisoquinoline-7-carboxylic acid from Example 341. ESI MS: Calc: 531.2. Found: 532.2 $(M+H)^+$.

Example 453

3-[(cis)-1-{4-(2-cyano-1H-pyrrol-1-yl)-2-[(1H-indol-4-ylsulfonyl)amino]butanoyl}-4-methylpiperidin-3-yl]propanoic acid from Example 347. ESI MS: Calc: 525.2. Found: 526.3 $(M+H)^+$.

Example 454

[(2-{4-(2-cyano-1H-pyrrol-1-yl)-2-[(1H-indol-4-ylsulfonyl)amino]butanoyl}-1,2,3,4-tetrahydroisoquinolin-6-yl)oxy]acetic acid from Example 399. ESI MS: Calc: 561.2. Found: 562.2 $(M+H)^+$.

Example 455

2-[(2-{4-(2-cyano-1H-pyrrol-1-yl)-2-[(1H-indol-4-ylsulfonyl)amino]butanoyl}-1,2,3,4-tetrahydroisoquinolin-7-yl)oxy]-2-methylpropanoic acid from Example 361. ESI MS: Calc: 589.2. Found: 590.3 $(M+H)^+$.

Procedures for Identification of CCR10 Antagonists
CCR10 FLIPR Assay

Preferred compounds have an $IC_{50}$ of 500 nM or lower in this assay.

To a 1 liter bottle of Hams F12 (Mediatech #10-080-CM) add 100 mL Fetal Bovine Serum (Mediatech #35-015-CV), 10 mL geneticin (Invitrogen #10131-027), and 2 mL Zeocin (Invitrogen #R250-05).

CHO-K1 hCCR10 cells (Euroscreen cat #ES-143-A) are diluted in media to a final concentration of $2.8 \times 10^5$ cells/mL and 25 µL of this suspension are added to each well of a BD384 well TC treated assay plate (VWR #62406-490). This will yield approximately 7,000 cells/well. The plate is incubated at 37° C./5% $CO_2$ overnight.

The $EC_{50}$ and $EC_{70}$ should be calculated each time the assay is performed. CTACK/CCL27 (R&D Systems #376-CT; 30 µM stock) is diluted to a working concentration of 10 µM (2.5 µM final) in peptide buffer (HBSS/1 mM CaCl/1 mM $MgSO_4$/0.1% BSA). This is serially diluted 1:3 in the same buffer for a total of 11 concentrations of peptide. The assay below is run and the $EC_{50}$ of the CCL27 is calculated. Test compounds are assayed at the $EC_{70}$.

Cell plates are removed from the incubator, inverted to "flick" out media and tapped dry on a paper towel. 25 µL 1×FLUO-4 dye/2 mM probenicid (Molecular probes Fluo-4 kit #F36206) are added to each well. The plates are then incubated 30 minutes at 37° C./5% $CO_2$, then removed and incubated 30 additional minutes at room temperature. 5 µL diluted (see below) test compound (final concentration based on 30 µL) are added to appropriate wells. The wells are mixed and incubated at room temperature for 15 minutes. The plates are then placed on FLIPR and 10 µL CCL27 (30 µM stock diluted to appropriate 4× of final concentration at $EC_{70}$) from a Greiner 384 well polypropylene plate are transferred.

Plate reader data are analyzed using ActivityBase software (ID Business Solutions, Ltd). The RFU signals from the plate reader are converted to percent of control (POC) values using the formula:

$$POC=100*(Signal-BCTRL)\div(PCTRL-BCTRL)$$

Where Signal is the test well signal, BCTRL is the average of background (negative control) well signals on the plate and PCTRL is the average of positive control well signals on the plate.

For the concentration responsive compounds, POC as a function of test compound concentration are fitted to a 4-parameter logistic equation of the form:

$$Y=A+(B-A)/[1+(x/C)^D]$$

Where A, B, C, and D are fitted parameters (parameter B is fixed at zero POC), and x and y are the independent and dependent variables, respectively. The $IC_{50}$ (50% inhibitory concentration) is determined as the inflection point parameter, C.

1× Assay Buffer: 1×HBSS (10×, Invitrogen #14185-027), 10 mM HEPES pH 7.4, 0.35 g/L sodium bicarbonate, 1 mM $CaCl_2$, 1 mM $MgSO_4$ Chemotaxis Assay Test compounds are evaluated for their ability to inhibit chemotaxis of Baf/3 cells expressing human CCR10 (hereinafter Baf/3-hCCR10 cells) in response to CCL27. Preferred compounds have $IC_{50}<1$ µM in this assay.

Test compounds are diluted (2× the final concentration) in CTX media (RPMI 1640 (Gibco-BRL #11875-093) supplemented with 0.1% BSA (Sigma #A3803)). Control solutions contain 1% DMSO in CTX media. Baf/3-hCCR10 cells are re-suspended in CTX media to a concentration of $4 \times 10^6$ cells/mL. In a 96 well plate, 100 µL the Baf/3-hCCR10 cell suspension is combined with 100 µL of the test compound solution and the plate is then incubated for 15 minutes at room temperature.

150 µL of a solution of the chemoattractant (2× the $EC_{70}$ for CCL27) in CTX media is added to appropriate wells of a 96-well chemotaxis chamber (Neuro Probe Cat. #:116-5, 5 µm pore size, 5.7 mm diameter size, 300 µL, 96 well plate).

CTX media without chemoattractant is added to control wells. 152 μL of 2× compound solution in CTX media is added to appropriate wells. The chamber is assembled according to manufacturer's instructions using the 5 micron pore size PVP-free polycarbonate filter. Care should be taken to avoid bubbles as they will cause variation.

80 μL of the cells plus compound incubation mixture is added to upper wells of the chamber. Care is taken to avoid forming bubbles at the level of the filter. The chamber is then incubated at 37° C. for 3 hours.

The chamber is then disassembled and the filter is removed. 150 μL of media is gently removed from each well of the chemotaxis chamber. The remaining 150 μL is then mixed and 100 μL of the resulting cell suspension is transferred into a 96 well Costar 3917 assay plate (Corning incorporated, cat #3917).

The cells are measured using a CyQUANT® NF Cell Proliferation Assay (Invitrogen, cat #C35006). 11 mL of 1×HBSS buffer is prepared by diluting 2.2 mL of 5×HBSS buffer (Component C) with 8.8 mL of deionized water. 1× dye binding solution is prepared by adding 22 microL of CyQUANT® NF dye reagent (Component A) and 22 microL of Component C to 11 mL of 1×HBSS buffer. 100 microL of 1× dye binding solution is dispensed into wells of the 96 well Costar plate containing the cell suspensions. The plate is covered and incubated at 37° C. for 60 minutes. Fluorescence measurement is quantitated using a multilabel plate reader (Wallac Victor2).

Methods of Therapeutic Use

In accordance with the invention, there are provided novel methods of using the compounds of the present invention. The compounds disclosed herein effectively block the interaction of CCR10 with its ligand CCL 27. The inhibition of this interaction is an attractive means for preventing and treating a variety of diseases or conditions associated with entry and activation of T-cells into the skin or other tissues where CCR10 is found to be expressed and associated with inflammatory conditions, such as lung tissue. Thus, the compounds of the present invention are useful for the treatment of diseases and conditions including psoriasis, contact sensitivity, dermatitis, systemic sclerosis, cutaneous systemic lupus erythematosus, and allergic asthma. The compounds of the invention will also be useful for treatment of melanomas that express CCR10.

These disorders have been well characterized in man, but also exist with a similar etiology in other mammals, and can be treated by pharmaceutical compositions of the present invention.

For therapeutic use, the compounds may be administered in a therapeutically effective amount in any conventional dosage form in any conventional manner Routes of administration include, but are not limited to, intravenously, intramuscularly, subcutaneously, intrasynovially, by infusion, sublingually, transdermally, orally, topically or by inhalation, tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems,* 5th ed., Lea and Febiger (1990)). A therapeutically effective amount can be determined by a skilled artisan based upon such factors as weight, metabolism, and severity of the affliction etc. Preferably the active compound is dosed at about 1 mg to about 500 mg per kilogram of body weight on a daily basis. More preferably the active compound is dosed at about 1 mg to about 100 mg per kilogram of body weight on a daily basis.

The compounds may be administered alone or in combination with adjuvants that enhance the stability of the inhibitors, facilitate administration of pharmaceutic compositions containing them in certain embodiments, provide increased dissolution or dispersion, increase inhibitory activity, provide adjunct therapy, and the like. Advantageously, such combinations may utilize lower dosages of the active ingredient, thus reducing possible toxicity and adverse side effects. Pharmaceutically acceptable carriers and adjuvants for use with compounds according to the present invention include, for example, ion exchangers, alumina, aluminum stearate, lecithin, serum proteins, buffer substances, water, salts or electrolytes and cellulose-based substances. This is not a complete list possible pharmaceutically acceptable carriers and adjuvants, and one of ordinary skilled in the art would know other possibilities, which are replete in the art.

We claim:
1. A compound formula (I):

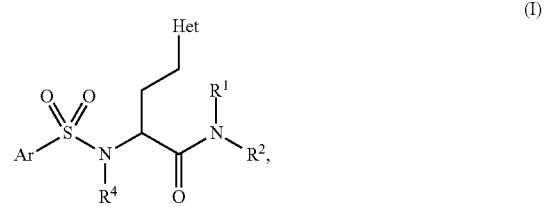

wherein:
Ar is phenyl, naphthyl or heteroaryl selected from indolyl, pyridyl, thienyl, pyrazolyl, oxazolyl, indazolyl, benzimidazolyl, isoquinolinyl, 1H-pyrrolo[2,3-b]pyridinyl, benzothienyl, benzofuranyl, 2,1,3-benzothiadiazolyl and 6H-imidazo[2,1-b]thiazolyl, wherein said phenyl naphthyl or heteroaryl is optionally substituted with one to four groups selected from $C_{1-6}$alkyl, $C_{1-6}$alkoxy, phenyl, heteroaryl, phenyloxy, halogen, —$NH_2$, —NHC(O)$NH_2$, —NHC(O)$C_{1-6}$alkyl, —$NO_2$, —$CF_3$, —$OCF_3$, —CN, —C(O)$C_{1-6}$alkyl, —$(CH_2)_{0-2}CO_2C_{1-6}$alkyl, —$(CH_2)_{0-2}CO_2H$, 5-tetrazolyl, —CHO, —C(O)$NH_2$, —C(O)NH($C_{1-6}$alkyl) and —C(O)N($C_{1-6}$alkyl)$_2$; or
if Ar is phenyl, two adjacent groups together with the phenyl they are bonded to may form a 2,3-dihydrobenzofuranyl, 1,3-dihydroindol-2-one, or 2-acetyl-3,4-dihydro-1H-isoquinolinyl group;
Het is a heteroaryl group selected from:

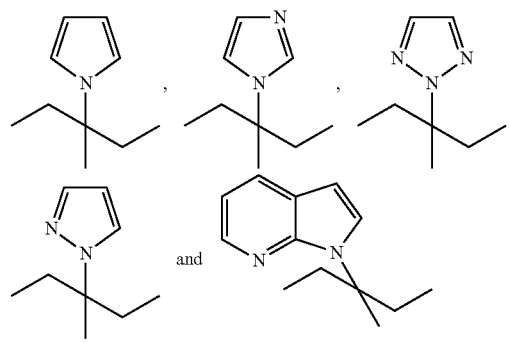

and is optionally substituted with one to two groups independently selected from —CN, —NO$_2$, halogen, —C$_{1-6}$alkyl, —C(O)NH$_2$ and CO$_2$Me;

R$^1$ and R$^2$ are independently selected from C$_{1-6}$alkyl, arylC$_{1-2}$alkyl, phenyl, naphthyl and C$_{3-8}$cycloalkyl, wherein said arylC$_{1-2}$alkyl is optionally substituted with one to two groups selected from halogen, C$_{1-6}$alkoxy, C$_{1-6}$alkyl, —CF$_3$, imidazolyl, pyridyl, pyrimidinyl, pyrazolyl, 5-methyloxadiazolyl, morpholinyl, piperidinyl and N-methyl-1,2,3,4-tetrahydroisoquinolinyl; or R$^1$ and R$^2$, together with the N they are bonded to form a heterocycle selected from piperidine, morpholine, tetrahydroisoquinoline, decahydroisoquinoline, piperazine, azepane, 6-aza-spiro[2.5]octane, 2,3,4,5-tetrahydro-1H-benzo[b]azepine, [1,4]-diazepane, [1,4]-oxazepane, thiomorpholine, thiomorpholine, thiomorpholine 1,1-dioxide, 4,5,6,7-tetrahydrothieno[3,2-c]pyridine, 5,6,7,8-tetrahydro-[1,2,4]triazolo[4,3-a]pyrazine, 5,6,7,8-tetrahydro-imidazo[1,5-a]pyrazine, 4,5,6,7-tetrahydro-thiazolo[5,4-c]pyridine, 1,2,3,6-tetrahydropyridine and octahydropyrido[1,2-a]pyrazine, wherein said heterocycle is optionally substituted by one to two groups selected from C$_{1-6}$alkyl, C$_{1-6}$alkenyl, phenyl, benzyl, hydroxyC$_{1-6}$alkyl, —OH, —CF$_3$, —CN, halogen, —NO$_2$, —NH$_2$, oxo, 1,3-dioxolane, —CH=NOCH$_3$, —SO$_2$NH$_2$, —SO$_2$N(C$_{1-6}$alkyl)$_2$, —SO$_3$H, —SO$_2$(C$_{1-6}$alkyl)$_2$, —C(O)N(C$_{1-6}$alkyl)$_2$, —C(O)NHC$_{1-6}$alkyl, —(CH$_2$)$_{0-2}$C(O)NH$_2$, —(CH$_2$)$_{0-4}$CO$_2$H, —(CH$_2$)$_{0-4}$CO$_2$C$_{1-6}$alkyl, =C—CO$_2$C$_{1-6}$ alkyl, —CH=CH—CO$_2$H, —CH=CH—CO$_2$C$_{1-6}$ alkyl, —OCH$_2$CO$_2$H, —OCH$_2$CO$_2$C$_{1-6}$alkyl, —OC(CH$_3$)$_2$CO$_2$H, —OC(CH$_3$)$_2$CO$_2$C$_{1-6}$alkyl, —C(O)CH$_2$CO$_2$H, —C(O)CH$_2$CO$_2$C$_{1-6}$alkyl, —C(O)C$_{1-6}$ alkyl, —C(O)C$_{1-4}$alkyl(OH), —CH$_2$OC$_{1-6}$alkyl, —(CH$_2$)$_{0-2}$NHC(O)C$_{1-6}$alkyl, —C(O)morpholinyl, thiazole, 3-methyl-1,2,4-oxadiazolyl, pyrimidine and 2-[1,2,4]oxadiazol-3-ylpyrazine; and R$^4$ is hydrogen or C$_{1-6}$alkyl;

or a pharmaceutically acceptable salt thereof.

2. The compound of claim 1, wherein:

Ar is phenyl, naphthyl or heteroaryl selected from indolyl, pyridyl, thienyl, pyrazolyl, indazolyl, isoquinolinyl, benzothienyl, benzofuranyl, and 6H-imidazo[2,1-b]thiazolyl, wherein said phenyl naphthyl or heteroaryl is optionally substituted with one to four groups selected from CH$_3$, —CH$_2$CH$_3$, —OCH$_3$, Cl, Br, F, —NH$_2$, C(O)CH$_3$, NHC(O)CH$_3$, —CF$_3$, —OCF$_3$, —CN and —CO$_2$CH$_3$; or if Ar is phenyl, two adjacent groups together with the phenyl they are bonded to may form a 2,3-dihydrobenzofuranyl or oxindolyl group;

Het is a heteroaryl group selected from

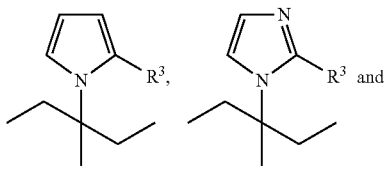

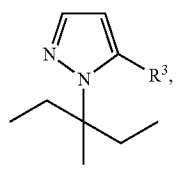

wherein R$^3$ is selected from —CN, —NO$_2$, Cl, Br, —C(O)NH$_2$ and CO$_2$Me;

R$^1$ is CH$_3$ and R$^2$ is benzyl, wherein said benzyl is optionally substituted with one to two groups selected from halogen, C$_{1-6}$alkoxy, C$_{1-6}$alkyl, —CF$_3$, imidazolyl, pyridyl, pyrimidinyl, pyrazolyl, 5-methyloxadiazolyl, morpholinyl, piperidinyl and N-methyl-1,2,3,4-tetrahydroisoquinolinyl; or R$^1$ and R$^2$, together with the N they are bonded to form a heterocycle selected from piperidine, tetrahydroisoquinoline, decahydroisoquinoline, piperazine, 6-aza-spiro[2.5]octane, azepane, [1,4]-diazepane and [1,4]-oxazepane, 4,5,6,7-tetrahydrothieno[3,2-c]pyridine, 5,6,7,8-tetrahydro-imidazo[1,5-a]pyrazine, 1,2,3,6-tetrahydropyridine, 5,6,7,8-tetrahydro-[1,2,4]triazolo[4,3-a]pyrazine, 2,3,4,5-tetrahydro-1H-benzo[b]azepine and 1,2,3,6-tetrahydropyridine, wherein said heterocycle is optionally substituted by one to two groups selected from C$_{1-6}$alkyl, C$_{1-6}$alkenyl, phenyl, benzyl, —CF$_3$, —CN, Cl, Br, F, —NO$_2$, oxo, —CH=NOCH$_3$, SO$_2$NH$_2$, —SO$_2$N(CH$_3$)$_2$, —SO$_3$H, —SO$_2$(CH$_3$), —C(O)N(CH$_3$)$_2$, —C(O)NHCH$_3$, —(CH$_2$)$_{0-2}$C(O)NH$_2$, —(CH$_2$)$_{0-4}$CO$_2$H, —(CH$_2$)$_{0-4}$CO$_2$C$_{1-2}$alkyl, —(CH$_2$)$_{0-4}$OH, —CH=CH—CO$_2$H, —CH=CH—CO$_2$C$_{1-2}$alkyl, —C—CO$_2$C$_{1-6}$alkyl, —OCH$_2$CO$_2$H, —OCH$_2$CO$_2$C$_{1-2}$alkyl, —OC(CH$_3$)$_2$CO$_2$H, —OC(CH$_3$)$_2$CO$_2$C$_{1-2}$alkyl, —C(O)CH$_2$CO$_2$H, —C(O)CH$_2$CO$_2$C$_{1-2}$alkyl, —C(O)CH$_3$, —C(O)C$_{1-4}$alkyl(OH), —CH$_2$OCH$_3$, —(CH$_2$)$_{0-2}$NHC(O)CH$_3$, —C(O)morpholinyl, thiazole, 3-methyl-1,2,4-oxadiazolyl, pyrimidine and 2-[1,2,4]oxadiazol-3-ylpyrazine; and R$^4$ is hydrogen;

or a pharmaceutically acceptable salt thereof.

3. The compound of claim 1, wherein:

Ar is phenyl, indolyl, thienyl or indazolyl, wherein each is optionally substituted with one to three groups selected from CH$_3$, —CH$_2$CH$_3$, —OCH$_3$, Cl, Br, F, —NH$_2$, and —CF$_3$;

Het is a heteroaryl group selected from

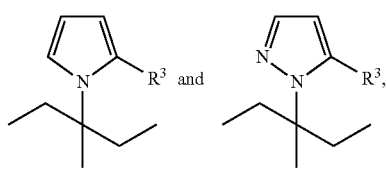

wherein R$^3$ is selected from —CN, —NO$_2$, Cl, Br, —C(O)NH$_2$ and CO$_2$Me;

R$^1$ and R$^2$, together with the N they are bonded to, form a heterocycle selected from piperidine, tetrahydroisoquinoline, decahydroisoquinoline, piperazine, 6-aza-spiro[2.5]octane, azepane, [1,4]-diazepane and [1,4]-oxazepane, 1,2,3,6-tetrahydrpyridine and 4,5,6,7-tetrahydrothieno[3,2-c]pyridine, wherein said heterocycle is optionally substituted by one to two groups selected from C$_{1-6}$alkyl, (CH$_2$)$_{0-2}$OH, —CF$_3$, —CN, Cl, Br, F, —(CH$_2$)$_{0-4}$CO$_2$H, —(CH$_2$)$_{0-4}$CO$_2$C$_{1-6}$ alkyl, —C(O)N(CH$_3$)$_2$, —C(O)NHCH$_3$, —C(O)NH$_2$, —C(O)CH$_3$, —CH=CH—CO$_2$H, —OC(CH$_3$)$_2$CO$_2$H, —OC(CH$_3$)$_2$CO$_2$H and —C(O)CH$_2$CO$_2$H; and
R$^4$ is hydrogen;
or a pharmaceutically acceptable salt thereof.

4. A pharmaceutical composition comprising the compound of claim 1, or a pharmaceutically acceptable salt thereof.

5. The compound of formula (I) according to claim 1 selected from the group consisting of:
N-{3-(2-cyano-1H-pyrrol-1-yl)-1-[(4-methylpiperidin-1-yl)carbonyl]propyl}thiophene-3-sulfonamide;
N-{3-(2-cyano-1H-pyrrol-1-yl)-1-[(4-methylpiperidin-1-yl)carbonyl]propyl}-2-methylbenzenesulfonamide;
N-{3-(2-cyano-1H-pyrrol-1-yl)-1-[(4-methylpiperidin-1-yl)carbonyl]propyl}-3-methylbenzenesulfonamide;
N-{3-(2-cyano-1H-pyrrol-1-yl)-1-[(4-methylpiperidin-1-yl)carbonyl]propyl}-4-methylbenzenesulfonamide;
N-{1-[(4-methylpiperidin-1-yl)carbonyl]-3-(1H-pyrazol-1-yl)propyl}-1H-indole-4-sulfonamide;
N-{3-(2-cyano-1H-pyrrol-1-yl)-1-[(4-methylpiperidin-1-yl)carbonyl]propyl}-2,4-dimethylbenzenesulfonamide;
N-{3-(2-cyano-1H-pyrrol-1-yl)-1[(4-methylpiperidin-1-yl)carbonyl]propyl}-2,5-dimethylbenzenesulfonamide;
N-{3-(2-cyano-1H-pyrrol-1-yl)-1-[(4-methylpiperidin-1-yl)carbonyl]propyl}-3,5-dimethylbenzenesulfonamide;
N-{3-(2-cyano-1H-pyrrol-1-yl)-1-[(4-methylpiperidin-1-yl)carbonyl]propyl}-2-methoxybenzenesulfonamide;
N-{3-(2-cyano-1H-pyrrol-1-yl)-1-[(4-methylpiperidin-1-yl)carbonyl]propyl}-3-methoxybenzenesulfonamide;
N-{3-(2-cyano-1H-pyrrol-1-yl)-1-[(4-methylpiperidin-1-yl)carbonyl]propyl}-4-methoxybenzenesulfonamide;
N-[1-{[4-(hydroxymethyl)piperidin-1-yl]carbonyl}-3-(1H-pyrazol-1-yl)propyl]-1H-indole-4-sulfonamide;
N-{3-(2-cyano-1H-pyrrol-1-yl)-1-[(4-methylpiperidin-1-yl)carbonyl]propyl}-1,3,5-trimethyl-1H-pyrazole-4-sulfonamide;
N-{3-(2-cyano-1H-pyrrol-1-yl)-1-[(4-methylpiperidin-1-yl)carbonyl]propyl}-4-fluoro-2-methylbenzenesulfonamide;
2-chloro-N-{3-(2-cyano-1H-pyrrol-1-yl)-1-[(4-methylpiperidin-1-yl)carbonyl]propyl}benzenesulfonamide;
3-chloro-N-{3-(2-cyano-1H-pyrrol-1-yl)-1-[(4-methylpiperidin-1-yl)carbonyl]propyl}benzenesulfonamide;
4-chloro-N-{3-(2-cyano-1H-pyrrol-1-yl)-1-[(4-methylpiperidin-1-yl)carbonyl]propyl}benzenesulfonamide;
N-{3-(2-cyano-1H-pyrrol-1-yl)-1-[(4-methylpiperidin-1-yl)carbonyl]propyl}-2,5-dimethylthiophene-3-sulfonamide;
2-chloro-N-{3-(2-cyano-1H-pyrrol-1-yl)-1-[(4-methylpiperidin-1-yl)carbonyl]propyl}pyridine-3-sulfonamide;
N-{3-(2-cyano-1H-pyrrol-1-yl)-1-[(4-methylpiperidin-1-yl)carbonyl]propyl}-1H-indole-3-sulfonamide;
2-cyano-N-{3-(2-cyano-1H-pyrrol-1-yl)-1-[(4-methylpiperidin-1-yl)carbonyl]propyl}-5-methylbenzenesulfonamide;
N-{3-(2-cyano-1H-pyrrol-1-yl)-1-[(4-methylpiperidin-1-yl)carbonyl]propyl}-1H-indole-4-sulfonamide;
N-{3-(2-cyano-1H-pyrrol-1-yl)-1-[(4-methylpiperidin-1-yl)carbonyl]propyl}-1H-indole-6-sulfonamide;
N-{3-(2-cyano-1H-pyrrol-1-yl)-1-[(4-methylpiperidin-1-yl)carbonyl]propyl}-1-benzofuran-7-sulfonamide;
N-{3-(2-cyano-1H-pyrrol-1-yl)-1-[(4-methylpiperidin-1-yl)carbonyl]propyl}-1H-indazole-4-sulfonamide;
N-{3-(2-cyano-1H-pyrrol-1-yl)-1-[(4-methylpiperidin-1-yl)carbonyl]propyl}-1H-indazole-6-sulfonamide;
N-{3-(2-cyano-1H-pyrrol-1-yl)-1-[(4-methylpiperidin-1-yl)carbonyl]propyl}-1H-indole-5-sulfonamide;
N-{3-(3-cyano-1H-pyrazol-1-yl)-1-[(4-methylpiperidin-1-yl)carbonyl]propyl}-1H-indole-4-sulfonamide;
N-{3-(5-cyano-1H-pyrazol-1-yl)-1-[(4-methylpiperidin-1-yl)carbonyl]propyl}-1H-indole-4-sulfonamide;
N-{3-(2-cyano-1H-pyrrol-1-yl)-1-[(4-methylpiperidin-1-yl)carbonyl]propyl}-2,4,6-trimethylbenzenesulfonamide; and
the pharmaceutically acceptable salts thereof.

* * * * *